US008389794B2

(12) United States Patent
Jørgensen et al.

(10) Patent No.: US 8,389,794 B2
(45) Date of Patent: Mar. 5, 2013

(54) TRANSGENIC PIG AS A MODEL OF ALZHEIMER'S DISEASE

(75) Inventors: Arne Lund Jørgensen, Højbjerg (DK); Ida Elisabeth Holm, Højbjerg (DK); Anders Lade Nielsen, Åbyhøj (DK); Marianne Gregers Johansen, Århus C (DK); Jannik Ejnar Jakobsen, Trige (DK)

(73) Assignee: Aarhus Universitet (DK)

( * ) Notice: Subject to any disclaimer, the term of this patent is extended or adjusted under 35 U.S.C. 154(b) by 481 days.

(21) Appl. No.: 12/529,963

(22) PCT Filed: Mar. 6, 2008

(86) PCT No.: PCT/DK2008/050054

§ 371 (c)(1),
(2), (4) Date: Nov. 30, 2009

(87) PCT Pub. No.: WO2008/106981

PCT Pub. Date: Sep. 12, 2008

(65) Prior Publication Data

US 2010/0138940 A1 Jun. 3, 2010

(30) Foreign Application Priority Data

Mar. 7, 2007 (DK) ................................ 2007 00352
Jul. 13, 2007 (DK) ................................ 2007 01038
Nov. 9, 2007 (DK) ................................ 2007 01582

(51) Int. Cl.
*G01N 33/00* (2006.01)
*C12N 15/00* (2006.01)
*A01K 67/027* (2006.01)

(52) U.S. Cl. ................................ 800/17; 800/24; 800/3

(58) Field of Classification Search ........................ None
See application file for complete search history.

(56) References Cited

U.S. PATENT DOCUMENTS 6,485,911 B1 11/2002 St. George-Hyslop et al.

FOREIGN PATENT DOCUMENTS

| | | | | |
|---|---|---|---|---|
| JP | 316420 | * 1/2000 | ......................... | 15/9 |
| WO | WO 96/40896 A1 | 12/1996 | | |
| WO | WO 2004/064768 A2 | 8/2004 | | |
| WO | WO 2007/124751 A2 | 11/2007 | | |

OTHER PUBLICATIONS

Focus Denmark, 2006, vol. 2, Trade Council, Ministry of Foreign Affairs of Denmark, "The Fight Against Alzheimer's," pp. 1 and 8-10.*

Lagutina et al. Birth of Cloned Pigs from Zona-Free Nuclear Transfer Blastocysts Developed in Vitro before Transfer. Cloning and Stem Cells, 2005, vol. 8, pp. 283-294.*

Citron et al. Mutant Presenilins of Alzheimer's diesase increase production of a 42-residue amyloi beta-protein in both transfected cells and transgenic mice. Nature Medicine, 1997, vol. 3, pp. 67-72.*

Takeuchi et al. Age-Related Amyloid b Deposition in Transgenic Mice Overexpressing Both Alzheimer Mutant Presenilin 1 and Amyloid b Precursor Protein Swedish Mutant Is Not Associated with Global Neuronal Loss American Journal of Pathology, 2000, vol. 157, pp. 331-339.*

Buttini et al. Journal of Neuroscience, 2005, vol. 25, pp. 9096-9101.*

Morgan. Birth of Cloned Pigs from Zona-Free Nuclear Transfer Blastocysts Developed In Vitro before Transfer. Expert Review Vaccines, 2003, vol. 2, pp. 89-95.*

Abad MA et al. (Dec. 2006), "Neuronal pentraxin 1 contributes to the neuronal damage evoked by amyloid-β and is overwxpressed in dystrophic neurites in alzheimer's brain." J Neurosci, 26 (49), 12735-12747.

Alberici A et al. (2007), "Dementia, delusions and seizures: storage disease or genetic AD?", Eur J Neurol, 14 (9), 1057-1059.

Alexander LJ et al. (1996), "Cloning and characterization of 414 polymorphic porcine microsatellites." Anim Genet, 27 (3), 137-48.

Andersen et al. (Nov. 2002), Mechanisms underlying targeted gene correction using chimeric RNA/DNA and single-stranded DNA oligonucleotides, J Mol Med, vol. 80, p. 770-781.

Anheim M et al. (2007), "Ataxic variant of alzheimer's disease caused by Pro117Ala PSEN1 mutation." J Neurol Neurosurg Psychiatr, 78 (12), 1414-1415.

Arango-Lasprilla JC et al. (2007), "Cognitive changes in the preclinical phase of familial alzheimer's disease." J Clin Exp Neuropsychol, 29 (8), 892-900.

Asami-Odaka A et al. (2005), "Passive immunization of the Aβ42(43) C-terminal-specific antibody BC05 in a mouse model of alzheimer's disease." Neurodegener Dis, 2 (1), 36-43.

Biswas SC et al. (Jan. 2007), "Bim is elevated in alzheimer's disease neurons and is required for β-amyloid-induced neuronal apoptosis.", 27 (4), 893-900.

Blechingberg J et al. (2007), "Identification and characterization of GFAP?, a novel Glial fibrillary acidic protein isoform.", GLIA, 55, 497-507.

Blechingberg J et al. (Nov. 2007), "Regulatory mechanisms for 3'-end alternative splicing and polyadenylation of the glial fibrillary acidic protein, GFAP, transcript.", Nucleic Acids Research, 35 (22), 7636-7650.

(Continued)

*Primary Examiner* — Deborah Crouch
(74) *Attorney, Agent, or Firm* — McLane, Graf, Raulerson & Middleton, PA

(57) ABSTRACT

The present invention relates to a modified pig as a model for studying Alzheimer's disease. The modified pig model displays one or more phenotypes associated with Alzheimer's disease. Disclosed is also a modified pig comprising a modified human and/or porcine APP gene, and/or PS1 gene, and/or a transcriptional and/or translational product or part thereof. The invention further relates to methods for producing the modified pig; and methods for evaluating the effect of a therapeutical treatment of Alzheimer's disease; methods for screening the efficacy of a pharmaceutical composition; and a method for treatment of a human being suffering from Alzheimer's disease are disclosed.

11 Claims, 40 Drawing Sheets

OTHER PUBLICATIONS

Bodyak N et al. (1999), "Performance of mice in an automated olfactometer: Odor detection, discrimination and odor memory.", 24, 637-645.
Book et al. (1974), The Fetal and Neonatal Pig in Biomedical Research, Joumal of Animal Science, vol. 38, No. 5, p. 997-1002.
Braak H et al. (1991), "Neuropathological stageing of alzheimer-related changes.", Acta Neuropathol (Berl), 82, 239-259.
Carey BW et al. (2007), "Presenilin/ ?-secretase and a-secretase-like peptidases cleave human MHC class I proteins.", Biochemical Journal, 401 (1), 121-127.
Chen Q et al. (Jul. 2002), "A novel mechanism for the regulation of amyloid precursor protein metabolism.", 158 (1), 79-89.
Czech et al. (Jul. 20, 1998), Characterization of Human Presenilin 1 Transgenic Rats: Increased Sensitivity to Apoptosis in Primary Neuronal Cultures, Neuroscience, New York, vol. 87, No. 2, p. 325-326.
Dobrinsky et al. (1996), Development of a Culture Medium (BECM-3) for Porcine Embryos: Effect of Bovine Serum Albumin and Fetal Bovine Serum on Embryo Development, Biol Reprod, vol. 55, p. 1069-1074.
Doty RL et al. (Feb. 1984), "University of Pennsylvania smell identification test: A rapid quantitative olfactory function test for the clinic.", Laryngoscope, 94 (2 pt. 1), 176-8.
Douglas WR et al. (1972), "Of pigs and men and research: A review of applications and analogies of the pig, sus scrofa, in human medical research." Space Life Sci, 3, 226-234.
Du et al. (2005), High overall In Vitro Efficiency of Porcine Handmade Cloning (HMC) Combining Partial Zona Digestion and Oocyte Trisection with Sequential Culture, Cloning and Stem Cells, vol. 7, No. 3, p. 199-204.
Dumanchin C et al. (Oct. 2006), "Biological effects of four PSEN1 gene mutations causing alzheimer's disease with spastic paraparesis and cotton wool plaques.", Hum Mutat, 27 (10), 1063.
Eibenstein A et al. (2005), "Modern psychophysical tests to assess olfactory function.", Neurol Sci, 26, 147-155.
Eibenstein A et al. (2005), "Olfactory screening test in mild cognitive impairment.", 26, 156-160.
Esaki et al. (2004), Cryopreservation of Porcine Embroys Derived from In Vitro-Matured Oocytes, Biology of Reproduction, vol. 71, p. 432-437.
Fang B et al. (2006), "Chinese presenilin-1 V97L mutation enhanced Aβ42 levels in SH-SY5Y neuroblastoma cells.", 406 (1-2), 33-37.
Feltrin et al. (2006), In Vitro Bovine Embryo Development After Nuclear Transfer by Handmade Cloning Using a Modified WOW Culture System, Reprod Fertil Dev 18(2), p. 126.
Games D et al. (Feb. 1995), "Alzheimer-type neuropathology in transgenic mice overexpressing V717F β-amyloid precursor protein.", 373 (6514), 523-7.
Hagl C et al. (2005), "Use of a maze to detect cognitive dysfunction in a porcine model of hypothermic circulatory arrest.", The Society of Thoracic Surgeons, 79, 1307-15.
Hardy J et al. (Jul. 2002), "The Amyloid Hypothesis of alzheimer's disease: Progress and problems on the road to therapeutics.", Science, 297 (5580), 353-6.
Hendriks L et al. (Jun. 1992), "Presenile dementia and cerebral haemorrhage linked to a mutation at codon 692 of the β-amyloid precursor protein gene.", Nature Genetics, 1 (3), 218-221.
Holm IE et al. (Feb. 1994), "Hippocampus of the domestic pig: A stereological study of subdivisional volumes and neuron numbers.", Hippocampus, 4 (1), 115-126.
Hoshino et al. (2005), Developmental Competence of Somatic Cell Nuclear Transfer Embryos Reconstructed from Oocytes Matured In Vitro with Follicle Shells in Miniature Pig, Cloning and Stem Cells, vol. 7, No. 1, p. 17-27.
Hyafil F et al. (1993), "In vitro and in vivo reversal of multidrug resistance by GF120918, an acridonecarboxamide derivative.", 53 (19), 4595-602.
Ivics et al. (Nov. 1997),Molecular Reconstruction of Sleeping Beauty, a Tc1-like Transposon from Fish, and Its Transposition in Human Cells, Cell, vol. 91, p. 501-510.
Jelsing J et al. (2005), "A volumetric screening procedure for the Gottingen minipig brain.", Exp Brain Res, 162 (4), 428-435.
Jones CT et al. (Jul. 1992), "Mutation in codon 713 of the β amyloid precursor protein gene presenting with schizophrenia.", Nature Genetics, 1 (4), 306-309.
Kamino K et al. (1992), "Linkage and mutational analysis of familial alzheimer disease kindreds for the APP gene region.", Am J Hum Genet, 51 (5), 998-1014.
Kikuchi et al. (1999), Developmental Competence, after Transfer to Recipients, of Porcine Oocytes Matured, Fertilized, and Cultured In Vitro, Biology of Reproduction, vol. 60, p. 336-340.
Kikuchi et al. (2002), Successful Piglet Production after Transfer of Blastocysts Produced by a Modified In Vitro System, Biology of Reproduction, vol. 66, p. 1033-1041.
Kim J et al. (Jan. 2007), "Aβ40 inhibits amyloid deposition in vivo.", J Neurosci, 27 (3), 627-633.
Kimura A et al. (1999), "Amyloid precursor protein 770.", Published only in Database.
Kragh et al. (2004), Production of Transgenic Porchine Blastocysts by Handmade Cloning, Reprod. Fert. Dev. 16. p. 290.
Kragh et al. (2004), Production of transgenic porchine blastocysts by hand-made cloning, Reprod. Fert. Dev. 16. p. 315-318.
Kragh et al. (2005), Efficient in vitro production of porcine blastocysts by handmade cloning with a combined electrical and chemical activation, Theriogenology 64, p. 1536-1545.
Levites Y et al. (Jan. 2006), "Anti-Aβ42- and anti Aβ40-specffic mAbs attenuate amyloid deposition in an alzheimer disease mouse model.", Journal of clinical investigation, 116 (1), 193-201.
Mant R et al. (Sep. 1992), "Schizophrenia scepticism.", Nat Genet, 2 (1), 12.
Mirra SS et al. (Apr. 1991), "The consortium to establish a regstry for alzheimer's disease (CERAD)." Neurology, 41 (4), 479-486.
Moustgaard A et al. (2002), "Spontaneous object recognition in the Göttingen minipig.", Natural Plasticity, 9 (4), 255-259.
Mullan M et al. (Aug. 1992), "A pathogenic mutation for probable alzheimer's disease in the APP gene at the N-terminus of β-amyloid.", 1 (5), 345-347.
Mullan M et al. (Sep. 1992), "In search of the soluble.", Nature, 359 (6393), 268-269.
Needleman SB et al. (1970), A General Method Applicable to the Search for Similarities in the Amino Acid Sequence of Two Proteins, J. Mol. Biol. 48, p. 443-453.
Neve RL et al. (Oct. 1988), "Expression of the alzheimer amyloid precursor gene transcripts in the human brain.", Neuron, 1 (8), 669-677.
Oback et al. (2003), Cloned Cattle Derived from a Novel Zona-Free Embryo Reconstruction System, Cloning and Stem Cells, vol. 5, No. 1, p. 3-12.
Oerum et al. (Jul. 1, 2006), Porcine APP cDNAs: Molecular cloning and characterization, expression analysis, choromosomal localization and SNP analysis, Biochimica et Biophysica Acta, vol. 1759, No. 7, p. 378-384.
Parisiadou L et al. (2004), "Presenilin 1 and cadherins: Stabilization of cell-cell adhesion and proteolysis-dependent regulation of transcription.", Neurodegenerer Dis, 1 (4-5), 184-191.
Peura et al. (1998), The Effect of Recipient Oocyte Volume on Nuclear Transfer in Cattle, Molecular Reproduction and Development, vol. 50, p. 185-191.
Peura et al. (2003), A Comparison of Established and New Approaches in Ovine and Bovine Nuclear Transfer, Cloning and Stem Cells, vol. 5, No. 4, 257-277.
Pillay P et al. (2007), "Order-specific quantitative patterns of cortical gyrification.", European Journal of Neuroscience, 25 (9), 2705-2712.
Pond WG et al. (2000), "Perinatal ontogeny of brain growth in the domestic pig.", Proc Soc Exp Biol Med, 223 (1), 102-8.
Price DL et al. (1991), "Aged non-human primates: An animal model of age-associated neurodegenerative disease.", Barin Pathol, 1 (4), 287-96.
Reed et al. (Jan. 1992), In Vitro Culture of Pig Embryos, Theriogeneology, vol. 37, No. 1, p. 95-109.

Rockenstein EM et al. (Nov. 1995), "Levels and alternative splicing of amyloid β protein precursor (APP) transcripts in brains of APP transgenic mice and humans with alzheimer's disease.", J Biol Chem, 270 (47), 28257-67.
Rohrer GA et al. (Jan. 1994), "A microsatellite linkage map of the porcine genome.", Genetics, 136 (1), 231-45.
Saganich MJ et al. (Dec. 2006), "Deficits in synaptic transmission and learning in amyloid precursor protein (APP) transgenic mice require C-terminal cleavage of APP.", J Neurosci, 26 (52), 13428-13436.
Sanchez-Valle R et al. (2007), "A novel mutation in the PSEN1 gene (L286P) associated with familial early-onset dementia of alzheimer type and lobar haematomas.", Eur J Neurol, 14 (12), 1409-1412.
Sasahara M et al. (Jan. 1991), "PDGF B-chain in neurons of the central nervous system, posterior pituitary, and in a transgenic model. ", Cell, 64 (1), 217-27.
Sato C et al. (Nov. 2006), "Structure of the catalytic pore of ?-secretase probed by the accessibility of substituted cysteines.", J Neurosci, 26 (46), 12081-12088.
Schellenberg GD et al. (1992), "Genetic association and linkage analysis of the apolipoprotein CII locus and falial alzheimer's disease.", Ann Neurol, 31 (2), 223-227.
Schellenberg GD et al. (Oct. 1992), "Genetic linkage evidence for a familial alzheimer's disease locus on chromosome 14.", Science, 258 (5082), 668-671.
Schenk D et al. (Jul. 1999), "Immunization with amyloid-β attenuates alzheimer-disease-like pathology in the PDAPP mouse.", Nature, 400 (6740), 173-7.
Selkoe DJ (1993), "Physiological production of the β-amyloid protein and the mechanism of alzheimer's disease.", Trends Neurosci, 16 (10), 403-9.
Selkoe DJ (1994), "Normal and abnormal biology of the β-amyloid precursor protein.", Annu Rev Neurosci, 17, 489-517.
Sherrer et al. (2004), Fertilization and blastocyst development in oocytes obtained from prepubertal and adult pigs, J Anim Sci, vol. 82, p. 102-108.
Sherrington R et al. (Jun. 1995), "Cloning of gene bearing missense mutations in early-onset familiaal alzheimer's disease.", Nature, 375, 754-760.
Sisodia SS (Nov. 1999), "Alzheimer's Disease: Perspectives for the new millennium.", J Clin Invest, 104 (9), 1169-70.
Slotnick B et al. (May 2002), "Odor discrimination and odor quality perception in rats with disruption of connections between the olfactory epithelium and olfactory bulbs.", J Neurosci, 22 (10), 4205-4216.
Smith DH et al. (Sep. 1999), "Accumulation of amyloid β and Tau and the formation of neurofilament inclusions following diffuse brain injury in the pig.", J Neuropathol Exp Neurol, 58 (9), 982-992.
Smith et al. (1981), Comparison of Biosequences, Advances in Applied Mathematics 2, p. 482-489.
Smith TF et al. (1981), "Identification of common molecular subsequences.", J Mol Biol, 147 (1), 195-7.
St. George-Hyslop P et al. (Dec. 1992), "Genetic evidence for a novel familial alzheimer's disease locus on chromosome 14.", Nat Genet, 2 (4), 330.334.
Sorensen et al. (2005), Site-specific strand bias in gene correction using single-stranded oligonucleotides, J Mol Med, vol. 83, p. 39-49.
Taniuchi N et al. (Nov. 2007), "Decreased proliferation of hippocampal progenitor cells in APPswe/PS1dE9 transgenic mice.", Neuroreport, 18 (17), 1801-1805.
Tanzi RE et al. (1993), "Cellular specificity and regional distribution of amyloid β protein precursor alternative transcripts are unaltered in alzheimer hippocampal formation.", Molecular Brain Research, 18 (3), 246-52.
The National Institute on Aging, and Reagan Institute Working Group on Diagnostic Criteria for the Neuropathological Assessment of Alzheimer's Disease (1997), "Consensus recommendations for the postmortem diagnosis of alzheimer's Disease.", Neurobiology of Aging, 18 (4 suppl), S1-S3.
Tsuchiya D et al. (Nov. 2006), "Morphological change by ocerexpression of D385A dominant negative presenilin 1 in human neuroblastoma SH-SY5Y cells.", J Pharmacol Sci, 102 (3), 354-358.
Umov et al. (Jun. 2005), Highly efficient endogenous human gene correction using designed zinc-finger nucleases, Nature, vol. 435, p. 646-651.
Vajta et al. (1997), Survival and development of bovine blastocysts produced in vitro after assisted hatching, vitrification and in-straw direct rehydration, Journal of Reproduction and Fertility, vol. 111, p. 65-70.
Vajta et al. (2004), Production of a healthy calf by somatic cell nuclear transfer without micromanipulators and carbon dioxide incubators using the Handmade Cloning (HMC) and the Submarine Incubation System (SIS), Theriogenology, vol. 62, p. 1465-1472.
Vajta et. al (2003), Handmade Somatic Cell Cloning Cattle: Analysis of Factors Contributing to High Efficiency In Vitro, Biology of Reproduction, vol. 68, p. 571-578.
Vajta G. (2000), Oocyte and Embryo Vitrification, Annual ESDAR Conference 1999, p. 45-48.
Vodicka et al. (May 2005), The Miniature Pig as an Animal Model in Biomedical Research, Annals of the New York Academy of Sciences, vol. 1049, p. 161-171.
Watanabe H et al. (2001), "MR-based statistical altas of the Göttingen minipig brain.", Neuroimage, 14 (5), 1089-96.
Wu et al. (2004), Birth of Piglets by in vitro fertilization of zona-free porcine oocytes, Theriogenology, vol. 62, p. 1544-1556.
Yoshioka et al. (2002), Birth of Piglets Derived from Porcine Zygotes Cultured in a Chemically Defined Medium, Biology of Reproduction, vol. 66, p. 112-119.

* cited by examiner

APP770 protein homology between human and pig

```
HsAPP   MLPGLALLLLAAWTARALEVPTDGNAGLLAEPQIAMFCGRLNMHMNVQNGKWDSDPSGTK
        ::::::: ::::::::::::::::::::::::: :::::: ::::::::::: :::::::
SsAPP   MLPGLALVLLAAWTARALEVPTDGNAGLLAEPQVAMFCGKLNMHMNVQNGKWESDPSGTK
                10        20        30        40        50        60

                70        80        90       100       110       120
HsAPP   TCIDTKEGILQYCQEVYPELQITNVVEANQPVTIQNWCKRGRKQCKTHPHFVIPYRCLVG
        ::: :::::::::::::::::::::::::::::::::::: ::::::: : :::::::::
SsAPP   TCIGTKEGILQYCQEVYPELQITNVVEANQPVTIQNWCKRSRKQCKTHTHIVIPYRCLVG
                70        80        90       100       110       120

               130       140       150       160       170       180
HsAPP   EFVSDALLVPDKCKFLHQERMDVCETHLHWHTVAKETCSEKSTNLHDYGMLLPCGIDKFR
        ::::::::::::::::::::::::::::::::::::::::::::::::::::::::::::
SsAPP   EFVSDALLVPDKCKFLHQERMDVCETHLHWHTVAKETCSEKSTNLHDYGMLLPCGIDKFR
               130       140       150       160       170       180

               190       200       210       220       230       240
HsAPP   GVEFVCCPLAEESDNVDSADAEEDDSDVWWGGADTDYADGSEDKVVEVAEEEEVAEVEEE
        ::::::::::::::: ::::::::::::::::::::::::::::::::::::::: ::::
SsAPP   GVEFVCCPLAEESDNIDSADAEEDDSDVWWGGADTDYADGSEDKVVEVAEEEEVADVEEE
               190       200       210       220       230       240

               250       260       270       280       290       300
HsAPP   EADDDEDDEDGDEVEEEAEEPYEEATERTTSIATTTTTTTESVEEVVREVCSEQAETGPC
        ::.:::::::::::::::::::::::::::::::::::::::::::::::::::::::::
SsAPP   EAEDDEDDEDGDEVEEEAEEPYEEATERTTSIATTTTTTTESVEEVVREVCSEQAETGPC
               250       260       270       280       290       300

               310       320       330       340       350       360
HsAPP   RAMISRWYFDVTEGKCAPFFYGGCGGNRNNFDTEEYCMAVCGSAMSQSLLKTTQEPLARD
        :::::::::::::::::::::::::::::::::::::::::::.::::::::::: :  :
SsAPP   RAMISRWYFDVTEGKCAPFFYGGCGGNRNNFDTEEYCMAVCGSVMSQSLLKTTQEHLPQD
               310       320       330       340       350       360

               370       380       390       400       410       420
HsAPP   PVKLPTTAASTPDAVDKYLETPGDENEHAHFQKAKERLEAKHRERMSQVMREWEEAERQA
        ::::::::::::::::::::::::::::::::::::::::::::::::::::::::::::
SsAPP   PVKLPTTAASTPDAVDKYLETPGDENEHAHFQKAKERLEAKHRERMSQVMREWEEAERQA
               370       380       390       400       410       420

               430       440       450       460       470       480
HsAPP   KNLPKADKKAVIQHFQEKVESLEQEAANERQQLVETHMARVEAMLNDRRRLALENYITAL
        ::::::::::::::::::::::::::::::::::::::::::::::::::::::::::::
SsAPP   KNLPKADKKAVIQHFQEKVESLEQEAANERQQLVETHMARVEAMLNDRRRLALENYITAL
               430       440       450       460       470       480
```

Fig. 1

```
               490       500       510       520       530       540
HsAPP   QAVPPRPRHVFNMLKKYVRAEQKDRQHTLKHFEHVRMVDPKKAAQIRSQVMTHLRVIYER
        ::::::::::::::::::::::::::::::::::::::::::::::::::::::::::::
SsAPP   QAVPPRPRHVFNMLKKYVRAEQKDRQHTLKHFEHVRMVDPKKAAQIRSQVMTHLRVIYER
               490       500       510       520       530       540

               550       560       570       580       590       600
HsAPP   MNQSLSLLYNVPAVAEEIQDEVDELLQKEQNYSDDVLANMISEPRISYGNDALMPSLTET
        ::::::::::::::::::::::::::::::::::::::::::::::::::::::::::::
SsAPP   MNQSLSLLYNVPAVAEEIQDEVDELLQKEQNYSDDVLANMISEPRISYGNDALMPSLTET
               550       560       570       580       590       600

               610       620       630       640       650       660
HsAPP   KTTVELLPVNGEFSLDDLQPWHSFGADSVPANTENEVEPVDARPAADRGLTTRPGSGLTN
        ::::::::::::::::::::: :: :::::::::::::::::::::::::::::::::::
SsAPP   KTTVELLPVNGEFSLDDLQPWHPFGVDSVPANTENEVEPVDARPAADRGLTTRPGSGLTN
               610       620       630       640       650       660

               670       680       690       700       710       720
HsAPP   IKTEEISEVKMDAEFRHDSGYEVHHQKLVFFAEDVGSNKGAIIGLMVGGVVIATVIVITL
        ::::::::::::::::::::::::::::::::::::::::::::::::::::::::::::
SsAPP   IKTEEISEVKMDAEFRHDSGYEVHHQKLVFFAEDVGSNKGAIIGLMVGGVVIATVIVITL
               670       680       690       700       710       720

               730       740       750       760       770
HsAPP   VMLKKKQYTSIHHGVVEVDAAVTPEERHLSKMQQNGYENPTYKFFEQMQN
        ::::::::::::::::::::::::::::::::::::::::::::::::::
SsAPP   VMLKKKQYTSIHHGVVEVDAAVTPEERHLSKMQQNGYENPTYKFFEQMQN
               730       740       750       760       770
```

Fig. 1 (cont.)

PS1 protein homology between human and pig

```
HsPS1    MTELPAPLSYFQNAQMSEDNHLSNTVRSQNDNRERQEHN-DRRSLGHPEPLSNGRPQGNS
         ::::::::::::::::::::: :: : :::: ::: ::   ::  :  :  ::::  ::::
SsPS1    MTELPAPLSYFQNAQMSEDNHVSNNVSSQNDSRERHEHSIERRRRGNSESLSNGGAQGNS
                 10        20        30        40        50        60

       60        70        80        90       100       110
HsPS1    RQVVEQDEEEDEELTLKYGAKHVIMLFVPVTLCMVVVVATIKSVSFYTRKDGQLIYTPFT
         :::::: :::::::::::::::::::::::::::::::::::::::::::::::::::::
SsPS1    RQVVEQEEEEDEELTLKYGAKHVIMLFVPVTLCMVVVVATIKSVSFYTRKDGQLIYTPFT
                 70        80        90       100       110       120

      120       130       140       150       160       170
HsPS1    EDTETVGQRALHSILNAAIMISVIVVMTILLVVLYKYRCYKVIHAWLIISSLLLLFFFSF
         ::::::::::::::::::::::::::::::::::::::::::::::::::::::::::::
SsPS1    EDTETVGQRALHSILNAAIMISVIVVMTILLVVLYKYRCYKVIHAWLIISSLLLLFFFSF
                130       140       150       160       170       180

      180       190       200       210       220       230
HsPS1    IYLGEVFKTYNVAVDYITVALLIWNFGVVGMISIHWKGPLRLQQAYLIMISALMALVFIK
         ::::::::::::: :::::::::::::::::: :::::::::::::::::::::::::::
SsPS1    IYLGEVFKTYNVAMDYITVALLIWNFGVVGMIAIHWKGPLRLQQAYLIMISALMALVFIK
                190       200       210       220       230       240

      240       250       260       270       280       290
HsPS1    YLPEWTAWLILAVISVYDLVAVLCPKGPLRMLVETAQERNETLFPALIYSSTMVWLVNMA
         ::::::::::::::::::::::::: ::::.:::::::::::::::::::::::::::::
SsPS1    YLPEWTAWLILAVISVYDLVAVLCPNGPLRLLVETAQERNETLFPALIYSSTMVWLVNMA
                250       260       270       280       290       300

      300       310       320       330       340       350
HsPS1    EGDPEAQRRVSKNSKYNAESTERESQDTVAENDDGGFSEEWEAQRDSHLGPHRSTPESRA
         :::::::: ::::: ::: ::  :::: : : ::::::::::::::: :::: :: ::: 
SsPS1    EGDPEAQRKVSKNSNYNAQSTG-ESQDSVTESDDGGFSEEWEAQRDSRLGPHHSTAESRS
                310       320       330       340       350

      360       370       380       390       400       410
HsPS1    AVQELSSSILAGEDPEERGVKLGLGDFIFYSVLVGKASATASGDWNTTIACFVAILIGLC
         ::: :: :: : ::::::::::::::::::::::::::::::::::::::::::::::::
SsPS1    AVQDLSRSIPATEDPEERGVKLGLGDFIFYSVLVGKASATASGDWNTTIACFVAILIGLC
      360       370       380       390       400       410

      420       430       440       450       460
HsPS1    LTLLLLAIFKKALPALPISITFGLVFYFATDYLVQPFMDQLAFHQFYI
         ::::::::::::::::::::::::::::::::::::::::::::::::
SsPS1    LTLLLLAIFKKALPALPISITFGLVFYFATDYLVQPFMDQLAFHQFYI
      420       430       440       450       460
```

Fig. 2

100 bp marker
1) Minipig no. 7 Cerebral cortex
2) Minipig no. 7 Cerebellum
3) Minipig no. 7 Hippocampus
4) Minipig no. 7 Basal ganglia
5) Minipig no. 7 Brain stem
6) Minipig no. 7 Heart
7) Minipig no. 7 Liver
8) $H_2O$ Lane 1: Cortex from Minipig no. 11 (normal non-transgenic pig)
Lane 2: Cortex from Minipig no. 7 (transgenic for human APPsw gene)

Antibody 6E10 (1:1.000)

A
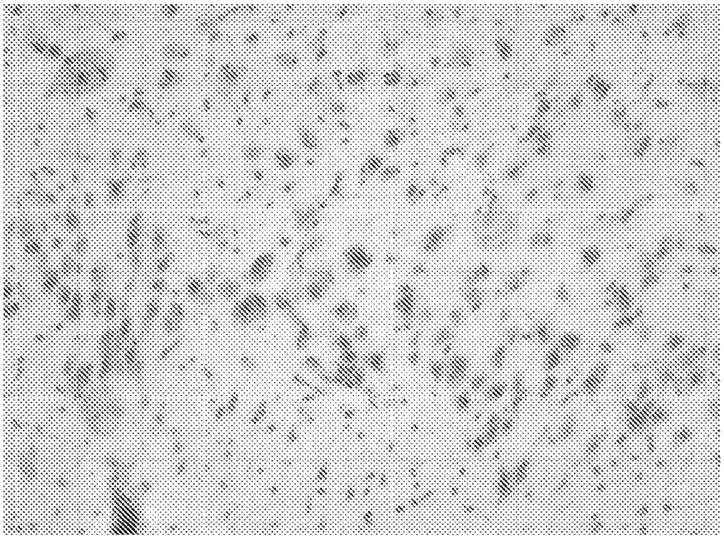
B
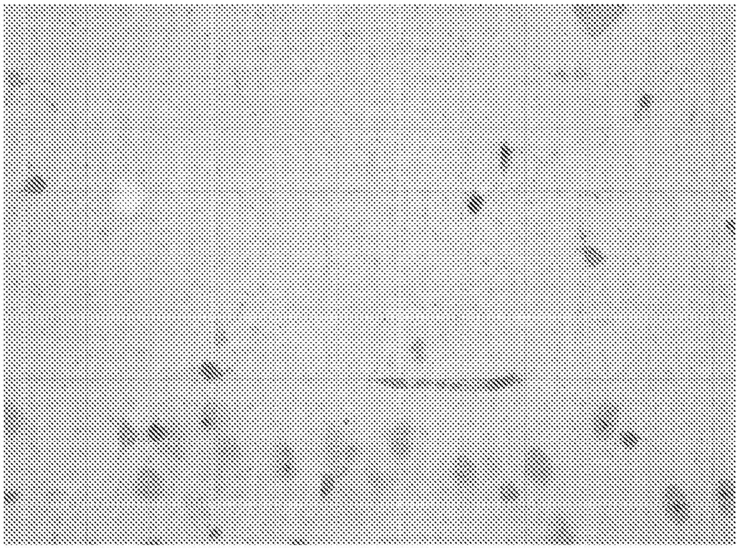
Fig. 13

Fig. 21

Gene-shift in the Hek 293 cell clone 4.

The GFP gene linked to a puromycin resistant gene is shifted with a RFP gene linked to a hygromycin gene

| A cell line containing the transposon was generated after 11 days of puromycin selection | The cells were split and transfected with the RFP donor plasmid and a FlPe plasmid | 5 days of selection with hygromycin. A small cell colony shows a faint sign of gene-shift. The red colour slowly replaces the green colour | The cell colony now shows clear evidence of gene-shifting, after continuous selection with hygromycin. No green colour is left only the red colour from the donor gene. | The cell colony undergone geneshift is no longer resistant to puromycin, as expected | colour |
|---|---|---|---|---|---|

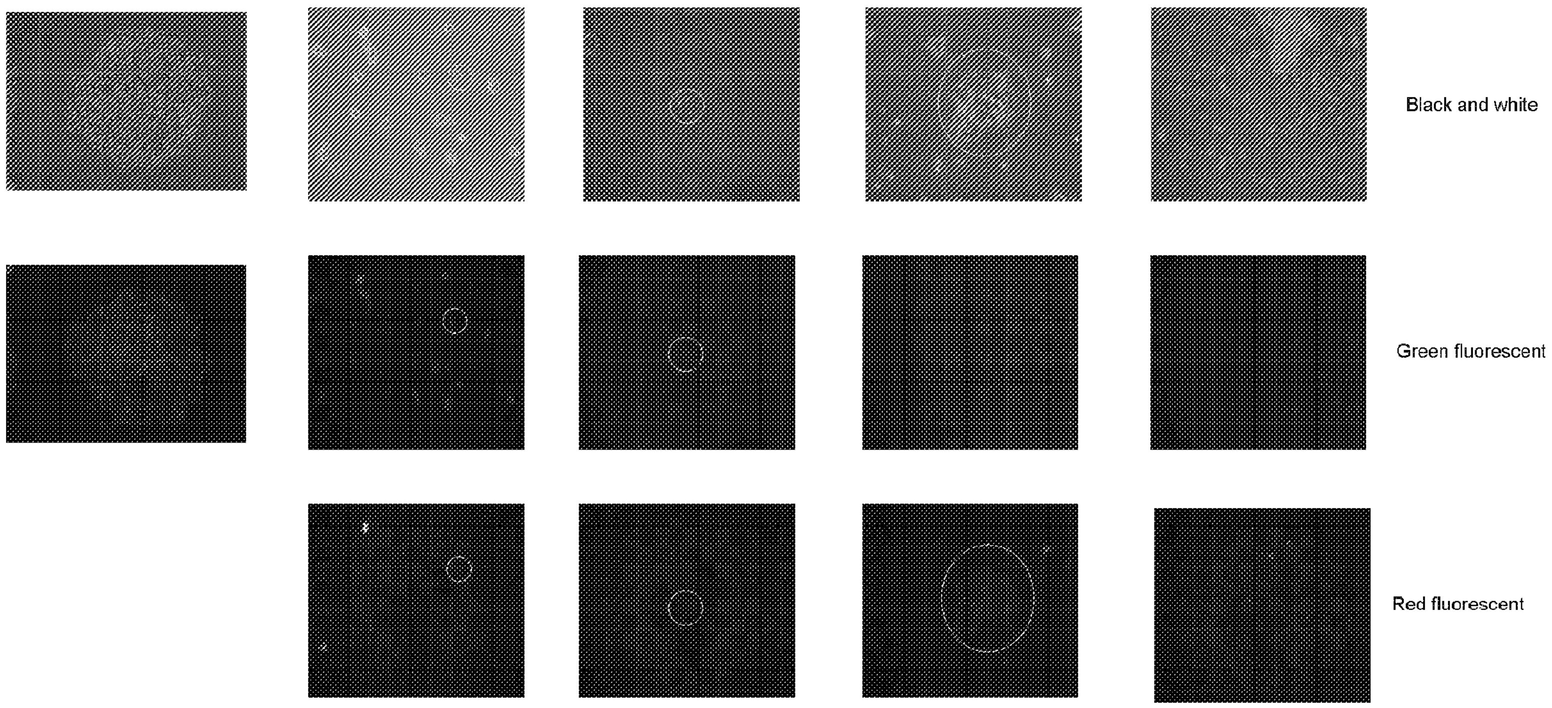

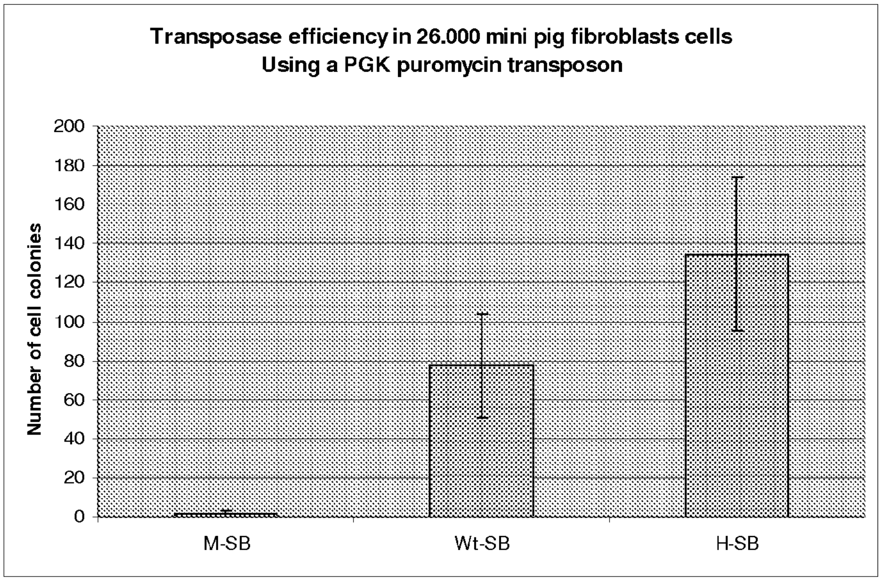
Transposition into minipig cells using a short PGK- puromycin transposon
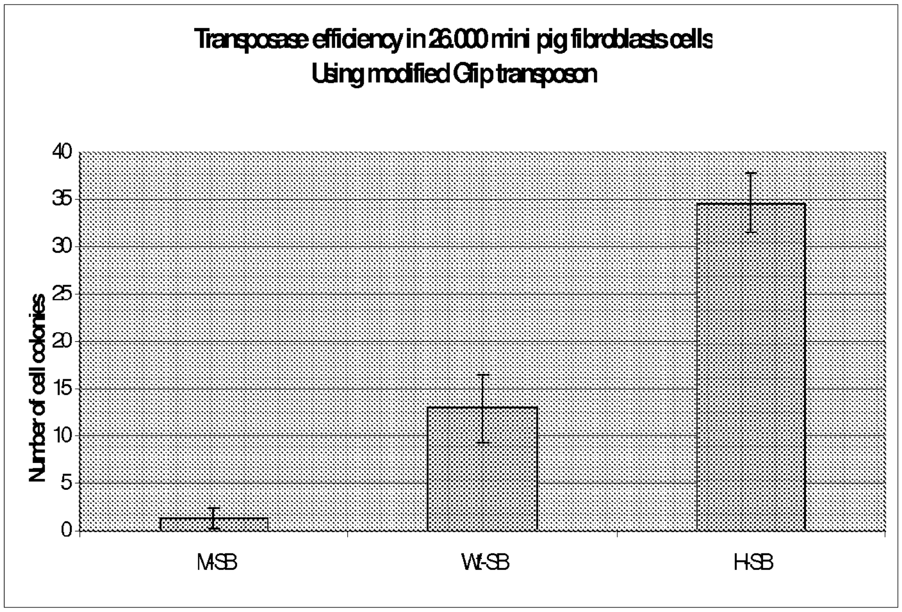
Transposition into minipig cells using the presented transposon
Fig. 22

A colony of green fluorescent minipig cells, containing the presented transposon. The cells were selected with puromycin for 10 days A green fluorescent blastocyst made from minipig cells containing the presented transposon A
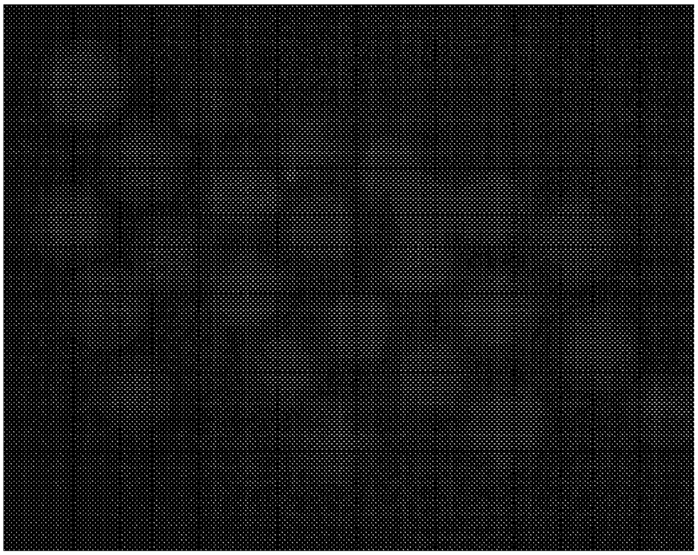
B
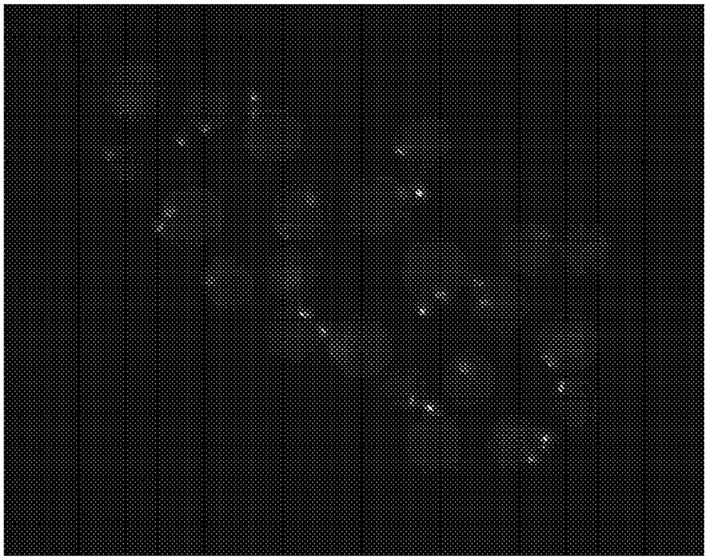
Fig. 27

```
Query  13    ATGCTGCCCGGTTTGGCACTGCTCCTGCTGGCCGCCTGGACGGCTCGGGCGCTGGAGGTA  72
             ||||||||||||||||||||||||||||||||||||||||||||||||||||||||||||
Sbjct  195   ATGCTGCCCGGTTTGGCACTGCTCCTGCTGGCCGCCTGGACGGCTCGGGCGCTGGAGGTA  254

Query  73    CCCACCGATGGTAATGCTGGCCTGCTGGCTGAACCCCAGATTGCCATGTTCTGTGGCAGA  132
             ||||| ||||||||||||||||||||||||||||||||||||||||||||||||||||||
Sbjct  255   CCCACTGATGGTAATGCTGGCCTGCTGGCTGAACCCCAGATTGCCATGTTCTGTGGCAGA  314

Query  133   CTGAACATGCACATGAATGTCCAGAATGGGAAGTGGGATTCAGATCCATCAGGGACCAAA  192
             ||||||||||||||||||||||||||||||||||||||||||||||||||||||||||||
Sbjct  315   CTGAACATGCACATGAATGTCCAGAATGGGAAGTGGGATTCAGATCCATCAGGGACCAAA  374

Query  193   ACCTGCATTGATACCAAGGAAGGCATCCTGCAGTATTGCCAAGAAGTCTACCCTGAACTG  252
             ||||||||||||||||||||||||||||||||||||||||||||||||||||||||||||
Sbjct  375   ACCTGCATTGATACCAAGGAAGGCATCCTGCAGTATTGCCAAGAAGTCTACCCTGAACTG  434

Query  253   CAGATCACCAATGTGGTAGAAGCCAACCAACCAGTGACCATCCAGAACTGGTGCAAGCGG  312
             ||||||||||||||||||||||||||||||||||||||||||||||||||||||||||||
Sbjct  435   CAGATCACCAATGTGGTAGAAGCCAACCAACCAGTGACCATCCAGAACTGGTGCAAGCGG  494

Query  313   GGCCGCAAGCAGTGCAAGACCCATCCCCACTTTGTGATTCCCTACCGCTGCTTAGTTGGT  372
             ||||||||||||||||||||||||||||||||||||||||||||||||||||||||||||
Sbjct  495   GGCCGCAAGCAGTGCAAGACCCATCCCCACTTTGTGATTCCCTACCGCTGCTTAGTTGGT  554

Query  373   GAGTTTGTAAGTGATGCCCTTCTCGTTCCTGACAAGTGCAAATTCTTACACCAGGAGAGG  432
             ||||||||||||||||||||||||||||||||||||||||||||||||||||||||||||
Sbjct  555   GAGTTTGTAAGTGATGCCCTTCTCGTTCCTGACAAGTGCAAATTCTTACACCAGGAGAGG  614

Query  433   ATGGATGTTTGCGAAACTCATCTTCACTGGCACACCGTCGCCAAAGAGACATGCAGTGAG  492
             ||||||||||||||||||||||||||||||||||||||||||||||||||||||||||||
Sbjct  615   ATGGATGTTTGCGAAACTCATCTTCACTGGCACACCGTCGCCAAAGAGACATGCAGTGAG  674

Query  493   AAGAGTACCAACTTGCATGACTACGGCATGTTGCTGCCCTGCGGAATTGACAAGTTCCGA  552
             ||||||||||||||||||||||||||||||||||||||||||||||||||||||||||||
Sbjct  675   AAGAGTACCAACTTGCATGACTACGGCATGTTGCTGCCCTGCGGAATTGACAAGTTCCGA  734

Query  553   GGGGTAGAGTTTGTGTGTTGCCCACTGGCTGAAGAAAGTGACAATGTGGATTCTGCTGAT  612
             ||||||||||||||||||||||||||||||||||||||||||||||||||||||||||||
Sbjct  735   GGGGTAGAGTTTGTGTGTTGCCCACTGGCTGAAGAAAGTGACAATGTGGATTCTGCTGAT  794

Query  613   GCGGAGGAGGATGACTCGGATGTCTGGTGGGGCGGAGCAGACACAGACTATGCAGATGGG  672
             ||||||||||||||||||||||||||||||||||||||||||||||||||||||||||||
Sbjct  795   GCGGAGGAGGATGACTCGGATGTCTGGTGGGGCGGAGCAGACACAGACTATGCAGATGGG  854

Query  673   AGTGAAGACAAAGTAGTAGAAGTAGCAGAGGAGGAAGAAGTGGCTGAGGTGGAAGAAGAA  732
             ||||||||||||||||||||||||||||||||||||||||||||||||||||||||||||
```

Fig. 31

```
Sbjct  855   AGTGAAGACAAAGTAGTAGAAGTAGCAGAGGAGGAAGAAGTGGCTGAGGTGGAAGAAGAA  914

Query  733   GAAGCCGATGATGACGAGGACGATGAGGATGGAGATGAGGTAGAGGAAGAGGCTGAGGAA  792
             |||||||||||||||||||||||||||||||| |||||||||||||||||||||||||||
Sbjct  915   GAAGCCGATGATGACGAGGACGATGAGGATGGTGATGAGGTAGAGGAAGAGGCTGAGGAA  974

Query  793   CCCTACGAAGAAGCCACAGAGAGAACCACCAGCATTGCCACCACCACCACCACCACCACA  852
             ||||||||||||||||||||||||||||||||||||||||||||||||||||||||||||
Sbjct  975   CCCTACGAAGAAGCCACAGAGAGAACCACCAGCATTGCCACCACCACCACCACCACCACA  1034

Query  853   GAGTCTGTGGAAGAGGTGGTTCGAGTTCCTACAACAGCAGCCAGTACCCCTGATGCCGTT  912
             ||||||||||||||||||||||||||||||||||||||||||||||||||||||||||||
Sbjct  1035  GAGTCTGTGGAAGAGGTGGTTCGAGTTCCTACAACAGCAGCCAGTACCCCTGATGCCGTT  1094

Query  913   GACAAGTATCTCGAGACACCTGGGGATGAGAATGAACATGCCCATTTCCAGAAAGCCAAA  972
             ||||||||||||||||||||||||||||||||||||||||||||||||||||||||||||
Sbjct  1095  GACAAGTATCTCGAGACACCTGGGGATGAGAATGAACATGCCCATTTCCAGAAAGCCAAA  1154

Query  973   GAGAGGCTTGAGGCCAAGCACCGAGAGAGAATGTCCCAGGTCATGAGAGAATGGGAAGAG  1032
             ||||||||||||||||||||||||||||||||||||||||||||||||||||||||||||
Sbjct  1155  GAGAGGCTTGAGGCCAAGCACCGAGAGAGAATGTCCCAGGTCATGAGAGAATGGGAAGAG  1214

Query  1033  GCAGAACGTCAAGCAAAGAACTTGCCTAAAGCTGATAAGAAGGCAGTTATCCAGCATTTC  1092
             ||||||||||||||||||||||||||||||||||||||||||||||||||||||||||||
Sbjct  1215  GCAGAACGTCAAGCAAAGAACTTGCCTAAAGCTGATAAGAAGGCAGTTATCCAGCATTTC  1274

Query  1093  CAGGAGAAAGTGGAATCTTTGGAACAGGAAGCAGCCAACGAGAGACAGCAGCTGGTGGAG  1152
             ||||||||||||||||||||||||||||||||||||||||||||||||||||||||||||
Sbjct  1275  CAGGAGAAAGTGGAATCTTTGGAACAGGAAGCAGCCAACGAGAGACAGCAGCTGGTGGAG  1334

Query  1153  ACACACATGGCCAGAGTGGAAGCCATGCTCAATGACCGCCGCCGCCTGGCCCTGGAGAAC  1212
             ||||||||||||||||||||||||||||||||||||||||||||||||||||||||||||
Sbjct  1335  ACACACATGGCCAGAGTGGAAGCCATGCTCAATGACCGCCGCCGCCTGGCCCTGGAGAAC  1394

Query  1213  TACATCACCGCTCTGCAGGCTGTTCCTCCTCGGCCTCGTCACGTGTTCAATATGCTAAAG  1272
             ||||||||||||||||||||||||||||||||||||||||||||||||||||||||||||
Sbjct  1395  TACATCACCGCTCTGCAGGCTGTTCCTCCTCGGCCTCGTCACGTGTTCAATATGCTAAAG  1454

Query  1273  AAGTATGTCCGCGCAGAACAGAAGGACAGACAGCACACCCTAAAGCATTTCGAGCATGTG  1332
             ||||||||||||||||||||||||||||||||||||||||||||||||||||||||||||
Sbjct  1455  AAGTATGTCCGCGCAGAACAGAAGGACAGACAGCACACCCTAAAGCATTTCGAGCATGTG  1514

Query  1333  CGCATGGTGGATCCCAAGAAAGCCGCTCAGATCCGGTCCCAGGTTATGACACACCTCCGT  1392
             ||||||||||||||||||||||||||||||||||||||||||||||||||||||||||||
Sbjct  1515  CGCATGGTGGATCCCAAGAAAGCCGCTCAGATCCGGTCCCAGGTTATGACACACCTCCGT  1574
```

Fig. 31 (Cont.)

```
Query  1393  GTGATTTATGAGCGCATGAATCAGTCTCTCTCCCTGCTCTACAACGTGCCTGCAGTGGCC  1452
             ||||||||||||||||||||||||||||||||||||||||||||||||||||||||||||
Sbjct  1575  GTGATTTATGAGCGCATGAATCAGTCTCTCTCCCTGCTCTACAACGTGCCTGCAGTGGCC  1634

Query  1453  GAGGAGATTCAGGATGAAGTTGATGAGCTGCTTCAGAAAGAGCAAAACTATTCAGATGAC  1512
             ||||||||||||||||||||||||||||||||||||||||||||||||||||||||||||
Sbjct  1635  GAGGAGATTCAGGATGAAGTTGATGAGCTGCTTCAGAAAGAGCAAAACTATTCAGATGAC  1694

Query  1513  GTCTTGGCCAACATGATTAGTGAACCAAGGATCAGTTACGGAAACGATGCTCTCATGCCA  1572
             ||||||||||||||||||||||||||||||||||||||||||||||||||||||||||||
Sbjct  1695  GTCTTGGCCAACATGATTAGTGAACCAAGGATCAGTTACGGAAACGATGCTCTCATGCCA  1754
```

Fig. 31 (Cont.)

```
Query  1573  TCTTTGACCGAAACGAAAACCACCGTGGAGCTCCTTCCCGTGAATGGAGAGTTCAGCCTG  1632
             ||||||||||||||||||||||||||||||||||||||||||||||||||||||||||||
Sbjct  1755  TCTTTGACCGAAACGAAAACCACCGTGGAGCTCCTTCCCGTGAATGGAGAGTTCAGCCTG  1814

Query  1633  GACGATCTCCAGCCGTGGCATTCTTTTGGGGCTGACTCTGTGCCAGCCAACACAGAAAAC  1692
             ||||||||||||||||||||||||||||||||||||||||||||||||||||||||||||
Sbjct  1815  GACGATCTCCAGCCGTGGCATTCTTTTGGGGCTGACTCTGTGCCAGCCAACACAGAAAAC  1874

Query  1693  GAAGTTGAGCCTGTTGATGCCCGCCCTGCTGCCGACCGAGGACTGACCACTCGACCAGGT  1752
             ||||||||||||||||||||||||||||||||||||||||||||||||||||||||||||
Sbjct  1875  GAAGTTGAGCCTGTTGATGCCCGCCCTGCTGCCGACCGAGGACTGACCACTCGACCAGGT  1934

Query  1753  TCTGGGTTGACAAATATCAAGACGGAGGAGATCTCTGAAGTGAATCTGGATGCAGAATTC  1812
             ||||||||||||||||||||||||||||||||||||||||||||   ||||||||||||||
Sbjct  1935  TCTGGGTTGACAAATATCAAGACGGAGGAGATCTCTGAAGTGAAGATGGATGCAGAATTC  1994

Query  1813  CGACATGACTCAGGATATGAAGTTCATCATCAAAAATTGGTGTTCTTTGCAGAAGATGTG  1872
             ||||||||||||||||||||||||||||||||||||||||||||||||||||||||||||
Sbjct  1995  CGACATGACTCAGGATATGAAGTTCATCATCAAAAATTGGTGTTCTTTGCAGAAGATGTG  2054

Query  1873  GGTTCAAACAAAGGTGCAATCATTGGACTCATGGTGGGCGGTGTTGTCATAGCGACAGTG  1932
             ||||||||||||||||||||||||||||||||||||||||||||||||||||||||||||
Sbjct  2055  GGTTCAAACAAAGGTGCAATCATTGGACTCATGGTGGGCGGTGTTGTCATAGCGACAGTG  2114

Query  1933  ATCGTCATCACCTTGGTGATGCTGAAGAAGAAACAGTACACATCCATTCATCATGGTGTG  1992
             ||||||||||||||||||||||||||||||||||||||||||||||||||||||||||||
Sbjct  2115  ATCGTCATCACCTTGGTGATGCTGAAGAAGAAACAGTACACATCCATTCATCATGGTGTG  2174

Query  1993  GTGGAGGTTGACGCCGCTGTCACCCCAGAGGAGCGCCACCTGTCCAAGATGCAGCAGAAC  2052
             ||||||||||||||||||||||||||||||||||||||||||||||||||||||||||||
Sbjct  2175  GTGGAGGTTGACGCCGCTGTCACCCCAGAGGAGCGCCACCTGTCCAAGATGCAGCAGAAC  2234

Query  2053  GGCTACGAAAATCCAACCTACAAGTTCTTTGAGCAGATGCAGAACTAG  2100
             ||||||||||||||||||||||||||||||||||||||||||||||||
Sbjct  2235  GGCTACGAAAATCCAACCTACAAGTTCTTTGAGCAGATGCAGAACTAG  2282
```

Fig. 32

```
PS1 wt       atgacagagttacctgcaccgttgtcctacttccagaatgcacagatgtctgaggacaac
             ||||||||||||||||||||||||||||||||||||||||||||||||||||||||||||
PS1 M146I    atgacagagttacctgcaccgttgtcctacttccagaatgcacagatgtctgaggacaac

PS1 wt       cacctgagcaatactgtacgtagccagaatgacaatagagaacggcaggagcacaacgac
             ||||||||||||||||||||||||||||||||||||||||||||||||||||||||||||
PS1 M146I    cacctgagcaatactgtacgtagccagaatgacaatagagaacggcaggagcacaacgac

PS1 wt       agacggagccttggccaccctgagccattatctaatggacgaccccagggtaactcccgg
             ||||||||||||||||||||||||||||||||||||||||||||||||||||||||||||
PS1 M146I    agacggagccttggccaccctgagccattatctaatggacgaccccagggtaactcccgg

PS1 wt       caggtggtggagcaagatgaggaagaagatgaggagctgacattgaaatatggcgccaag
             ||||||||||||||||||||||||||||||||||||||||||||||||||||||||||||
PS1 M146I    caggtggtggagcaagatgaggaagaagatgaggagctgacattgaaatatggcgccaag

PS1 wt       catgtgatcatgctctttgtccctgtgactctctgcatggtggtggtcgtggctaccatt
             ||||||||||||||||||||||||||||||||||||||||||||||||||||||||||||
PS1 M146I    catgtgatcatgctctttgtccctgtgactctctgcatggtggtggtcgtggctaccatt

PS1 wt       aagtcagtcagcttttatacccggaaggatgggcagctaatctataccccattcacagaa
             ||||||||||||||||||||||||||||||||||||||||||||||||||||||||||||
PS1 M146I    aagtcagtcagcttttatacccggaaggatgggcagctaatctataccccattcacagaa

PS1 wt       gataccgagactgtgggccagagagccctgcactcaattctgaatgctgccatcatgatc
             ||||||||||||||||||||||||||||||||||||||||||||||||||||||||||||
PS1 M146I    gataccgagactgtgggccagagagccctgcactcaattctgaatgctgccatcatgatc

PS1 wt       agtgtcattgttgtcatgactatcctcctggtggttctgtataaatacaggtgctataag
             ||||||||||||||||| ||||||||||||||||||||||||||||||||||||||||||
PS1 M146I    agtgtcattgttgtcataactatcctcctggtggttctgtataaatacaggtgctataag

Ps1 wt       gtcatccatgcctggcttattatatcatctctattgttgctgttctttttttcattcatt
             ||||||||||||||||||||||||||||||||||||||||||||||||||||||||||||
Ps1 M146I    gtcatccatgcctggcttattatatcatctctattgttgctgttctttttttcattcatt

PS1 wt       tacttgggggaagtgtttaaaacctataacgttgctgtggactacattactgttgcactc
             ||||||||||||||||||||||||||||||||||||||||||||||||||||||||||||
PS1 M146I    tacttgggggaagtgtttaaaacctataacgttgctgtggactacattactgttgcactc

PS1 wt       ctgatctggaattttggtgtggtgggaatgatttccattcactggaaaggtccacttcga
             ||||||||||||||||||||||||||||||||||||||||||||||||||||||||||||
PS1 M146I    ctgatctggaattttggtgtggtgggaatgatttccattcactggaaaggtccacttcga

PS1 wt       ctccagcaggcatatctcattatgattagtgccctcatggccctggtgtttatcaagtac
             ||||||||||||||||||||||||||||||||||||||||||||||||||||||||||||
PS1 M146I    ctccagcaggcatatctcattatgattagtgccctcatggccctggtgtttatcaagtac

PS1 wt       ctccctgaatggactgcgtggctcatcttggctgtgatttcagtatatgatttagtggct
             ||||||||||||||||||||||||||||||||||||||||||||||||||||||||||||
PS1 M146I    ctccctgaatggactgcgtggctcatcttggctgtgatttcagtatatgatttagtggct
```

Fig. 33

```
PS1 wt       gttttgtgtccgaaaggtccacttcgtatgctggttgaaacagctcaggagagaaatgaa
             ||||||||||||||||||||||||||||||||||||||||||||||||||||||||||||
PS1 M146I    gttttgtgtccgaaaggtccacttcgtatgctggttgaaacagctcaggagagaaatgaa

PS1 wt       acgctttttccagctctcatttactcctcaacaatggtgtggttggtgaatatggcagaa
             ||||||||||||||||||||||||||||||||||||||||||||||||||||||||||||
PS1 M146I    acgctttttccagctctcatttactcctcaacaatggtgtggttggtgaatatggcagaa

PS1 wt       ggagacccggaagctcaaaggagagtatccaaaaattccaagtataatgcagaaagcaca
             ||||||||||||||||||||||||||||||||||||||||||||||||||||||||||||
PS1 M146I    ggagacccggaagctcaaaggagagtatccaaaaattccaagtataatgcagaaagcaca

PS1 wt       gaaagggagtcacaagacactgttgcagagaatgatgatggcgggttcagtgaggaatgg
             ||||||||||||||||||||||||||||||||||||||||||||||||||||||||||||
PS1 M146I    gaaagggagtcacaagacactgttgcagagaatgatgatggcgggttcagtgaggaatgg

PS1 wt       gaagcccagagggacagtcatctagggcctcatcgctctacacctgagtcacgagctgct
             ||||||||||||||||||||||||||||||||||||||||||||||||||||||||||||
PS1 M146I    gaagcccagagggacagtcatctagggcctcatcgctctacacctgagtcacgagctgct

PS1 wt       gtccaggaactttccagcagtatcctcgctggtgaagacccagaggaaaggggagtaaaa
             ||||||||||||||||||||||||||||||||||||||||||||||||||||||||||||
PS1 M146I    gtccaggaactttccagcagtatcctcgctggtgaagacccagaggaaaggggagtaaaa

PS1 wt       cttggattgggagatttcattttctacagtgttctggttggtaaagcctcagcaacagcc
             ||||||||||||||||||||||||||||||||||||||||||||||||||||||||||||
PS1 M146I    cttggattgggagatttcattttctacagtgttctggttggtaaagcctcagcaacagcc

PS1 wt       agtggagactggaacacaaccatagcctgtttcgtagccatattaattggtttgtgcctt
             ||||||||||||||||||||||||||||||||||||||||||||||||||||||||||||
PS1 M146I    agtggagactggaacacaaccatagcctgtttcgtagccatattaattggtttgtgcctt

PS1 wt       acattattactccttgccattttcaagaaagcattgccagctcttccaatctccatcacc
             ||||||||||||||||||||||||||||||||||||||||||||||||||||||||||||
PS1 M146I    acattattactccttgccattttcaagaaagcattgccagctcttccaatctccatcacc

PS1 wt       tttgggcttgttttctactttgccacagattatcttgtacagccttttatggaccaatta
             ||||||||||||||||||||||||||||||||||||||||||||||||||||||||||||
PS1 M146I    tttgggcttgttttctactttgccacagattatcttgtacagccttttatggaccaatta

PS1 wt       gcattccatcaattttatatctag
             ||||||||||||||||||||||||
PS1 M146I    gcattccatcaattttatatctag
```

Fig. 33 (Cont.)

```
PS1 wt      MTELPAPLSYFQNAQMSEDNHLSNTVRSQNDNRERQEHNDRRSLGHPEPLSNGRPQGNSR
            ||||||||||||||||||||||||||||||||||||||||||||||||||||||||||||
PS1 M146I   MTELPAPLSYFQNAQMSEDNHLSNTVRSQNDNRERQEHNDRRSLGHPEPLSNGRPQGNSR

PS1 wt      QVVEQDEEEDEELTLKYGAKHVIMLFVPVTLCMVVVVATIKSVSFYTRKDGQLIYTPFTE
            ||||||||||||||||||||||||||||||||||||||||||||||||||||||||||||
PS1 M146I   QVVEQDEEEDEELTLKYGAKHVIMLFVPVTLCMVVVVATIKSVSFYTRKDGQLIYTPFTE

PS1 wt      DTETVGQRALHSILNAAIMISVIVVMTILLVVLYKYRCYKVIHAWLIISSLLLLFFFSFI
            ||||||||||||||||||||||||| ||||||||||||||||||||||||||||||||||
PS1 M146I   DTETVGQRALHSILNAAIMISVIVVITILLVVLYKYRCYKVIHAWLIISSLLLLFFFSFI

PS1 wt      YLGEVFKTYNVAVDYITVALLIWNFGVVGMISIHWKGPLRLQQAYLIMISALMALVFIKY
            ||||||||||||||||||||||||||||||||||||||||||||||||||||||||||||
PS1 M146I   YLGEVFKTYNVAVDYITVALLIWNFGVVGMISIHWKGPLRLQQAYLIMISALMALVFIKY

PS1 wt      LPEWTAWLILAVISVYDLVAVLCPKGPLRMLVETAQERNETLFPALIYSSTMVWLVNMAE
            ||||||||||||||||||||||||||||||||||||||||||||||||||||||||||||
PS1 M146I   LPEWTAWLILAVISVYDLVAVLCPKGPLRMLVETAQERNETLFPALIYSSTMVWLVNMAE

PS1 wt      GDPEAQRRVSKNSKYNAESTERESQDTVAENDDGGFSEEWEAQRDSHLGPHRSTPESRAA
            ||||||||||||||||||||||||||||||||||||||||||||||||||||||||||||
PS1 M146I   GDPEAQRRVSKNSKYNAESTERESQDTVAENDDGGFSEEWEAQRDSHLGPHRSTPESRAA

PS1 wt      VQELSSSILAGEDPEERGVKLGLGDFIFYSVLVGKASATASGDWNTTIACFVAILIGLCL
            ||||||||||||||||||||||||||||||||||||||||||||||||||||||||||||
PS1 M146I   VQELSSSILAGEDPEERGVKLGLGDFIFYSVLVGKASATASGDWNTTIACFVAILIGLCL

PS1 wt      TLLLLAIFKKALPALPISITFGLVFYFATDYLVQPFMDQLAFHQFYI
            |||||||||||||||||||||||||||||||||||||||||||||||
PS1 M146I   TLLLLAIFKKALPALPISITFGLVFYFATDYLVQPFMDQLAFHQFYI
```

Fig. 34

TRANSGENIC PIG AS A MODEL OF ALZHEIMER'S DISEASE

FIELD OF INVENTION

The present invention relates to a modified pig as a model for studying Alzheimer's disease, wherein the pig model expresses at least one phenotype associated with said disease. The invention further relates to methods by which the modified pig is produced. In addition, methods for evaluating the response of a therapeutical treatment of Alzheimer's disease, for screening the efficacy of a pharmaceutical composition, and a method for treatment of human being suffering from Alzheimer's disease are disclosed.

BACKGROUND OF INVENTION

Transgenic, non-human animals can be used to understand the action of a single gene or genes in the context of the whole animal and the interrelated phenomena of gene activation, expression, and interaction. The technology has also led to the production of models for various diseases in humans and other animals which contributes significantly to an increased understanding of genetic mechanisms and of genes associated with specific diseases.

Traditionally, smaller animals such as mice have been used as disease models for human diseases and have been found to be suitable as models for certain diseases. However, their value as animal models for many human diseases is quite limited due to differences in mice compared to humans. Larger transgenic animals are much more suitable than mice for the study of many of the effects and treatments of most human diseases because of their greater similarity to humans in many physiological and genetic aspects. Particularly, pigs are believed to be valuable as disease models for human diseases.

Many human diseases are hereditary. The inheritance of genetic disorders, abnormalities, or traits is a function of both the type of chromosome on which the abnormal gene resides (autosomal or sex chromosome), and of the trait itself, i.e. whether the trait is dominant or recessive. The trait can be due to a single defective gene from one parent (dominant inheritance) or the trait can arise when two copies of the gene (one from each parent) are defective (recessive inheritance).

Dominant inheritance occurs when an abnormal gene from one parent is capable of causing disease even though the matching gene from the other parent is normal. Accordingly, the abnormal gene dominates the outcome of the gene pair and one copy of the mutant gene is sufficient for expression of the abnormal phenotype.

Several distinct characteristics of autosomal dominant inheritance include: Every affected individual has an affected parent (except in cases of new mutations or incomplete penetrance); males and females are equally likely to inherit the allele and be affected (as the genes are located on autosomes, of which each male and female has two copies); and recurrence risk (the probability that a genetic disorder that is present in a patient will recur in another member of the family) for each child of an affected parent is ½ (as only one copy of a gene is necessary for development of the disease). If one parent is a heterozygote for a particular gene, their offspring will either inherit the gene or they will not, with each outcome equally likely. Accordingly, if an affected individual's siblings are not affected, they do not carry the mutation and cannot therefore pass it on to their own offspring.

Transgenic animals carrying a dominant disease gene which is expressed in the animal makes it possible to study the phenotype associated with said dominant disease gene. Transgenic animals have traditionally been used for the improvement of livestock, and for the large scale production of biologically active pharmaceuticals. Historically, transgenic animals have been produced almost exclusively by microinjection of the fertilized egg. The pronuclei of fertilized eggs are microinjected in vitro with foreign, i.e., xenogeneic or allogeneic DNA or hybrid DNA molecules. The microinjected fertilized eggs can then be transferred to the genital tract of a pseudopregnant female.

Alzheimer's disease has been classified as a protein misfolding disease due to the accumulation of abnormally folded amyloid beta (Abeta or Aβ) protein in the brains of Alzheimer's disease patients. Amyloid beta is a short peptide that is an abnormal proteolytic byproduct of the transmembrane protein amyloid precursor protein (APP), which seems to be involved in neuronal development. The presenilins are components of proteolytic complex involved in APP processing and degradation. Although amyloid beta monomers are soluble and harmless, they undergo a dramatic conformational change at sufficiently high concentration to form a beta sheet-rich tertiary structure that aggregates to form fibrils of amyloid, depositing outside neurons in dense formations. Abnormal aggregation of the tau protein is thought also to be involved in Alzheimer's disease as hyperphosphorylated tau accumulated and aggregates into masses inside nerve cell bodies known as neurofibrillary tangles.

"Alzheimer's disease" (AD) is used herein to refer to any neurodegenerative brain disorder characterized by progressive memory loss and severe dementia in advanced cases. Alzheimer's disease is associated with certain abnormalities in brain tissue, involving a particular protein, beta-amyloid. Memory impairment is a necessary feature for the diagnosis of this type of dementia. Change in one of the following areas must also be present: language, decision-making ability, judgment, attention, and other areas of mental function and personality.

Alzheimer's disease is a progressive neurodegenerative disease of the brain and the most common cause of dementia after the age of 65 years. The pathological criteria of AD include intraneuronal neurofibrillary tangles (NFT) composed of paired helical filaments of hyperphosphorylated tau protein, deposits of the proteolytic fragments Ab40 and Ab42 of the amyloid precursor protein (APP) in form of extracellular neuritic (senile) plaques and congophilic angiopathy, and loss of neurons (Mirra et al 1991). The lesions develop in the hippocampal region and spread to other brain regions in a characteristic spatio-temporal pattern (J L Price et al. 1991, Braak & Braak, 1991). The degree of dementia appears to correlate with the number of NFT lesions rather than with the burden of neuritic plaques, and definite neuropathological diagnosis of AD can be established only in combination with the clinical diagnosis.

The rate of progression is different for each person. If Alzheimer's disease develops rapidly, it is likely to continue to progress rapidly. If it has been slow to progress, it will likely continue on a slow course. There are two types of Alzheimer's disease—early onset and late onset. In early onset Alzheimer's disease, symptoms first appear before age 60. Early onset Alzheimer's disease is much less common, accounting for only 5-10% of cases. However, it tends to progress rapidly.

Early onset disease can run in families and involves autosomal dominant, inherited mutations that may be the cause of the disease. So far, three early onset genes have been identified. Late onset Alzheimer's disease, the most common form of the disease, develops in people 60 and older and is thought to be less likely to occur in families. Late onset Alzheimer's disease may run in some families, but the role of genes is less direct and definitive. These genes may not cause the disease itself, but simply increase the likelihood of formation of plaques and tangles or other Alzheimer's disease-related pathologies in the brain.

The etiology of AD is multifactorial, but in certain rare families AD segregates as an autosomal dominant disorder with age of onset in the 40s and 50s. Disease-causing mutations have been identified in the amyloid precursor protein gene (APP), and in the presenilin 1 and presenilin 2 genes (PSEN1 and PSEN2). At the biochemical level these mutations are associated with a change in the proteolytic cleavage of APP increasing the production of either total Abeta or selectively the highly amyloidogenic fragment Ab42 (for review see Sisodia et al. 1999). This change in Ab production and the extent to which Ab initiate the pathogenic process leading to neuritic plaques and, most importantly, to formation of intraneuronal NFT and neuron loss has been studied intensively (Selkoe & Hardy, 2002). Any suitable prevention of AD or therapeutic intervention must remove or halt development of NFT as tau pathology per se is sufficient to cause neurodegeneration.

The cause of Alzheimer's disease is not entirely known but is thought to include both genetic and environmental factors. A diagnosis of Alzheimer's disease is made based on characteristic symptoms and by excluding other causes of dementia. The only way to validate a case of Alzheimer's disease is by microscopic examination of a sample of brain tissue after death.

The brain tissue shows "neurofibrillary tangles", "neuritic plaques" (abnormal clusters of dead and dying nerve cells, other brain cells, and protein), and "senile plaques" (areas where products of dying nerve cells have accumulated around protein). Although these changes occur to some extent in all brains with age, there are many more of them in the brains of people with Alzheimer's disease.

The destruction of nerve cells (neurons) leads to a decrease in neurotransmitters (substances secreted by a neuron to send a message to another neuron). The correct balance of neurotransmitters is critical to the brain. By causing both structural and chemical problems in the brain, Alzheimer's disease appears to disconnect areas of the brain that normally work together.

There is a need for improved animal models for human diseases in order to gain more information of the onset, progression and treatment regimes of hereditary diseases in humans of which Alzheimer's disease is one of them.

Even though the genes (or mutations therein) responsible for Alzheimer's disease or the genes involved in the onset and progression of Alzheimer's have been identified in humans it does not necessarily follow that animals transgenic for said mutations display a phenotype comparable to that of human disease. However, the present invention has surprisingly shown that the modified pig model display the Alzheimer's disease phenotype.

SUMMARY OF INVENTION

The present invention concerns a genetically modified pig model which allows for the study of Alzheimer's disease.

Thus, one aspect of the present invention relates to a genetically modified pig as a model for studying Alzheimer's disease, wherein the pig model expresses at least one phenotype associated with said disease and/or a modified pig comprising at least one modified i) human APP gene or part thereof and/or ii) human PS1 gene or part thereof and/or iii) porcine APP gene or part thereof and/or iv) porcine PS1 gene or part thereof and/or v) APP gene or part thereof and at least one modified PS1 gene or part thereof and/or vi) human APP gene or part thereof comprising a Swedish mutation and/or vii) human APP gene or part thereof being the APPsw695 gene and/or viii) human PS1 gene or part thereof comprising a mutation encoding a PS1 protein harbouring a Pro117Leu mutation and/or ix) human APP gene or part thereof comprising a Swedish mutation and at least one modified PS1 gene or part thereof comprising a mutation encoding a PS1 protein harbouring a Pro117Leu mutation and/or x) human APP gene or part thereof being the APPsw695 gene and at least one modified PS1 gene or part thereof comprising a mutation encoding a PS1 protein harbouring a Pro117Leu mutation, transcriptional and/or translational product or part thereof.

A second aspect of the present invention relates to a genetically modified porcine blastocyst derived from derived from the genetically modified pig model as defined herein and/or a modified porcine blastocyst comprising at least one modified i) human APP gene or part thereof and/or ii) human PS1 gene or part thereof and/or iii) porcine APP gene or part thereof and/or iv) porcine PS1 gene or part thereof and/or v) APP gene or part thereof and at least one modified PS1 gene or part thereof and/or vi) human APP gene or part thereof comprising a Swedish mutation and/or vii) human APP gene or part thereof being the APPsw695 gene and/or viii) human PS1 gene or part thereof comprising a mutation encoding a PS1 protein harbouring a Pro117Leu mutation and/or ix) human APP gene or part thereof comprising a Swedish mutation and at least one modified PS1 gene or part thereof comprising a mutation encoding a PS1 protein harbouring a Pro117Leu mutation and/or x) human APP gene or part thereof being the APPsw695 gene and at least one modified PS1 gene or part thereof comprising a mutation encoding a PS1 protein harbouring a Pro117Leu mutation, transcriptional and/or translational product or part thereof.

A third aspect of the present invention pertains to a genetically modified porcine embryo derived from the genetically modified pig model as defined herein and/or a modified porcine embryo comprises at least one modified i) human APP gene or part thereof and/or ii) human PS1 gene or part thereof and/or iii) porcine APP gene or part thereof and/or iv) porcine PS1 gene or part thereof and/or v) APP gene or part thereof and at least one modified PS1 gene or part thereof and/or vi) human APP gene or part thereof comprising a Swedish mutation and/or vii) human APP gene or part thereof being the APPsw695 gene and/or viii) human PS1 gene or part thereof comprising a mutation encoding a PS1 protein harbouring a Pro117Leu mutation and/or ix) human APP gene or part thereof comprising a Swedish mutation and at least one modified PS1 gene or part thereof comprising a mutation encoding a PS1 protein harbouring a Pro117Leu mutation and/or x) human APP gene or part thereof being the APPsw695 gene and at least one modified PS1 gene or part thereof comprising a mutation encoding a PS1 protein harbouring a Pro117Leu mutation, transcriptional and/or translational product or part thereof.

A fourth aspect relates to a genetically modified porcine fetus derived from the genetically modified pig model as defined herein and/or a modified porcine fetus comprising at least one modified A fifth aspect of the present invention relates to a genetically modified donor cell and/or cell nucleus derived from the genetically modified pig model as defined herein and/or a donor cell and/or cell nucleus comprising at least one modified i) human APP gene or part thereof and/or ii) human PS1 gene or part thereof and/or iii) porcine APP gene or part thereof and/or iv) porcine PS1 gene or part thereof and/or v) APP gene or part thereof and at least one modified PS1 gene or part thereof and/or vi) human APP gene or part thereof comprising a Swedish mutation and/or vii) human APP gene or part thereof being the APPsw695 gene and/or viii) human PS1 gene or part thereof comprising a mutation encoding a PS1 protein harbouring a Pro117Leu mutation and/or ix) human APP gene or part thereof comprising a Swedish mutation and at least one modified PS1 gene or part thereof comprising a mutation encoding a PS1 protein harbouring a Pro117Leu mutation and/or x) human APP gene or part thereof being the APPsw695 gene and at least one modified PS1 gene or part thereof comprising a mutation encoding a PS1 protein harbouring a Pro117Leu mutation, transcriptional and/or translational product or part thereof.

Embodiments for the present invention comprises, minipigs for example selected from the group consisting of Goettingen, Yucatan, Bama Xiang Zhu, Wuzhishan and Xi Shuang Banna, including any combination thereof. However, another embodiment relates to pigs that are not a mini-pig, such as the species of Sus domesticus, for example where the pig is selected from the group consisting of Landrace, Yorkshire, Hampshire, Duroc, Chinese Meishan, Berkshire and Piêtrain, including any combination thereof. In a preferred embodiment the pig, embryo, fetus, blastocyst and/or donor cell is a Goettingen minipig or from a Goettingen minipig.

Embodiments of the present invention comprise the modified pig, wherein the pig comprises at least one modified human APP gene or part thereof, transcriptional and/or translational product or part thereof, and/or wherein the pig comprises at least one modified human PS1 gene or part thereof, transcriptional and/or translational product or part thereof, and/or wherein the pig comprises at least one modified porcine APP gene or part thereof, transcriptional and/or translational product or part thereof, and/or wherein the pig comprises at least one modified porcine PS1 gene or part thereof, transcriptional and/or translational product or part thereof, and/or wherein the pig comprises at least one modified APP gene or part thereof and at least one modified PS1 gene or part thereof, transcriptional and/or translational product or part thereof, and/or wherein the pig comprises at least one modified human APP gene or part thereof comprising a Swedish mutation, transcriptional and/or translational product or part thereof, transcriptional and/or translational product or part thereof, and/or wherein the pig comprises at least one modified human APP gene or part thereof, being the APP695sw gene, transcriptional and/or translational product or part thereof, and/or wherein the pig comprises at least one modified human PS1 gene or part thereof comprises a mutation encoding a PS1 protein harbouring a Pro117Leu mutation, transcriptional and/or translational product or part thereof, and/or wherein the pig comprising at least one modified human APP gene or part thereof comprising a Swedish mutation and wherein said at least one modified PS1 gene or part thereof is at least one modified human PS1 gene or part thereof comprising a mutation encoding a PS1 protein harbouring a Pro117Leu mutation, transcriptional and/or translational product or part thereof, and/or wherein the pig comprises at least one modified APP gene or part thereof being the APP695sw and wherein said at least one modified PS1 gene or part thereof is at least one modified human PS1 gene or part thereof comprising a mutation encoding a PS1 protein harbouring a Pro117Leu mutation, transcriptional and/or translational product or part thereof.

Embodiments of the present invention includes a modified pig wherein at least one phenotype is at least 10% reduced olfaction as compared to a standard level of olfaction observed for said pig, and/or wherein at least one phenotype is at least 10% reduced semantic memory as compared to a standard level of semantic memory observed for said pig, and/or wherein at least one phenotype is at least 10% reduced visio-spatial memory compared to the standard level of visio-spatial memory observed for said pig, and/or wherein at at least one phenotype is the accumulation of abeta protein and/or tau protein.

A sixth aspect of the present invention relates to the genetically modified pig model, porcine blastocyst, embryo and/or fetus as disclosed herein obtainable by nuclear transfer comprising the steps of i) establishing at least one oocyte having at least a part of a modified zona pellucida, ii) separating the oocyte into at least two parts obtaining an oocyte having a nucleus and at least one cytoplast, iii) establishing a donor cell or cell nucleus with desired genetic properties, iv) fusing at least one cytoplast with the donor cell or membrane surrounded cell nucleus, v) obtaining a reconstructed embryo, vi) activating the reconstructed embryo to form an embryo; culturing said embryo; and vii) transferring said cultured embryo to a host mammal such that the embryo develops into a genetically modified fetus, wherein said genetically modified embryo obtainable by nuclear transfer comprises steps i) to v) and/or vi), wherein said genetically modified blastocyst obtainable by nuclear transfer comprises steps i) to vi) and/or vii), wherein said genetically modified fetus obtainable by nuclear transfer comprises steps i) to vii).

A seventh aspect relates to a method for producing a transgenic pig, porcine blastocyst, embryo and/or fetus as a model for Alzheimer's disease comprising: i) establishing at least one oocyte, ii) separating the oocyte into at least three parts obtaining at least one cytoplast, iii) establishing a donor cell or cell nucleus having desired genetic properties, iv) fusing at least one cytoplast with the donor cell or membrane surrounded cell nucleus, v) obtaining a reconstructed embryo, vi) activating the reconstructed embryo to form an embryo; vii) culturing said embryo; and viii) transferring said cultured embryo to a host mammal such that the embryo develops into a genetically modified fetus, wherein said transgenic embryo comprises steps i) to v) and/or vi), wherein said transgenic blastocyst comprises steps i) to vi) and/or vii), wherein said transgenic fetus comprises steps i) to vii).

Embodiments of the sixth and seventh aspects comprise one or more of the features, wherein the method for activation of the reconstructed embryo is selected from the group of methods consisting of electric pulse, chemically induced shock, increasing intracellular levels of divalent cations and reducing phosphorylation. Further embodiments of the sixth and seventh aspects comprise one or more of the features as defined above, wherein steps d) and f) are performed sequentially or simultaneously, and embodiments comprising one or more of the features, wherein the embryo is cultured in vitro. Such embryo may be cultured in sequential culture. The embryo, for example at the blastocyst stage, is cryopreserved prior to transfer to a host mammal. For the methods of the present invention embodiments cover pigs, mini-pigs for example selected from the group consisting of Goettingen, Yucatan, Bama Xiang Zhu, Wuzhishan and Xi Shuang Banna, including any combination thereof. However, another embodiment relates to pigs that are not a mini-pig, such as the species of Sus scrofa domesticus, for example where the pig is selected from the group consisting of Landrace, Yorkshire, Hampshire, Duroc, Chinese Meishan, Berkshire and Piêtrain, including any combination thereof.

A further aspect of the present invention pertains to method for evaluating the effect of a therapeutical treatment of Alzheimer's disease, said method comprising the steps of i) providing the pig model as disclosed herein, ii) treating said pig model with a pharmaceutical composition exerting an effect on said phenotype, and iii) evaluating the effect observed.

In one embodiment the method further comprises a step of advising on medical treatment based on the afore-mentioned observed effects.

Yet a further aspect of the present invention relates to a method for screening the efficacy of a pharmaceutical composition for Alzheimer's disease, said method comprising the steps of i) providing the pig model as disclosed herein, ii) expressing in said pig model said genetic determinant and exerting said phenotype for said disease, iii) administering to said pig model a pharmaceutical composition the efficacy of which is to be evaluated, and iv) evaluating the effect, if any, of the pharmaceutical composition on the phenotype exerted by the genetic determinant when expressed in the pig model.

Furthermore the present invention in another aspect relates to a method for treatment of a human being suffering from Alzheimer's disease, said method comprising the initial steps of i) providing the pig model as disclosed herein, ii) expressing in said pig model said genetic determinant and exerting said phenotype for said disease, iii) administering to said pig model a pharmaceutical composition the efficacy of which is to be evaluated, and iv) evaluating the effect observed, and v) treating said human being suffering from Alzheimer's disease based on the effects observed in the pig model.

DESCRIPTION OF DRAWINGS

FIG. 1 shows an alignment of the human and the porcine APP770 protein.

FIG. 2 shows an alignment of the human and the porcine PS1 protein.

FIG. 8 a) shows an agarose gel of a cDNA derived from a full-length transcript of the transgene is present in the transgenic donor cell and in fibroblasts from the 7 piglets b) shows the DNA sequence of the mutated APP transgene of one of the transgenic piglets. A silent nucleotide polymorphism (T to C) at position 260 and the Swedish mutation at positions 2204 (G to T) and 2205 (A to C) are evident.

FIG. 9

Figure 8:
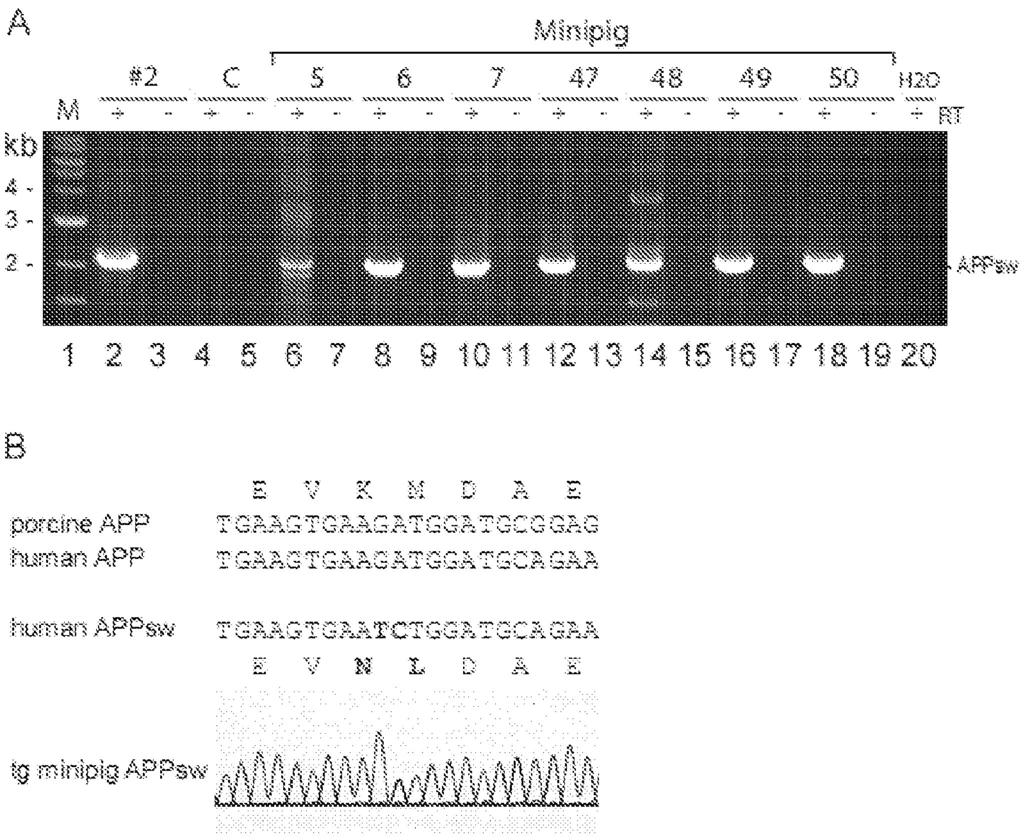
Figure 9:
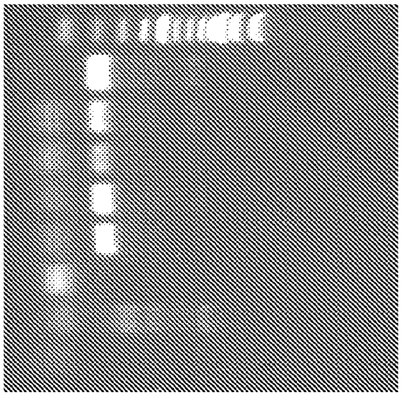

In order to study transgene expression in brain tissue and other tissues we sacrificed piglet No. 7 at the age of 3 months. cDNA was produced from total RNA extracted from cerebral cortex, cerebellum, the hippocampus, basal ganglia, brain stem, heart, and liver. PCR was done on these cDNAs with the same primers 6 and 4 (primer combination C in FIG. 5) that were used for quantitation of the transcript of the transgene (FIG. 8*b*). The agarose gel in FIG. 9 shows that the transgene is highly expressed in all the brain regions and not in heart and liver tissue.

Figure 10:
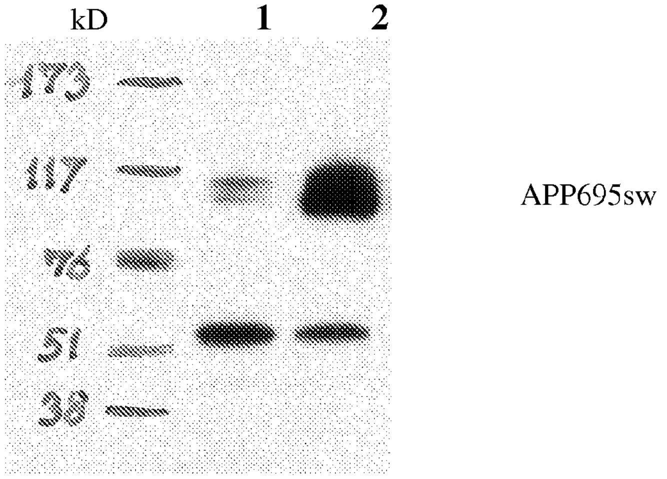

FIG. 10 shows a Western blot of protein extract from cerebral cortex of a non-transgenic minipig (lane 1) and protein extract from cerebral cortex of transgenic minipig no. 7 (lane 2). The anti-APP antibody 6E10 was used in the Western blot.

Figure 11:
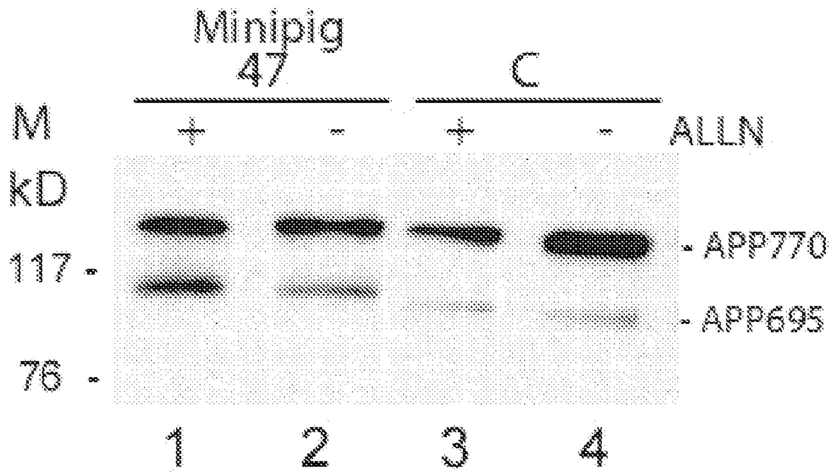

FIG. 11 shows the presence of the mutation of the APPsw gene following sequencing and in addition showing a Western blot of extracts obtained from transgenic and wt pigs following treatment with ALLN as described. Lanes 1 and 2 represent fibroblasts from the transgenic piglet and lanes 3 and 4 represent non-transgenic donor cells. The cells in lanes 1 and 3 have been grown in the presence of the protease inhibitor ALLN.

Figure 12:
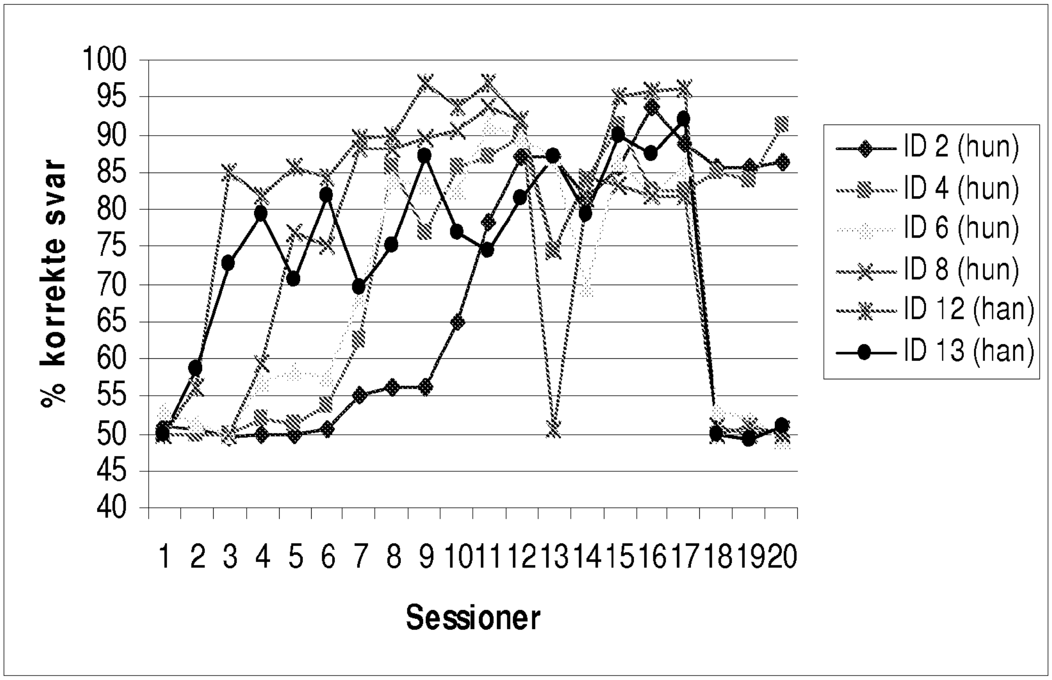

FIG. 12 shows the results of the training of the 6 pigs. After session 12, the olfactometer was adjusted causing a break in the training lasting 1 month. Sessions 13 to 17 represent renewed training after adjusting the apparatus. Bulbectomy was performed after session 17 in 4 pigs and sessions 18 to 20 represent testing after the operation. The bulbectomized pigs have only 50% correct answers whereas the sham-operated pigs still have 85% correct answers.

FIG. 13 a) shows the accumulation of protein in brain tissue that stains positive with an antibody raised against Abeta 1-42 (Signet Lab—SIG-39142-500 batch 06KCO2476). The protein is located in neuronal somata in the cortex including the hippocampus as well as in the neurpil surrounding small blood vessels in the tissue; b) shows a similar neurological tissue section from the hippocampus of 3 month old Göttingen minipig (normal control) stained with the same antibody against Abeta1-42 in the same staining procedure. There are no plaque-like immunoreactive deposits in the tissue and no staining of neuronal somata in any parts of the brain examined.

Figure 14:
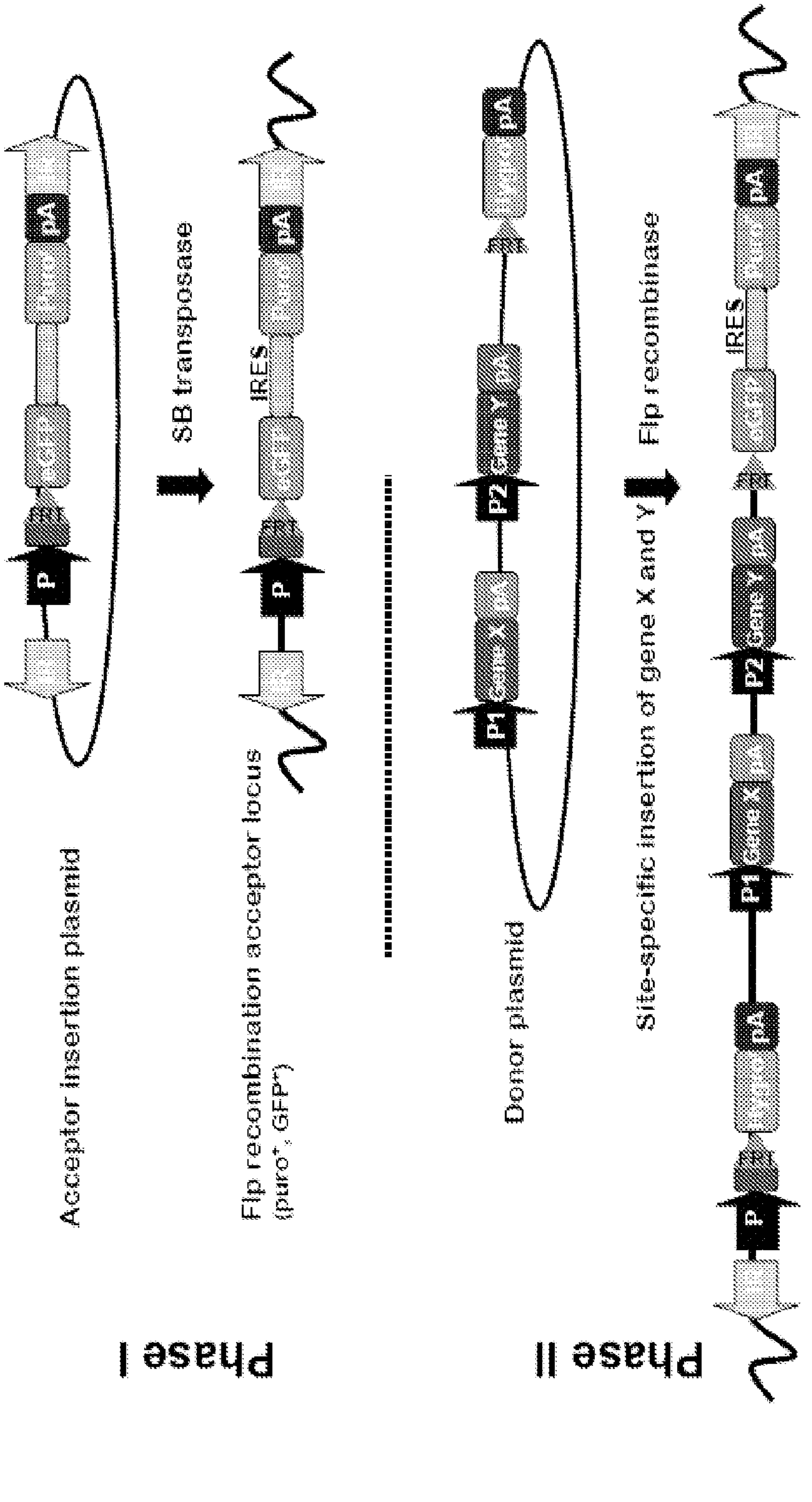

FIG. 14 shows the bi-phased technology of the present invention in which an integrating SB vector, carrying a reporter gene and a selective marker gene, serves as a reporter for continuous gene expression and hence as a target for gene insertion. In a second modification step this vector may serve as a target for insertion of one or more gene expression cassettes in a well-characterized locus.

Figure 15:
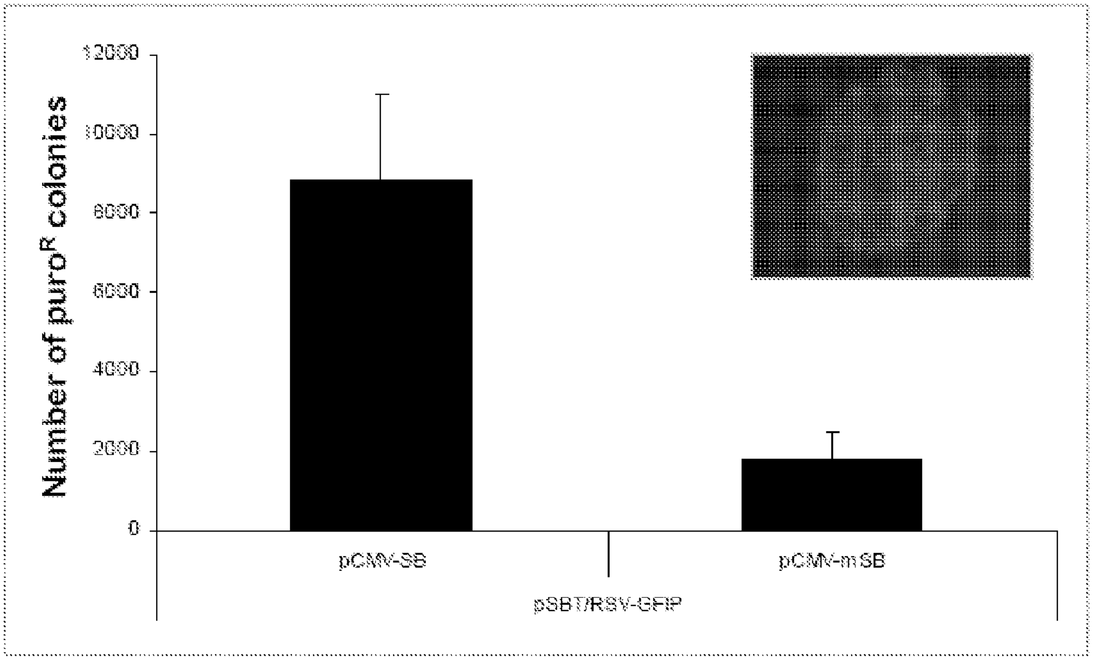

FIG. 15 shows a schematic representation of pSBT/RSV-GFIP.

Figure 16:
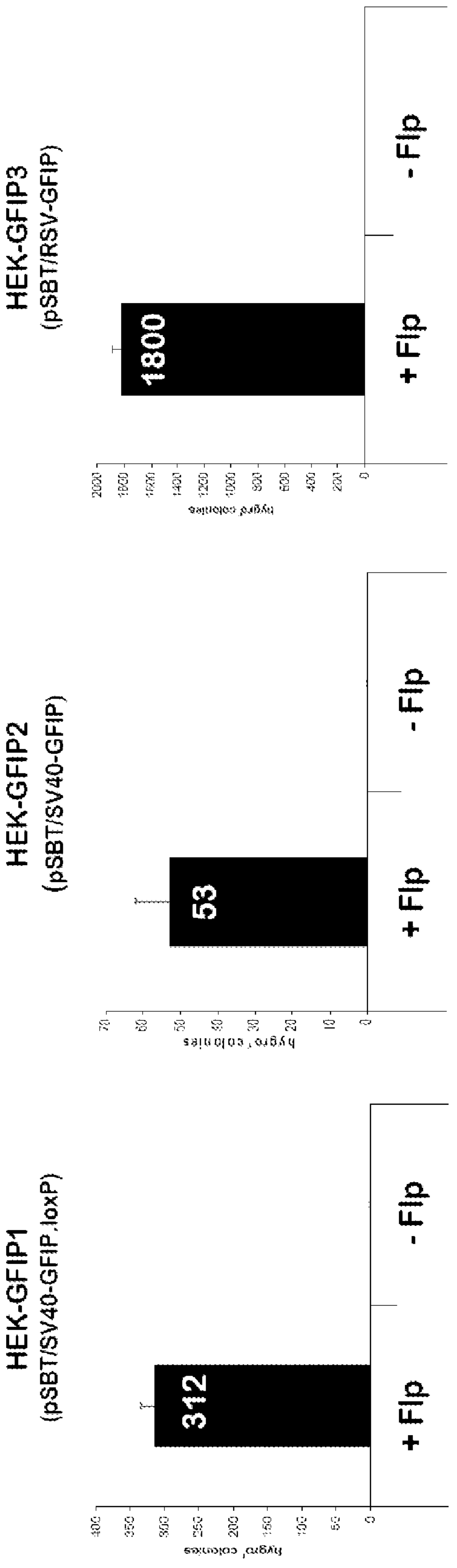

FIG. 16 shows transposition of SB vectors in porcine fibroblasts. A standard transposon encoding a puromycin resistance gene (SBT/PGK-puro) was employed and varying levels of transposition were detected, resulting in about 75 drug-resistant colonies in cultures of fibroblasts co-transfected with pSBT/PGK-puro and pCMV-SB, less than 3 colonies appeared after transfection with pSBT/PGK-puro and pCMV-mSB, the latter which encodes an inactive version of the transposase. Interestingly, a mean of almost 140 colonies was obtained using the hyperactive transposase variant HSB3, indicating that HSB3 also in porcine cells mediates higher levels of transposition compared to the original SB transposase.

Figure 17:
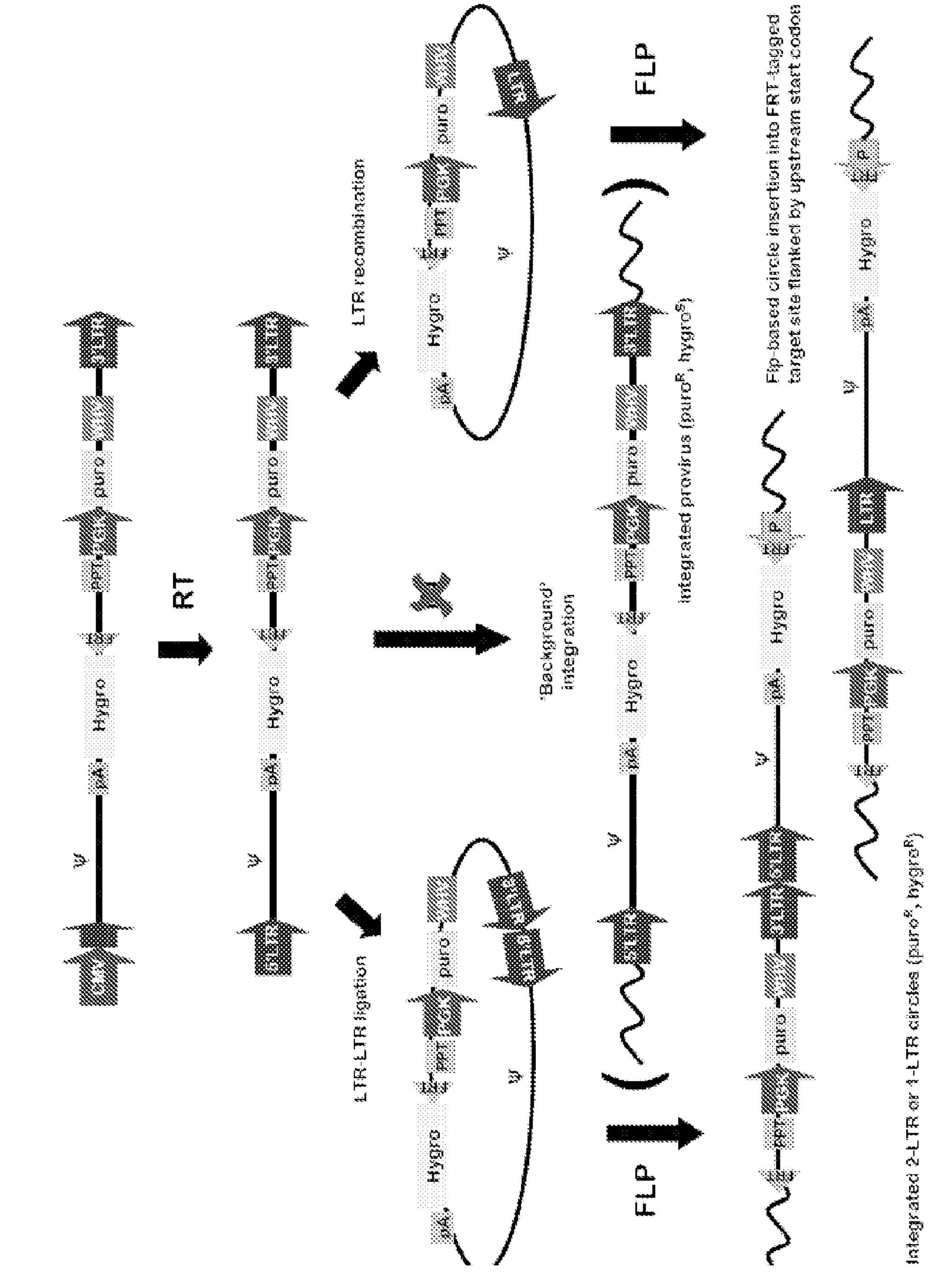

FIG. 17 shows a schematic representation of circular DNA intermediates that are generated during lentivirus infection and which are often considered dead-end reverse-transcribed products of infection. 2-LTR DNA circles are generated by DNA repair and ligation of the full-length linear viral DNA (FIG. 17, left), whereas 1-LTR DNA circles are generated by homologous recombination between the two LTRs of the episomal and linear viral DNA (FIG. 17, right). These circles, generated during lentiviral vector transduction, may support Flp-based recombination, allowing site-specific integration of DNA circles devoid of bacterial sequences (FIG. 17, bottom).

Figure 18:
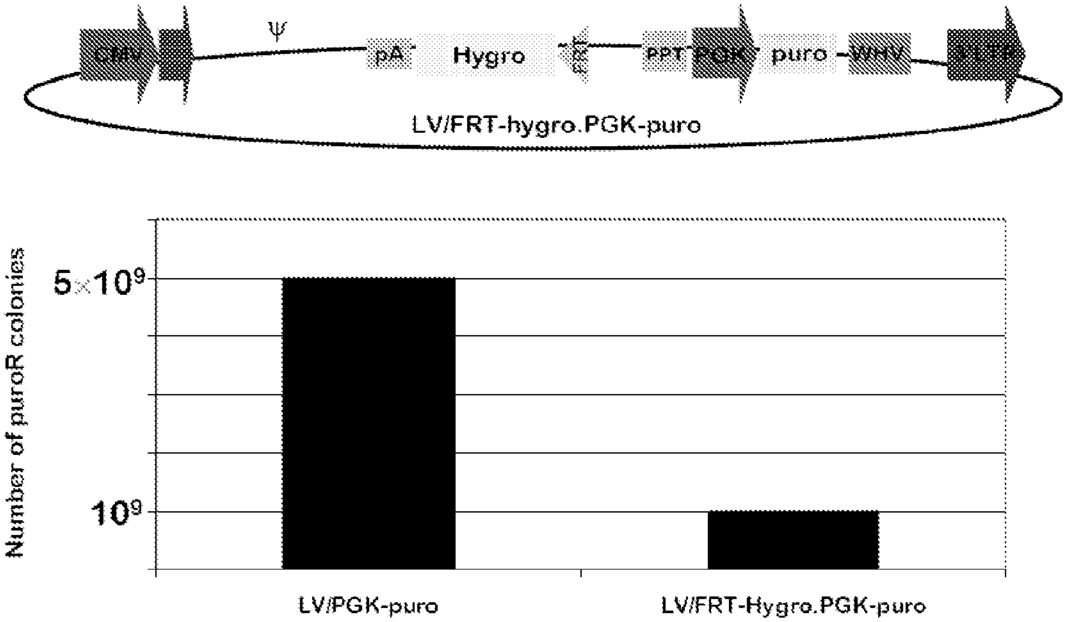

FIG. 18. Integration-defective lentiviral vectors (ID-LVs) were generated which contained a mutated inactive integrase protein. A lentiviral vector, pLV/FRT-hygro.PGK-puro, was generated that contains the FRT-hygro recombination sequence and found in transduction titer assays that this vector was only slightly less efficiently transferred in comparison to the original vector.

Figure 19:
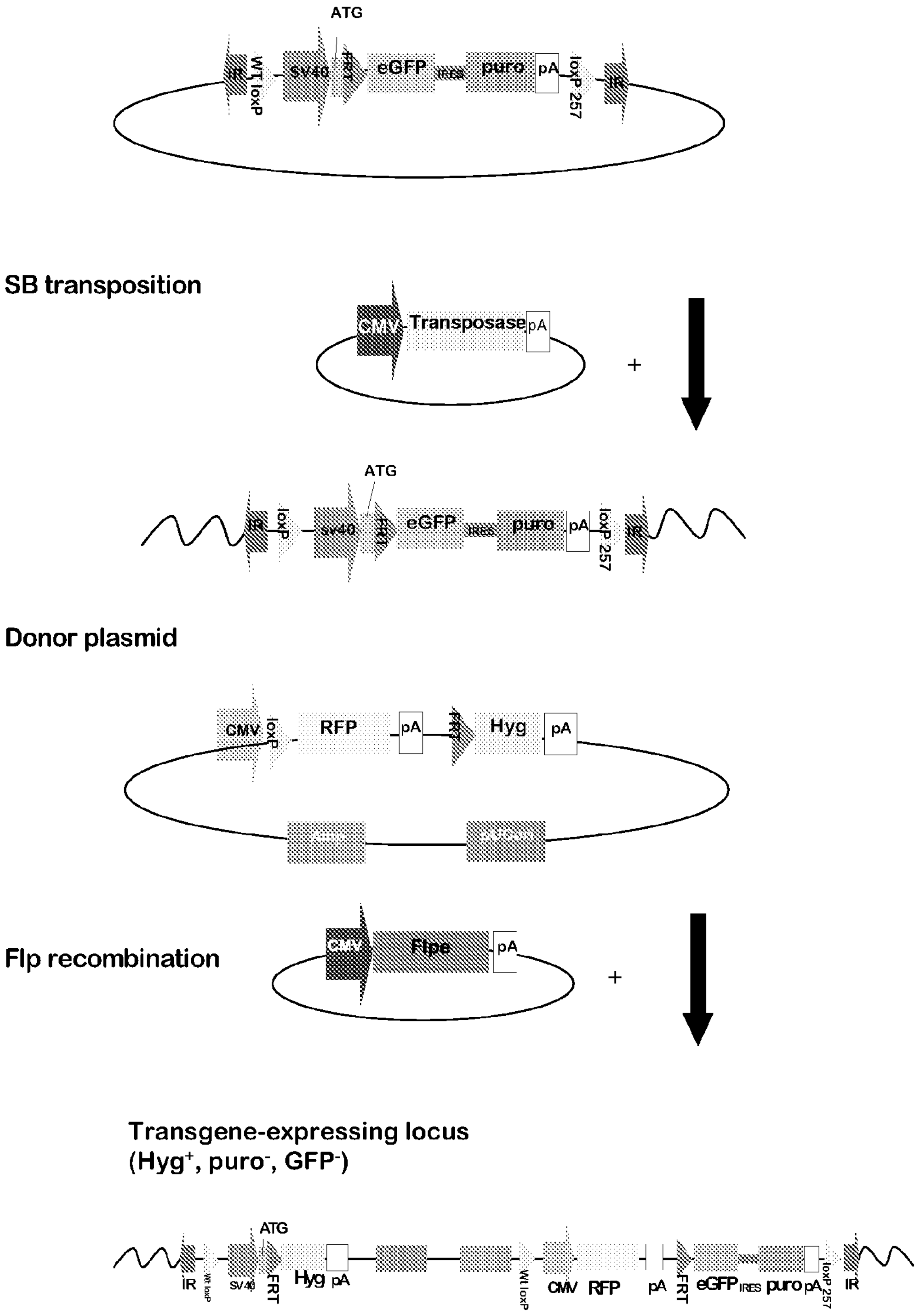

FIG. 19 shows a gene shift with the help of the Sleeping Beauty (SB) DNA transposon technology and Flpe recombination is presented in this example. An SB transposon containing an eGFP gene and an frt site was inserted into HEK 293 cells. The frt site enables gene shifting with a donor plasmid containing the RFP gene as well as an frt site.

Figure 20:
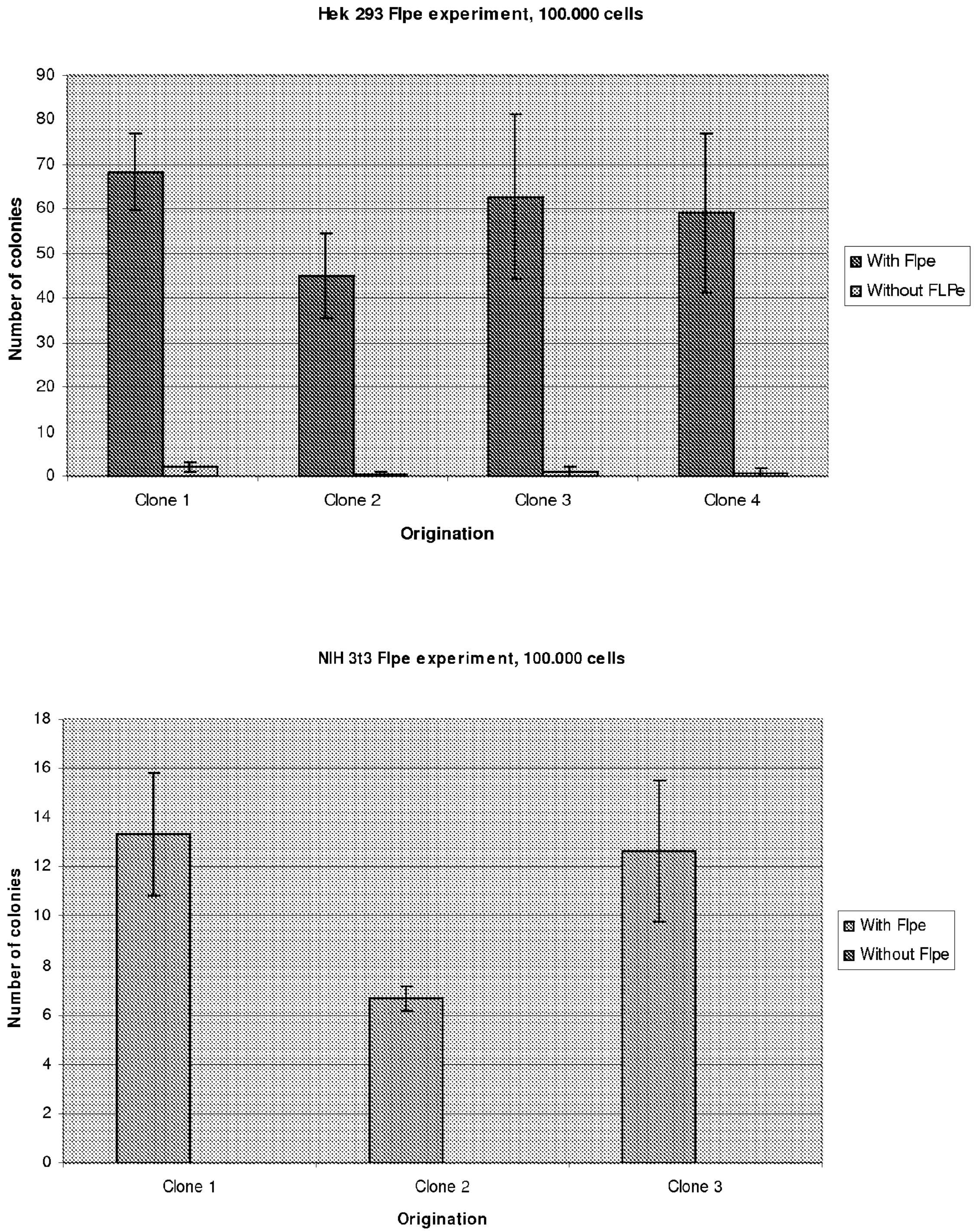

FIG. 20 shows efficient insertion of a FRT-tagged SB vector in pig fibroblasts SB-tagged cell clones containing a Flp recombination target site for site-specific gene insertion were co-transfected the pSBT/IoxP.SV40-IopP257 plasmid with pCMV-mSB, pCMV-SB, and pCMV-HSB3, respectively. HSB3 again showed the highest activity, resulting in about 30 drug-resistant colonies after transfection of 3 H $10^4$ fibroblasts.

FIG. 21 shows clone analysis by fluorescence microscopy of isolated and expanded puromycin-resistant colonies demonstrates efficient FRTeGFP expression FIG. 22 upper panel shows the transposase efficiency in fibroblast cells of a mini pig, using a PGK (phosphoglycerate kinase) promoter—puromycin transposon; FIG. 22 lower panel shows the transposase efficiency in fibroblast cells of a mini pig, using a modified GFIP transposon.

Figure 23:
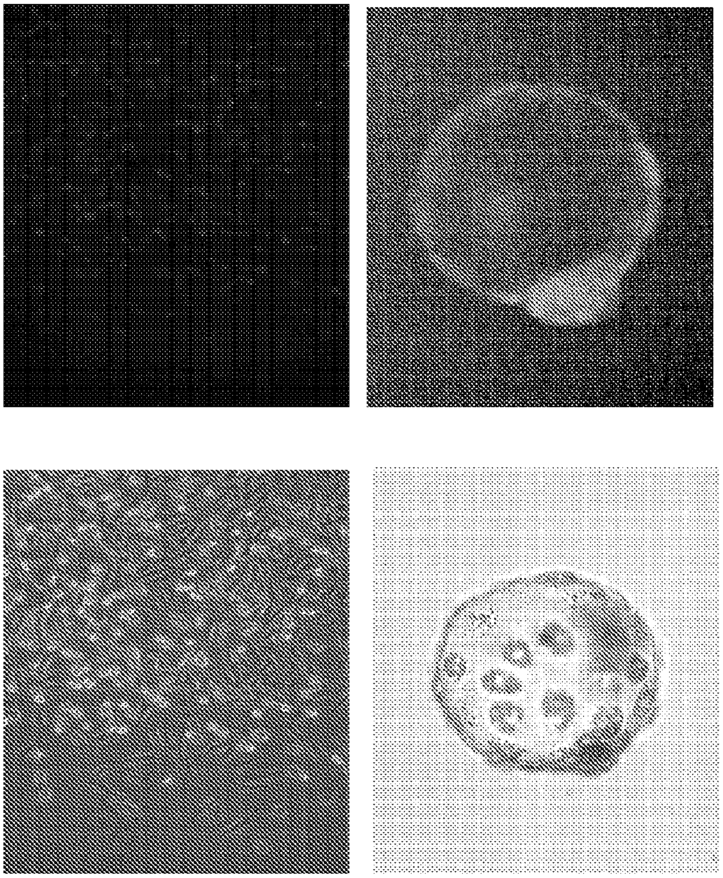

FIG. 23 shows viable cells and blastocysts comprising a transposon tagged genome carrying an eGFP gene.

Figure 24:
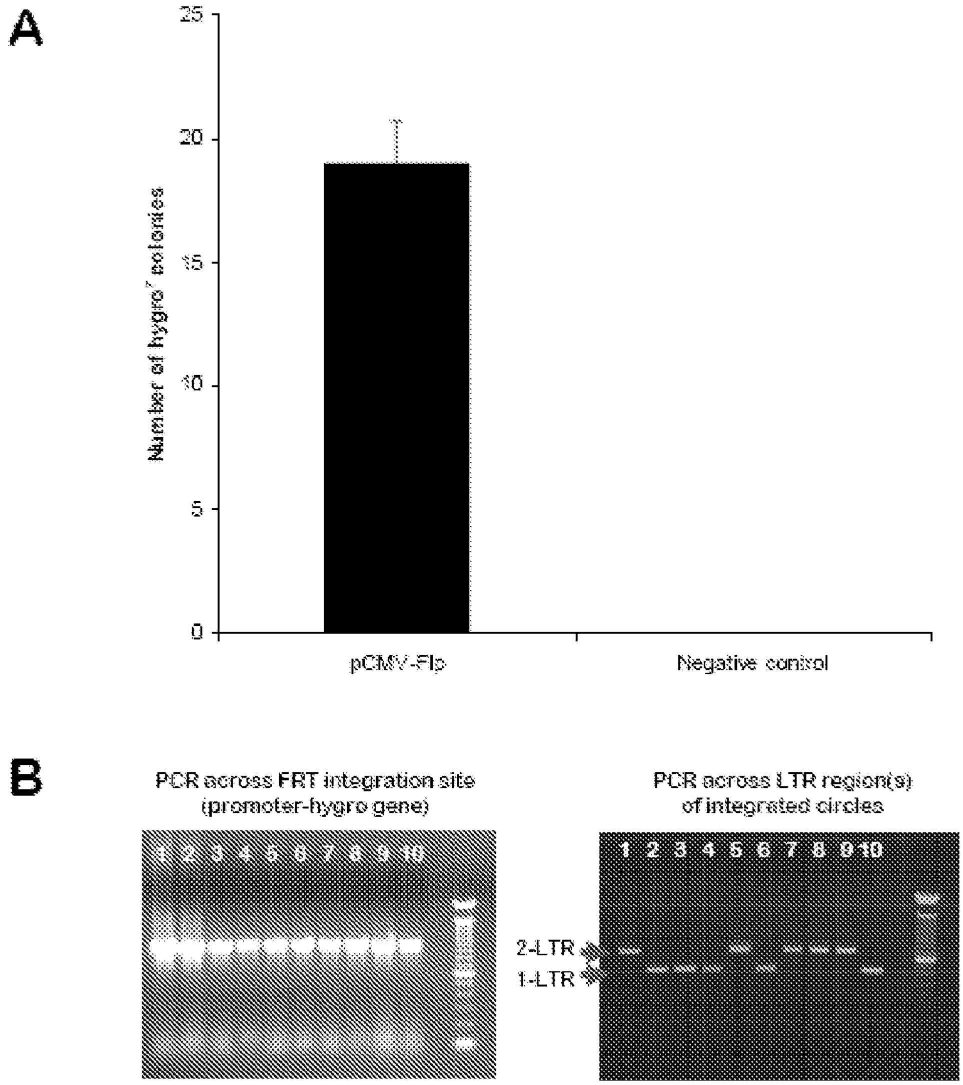

FIG. 24 shows results of an experiment in which HEK-GFIP3 cells were transfected with pCMV-Flpx9. On the following day, the transfected cells were transduced with ID-LV/FRT-hygro.PGK-puro at a MOI-100. Approximately 20 hygromycin B-resistant colonies were obtained (FIG. 24A). PCR amplifications using as template genomic DNA from the hygromycin B-resistant colonies verified that DNA circles had been inserted site-specifically into SB-tagged loci (FIG. 24B). PCR across the FRT integration site resulted in band sizes indicative of specific gene insertion, whereas primers that amplified sequences containing the LTR region(s) of the integrated circles resulted in amplicons with either one or two LTRs (FIG. 24B).

Figure 25:
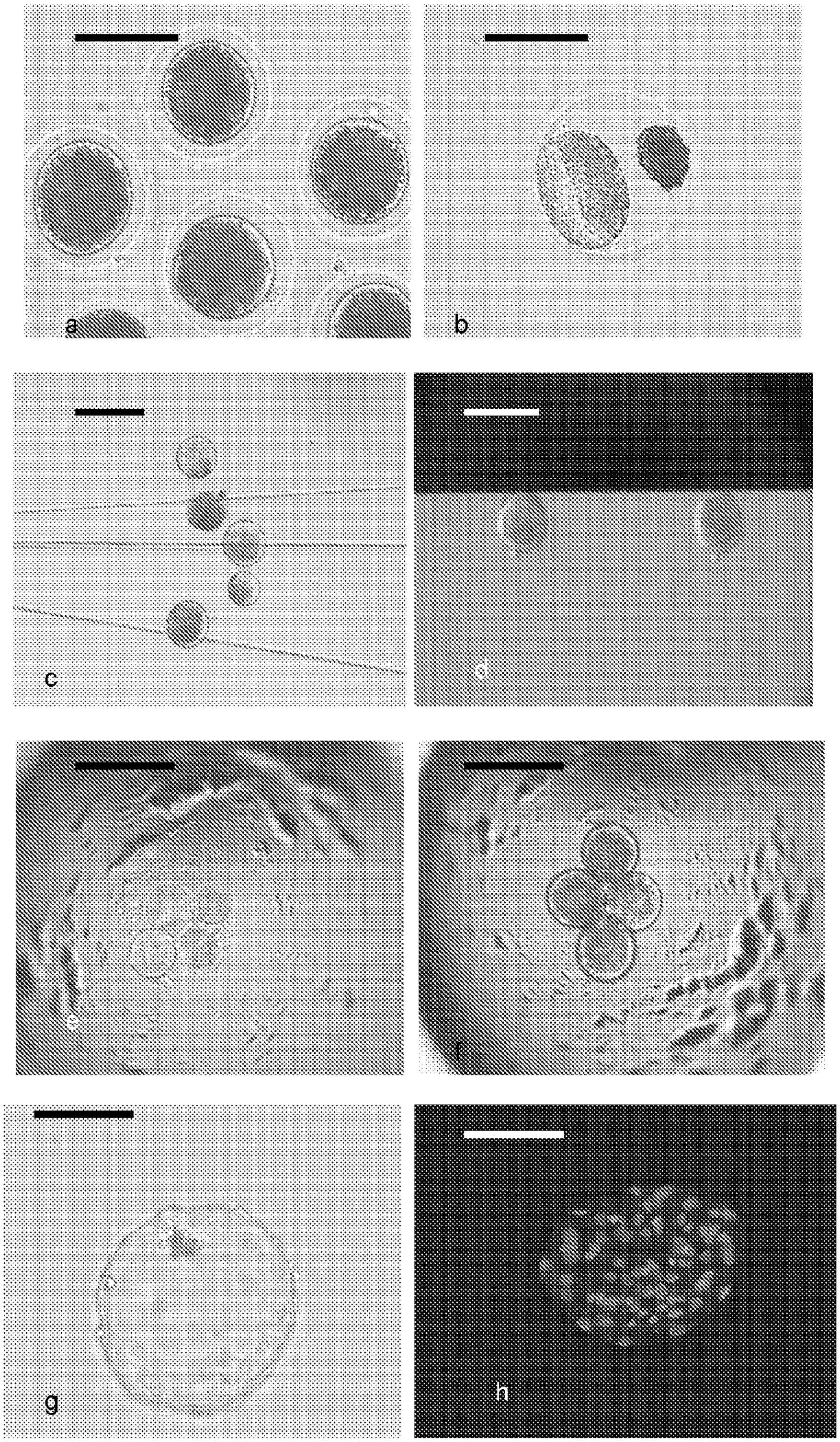
Figure 26:
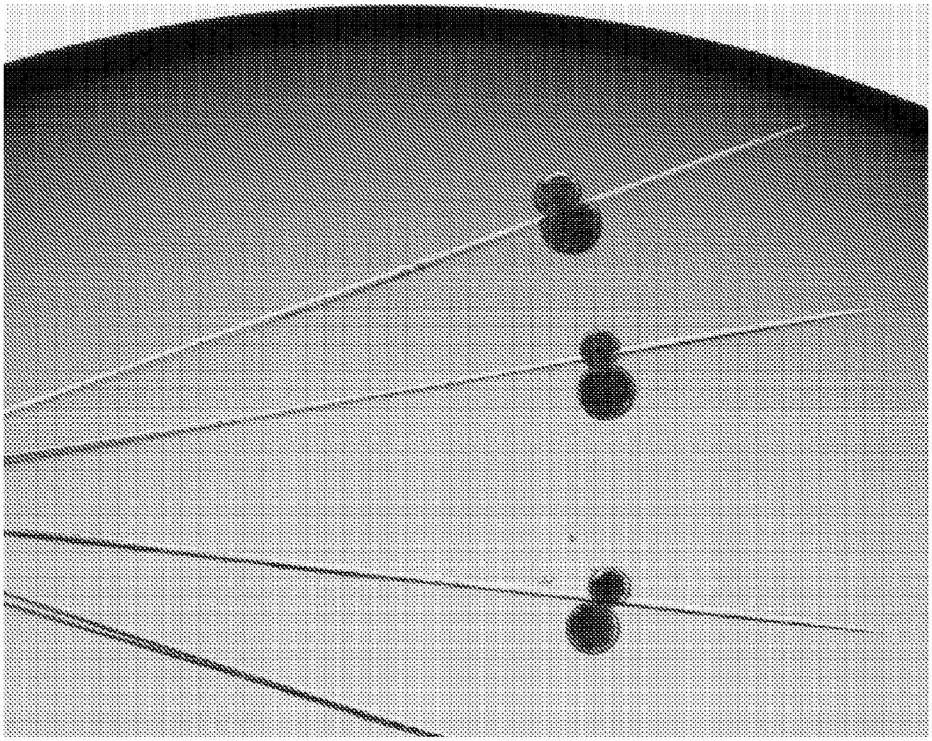

FIG. 26. (a) Oocytes trisection; (b) couplets of fibroblast-oocyte fragment for the first fusion; (c) embryos reconstructed with triplets (note elongation under the AC currency); (d) triplets fusion. Scale bar=50 μm FIG. 25. (a) In vitro matured oocytes after partial zona digestion. (b) Delipated oocytes after centrifugation. (c) Bisection of delipated oocytes. (d) Couplets of fibroblast-oocyte fragment for the first fusion. (e) Four-cell stage reconstructed embryos developed from delipated oocytes. (f) Four-cell stage reconstructed embryos developed from intact oocytes. (g) Re-expanded blastocysts from delipated embryos after warming. (h) Hoechst staining and UV illumination of re-expanded blastocysts from delipated embryos after warming. Bar represents 100 μm.

Bisection at chemically assisted enucleation. Note the extrusion cone or polar body connected to the smaller part (putative karyoplast). Stereomicroscopic picture. Bar represents 50 μm.

FIG. 27. Hoechst staining and UV illumination of the absence and presence of chromatin. UV light, inverted fluorescent microscopic picture. Bar represents 50 μm. (a) The absence of chromatin in putative cytoplasts (b) The presence of chromatin in putative karyoplasts.

Figure 28:
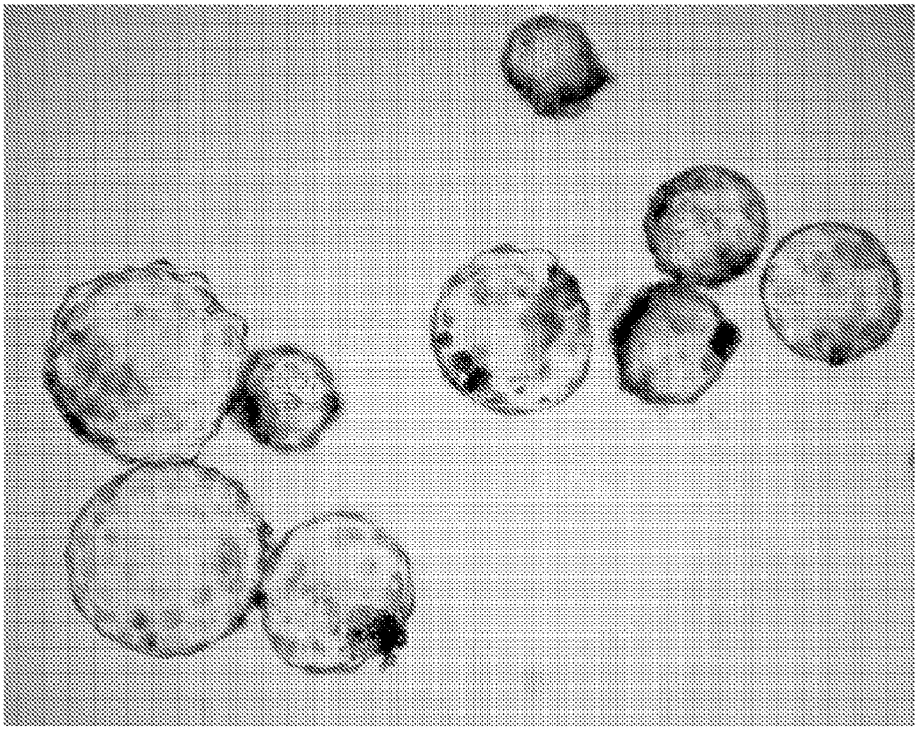

FIG. 28. Stereomicroscopic picture of Day 7 blastocysts produced with chemically assisted handmade enucleation (CAHE). Bar represents 50 μm.

Figure 29:
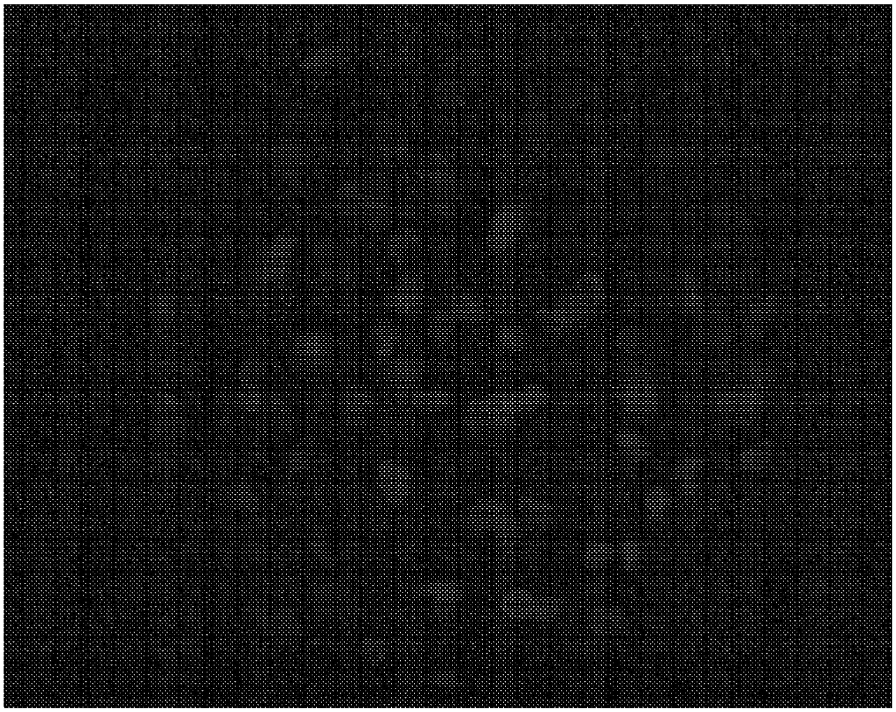

FIG. 29. Hoechst staining and UV illumination of blastocyst developed after chemically assisted handmade enucleation (CAHE). Bar represents 50 μm.

Figure 30:
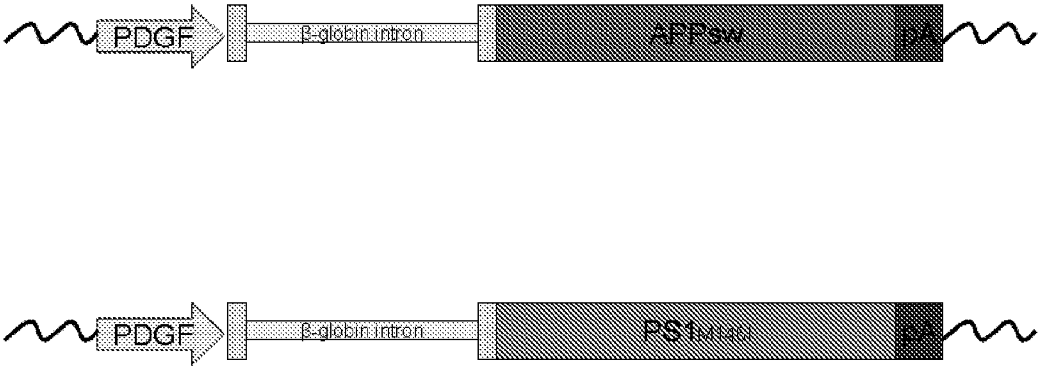

FIG. 30 Schematic presentation of constructs used to express mutated genes according to the present invention, PDGF (1 kb promoter from the human platelet derived growth factor beta gene incl. 27 bp of the 5'UTR), beta globin intron (intron 2 of beta globin gene and flanking exon sequences but no ATG codon), APPsw (transgene, see below), PS1 (M146I) (transgene, see below), pA (polyadenylation signal from SV40).

FIG. 31 Alignment of coding DNA sequence of human APP wildtype (Sbjct) and mutated human APPSW (Query)

FIG. 32 Alignment of amino acid sequence of human APP wildtype (Sbjct) and APPSW (Query)

FIG. 33 Alignment of coding DNA sequence of human PS1 wildtype (wt) and mutated human PS1 (M146I)

FIG. 34 Alignment of amino acid sequence of human PS1 wildtype (wt) and mutated human PS1 (M146I)

Figure 35:
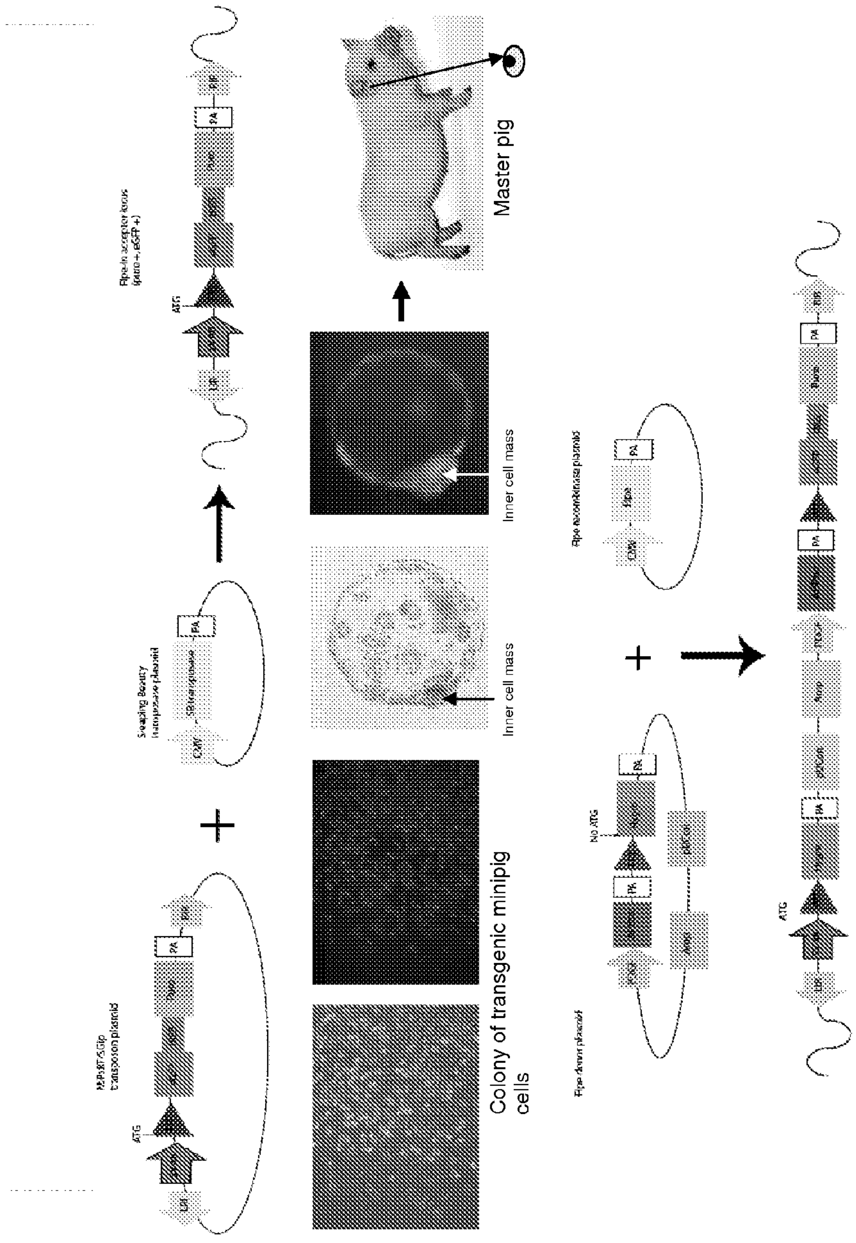

FIG. 35 shows schematically the events and constructs used for the production of a genetically modified pig as a model for studying Alzheimer's disease.

Figure 36:
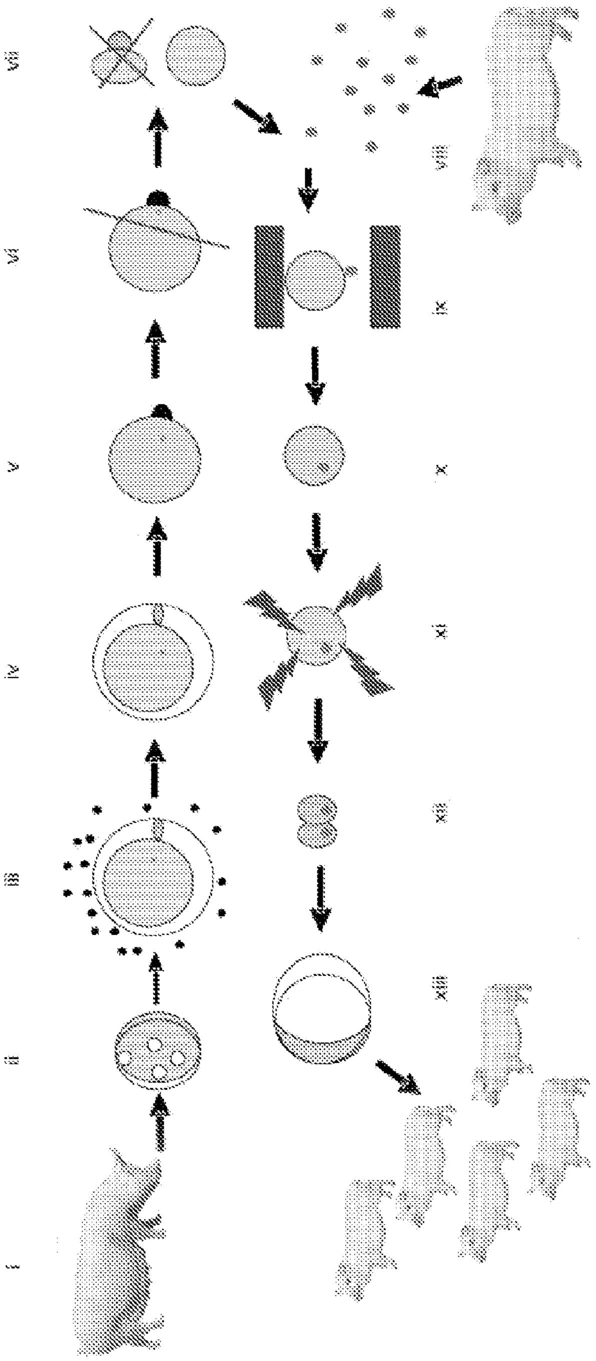

FIG. 36 shows schematically the cloning process for the production of a pig model for studying Alzheimer's disease.

DETAILED DESCRIPTION OF THE INVENTION

Definitions

Amyloid beta (Aβ or Abeta) is a peptide of 39-43 amino acids that is the main constituent of amyloid plaques in the brains of Alzheimer's disease patients.

Aβ is formed after sequential cleavage of the amyloid precursor protein (APP), a transmembrane glycoprotein of undetermined function. APP can be processed by α-, β- and γ-secretases; Aβ protein is generated by successive action of the β and γ secretases. The γ secretase, which produces the C-terminal end of the Aβ peptide, cleaves within the transmembrane region of APP and can generate a number of isoforms of 39-43 amino acid residues in length. The most common isoforms are Aβ40 and Aβ42.

The term "genetic determinant" is used herein to refer to a single-stranded or double-stranded "polynucleotide molecule" or "nucleic acid" comprising a structural gene of interest. The "genetic determinant" encodes a protein not ordinarily made in appreciable amounts in the target cells. Thus, "genetic determinants" include nucleic acids which are not ordinarily found in the genome of the target cell. "Genetic determinants" also include nucleic acids which are ordinarily found within the genome of the target cell, but is in a form which allows for the expression of proteins which are not ordinarily expressed in the target cells in appreciable amounts. Alternatively, "genetic determinants" may encode a variant or mutant form of a naturally-occurring protein.

The terms "polynucleotide" and "nucleic acid" are used interchangeably, and, when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The terms 'transgenic' pig and 'genetically modified' pig are used in identical meaning herein.

The presenilin 1 protein is herein abbreviated PS1 or alternatively PSEN1. The gene encoding presenilin 1 is abbreviated PS1 gene. The amyloid precursor protein is abbreviated APP and the gene encoding the APP protein is referred to as the APP gene.

The present invention pertains to a modified pig model for studying Alzheimer's disease, wherein the pig model expresses at least one phenotype associated with Alzheimer's disease.

It will be appreciated that the invention does not comprise processes for modifying the genetic identity of pigs which are likely to cause them suffering without any substantial medical benefit to man or animal, or animals resulting from such processes.

The present invention also relates to modified pig embryos, blastocysts, donor cells and/or fetuses obtainable by the methods described herein.

The methods for producing the pig model for studying Alzheimer's disease described herein do not encompass a surgical step performed on the pig.

Pigs

The present invention relates to a modified pig as a model for studying Alzheimer's disease, wherein the pig model expresses at least one phenotype associated with Alzheimer's disease. The pig of the present invention may be any pig.

The pig is evolutionary close to humans as compared to for example rodentia. Furthermore, the pig has been widely used in bio-medical research because of the similarities between human and porcine physiology (Douglas, 1972; Book & Bustad, 1974). The porcine brain is about 100 $cm^3$ big and highly gyrencephalic (Pillay & Manger, 2007) and has a developmental growth curve similar to that of the human brain (Pond et al., 2000). Also the relative size and cytoarchitecture of the hippocampal formation is similar to that of the human brain (Mark og Ida). Most importantly, a porcine model of diffuse brain injury demonstrates that AD-like pathology including accumulation of a-beta and tau can be produced in the porcine brain (Smith et al. J Neuropathol Exp Neurol. 1999).

In one embodiment the pig of the present invention is a wild pig. In another embodiment the pig is the domestic pig, *Sus scrofa*, such as *S. domesticus*. In yet another embodiment the invention relates to mini pigs, as well as to inbred pigs. The pig can be selected e.g. from the group consisting of Landrace, Yorkshire, Hampshire, Duroc, Chinese Meishan, Berkshire and Piêtrain, such as the group consisting of Landrace, Yorkshire, Hampshire and Duroc, for example the group consisting of Landrace, Duroc and Chinese Meishan, such as the group consisting of Berkshire, Pietrain, Landrace and Chinese Meishan, for example the group consisting of Landrace and Chinese Meishan. In one embodiment, the pig is not a mini-pig. In another embodiment the pig of the present invention is an inbred pig.

In another embodiment of the present invention the pig is a mini-pig and the mini-pig is preferably selected from the group consisting of Goettingen, Yucatan, Bama Xiang Zhu, Wuzhishan and Xi Shuang Banna. Thus, the present invention relates to any of Goettingen, Yucatan, Bama Xiang Zhu, Wuzhishan and Xi Shuang Banna separately, or in any combination.

Due to its size and weight of about 200 kg the domestic pig is not easily handled in a laboratory setting. A preferred alternative to the domestic pig is the Goettingen (Göttingen) mini-pig that weighs about 30 kg. The Goettingen minipig has a brain with almost the same brain size and identical morphology to the domestic pig, although differences may exist in the postnatal development (Jelsing et al. J. Exp. Biol. 2006). Thus, the Göttingen minipig is increasingly used in neuroscience and has served as experimental models for functional imaging studies, and a volumetric screening procedure and a magnetic resonance-based stereotaxic atlas has been developed (Jelsing et al. Exp Brain Res 2005; Watanabe et al. NeuroImage 2001). Therefore, a preferred embodiment the pig of the present invention is the Goettingen mini pig.

Genetically Modified

The modifications are introduced in the somatic cell prior to cell nuclear transfer. However, the modification may in another embodiment be introduced during the cell nuclear transfer process, for example by addition of transgenes at different steps of the hand made cloning (HMC) procedure that will then find their way to the genome of the embryo.

The genetic modifications comprise random integration of a disease-causing gene, mutated gene, into the genome of the somatic cell. It could also be random integration of a normal non-mutated gene that will cause a disease when expressed in a specific tissue or at a specific expression level.

However, the invention also pertains to modified pigs, embryos, donor cells, blastocysts and/or fetuses obtained by transfer of mRNA and/or protein of the genes disclosed herein. Thus, the modification of the pig is in one embodiment does not lead to integration of a transgene into the genome of the pig, embryo, blastocyst and/or fetus.

The introduced gene or transgene, transcriptional and/or translational product or part thereof may originate from any species, including bacteria, pig, human, mouse, rat, yeast, invertebrates, or plants. Regulatory sequences of the transgene may drive ubiquitous or inducible or tissue- and/or time-specific expression and may also originate from any species including pig, human, mouse, rat, yeast, invertebrates, or plants.

Importantly, the genetic modification in the somatic cell may be targeted to a specific region in the porcine genome by homologous recombination of a targeting construct or by gene editing procedures. This could be inactivation (e.g. knock-out) of specific genes that will cause a disease or phenotype, or it could be integration (knock-in) of specific mutations to specific genes that will then cause disease. Also, disease causing transgenes can be integrated into specific regulatory regions of the porcine genome by homologous recombination methods.

Homologous recombination occurs between two homologous DNA molecules. It is also called DNA crossover. By homologous recombination, one DNA segment can replace another DNA segment with a similar sequence. The process involve breakage and reunion between the homologous regions of DNA, which is mediated by specialized enzymes. The technique allows replacing one allele with an engineered construct without affecting any other locus in the genome. Using homologous recombination it is possible to direct the insertion of a transgene to a specific known locus of the host cells genome. Knowing the DNA sequence of the target locus, it is possible to replace any gene with a genetically modified DNA construct, thereby either replacing or deleting the target sequence. The technique comprises discovering and isolating the normal gene and then determining its function by replacing it in vivo with a defective copy. This procedure is known as ‘gene knock-out’, which allows for specific gene targeting by taking advantage of homologous recombination. Cloned copies of the target gene are altered to make them nonfunctional and are then introduced into ES cells where they recombine with the homologous gene in the cell’s genome, replacing the normal gene with a nonfunctional copy.

Homologous recombination can similarly be exploited to generate fusion genes or insertion of point mutations in a ‘knock-in’ strategy, in which a targeting vector, comprising a relevant exon of the target locus fused with the cDNA sequence of chromosomal translocation-fusion partner, is transfected into embryonic stem cells, whereby the recombinant sequence is fused to an endogenous gene to generate fusion a gene.

Another applicable technique to exploits the phenomenon called RNA interference (RNAi), in which 21 nucleotide small interfering RNAs (siRNA) can elicit an effective degradation of specific mRNAs. RNA interference constitutes a new level of gene regulation in eukaryotic cells. It is based on the fact that presence of double stranded RNA in a cell eliminates the expression of a gene of the same sequence, whereas expression of other unrelated genes is left undisturbed. The siRNA stimulates the cellular machinery to cut up other single-stranded RNA having the same sequence as the siRNA.

The genetic modifications introduced into the porcine genome prior or during the HMC procedure could also be epigenetic modifications (e.g. methylation of DNA or methylation or acetylation/deacetylation of histones) by incubating somatic cells, oocytes or reconstructed HMC embryos with chemical components such as Tricostatin or compounds with similar effect.

The present invention relates to a modified pig, comprising a genetic determinant in the form of modified porcine and/or human APP gene or part thereof, and/or modified porcine and/or human PS1 gene or part thereof, separately or in combination as described in detail herein.

The present invention also relates to porcine embryos, blastocysts and/or fetuses derived from a modified pig expressing at least one phenotype associated with Alzheimer’s disease.

In one embodiment of the present invention the transgenic pig, embryo, blastocyst, donor cell and/or fetus is transgenic for at least one gene selected from a human amyloid precursor protein (APP) gene (SEQ ID NO: 1) or part thereof, human presenilin 1 (PS1) gene (SEQ ID NO: 2) or part thereof, porcine amyloid precursor protein (APP) gene (SEQ ID NO: 3) or part thereof or porcine presenilin 1 (PS1) gene (SEQ ID NO: 4) or part thereof. However, in another embodiment the transgenic pig is transgenic for a combination of genes, for example the modified human APP gene or part thereof in combination with the modified human PS1 gene and/or the modified porcine PS1 gene or part thereof.

In another embodiment of the present invention the transgenic pig, embryo, blastocyst, donor cell and/or fetus is transgenic for at least one gene selected from a modified human amyloid precursor protein (APP) gene or part thereof, modified human presenilin 1 (PS1) gene or part thereof, modified porcine amyloid precursor protein (APP) gene or part thereof or modified porcine presenilin 1 (PS1) gene or part thereof. However, in another embodiment the transgenic pig is transgenic for a combination of genes, for example the modified human APP gene or part thereof in combination with the modified human PS1 gene and/or the modified porcine PS1 gene or part thereof. In a specific embodiment the modified pig, embryo, blastocyst, donor cell and/or fetus is transgenic due to insertion of at least one modified human APP gene or part thereof. In another embodiment the modified pig, embryo, blastocyst, donor cell and/or fetus is transgenic due to insertion of at least one modified human PS1 gene or part thereof. However, in another embodiment the modified pig, embryo, blastocyst, donor cell and/or comprises at least one modified porcine APP gene or part thereof. Furthermore, in a further embodiment the modified pig comprises at least one modified porcine PS1 gene or part thereof.

The below indicated substitutions are believed to be relevant regarding transgenic porcine models for Alzheimer’s disease.

TABLE 1

Mutations in APP (NM_000484) causing Alzheimer’s disease

| Mutation # | Mutation |
|---|---|
| 1 | Duplication of APP |
| 2 | LysMet670/671AsnLeu |

TABLE 1-continued

Mutations in APP (NM_000484) causing Alzheimer's disease

| Mutation # | Mutation |
|---|---|
| 3 | Ala673Thr |
| 4 | Asp678Asn |
| 5 | Ala692Gly |
| 6 | Glu693Lys |
| 7 | Glu693Gln |
| 8 | Glu693Gly |
| 9 | Asp694Asn |
| 10 | Leu705Val |
| 11 | Ala713Thr |
| 12 | Ala713val |
| 13 | Thr714Ala |
| 14 | Thr714Ile |
| 15 | Val715Ala |
| 16 | Ile716Thr |
| 17 | Val717Ile |
| 18 | Val717Leu |
| 19 | Val 717Phe |
| 20 | Val717Gly |
| 21 | Leu723Pro |

TABLE 2

Mutations causing Alzheimer's disease in PSEN1 (NM_000021)

| Mutation # | Mutation |
|---|---|
| 1 | Ala79Val |
| 2 | Val82Leu |
| 3 | delIle83/Met84 |
| 4 | Leu85Pro |
| 5 | Val89Leu |
| 6 | Cys92Ser |
| 7 | Val94Met |
| 8 | Val96Phe |
| 9 | Phe105Ile |
| 10 | Phe105Leu |
| 11 | Leu113Gln |
| 12 | Leu113Pro |
| 13 | Intron4; InsTAC |
| 14 | Tyr115Asp |
| 15 | Tyr115Cys |
| 16 | Tyr115Asp |
| 17 | Thr116Asn |
| 18 | Thr116Ile |
| 19 | Pro117Ser |
| 20 | Pro117Arg |
| 21 | Pro117Leu |
| 22 | Glu120Lys |
| 23 | Glu120Asp |
| 24 | Glu123Lys |
| 25 | Asn135Asp |
| 26 | Asn135Ser |
| 27 | Met139Val |
| 28 | Met139Lys |
| 29 | Met139Thr |
| 30 | Met139Ile |
| 31 | Ile143Phe |
| 32 | Ile143Asn |
| 33 | Ile143The |
| 34 | Ile143Met |
| 35 | Met146Leu |
| 36 | Met146Val |
| 37 | Met146Leu |
| 38 | Met146Ile |
| 39 | Thr147Ile |
| 40 | Leu153Val |
| 41 | Tyr154Asn |
| 42 | Tyr154Cys |
| 43 | InsPhe/Ile |
| 44 | His163Tyr |
| 45 | His163Arg |
| 46 | Trp165Gly |
| 47 | Trp165Cys |

TABLE 2-continued

Mutations causing Alzheimer's disease in PSEN1 (NM_000021)

| Mutation # | Mutation |
|---|---|
| 48 | Leu166Pro |
| 49 | Leu166Arg |
| 50 | Del_Ile197 |
| 51 | Ser169Pro |
| 52 | Ser170Phe |
| 53 | Leu171Pro |
| 54 | Leu173Trp |
| 55 | Leu174Met |
| 56 | Leu174Arg |
| 57 | Phe177Leu |
| 58 | Phe177Ser |
| 59 | Ser178Pro |
| 60 | Gly183Val |
| 61 | Glu184Asp |
| 62 | Gly206Ser |
| 63 | Gly206Asp |
| 64 | Gly206Ala |
| 65 | Gly206Val |
| 66 | Gly209Val |
| 67 | Gly209Arg |
| 68 | Gly209Glu |
| 69 | Ile213Leu |
| 70 | Ile213Phe |
| 71 | Ile213Thr |
| 72 | His214Tyr |
| 73 | Gly217Asp |
| 74 | Leu219Phe |
| 75 | Leu219Pro |
| 76 | Gln222Arg |
| 77 | Gln222His |
| 78 | Leu226Arg |
| 79 | Ile229Phe |
| 80 | Ala231Thr |
| 81 | Ala231Val |
| 82 | Met233Leu |
| 83 | Met233Val |
| 84 | Met233Thr |
| 85 | Leu235Val |
| 86 | Leu235Pro |
| 87 | Phe237Leu |
| 88 | Ala246Glu |
| 89 | Leu250Val |
| 90 | Leu250Ser |
| 91 | Tyr256Ser |
| 92 | Ala260Val |
| 93 | Val261Phe |
| 94 | Leu262Phe |
| 95 | Cys263Arg |
| 96 | Cys263Phe |
| 97 | Pro264Leu |
| 98 | Pro267Ser |
| 99 | Pro267Leu |
| 100 | Arg269Gly |
| 101 | Arg269His |
| 102 | Leu271Val |
| 103 | Val272Ala |
| 104 | Glu273Ala |
| 105 | Thr274Arg |
| 106 | Arg278Lys |
| 107 | Arg278Thr |
| 108 | Glu280Ala |
| 109 | Glu280Gly |
| 110 | Leu282Val |
| 111 | Leu282Arg |
| 112 | Pro284Leu |
| 113 | Ala285Val |
| 114 | Leu286Val |
| 115 | Deletions in intron 8 |
| 116 | InsArg(g63786_63787) |
| 117 | Thr354Ile |
| 118 | Arg358Gln |
| 119 | Ser365Tyr |
| 120 | Arg377Met |
| 121 | Gly378Glu |
| 122 | Gly378Val |
| 123 | Leu381Val |

TABLE 2-continued

| Mutations causing Alzheimer's disease in PSEN1 (NM_000021) | |
|---|---|
| Mutation # | Mutation |
| 124 | Gly384Ala |
| 125 | Phe386Ser |
| 126 | Ser390Ile |
| 127 | Val391Phe |
| 128 | Leu392Val |
| 129 | Leu392Pro |
| 130 | Gly394Val |
| 131 | Asn405Ser |
| 132 | Ala409The |
| 133 | Cys410Tyr |
| 134 | Leu418Phe |
| 135 | Leu424His |
| 136 | Leu424Arg |
| 137 | Ala426Pro |
| 138 | Ala431Glu |
| 139 | Ala431Val |
| 140 | Ala434Cys |
| 141 | Leu435Phe |
| 142 | Pro436Ser |
| 143 | Pro436Gln |
| 144 | Ile439Val |
| 145 | DelThr440 |

It is appreciated that the modified pig, embryo, blastocyst and/or fetus comprises at least one, such as two, three, four, five, six, seven, eight, nine, ten, 11, 12, 13, 14, 15, 16, 17, 18, 19, 20 or 21 mutations in the human or porcine APP gene or part thereof, where the mutations are known as disease-causing mutations in humans, for example selected from any of the mutations listed in table 1, in separate embodiments, or in any combination with the mutations listed in table 1 and/or table 2.

In a preferred embodiment the modified pig, embryo, blastocyst, donor cell and/or fetus of the present invention comprises at least one modified human APP gene or part thereof, wherein at least one mutation is the socalled Swedish mutation, corresponding to mutation #2 of table 1 which is a double mutation known by the person skilled in the art as LysMet670/671AsnLeu, transcriptional and/or translational product or part thereof (SEQ ID NO: 5, 6, 7, respectively)

In another preferred embodiment the modified pig, embryo, blastocyst, donor cell and/or fetus of the present invention comprises at least one modified human APP gene or part thereof, wherein said modified human APP gene is the APP695sw gene, transcriptional and/or translational product or part thereof. APP695sw is the neuron specific splice variant of the human amyloid precursor protein gene, APP695, which lacks exons 7 and 8 of the 19 exons of the APP gene (Neve et al. Neuron 1988; Tanzi et al. Brain Res Mol Brain Res 1993; Selkoe Rev Neurosci 1994) and including the so-called Swedish mutation (APP695sw) (SEQ ID NO.: 8, 9, 10, respectively).

In another preferred embodiment the modified pig, embryo, blastocyst, donor cell and/or fetus of the present invention comprises at least one modified human APP gene or part thereof, wherein at least one mutation is the Swedish mutation and at least one further mutation, such as Ala673Thr, Asp678Asn, Ala692Gly, Glu693Lys, Glu693Gln, Glu693Gly, Asp694Asn, Leu705Val, Ala713Thr, Ala713val, Thr714Ala, Thr714Ile, Val715Ala, Ile716Thr, Val717Ile, Val717Leu, Val 717Phe, Val717Gly and/or Leu723Pro, transcriptional and/or translational product or part thereof.

It is understood that the modified pig, embryo, blastocyst, donor cell and/or fetus of the present invention comprises at least one modified porcine APP gene or part thereof, wherein at least one mutation corresponds to the Swedish mutation known in human APP, transcriptional and/or translational product or part thereof (SEQ ID NO: 11, 12, 13, respectively).

In another embodiment the modified pig, embryo, blastocyst, donor cell and/or fetus of the present invention comprises at least one modified porcine APP gene or part thereof, wherein the modified porcine APP gene corresponds to the human APP695sw, transcriptional and/or translational product or part thereof.

In another preferred embodiment the modified pig of the present invention comprises at least one modified porcine APP gene or part thereof, wherein at least one mutation is the Swedish mutation and at least one further mutation, such as Ala673Thr, Asp678Asn, Ala692Gly, Glu693Lys, Glu693Gln, Glu693Gly, Asp694Asn, Leu705Val, Ala713Thr, Ala713val, Thr714Ala, Thr714Ile, Val715Ala, Ile716Thr, Val717Ile, Val717Leu, Val 717Phe, Val717Gly and/or Leu723Pro, transcriptional and/or translational product or part thereof.

An alignment of the human and the porcine APP770 protein is shown in FIG. 1.

It is understood that the modified pig comprises at least one, such as two, three, four, five, six, seven, eight, nine, ten, 11, 12, 13, 14, 15, 16, 17, 18, 19, 20, 25, 30, 35, 40, 45, 50, 55, 60, 65, 70, 75, 80, 85, 90, 95 or 100 mutations in the human or porcine PS1 gene or part thereof, where the mutations are known as disease-causing mutations in humans, for example selected from any of the mutations listed in table 2, in separate embodiments, or in any combination with the mutations listed in table 1 and/or table 2.

In a preferred embodiment the modified pig, embryo, blastocyst, donor cell and/or fetus of the present invention comprises at least one modified human PS1 gene or part thereof, comprises a mutation encoding a PS1 protein harbouring a Pro117Leu mutation, transcriptional and/or translational product or part thereof. (SEQ ID NO: 17, 18, 19, respectively).

In another preferred embodiment the modified pig, embryo, blastocyst and/or fetus of the present invention comprises at least one modified porcine PS1 gene or part thereof, wherein at least one mutation gives rise to a PS1 protein harbouring a Pro117Leu mutation and at least one further mutation.

It is understood that the modified pig, embryo, blastocyst, donor cell and/or fetus of the present invention comprises at least one modified porcine PS1 gene or part thereof, wherein at least one mutation gives rise to a PS1 protein harbouring a Pro117Leu mutation, transcriptional and/or translational product or part thereof (SEQ ID NO: 20, 21, 22, respectively).

In another preferred embodiment the modified pig, embryo, blastocyst, donor cell and/or fetus of the present invention comprises at least one modified porcine PS1 gene or part thereof, wherein at least one mutation gives rise to a PS1 protein harbouring a Pro117Leu mutation and at least one further mutation.

PS1 protein homology between human and pig is shown in FIG. 2.

It is also within the scope of the present invention that the modified pig, embryo, blastocyst, donor cell and/or fetus comprises any combination of at least two mutations in human and/or porcine APP gene or part thereof, and/or in the human and/or porcine PS1 gene or part thereof. The combination is for example three, four, five, six, seven, eight, nine, ten, 11, 12, 13, 14, 15, 16, 17, 18, 19, 20, 25, 30, 35, 40, 45, 50, 55, 60, 65, 70 or 75 mutations.

In a preferred embodiment the modified pig, embryo, blastocyst, donor cell and/or fetus comprises at least one modified APP gene or part thereof is at least one modified human APP gene or part thereof comprising a Swedish mutation and wherein said at least one modified PS1 gene or part thereof is at least one modified human PS1 gene or part thereof comprising a mutation encoding a PS1 protein harbouring a Pro117Leu mutation, transcriptional and/or translational product or part thereof.

In another preferred embodiment the modified pig, embryo, blastocysts, donor cell and/or fetus comprises at least one modified APP gene or part thereof being APP695sw and wherein said at least one modified PS1 gene or part thereof is at least one modified human PS1 gene or part thereof comprising a mutation encoding a PS1 protein harbouring a Pro117Leu mutation, transcriptional and/or translational product or part thereof.

In another preferred embodiment the Met146Ile variant of PS1 is introduced into the modified pig, embryo, blastocyst and/or fetus of the present invention.

It is appreciated that the cDNA or part thereof of the modified human APP gene and/or the cDNA or part thereof of the modified porcine APP gene and/or the cDNA or part thereof of the modified human PS1 gene and/or the cDNA or part thereof of the modified porcine PS1 gene, and combinations as outlined herein is within the scope of the present invention. Furthermore in another embodiment, the modified pig comprises the transcriptional product or part thereof and/or the translational product or part thereof encoded by the modified porcine and/or human APP gene. In yet a further embodiment the modified pig comprises the transcriptional product or part thereof and/or the translational product or part thereof of the porcine and/or human APP gene, or combination thereof as described herein.

Sequence Identity

Functional equivalents and variants are used interchangeably herein. In one preferred embodiment of the invention there is also provided variants of the modified human and/or porcine APP gene and/or modified human and/or porcine PS1 gene and variants of fragments thereof. When being polypeptides, variants are determined on the basis of their degree of identity or their homology with a predetermined amino acid sequence of the present invention, or, when the variant is a fragment, a fragment of any of the aforementioned amino acid sequences, respectively.

Accordingly, variants preferably have at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined sequence.

The following terms are used to describe the sequence relationships between two or more polynucleotides: "predetermined sequence", "comparison window", "sequence identity", "percentage of sequence identity", and "substantial identity".

A "predetermined sequence" is a defined sequence used as a basis for a sequence comparison; a predetermined sequence may be a subset of a larger sequence, for example, as a segment of a full-length DNA or gene sequence given in a sequence listing, such as a polynucleotide sequence of porcine or human PS1 sequence, or porcine or human APP sequence or may comprise a complete DNA or gene sequence. Generally, a predetermined sequence is at least 20 nucleotides in length, frequently at least 25 nucleotides in length, and often at least 50 nucleotides in length.

Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a predetermined sequence of at least 20 contiguous nucleotides and wherein the portion of the polynucleotide sequence in the comparison window may comprise additions or deletions (i.e., gaps) of 20 percent or less as compared to the predetermined sequence (which does not comprise additions or deletions) for optimal alignment of the two sequences.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a predetermined sequence over a comparison window of at least 20 nucleotide positions, frequently over a window of at least 25-50 nucleotides, wherein the percentage of sequence identity is calculated by comparing the predetermined sequence to the polynucleotide sequence which may include deletions or additions which total 20 percent or less of the predetermined sequence over the window of comparison. The predetermined sequence may be a subset of a larger sequence, for example, as a segment of the full-length modified porcine or human Ps1 sequence, or porcine or human APP sequence polynucleotide sequence illustrated herein.

Sequence identity is determined in one embodiment by utilising fragments of porcine or human PS1 sequence, or porcine or human APP peptides comprising at least 25 contiguous amino acids and having an amino acid sequence which is at least 80%, such as 85%, for example 90%, such as 95%, for example 96%, such as 97%, for example 98%, such as 99% identical to the amino acid sequence of SEQ ID NO: 23, SEQ ID NO: 24, SEQ ID NO: 25, or SEQ ID NO: 26 wherein the percent identity is determined with the algorithm GAP, BESTFIT, or FASTA in the Wisconsin Genetics Software Package Release 7.0, using default gap weights.

Conservative Amino Acid Substitutions:

Substitutions within the groups of amino acids, shown below, are considered conservative amino acid substitutions. Substitutions between the different groups of amino acids are considered non-conservative amino acid substitutions.

P, A, G, S, T (neutral, weakly hydrophobic)
Q, N, E, D, B, Z (hydrophilic, acid amine)
H, K, R (hydrophilic, basic)
F, Y, W (hydrophobic, aromatic)
L, I, V, M (hydrophobic)
C (cross-link forming)

By the term "transcriptional or translational products" is meant herein products of gene transcription, such as a RNA transcript, for example an unspliced RNA transcript, a mRNA transcript and said mRNA transcript splicing products, and products of gene translation, such as polypeptide(s) translated from any of the gene mRNA transcripts and various products of post-translational processing of said polypeptides, such as the products of post-translational proteolytic processing of the polypeptide(s) or products of various post-translational modifications of said polypeptide(s).

As used herein, the term "transcriptional product of the gene" refers to a pre-messenger RNA molecule, pre-mRNA, that contains the same sequence information (albeit that U nucleotides replace T nucleotides) as the gene, or mature messenger RNA molecule, mRNA, which was produced due to splicing of the pre-mRNA, and is a template for translation of genetic information of the gene into a protein.

Phenotypes

The phenotypes associated with Alzheimer's disease are many. It is appreciated that the pig model of the present invention expresses at least one phenotype associated with Alzheimer's disease, such as three, for example four, five, six, seven, eight, nine, ten, eleven, 12, 13, 14, 15, 16, 17, 18, 19 or 20 phenotypes associated with Alzheimer's disease. Non-limiting examples of said phenotypes are short term memory loss, deterioration of musculature and mobility, accumulation of amyloid plaques and neurofibrillary tangles in brain sections, reduced olfaction, reduced semantic memory, reduced visio-spatial memory and/or increased levels of amyloid beta and/or tau protein in the cerebrospinal fluid.

The phenotypes associated with Alzheimer's comprise short term memory loss which progresses from seemingly simple and often fluctuating forgetfulness to a more pervasive loss of short-term memory, then of familiar and well-known skills or objects. In humans, loss of olfaction is an early symptom. Loss of memory is often followed by aphasia and disorientation. Alzheimer's disease may also include behavioral changes, such as outbursts of violence or excessive passivity in people/pigs having no previous history of such behavior. In the later stages of the disease deterioration of musculature and mobility is observed.

The diagnosis is made primarily on the basis of clinical observation and tests of memory and intellectual functioning over a series of weeks or months. No medical tests are available to diagnose Alzheimer's disease conclusively pre-mortem. However, Alzheimer's disease can now be diagnosed by experts skilled in memory disorders with high accuracy. Functional neuroimaging studies such as positron emission tomography (PET), including Pittsburgh compound scan and single photon emission computed tomography (SPECT) scans can provide a supporting role.

Characterisation of the phenotype of the porcine model of Alzheimer's disease:

Parameters to be studied at various ages, for example age 6, 12, 18, 24 months of age, or 2.5, 3, 3.5, 4, 4.5, 5, 5.5, 6, 6.5 or 7 years of age:

Biochemistry

Transgene (APP or PS1) mRNA detection by Northern blotting, RT-PCR, in situ RNA hybridisation to cryostat brain sections.

Transgene protein detection by Western blotting, immunohistochemistry on paraffin embedded brain sections, sandwich ELISA for detection of Abeta in cerebro-spinal fluid.

Alzheimer's disease has been identified as a protein misfolding disease, or proteopathy, due to the accumulation of abnormally folded A-beta and tau proteins in the brains of AD patients. AD is also considered a tauopathy due to abnormal aggregation of the tau protein. Healthy neurons have an internal support structure, or cytoskeleton, partly made up of microtubules. These microtubules act like tracks, guiding nutrients and molecules from the body of the cell down to the ends of the axon and back. Tau protein stabilizes the microtubules stable during phosphorylation. In AD, tau is changed chemically, becoming hyperphosphorylated. Hyperphosphorylated tau begins to pair with other threads of tau and they become tangled up together inside nerve cell bodies in masses known as neurofibrillary tangles, resulting in disintegration of microtubules and thus malfunction in communication between neurons and later in the death of the cells.

Neuropathology

H+E and Bielchowsky staining of brain sections to detect specific AD pathology (amyloid plaques and neurofibrillary tangles). Immunohistochemistry to detect Abeta, tau, ubiquitin. Diagnosis according to standardized neuropathological criteria for Alzheimer's disease (Reagan criteria with CERAD score and Braak & Braak stadium).

Behavioral Analysis

Base-line studies and validation of the following tests are currently conducted on 16 normal pigs as well as on modified pigs according to the present invention, In order to examine the transgenic pigs for signs of AD symptoms three different behavioural tests are used:

1) Test of olfaction with an Olfactometer Test
2) Test of semantic memory with Object-Recognition Test
3) Test of visuo-spatial memory with Labyrinth Test All three tests are based on knowledge about the neuropsychological deficits in AD in humans and the assumption that development of AD in pigs will result in comparable deficits.

The test of visuo-spatial memory with labyrinth test is based on the fact that in addition to affection of memory, cognitive disturbances develop as a consequence of affection of more widespread cortical areas in the brain. AD patients particularly suffer from visuo-spatial disturbances and this is commonly tested with the clock-drawing test in which the patients are asked to draw a clock with correct numbers and arms. AD patients are unable to do this. A correlate to this test in animals is the Morris Water Maze designed for rodents and several tests have been designed for pigs (e.g. Hagl et al., 2005). Briefly, the pigs learn in which of different compartments food is stored in order to obtain a reward (food). The complexity of the test can be varied to increase the difficulty. This test is applied to the transgenic pigs at the same times as above. Spatial memory of the pigs is tested in an eight-room labyrinth (central hall-way with 4 rooms on each side). In 4 to 6 rooms is placed reward. The animal learns in which rooms rewards never occur and remember which rooms it has visited. The modified pig model for studying Alzheimer's disease expresses at least one phenotype associated with Alzheimer's disease in the form of reduced visio-spatial memory measured by the eight room labyrinth test. The reduction of visio-spatial memory is at least 10% compared to the standard level of visio-spatial memory observed in the pig i.e. prior to onset of at least one phenotype of Alzheimer's disease, such as at least 15%, for example at least 16%, such as at least 18%, for example at least 20%, such as at least 25%, for example at least 26%, such as at least 27%, for example at least 28%, such as at least 29%, for example at least 30%, such as at least 32%, for example at least 34%, such as at least 35%, for example at least 40%, such as at least 50% compared to the standard level of visio-spatial memory observed in the pig prior to onset of at least one phenotype of Alzheimer's disease. In a preferred embodiment the reduction in visio-spatial memory is reduced in the range of 30% to 60% compared to the standard level of visio-spatial memory observed in the pig prior to onset of at least one phenotype of Alzheimer's disease.

Thus, a 10% reduction in visio-spatial memory of a standard level observed in a particular pig being 80% correct choices, corresponds to a level of visio-spatial memory being 72% correct choices.

It is appreciated that a level of 50% correct choices in the visio-spatial memory test corresponds to a random behaviour by the pig.

The test of semantic memory with object-recognition test is based on cardinal symptom of AD in humans is affection of the memory. Several neuropsychological tests can be used in humans to test different elements of memory (i.e. episodic memory, semantic memory, working memory, perceptual speed test), but a rather simple test of semantic memory, the Mini Mental State Examination (MMSE), has found widespread use in the day-to-day testing of humans. The test consists of a total of 30 different questions and is easily performed. A score below 23 indicates memory deficit corresponding to dementia. A correlate to this test in animals is the object-recognition test in which spontaneous exploration of objects is evaluated. The animals are initially allowed to explore two identical objects. After a certain time lapse, the animals are exposed to two objects—one identical with the objects in the initial session—the other differing from them. The difference in time spent to explore the two objects indicates recognition of the object from the first session. Application of such a test for pigs has already been described by others (Moustgaard et al., 2002) and is used to test the transgenic pigs at the same times as above. Briefly, object recognition test takes place in an arena where two identical objects are presented to the pig for a well defined period of time. The pig is removed from the arena in a delay-period while one of the familial objects is substituted by a new object. The pig returns to the arena and the time the pig uses to explore the known and unknown objects is measured. The modified pig model for studying Alzheimer's disease expresses at least one phenotype associated with Alzheimer's disease in the form of reduced semantic memory measured by the object recognition test. The reduction of semantic memory is at least 10% compared to the standard level of semantic memory observed in the pig i.e. prior to onset of at least one phenotype of Alzheimer's disease, such as at least 15%, for example at least 16%, such as at least 17%, for example at least 18%, such as at least 19%, for example at least 20%, such as at least 21%, for example at least 22%, such as at least 23%, for example at least 24%, such as at least 25%, for example at least 26%, such as at least 27%, for example at least 28%, such as at least 29%, for example at least 30%, such as 31%, for example 32%, such as 35% compared to the standard level of semantic memory observed in the pig prior to onset of at least one phenotype of Alzheimer's disease. In a preferred embodiment the reduction in semantic memory is reduced in the range of 15% to 30% compared to the standard level of semantic memory observed in the pig prior to onset of at least one phenotype of Alzheimer's disease. Thus, a 10% reduction in semantic memory of a standard level observed of a particular pig being 80% correct choices corresponds to a level of semantic memory being 72% correct choices.

It is appreciated that a level of 50% correct choices in the semantic memory test corresponds to a random behaviour by the pig.

Olfaction

Test of olfaction with an olfactometer test is based on information originally observed in humans. In humans, one of the first signs of AD is affection of olfactory system (Eibenstein et al., 2005a,b) and a relatively simple test has been developed for testing olfaction in humans (Pocket Smell Test, Sensonics) (Doty et al., 1984). In animals, testing of olfaction is often performed using an olfactometer (Knosys Inc.), in which airborne odorants in varying concentrations are presented to the animal placed in a designated test chamber. Olfaction is tested in an olfactometer where the animal is presented to an odorant in various concentrations (+stimulus) or is presented to air without odorant (−stimulus). The animal has already been trained, by operant conditioning, to press a pedal (A) when +stimulus and a pedal (B) if −stimulus. When threshold for detection is reached the pig will perform a −response (press pedal B) in spite of the presence of a small amount of odorant.

We have developed an olfactometer for pigs and a total of 6 normal pigs have been tested with different odorants (ethanol and ethyl acetate). The pigs have been trained using operant conditioning to push a pedal when receiving the odorant, and are rewarded with chocolate (M&Ms) for a right answer. The threshold for detection of the odorant has been determined in the pigs.

The modified pigs are tested using the same olfactometer and we have chosen a level of 80% correct answers as normal, implicating that olfaction is decreased when the number of correct answers is below 80%. The transgenic pigs are for example tested at 6, 12, 18, 24, and 24+ months and each animal serves as it own control. A decrease in olfaction is anticipated as the first symptom of AD in the pigs to be reflected in a decreased number of correct answers (i.e. the % correct answers decreases below 80%).

Thus, in one embodiment of the present invention the modified pig as a model for studying Alzheimer's disease expresses at least one phenotype in the form of reduced olfaction. In the present context the level of olfacaction for a particular pig is reduced by at least 10% when the particular pig displays at least one phenotype associated with Alzheimer's disease, as compared to the pig prior to onset of the at least one phenotype of Alzheimer's disease (standard level of correct answers as observed during several sessions). Thus, the modified pig as a model for studying Alzheimer's disease expresses at least one phenotype in the form of at least 10% reduction in olfaction compared to a standard level of olfaction of said pig, such as at least 15% reduction in olfaction, for example at least 16% reduction in olfaction, such as at least 17% reduction in olfaction, such as at least 18% reduction in olfaction, for example at least 19% reduction in olfaction, such as at least 20% reduction in olfaction, for example at least 21% reduction in olfaction, such as at least 22% reduction in olfaction, such as at least 23% reduction in olfaction, for example at least 24% reduction in olfaction, such as at least 25% reduction in olfaction, for example at least 26% reduction in olfaction, such as at least 27% reduction in olfaction, such as at least 28% reduction in olfaction, for example at least 29% reduction in olfaction, such as at least 30% reduction in olfaction, for example at least 31% reduction in olfaction, such as at least 32% reduction in olfaction, such as at least 33% reduction in olfaction as compared to the pig prior to onset of the at least one phenotype of Alzheimer's disease.

Thus, a 10% reduction in olfaction of a standard level observed of a particular pig being 80% correct answers corresponds to a level of olfaction being 72% correct answers.

It is appreciated that a level of 50% correct answers in the olfaction test corresponds to a random behaviour by the pig.

In a preferred embodiment the level of olfaction of a modified pig of the present invention is reduced by at least 25%.

The standard level of olfaction in a pig that does not display an Alzheimer phenotype is is determined to exhibit about 80% correct answers when tested in the olfactometer as described herein. A modified pig as a model for studying Alzheimer's disease expresses at least one phenotype associated with Alzheimer's disease, wherein said pig exhibits 50% correct answers in the olfactometer test, for example 51% correct answers, such as 52% correct answers, for example 53% correct answers, such as 54% correct answers, for example 55% correct answers, such as 56% correct answers, for example 57% correct answers, such as 58% correct answers, for example 59% correct answers, such as 60% correct answers, for example 61% correct answers, such as 62% correct answers, for example 63% correct answers, such as 64% correct answers, for example 65% correct answers, such as 66% correct answers, for example 67% correct answers, such as 68% correct answers, for example 69% correct answers, such as 70% correct answers, for example 71% correct answers, such as 72% correct answers, for example 73% correct answers, such as 74% correct answers, for example 75% correct answers in the olfactometer test described herein. In a preferred embodiment the modified pig as a model for studying Alzheimer's disease expresses at least one phenotype associated with Alzheimer's disease, wherein said pig exhibits in the range of 50% to 60% correct answers in the olfactometer test. In another preferred embodiment the modified pig as a model for studying Alzheimer's disease expresses at least one phenotype associated with Alzheimer's disease, wherein said pig exhibits at the most 60% correct answers, for example at the most 59% correct answers, such as at the most 58% correct answers, for example at the most 57% correct answers, such as at the most 56% correct answers, for example at the most 55% correct answers, such as at the most 54% correct answers, for example at the most 53% correct answers, such as at the most 52% correct answers, for example at the most 51% correct answers, such as at the most 50% correct in the olfactometer test.

Brain Imaging PET and MRI Studies

The criteria of success: The model is considered successful if it fulfils the diagnostic criteria in humans: the presence of specific behavioural changes and corresponding neuropathological lesions. The protocol for monitoring general health and welfare will be continued throughout the period.

The pig model of the present invention displays accumulation of abnormally folded A-beta and tau proteins in the brains of modified pigs for studying of Alzheimer's disease. In another embodiment the pig model displays increased levels of amyloid beta and/or tau protein in the cerebrospinal fluid of said pig as compared to a standard level observed in the pig previously.

Methods for Producing Pig Model for Studying Alzheimer's Disease

The modified pig of the present invention may be produced using any technique in which modified genetic material, transcriptional product and/or translational product or part thereof is transferred from at donor cell to a host cell, such as an enucleated oocyte. A number of techniques exist such as introducing genetic material from a genetically modified somatic cell into an enucleated oocyte by for example microinjection or by nuclear transfer. The present invention provides improved procedures for cloning pigs by nuclear transfer which refers to the introduction of a full complement of nuclear DNA from one cell to an enucleated cell.

The present invention provides improved procedures for cloning mammals by nuclear transfer which refers to the introduction of a full complement of nuclear DNA from one cell to an enucleated cell.

In cloning, the transfer of the nucleus of a somatic (body) cell or somatic cell into an egg cell (oocyte) which has had its own nucleus removed (denucleated or enucleated) is called somatic cell nuclear transfer. The new individual will develop from this reconstructed embryo and be genetically identical to the donor of the somatic cell. In the present invention the modified pig model, porcine embryo, blastocyst and/or fetus is obtainable by somatic cell nuclear transfer comprising the steps of a) establishing at least one oocyte having at least a part of a modified zona pellucida, b) separating the oocyte into at least two parts obtaining at least one cytoplast, c) establishing a donor cell or cell nucleus having desired genetic properties, d) fusing at least one cytoplast with the donor cell or membrane surrounded cell nucleus, e) obtaining a reconstructed embryo, f) activating the reconstructed embryo to form an embryo; and g) transferring said cultured embryo to a host mammal such that the embryo develops into a genetically modified fetus, wherein said genetically modified embryo obtainable by nuclear transfer comprises steps a) to e) and/or f), wherein said genetically modified blastocyst obtainable by nuclear transfer comprises steps a) to e) and/or f), wherein said genetically modified fetus obtainable by nuclear transfer comprises steps a) to g)

It is appreciated that the donor cell or cell nucleus of c) harbours genetic determinants for Alzheimers disease, for example in the form of modified human or porcine APP gene or part thereof and/or modified human or porcine PS1 gene or part thereof and/or transcriptional and/or translational products thereof. The host mammal of g) is in one embodiment a pig, preferably a Goettingen mini pig.

However, the present invention also relates to a method for producing a transgenic pig, porcine blastocyst, embryo and/or fetus as a model for Alzheimer's disease comprising the steps of a) establishing at least one oocyte, b) separating the oocyte into at least three parts obtaining at least one cytoplasts, c) establishing a donor cell or cell nucleus having desired genetic properties, d) fusing at least one cytoplast with the donor cell or membrane surrounded cell nucleus, e) obtaining a reconstructed embryo, f) activating the reconstructed embryo to form an embryo; and g) transferring said cultured embryo to a host mammal such that the embryo develops into a genetically modified fetus, wherein said genetically modified embryo obtainable by nuclear transfer comprises steps a) to e) and/or f), wherein said genetically modified blastocyst obtainable by nuclear transfer comprises steps a) to e) and/or f), wherein said genetically modified fetus obtainable by nuclear transfer comprises steps a) to g).

The oocyte of b) may in another embodiment be separated into at least three parts obtaining at least two cytoplasts. It is appreciated that the donor cell or cell nucleus of c) harbours genetic determinants for Alzheimers disease, for example in the form of modified human or porcine APP gene or part thereof and/or modified human or porcine PS1 gene or part thereof. The host mammal of g) is in one embodiment a pig, preferably a Goettingen mini pig.

The various parameters are described in detail below.

Oocyte

The term 'oocyte' according to the present invention means an immature female reproductive cell, one that has not completed the maturing process to form an ovum (gamete). In the present invention an enucleated oocyte is the recipient cell in the nuclear transfer process.

The oocytes according to the present invention are isolated from oviducts and/or ovaries of a mammal. Normally, oocytes are retrieved from deceased pigs, although they may be isolated also from either oviducts and/or ovaries of live pigs. In one embodiment the oocytes are isolated by oviductal recovery procedures or transvaginal recovery methods. In a preferred embodiment the oocytes are isolated by aspiration. Oocytes are typically matured in a variety of media known to a person skilled in the art prior to enucleation. The oocytes can also be isolated from the ovaries of a recently sacrificed animal or when the ovary has been frozen and/or thawed. Preferably, the oocytes are freshly isolated from the oviducts.

Oocytes or cytoplasts may also be cryopreserved before use. While it will be appreciated by those skilled in the art that freshly isolated and matured oocytes are preferred, it will also be appreciated that it is possible to cryopreserve the oocytes after harvesting or after maturation. If cryopreserved oocytes are utilised then these must be initially thawed before placing the oocytes in maturation medium. Methods of thawing cryopreserved materials such that they are active after the thawing process are well-known to those of ordinary skill in the art. However, in general, cryopreservation of oocytes and cytoplasts is a very demanding procedure, and it is especially difficult in pigs, because of the above mentioned general fragility of pig oocytes and cytoplasts, and because of the high lipid content that makes them very sensitive to chilling injury (i.e. injury that occurs between +15 and +5° C. during the cooling and warming procedure).

In another embodiment, mature (metaphase II) oocytes that have been matured in vivo, may be harvested and used in the nuclear transfer methods disclosed herein. Essentially, mature metaphase II oocytes are collected surgically from either nonsuperovulated or superovulated pigs 35 to 48 hours past the onset of estrus or past the injection of human chorionic gonadotropin (hCG) or similar hormone.

Where oocytes have been cultured in vitro, cumulus cells that are surrounding the oocytes in vivo may have accumulated may be removed to provide oocytes that are at a more suitable stage of maturation for enucleation. Cumulus cells may be removed by pipetting or vortexing, for example, in the presence of in the range of 0.1 to 5% hyaluronidase, such as in the range of 0.2 to 5% hyaluronidase, for example in the range of 0.5 to 5% hyaluronidase, such as in the range of 0.2 to 3% hyaluronidase, for example in the range of 0.5 to 3% hyaluronidase, such as in the range of 0.5 to 2% hyaluronidase, for example in the range of 0.5 to 1% hyaluronidase, such as 0.5% hyaluronidase.

The first step in the preferred methods involves the isolation of a recipient oocyte from a suitable pig. In this regard, the oocyte may be obtained from any pig source and at any stage of maturation.

The stage of maturation of the oocyte at enucleation and nuclear transfer has been reported to be of significance for the success of nuclear transfer methods. Immature (prophase I) oocytes from pig ovaries are often harvested by aspiration. In order to employ techniques such as genetic engineering, nuclear transfer and cloning, such harvested oocytes are preferably matured in vitro before the oocyte cells may be used as recipient cells for nuclear transfer.

Preferably, successful pig embryo cloning uses the metaphase II stage oocyte as the recipient oocyte because it is believed that at this stage of maturation the oocyte can be or is sufficiently activated to treat the introduced nucleus as if it were a fertilizing sperm. However, the present invention relates to any maturation stage of the oocyte which is suitable for carrying out somatic cell nuclear transfer, embryos, blastocysts, and/or transgenic pigs obtainable by the method of somatic cell nuclear transfer of the present invention.

The in vitro maturation of oocytes usually takes place in a maturation medium until the oocyte has reached the metaphase II stage or has extruded the first polar body. The time it takes for an immature oocyte to reach maturation is called the maturation period.

In a preferred embodiment of the present invention the oocyte is from sow or gilt, preferably from a sow.

The donor (somatic cell or nucleus of somatic cell) and recipient (cytoplast) involved in the cell nuclear transfer method according to the present invention is a pig. Likewise, reconstructed embryos may be implanted in a pig according to the present invention. The different pigs suitable as donor, recipient or foster mother are described elsewhere herein.

The donor pig according to the present invention may be female, or male. The age of the pig can be any age such as an adult, or for example a fetus.

Embryo

According to the present invention a reconstructed embryo (i.e. single cell embryo) contains the genetic material of the donor cell. Subsequently, the reconstructed embryo divides progressively into a multi-cell embryo after the onset of mitosis. In vitro the onset of mitosis is typically induced by activation as described herein.

In the present invention the term 'embryo' also refers to reconstructed embryos which are embryos formed after the process of nuclear transfer after the onset of mitosis by activation. Reconstructed embryos are cultured in vitro.

When the embryo contains about 12-16 cells, it is called a "morula". Subsequently, the embryo divides further and many cells are formed, and a fluid-filled cystic cavity within its center, blastocoele cavity. At this stage, the embryo is called a "blastocyst". The developmental stage of the "fertilized" oocyte at the time it is ready to implant; formed from the morula and consists of an inner cell mass, an internal cavity, and an outer layer of cells called trophectodermal cells.

The blastocyst according to the present invention may be implanted into the uterus of a host mammal, in particular a pig, preferably a Goettingen minipig and continues to grow into a fetus and then an animal.

In the methods provided herein for producing genetically modified or transgenic non-human mammal, for cloning a non-human mammal, for culturing a reconstructed embryo, and/or for cryopreservation of a pig embryo, the embryo may be cultured in vitro. The embryo may for example be cultured in sequential culture. It will be appreciated that the embryo may be a normal embryo, or a reconstructed embryo as defined elsewhere herein.

The present invention thus relates to a modified porcine embryo, blastocyst and/or fetus derived from the genetically modified pig model as disclosed herein and/or the modified porcine embryo comprises at least one modified human APP gene or part thereof and/or, human PS1 gene or part thereof and/or, porcine APP gene or part thereof and/or, porcine PS1 gene or part thereof and/or, APP gene or part thereof and at least one modified PS1 gene or part thereof and/or, human APP gene or part thereof comprising a Swedish mutation and/or, human APP gene or part thereof being the APPsw695 gene and/or, human PS1 gene or part thereof comprising a mutation encoding a PS1 protein harbouring a Pro117Leu mutation and/or, human APP gene or part thereof comprising a Swedish mutation and at least one modified PS1 gene or part thereof comprising a mutation encoding a PS1 protein harbouring a Pro117Leu mutation and/or, human APP gene or part thereof being the APPsw695 gene and at least one modified PS1 gene or part thereof comprising a mutation encoding a PS1 protein harbouring a Pro117Leu mutation.

It is appreciated that the modified porcine embryo, blastocyst and/or fetus derivable from the modified pig model for studying Alzheimer's disease, expressing at least one phenotype associated with Alzheimer's disease may have been the result of the crossing of for example a pig transgenic for at least one APP mutation and a pig transgenic for at least one PS1 mutation, in particular a pig comprising at least one human APP gene or part thereof being the APPsw695 gene and a pig comprising at least one modified PS1 gene or part thereof comprising a mutation encoding a PS1 protein harbouring a Pro117Leu mutation.

Cytoplast

An oocyte or a part of an oocyte from which the nucleus has been removed.

Donor Cell

By the term 'donor cell' of the present invention is meant somatic cell and/or cells derived from the germ line.

By the term 'somatic cell' of the present invention is meant any (body) cell from an animal at any stage of development. For example somatic cells may originate from fetal, neonatal or adult tissue. Especially preferred somatic cells are those of foetal or neonatal origin. However, cells from a germ line may also be used. According to the present invention a donor cell is a somatic cell. In another embodiment of the present invention the donor cell is a cell derived from a germ cell line.

In a preferred embodiment of the present invention the donor cell harbours desired genetic properties. However, the donor cell may harbour desired genetic properties which have been gained by genetic manipulation as described elsewhere herein.

Somatic cells are selected from the group consisting of epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells.

These may be obtained from different organs, e.g., skin, lung, pancreas, liver, stomach, intestine, heart, reproductive organs, bladder, kidney, urethra and other urinary organs.

The pigs from which the somatic cells may be derived are described elsewhere herein. A preferred embodiment of the invention is the use of somatic cells originating from the same species as the recipient oocyte (cytoplast).

Preferably, the somatic cells are fibroblast cells as the can be obtained from both developing fetuses, newborn piglets and adult animals in large quantities. Fibroblasts may furthermore be easily propagated in vitro. Most preferably, the somatic cells are in vitro cultured fibroblasts of foetal or neonatal origin.

In a preferred embodiment the somatic cells are modified. In yet a further preferred embodiment of the present invention the somatic cells are preferably of foetal or neonatal origin, or for example from adults.

One aspect of the present invention relates to A modified donor cell and/or cell nucleus derived from the modified pig model as disclosed herein and/or a modified donor cell and/or cell nucleus comprising at least one modified human APP gene or part thereof and/or, human PS1 gene or part thereof and/or, porcine APP gene or part thereof and/or, porcine PS1 gene or part thereof and/or, APP gene or part thereof and at least one modified PS1 gene or part thereof and/or, human APP gene or part thereof comprising a Swedish mutation and/or, human APP gene or part thereof being the APPsw695 gene and/or, human PS1 gene or part thereof comprising a mutation encoding a PS1 protein harbouring a Pro117Leu mutation and/or, human APP gene or part thereof comprising a Swedish mutation and at least one modified PS1 gene or part thereof comprising a mutation encoding a PS1 protein harbouring a Pro117Leu mutation and/or, human APP gene or part thereof being the APPsw695 gene and at least one modified PS1 gene or part thereof comprising a mutation encoding a PS1 protein harbouring a Pro117Leu mutation. It is appreciated that the modified donor cell may be any type of tissue as described elsewhere herein, however, the preferred donor cell is a porcine fibroblast cell.

It is appreciated that the modified porcine donor cell or cell nucleus derivable from the modified pig model for studying Alzheimer's disease, expressing at least one phenotype associated with Alzheimer's disease may have been the result of the crossing of for example a pig transgenic for at least one APP mutation and a pig transgenic for at least one PS1 mutation, in particular a pig comprising at least one human APP gene or part thereof being the APPsw695 gene and a pig comprising at least one modified PS1 gene or part thereof comprising a mutation encoding a PS1 protein harbouring a Pro117Leu mutation.

Type of Genetic Modification

The donor cells may be genetically modified by any of standard method known in the art. The genetic modification may be a modification of the genomic DNA by deletion, insertion, duplication and/or other forms of mutation, including point mutation. The modification may be made in coding sequences and/or non-coding sequences. DNA constructs for insertion may harbour a gene of interest and/or regulatory sequences such as promoters, insulators, enhancers, repressors or ribosomal entry sites. In some embodiments, only one genetic modification is introduced in the genome. In other embodiments, however, the genome may be modified at more than one site. Suitable techniques for genetic modification of mammalian cells, such as fibroblasts, include techniques such as gene addition by nonhomologous recombination, gene replacement by homologous recombination, and gene editing. This may include the use of retroviral insertion, transposon transfer and/or artificial chromosome techniques. Nonhomologous DNA recombination may e.g. be carried out as described in Kragh et al. (2004) Reprod. Fert. Dev. 16:290 or Kragh et al. (2004) Reprod. Fert. Dev. 16:315, Transposon-based gene transfer may be carried out as described in Izsvak et al. (1997) Cell 91:501. Gene replacement by homologous recombination may e.g. involve the techniques described by Urnow et al. (2005) Nature 435:646. Techniques for gene editing have been described in Andersen et al. (2002) J. Mol. Med. 80:770, Liu et al (2002) Gene Ther. 9:118 and Sørensen et al. (2005) J. Mol. Med. 83:39.

In a preferred embodiment the donor cell is genetically modified by random integration of the genes disclosed herein into the genome of the donor cell.

In another preferred embodiment of the present invention the donor cell is genetically modified (as described in a copending application).

The donor cell or nucleus carries a SB tagged genome containing a Flp recombination target site for site specific gene insertion or integration. The SB tagged genome result from the integration of a recombinant target vector comprising a DNA transposon construct and a bicistronic gene cassette comprising (i) a FRT recombination site and (ii) an IRES-driven selection gene. The DNA transposon construct may be any construct in which any DNA transposon is present. In the present invention the DNA transposon construct is the Sleeping Beauty (SB) DNA transposon vector. The FRT recombination site may be embedded in the coding sequence of a selection gene which allows for detecting whether a transposition has occurred. The selection gene of the present invention is not limited to any particular selection gene. In preferred embodiments the selection gene are genes conferring resistance to antibiotics or drugs, such as puromycin, tetracycline, streptomycin or hygromycin resistance genes, or the enhanced green fluorescent protein (eGFP) gene, red fluorescent protein genes or the like.

The FRT recombination site may thus be embedded in a SV40 promoter driven fusion variant of the selection gene. However, any promoter suitable for conferring expression of a selection gene may be used according to the present invention. Non-limiting examples of such promoters are CMV (cytomegalovirus) or PGK promoter.

The IRES-driven selection gene is similarly not limited to any particular selection gene. In preferred embodiments the selection gene are genes conferring resistance to antibiotics or drugs, such as puromycin, tetracycline, streptomycin or hygromycin resistance genes, or the enhanced green fluorescent protein (eGFP) gene, red fluorescent protein genes or the like.

The recombinant vector construct may also comprise at least one site for Cre recombinase. The at least one site for Cre recombinase may be located as disclosed in the examples herein.

The donor cell or nucleus may also originate from a genetically modified pig comprising at least one site for integration of at least one transgene. A preferred embodiment is a donor cell or nucleus in the form of a fibroblast, such as a primary fibroblast.

The present invention also relates to a method for producing a porcine cell comprising a SB tagged genome containing a Flp recombination target site for site-specific gene insertion. The method comprises the steps of a) providing a mammalian cell, b) transfecting the cell of a) with a plasmid expressing a transposase and a recombinant target vector comprising a DNA transposon construct and a bicistronic gene cassette comprising (i) a FRT recombination site and ii) an IRES-driven selection gene, c) selecting SB tagged cells.

As described elsewhere herein the mammalian cell may be any cell. In one embodiment in which the porcine cell is subsequently to be used for producing a genetically modified pig by nuclear transfer according to the hand-made protocol as described herein, the porcine cell is in a preferred embodiment a fibroblast and most preferred a porcine primary fibroblast.

It is appreciated that a desired transgene may be integrated directly into the at least one site for integration present in the genome of the cell. However, the cell in which the genome carries the at least one site for integration is in another embodiment used as a donor cell for the production of a genetically modified pig by for example microinjection of the donor cell or nucleus thereof into a oocyte or by for example somatic nuclear transfer. In a preferred embodiment the donor cell or the nucleus thereof is used for the production of a genetically modified pig by somatic nuclear transfer using the procedure as described elsewhere herein.

The transgene or gene of interest to be integrated in the targeted cells of the present invention is not limited to any particular gene. In one embodiment the gene to be integrated is a disease-causing gene which results in the formation of a genetically modified pig displaying a phenotype of interest. According to the present invention the gene of interest to be integrated into the porcine cell is the human APP or part thereof, or porcine APP or part thereof, or human PS1 or part thereof, or porcine PS1 or part thereof, modified variants thereof. As described elsewhere herein the combination of said APP and PS1 is also within the scope of the present invention.

The integration of the transgene into the at least one site for integration present in the genome of the cell is employed by transfection into the cell of plasmid DNA containing the gene of interest and also FRT sites, and a plasmid expressing the Flp-recombinase used to support integration at the FRT sites.

Enucleation

The method of enucleation of an oocyte may be selected from the group of methods consisting of aspiration, physical removal, use of DNA-specific fluorochromes, exposure to ultraviolet light and/or chemically assisted enucleation. In one embodiment the present invention relates to the use of DNA-specific fluorochromes. Enucleation may, however, be performed by exposure with ultraviolet light. In a particular embodiment enucleation is chemically assisted prior to physical removal of the nucleus. Chemically assisted enucleation using for example antineoplastic agents, such as demecolcine (N-deacetyl-N-methyl 1 colchicine), and/or for example etoposide or related agents may be performed prior to enzymatic modification of zona pellucida.

Chemically assisted enucleation comprises culturing matured COCs in maturation medium as described elsewhere herein supplemented with demecolcine for a particular period of time. In the range of 0.1 μg/ml to 10 μg/ml demecolcine, such as 0.2 μg/ml to 10 μg/ml, for example 0.3 μg/ml to 10 μg/ml, such as 0.25 μg/ml to 5 μg/ml, for example 0.3 μg/ml to 1 μg/ml, such as 0.25 μg/ml to 0.5 μg/ml, for example 0.4 μg/ml demecolcin may be supplemented to the maturation medium. Similarly, maturation medium may be supplemented with etoposide for example in the range of 0.1 μg/ml to 10 μg/ml etoposide, such as 0.2 μg/ml to 10 μg/ml, for example 0.3 μg/ml to 10 μg/ml, such as 0.25 μg/ml to 5 μg/ml, for example 0.3 μg/ml to 1 μg/ml, such as 0.25 μg/ml to 0.5 μg/ml, for example 0.4 μg/ml etoposide may be supplemented to the maturation medium. The time for culturing the COCs in the presence of antineoplastic agents ranges from 10 min to 5 hrs, such as 30 minutes to 5 hrs, for example 10 minutes to 2 hrs, such as 30 min to 2 hrs, for example 10 min to 1.5 hrs, such as 20 min to 3 hrs, for example 10 min to 3 hrs, such as 30 min to 1.5 hrs, for example 45 min.

In a particular embodiment chemically assisted enucleation is performed using 0.45 μg/ml demecolcine and/or etoposide added to the maturation medium for 45 min.

In a particular embodiment it is preferred that the enucleation is by physical removal of the nucleus. The physical removal may be by separation for example by bisection of the oocyte into two halves (two parts), one which contains the nucleus and the enucleated oocyte half, known as the cytoplast, removing the nucleated half of the oocyte and selecting the resulting cytoplast for further procedures of the invention. Alternatively the separation is by trisection, resulting in three parts of which two parts are cytoplasts. In another embodiment the oocyte may be separated into four parts, resulting in the production of three cytoplasts. The oocyte may even be separated into five parts by physical removal, resulting in four cytoplasts. Similarly, the oocyte may be separated into six parts, for example seven parts, such as eight parts, for example nine parts, such as ten or more parts.

The physical separation of the oocyte and subsequent removal of the nucleus-bearing part of the oocyte may be achieved by the use of a microsurgical blade.

The oocytes may be screened to identify which oocytes have been successfully enucleated. Oocyte parts that harbour nuclear DNA may be identified by staining with Hoechst flourochrome, the staining procedure of which is known to a person skilled in the art. Oocyte parts harbouring nuclear DNA are discarded and the enucleated oocytes (cytoplasts) are selected for further procedures.

Zona Pellucida

Zona pellucida is a thick, transparent, noncellular layer or envelope of uniform thickness surrounding an oocyte Generally, an intact zona pellucida is considered to be important in cell nuclear transfer due to a number of parameters. One parameter is to keep the polar body close to the metaphase plate of the oocyte in order to indicate the appropriate site for enucleation. Another parameter relates to the keeping of the donor cell close to the oocyte cytoplast before and during fusion. The zona is also believed to confer protection for the donor cell and cytoplast during fusion. Finally, embryo development after reconstitution and activation is believed to be supported by the zona pellucida.

Modification of at least a part of the zona pellucida can be performed by a number of methods. For example physical manipulation can be used to modify the zona. But also chemical treatment with agents such as acidic solutions (acidic Tyrode) can be employed. One example of chemical agents that can be employed in the present invention is acidic solutions, for example Tyrode. In a particular embodiment of the invention the zona pellucida is modified by enzymatic digestion. Such enzymatic digestion may be performed by enzymes comprising for example trypsin. Alternatively a specific protease may be used, such as pronase.

In a preferred embodiment the enzymatic digestion results in at least a partial digestion of a part of zona pellucida which in a preferred embodiment of the present invention means that at least a part of the zona pellucida is being removed, or that the zona pellucida is partly removed. In the present context the zona pellucida is not completely removed.

According to an especially preferred embodiment of the present invention the partially digested part of zona pellucida is characterized by the zona pellucida still being visible and by the fact that the oocyte has not become misshaped.

The partial digestion may be achieved by exposure to a protease. In another embodiment of the present invention the partial digestion may be accomplished by the use of a pronase. In yet another embodiment the partial digestion may be achieved by a combination of a protease and pronase.

In a preferred embodiment the concentration of pronase is in the range of 0.1 mg/ml to 10 mg/ml, such as 0.5 mg/ml to 10 mg/ml, for example 1 mg/ml to 10 mg/ml, such as 1.5 mg/ml to 10 mg/ml, for example 2 mg/ml to 10 mg/ml, such as 2.5 mg/ml to 10 mg/ml, for example 2.75 mg/ml to 10 mg/ml, such as 3 mg/ml to 10 mg/ml, for example 3.25 mg/ml to 10 mg/ml, such as 3.3 mg/ml to 10 mg/ml, for example 3.5 mg/ml to 10 mg/ml.

A preferred embodiment is a pronase concentration in the range of 2 mg/ml to 5 mg/ml, such as 2.25 mg/ml to 5 mg/ml, for example 2.5 mg/ml to 5 mg/ml, such as 2.75 mg/ml to 5 mg/ml, for example 2.8 mg/ml to 5 mg/ml, such as 2.9 mg/ml to 5 mg/ml, for example 3 mg/ml to 5 mg/ml, such as 3.1 mg/ml to 5 mg/ml, for example 3.2 mg/ml to 5 mg/ml, such as 3.3 mg/ml to 5 mg/ml.

A particular embodiment of the present invention is a pronase concentration in the range of 1 mg/ml to 4 mg/ml, for example 1 mg/ml to 3.9 mg/ml, such as 1 mg/ml to 3.8 mg/ml, for example 1 mg/ml to 3.7 mg/ml, such as 1 mg/ml to 3.6 mg/ml, for example 1 mg/ml to 3.5 mg/ml such as 1 mg/ml to 3.4 mg/ml, for example 1 mg/ml to 3.3 mg/ml.

In a preferred embodiment the pronase concentration is in the range of 2.5 mg/ml to 3.5 mg/ml, such as 2.75 mg/ml to 3.5 mg/ml, for example 3 mg/ml to 3.5 mg/ml. In a special embodiment the pronase concentration is 3.3 mg/ml.

It is clear to the skilled person that the pronase should be dissolved in an appropriate medium, one preferred medium according to the present invention is T33 (Hepes buffered TCM 199 medium containing 33% cattle serum (as described earlier—Vajta, et al., 2003).

The time of incubation of the oocyte in the pronase solution is in the range of 1 second to 30 seconds, such as 2 seconds to 30 seconds, for example 3 seconds to 30 seconds, such as 4 seconds to 30 seconds, such as 5 seconds to 30 seconds.

In another embodiment of the present invention the incubation time is in the range of 2 seconds to 15 seconds, such as 2 seconds to 14 seconds, for example 2 seconds to 13 seconds, such as 2 seconds to 12 seconds, for example 2 seconds to 11 seconds, such as 2 seconds to 10 seconds, for example 2 seconds to 9 seconds, such as 2 seconds to 8 seconds, for example 2 seconds to 7 seconds, such as 2 seconds to 6 seconds, for example 2 seconds to 5 seconds.

In a particular embodiment of the present invention the incubation time is in the range of 3 seconds to 10 seconds, such as 3 seconds to 9 seconds, for example 4 seconds to 10 seconds, such as 3 seconds to 8 seconds, for example 4 seconds to 9 seconds, such as 3 seconds to 7 seconds, for example 4 seconds to 8 seconds, such as 3 seconds to 6 seconds, for example 4 seconds to 7 seconds, such as 3 seconds to 5 seconds, for example 4 seconds to 6 seconds, such as 4 seconds to 5 seconds. An especially preferred incubation time is 5 seconds.

In a preferred embodiment of the present invention the oocyte is treated for 5 seconds in a 3.3 mg/ml pronase solution at 39° C.

Reconstructed Embryo

By the term 'reconstructed embryo' is meant the cell which is formed by insertion of the donor cell or nucleus of the donor cell into the enucleated oocyte which corresponds to a zygote (during normal fertilization). However, the term 'reconstructed embryo' is also referred to as the 'reconstituted cell'. In the present invention the donor cell is a somatic cell. However, the donor cell may also be derived from a germ line cell.

Fusion

The transfer of a donor cell or a membrane surrounded nucleus from a donor cell to at least cytoplast is according to the present invention performed by fusion. In the scenarios described below the term 'donor cell' also refers to a membrane surrounded nucleus from a donor cell. Fusion may be achieved by a number of methods.

Fusion may be between a donor cell and at least one cytoplast, such as between a donor cell and at least two cytoplasts, for example between a donor cell and at least two cytoplasts, such as between a donor cell and at least three cytoplasts, such as between a donor cell and at least four cytoplasts, for example between a donor cell and at least five cytoplasts, such as between a donor cell and at least six cytoplasts, for example between a donor cell and at least seven cytoplasts, such as between a donor cell and at least eight cytoplasts.

Fusion may be performed according to the listed combinations above simultaneously or sequentially. In one embodiment of the present invention the fusion is performed simultaneously. In another embodiment fusion of the at least one cytoplast and a donor cell is performed sequentially.

For example fusion may be achieved by chemical fusion, wherein a donor cell and the at least one cytoplast are exposed to fusion promoting agents such as for example proteins, glycoproteins, or carbohydrates, or a combination thereof. A variety of fusion-promoting agents are known for example, polyethylene glycol (PEG), trypsin, dimethylsulfoxide (DMSO), lectins, agglutinin, viruses, and Sendai virus. Preferably phytohemaglutinin (PHA) is used. However mannitol and, or polyvinylalcohol may be used.

Alternatively, fusion may be accomplished by induction with a direct current (DC) across the fusion plane. Often an alternating current (AC) is employed to align the donor and recipient cell. Electrofusion produces a sufficiently high pulse of electricity which is transiently able to break down the membranes of the cytoplast and the donor cell and to reform the membranes subsequently. As a result small channels will open between the donor cell and the recipient cell. In cases where the membranes of the donor cell and the recipient cell connect the small channels will gradually increase and eventually the two cells will fuse to one cell.

Alignment of the at least one cytoplast and the donor cell may be performed using alternating current in the range of 0.06 to 0.5 KV/cm, such as 0.1 to 0.4 KV/cm, for example 0.15 to 0.3 KV/cm. In a preferred embodiment alignment of the at least one cytoplast and the donor cell may be performed using alternating current at 0.2 KV/cm.

Fusion may be induced by the application of direct current across the fusion plane of the at least one cytoplast and the donor cell. Direct current in the range of 0.5 to 5 KV/cm, such as 0.75 to 5 KV/cm, for example 1 to 5 KV/cm, such as 1.5 to 5 KV/cm, for example 2 to 5 KV/cm. Another preferred embodiment of the present invention is the application of direct current in the range of 0.5 to 2 KV/cm. In a further preferred embodiment the direct current may be 2 KV/cm.

The direct current may preferably be applied for in the range of 1-15 micro seconds, such as 5 to 15 micro seconds, for example 5 to 10 micro seconds. A particular embodiment may be 9 micro seconds.

In an especially preferred embodiment fusion with direct current may be using a direct current of 2 KV/cm for 9 micro seconds.

Electrofusion and chemical fusion may however be also be combined.

Typically electrofusion is performed in fusion chambers as known to the skilled person.

Fusion may be performed in at least one step, such as in two steps, for example three steps, such as in four steps, for example in five steps, such as six steps, for example seven steps, such as in eight steps.

Fusion may be performed in for example a first step wherein the at least one cytoplast is fused to the donor cell. A second step of fusion may comprise fusion of the fused pair (cytoplast-donor cell, reconstructed embryo) with at least one cytoplast, such as at least two cytoplasts, for example three cytoplasts, such as four cytoplasts, for example five cytoplasts, such as six cytoplasts, for example seven cytoplasts, such as eight cytoplasts. The second step of fusion with fusion of at least one cytoplast and the fused pair may be performed sequentially or simultaneously. In one embodiment the at least two cytoplasts are fused to the fused pair simultaneously. In another embodiment the at least two cytoplasts are fused to the fused pair sequentially.

In one embodiment of the invention the second step of fusion may also be an activation step wherein the reconstructed embryo is activated to enter mitosis. As described elsewhere herein.

Activation

In a preferred embodiment the reconstructed embryo may be allowed to rest prior to activation for a period of time in order to allow for the nucleus of the donor cell to reset its genome and gain toti potency in the novel surroundings of the enucleated cytoplast. The reconstructed embryo may for example rest for one hour prior to activation.

Preferably, the reconstructed embryo may be activated in order to induce mitosis. Methods for activation may preferably be selected from the group of consisting of electric pulse, chemically induced shock, increasing intracellular levels of divalent cations and reducing phosphorylation. A combination of methods may be preferred for activation.

In one particular embodiment of the invention the activation and the second step of fusion may be performed simultaneously. However, the activation of the reconstituted embryo and the at least one additional step of fusion between the reconstructed embryo and the at least one cytoplast may be performed sequentially.

Reducing the phosphorylation of cellular proteins in the reconstructed embryo by known methods such as for example by the addition of kinase inhibitors may activate the reconstituted embryo. A preferred embodiment may involve the use of agents that inhibit protein synthesis, for example cycloheximide. A further preferred embodiment may be using agents that inhibit spindle body formation, for example cytochalasin B.

In one embodiment of the invention the intracellular levels of divalent cations may be increased. Divalent cations such as for example calcium may be in comprised in the activation medium. Preferably, the cations may enter the reconstructed embryo, particularly upon subjecting the reconstructed embryo to an electric pulse. In a preferred embodiment the electric pulse may cause entering of calcium into the reconstructed embryo.

The application of an electrical pulse using direct current may be an activation step. However, in a preferred embodiment the electrical pulse applied for activation may also serve as an additional fusion step.

Prior to applying an electrical pulse using direct current the at least one cytoplast and the at least one reconstructed embryo may be aligned by the application of alternating current. The alternating current may be in the range of the range of 0.06 to 0.5 KV/cm, such as 0.1 to 0.4 KV/cm, for example 0.15 to 0.3 KV/cm. In a preferred embodiment alignment of the at least one cytoplast and the donor cell may be performed using alternating current at 0.2 KV/cm.

Activation may be induced by the application of direct current across the fusion plane of the at least one cytoplast and the donor cell. Direct current in the range of 0.2 to 5 KV/cm, such as 0.4 to 5 KV/cm, for example 0.5 to 5 KV/cm. Another preferred embodiment of the present invention is the application of direct current in the range of 0.5 to 2 KV/cm. In a further preferred embodiment the direct current may be 0.7 KV/cm.

The direct current may preferably be applied for in the range of 10 to 200 micro seconds, such as 25 to 150 micro seconds, for example 50 to 100 micro seconds. A particular embodiment may be 80 micro seconds.

In an especially preferred embodiment fusion with direct current may be using a direct current of 0.7 KV/cm for 80 micro seconds.

An especially preferred embodiment of activation according to the present invention may be use of an electrical pulse in combination with subjecting the reconstructed embryo to agents that inhibit protein synthesis, spindle body formation, and divalent cations.

Activation may be performed by any combination of the methods described above.

In Vitro Culture of Embryos

One aspect of the invention relates to a method of in vitro culturing embryos, whereby the blastocyst rate increased to 25.3%. Thus, a method of culturing a reconstructed embryo is within the scope of the present invention, comprising the steps of a) establishing at least one oocyte having at least a part of zona pellucida, b) separating the oocyte into at least two parts obtaining an oocyte having a nucleus and at least one cytoplast, c) establishing a donor cell or cell nucleus having desired genetic properties, d) fusing at least one cytoplast with the donor cell or membrane surrounded cell nucleus, e) obtaining the reconstructed embryo, f) activating the reconstructed embryo to form an embryo, and e) culturing said embryo.

Another aspect of the invention relates to a method of cell nuclear transfer in which a step of culturing the embryo is included.

In a preferred embodiment in relation to the methods described herein embryos are cultured in vitro in a sequential set of media. Preferably the blastocysts are grown in traditional medium such as for example NCSU37 or equivalent medium as known to a person skilled in the art, wherein glucose is removed and substituted by other agents. One agent may be pyruvate. Another agent may be lactate. The agents may also be combined and replace glucose in the traditional medium.

The embryos may be cultured in the substituted media as described above from Day 0 to Day 3, such as from Day 0 to Day 2.

The pyruvate concentration may range from 0.05 to 1 mM, such as 0.1 to 1 mM, for example 0.125 to 1 mM, such as 0.15 to 1 mM. However the concentration of sodium pyruvate may also range from 0.05 mM to 0.9 mM, such as 0.05 to 0.8 mM, for example 0.05 to 0.7 mM, such as 0.05 to 0.6 mM, for example 0.05 to 0.5 mM, such as 0.05 to 0.4 mM, for example 0.05 to 0.3 mM, such as 0.05 to 0.2 mM. Preferably the concentration ranges between 0.05 to 0.17 mM. A preferred concentration of sodium pyruvate is 0.17 mM.

The lactate concentration may range from 0.5 to 10 mM, such as 0.75 to 10 mM, for example 1 to 10 mM, such as 1.5 to 10 mM, such as 1.75 to 10 mM, for example 2 to 10 mM, such as 2.5 to 10 mM. However the concentration of sodium lactate may also range from 0.5 mM to 9 mM, such as 0.5 to 8 mM, for example 0.5 to 7 mM, such as 0.5 to 6 mM, for example 0.5 to 5 mM, such as 0.5 to 4 mM, for example 0.5 to 03 mM. Preferably the concentration ranges between 1 to 5 mM, such as 2 to 4 mM, for example 2 to 3 mM. A preferred concentration of sodium lactate is 2.73 mM.

After the initial glucose-free incubation medium glucose is again replacing the pyruvate and lactate. The embryos may be cultured in the glucose containing medium from Day 4 to Day 3, preferably from Day 3 to Day 7. The glucose concentration may range from 1 to 10 mM, such as 2 to 10 mM, for example 3 to 10 mM, such as 4 to 10 mM, for example 5 to 10 mM. However, the glucose concentration may also range from 1 to 9 mM, such as 2 to 8 mM, for example 3 to 7 mM, such as 4-6 mM. A preferred concentration of glucose according to the present invention is 5.5 mM of glucose.

Organ or Tissue Donation

In one embodiment, the animals of the invention may be used as a source for organ or tissue donation for humans or other animals, either animals of the same species or animal of other species. Transfer between species is usually termed xenotransplantation. Entire organs that may be transplanted include the heart, kidney, liver, pancreas or lung. Alternatively, parts of organs, such as specific organ tissues may be transplanted or transferred to humans or other animals. In a yet further embodiment, an individual cell or a population of individual cells from an animal of the invention may be transferred to a human being or another animal for therapeutic purposes.

Cryopreservation

The term 'cryopreserving' as used herein can refer to vitrification of an oocyte, cytoplast, a cell, embryo, or pig of the invention. The temperatures employed for cryopreservation is preferably lower than −80 degree C., and more preferably at temperatures lower than −196 degree C. Oocytes, cells and embryos of the invention can be cryopreserved for an indefinite amount of time. It is known that biological materials can be cryopreserved for more than fifty years.

It is within the scope of the present invention that embryos may be cryopreserved prior to transfer to a host pig when employing methods for producing a genetically engineered or transgenic non-human mammal. Such cryopreservation prior to transfer may be at the blastocyst stage the of embryo development. Vitrification is a form of cryopreservation where living cells are rapidly cooled so that the fluid of the cell does not form into ice. Thus, vitrification relates to the process of cooling where cells or whole tissues are preserved by cooling to low sub-zero temperatures, such as (typically) −80° C. or −196° C.

In particular the invention relates to the vitrification of an oocyte, however, the invention also relates to the vitrification of embryos, preferably embryos at the blastocyst stage. I one embodiment, the embryo is cultured to blastocyst stage prior to vitrification. Especially pig embryos are covered by the present invention. Also vitrified cytoplasts are covered by the present invention, as are cells.

Yet another aspect of the invention relates to the cryopreservation of a pig embryo derived by a method for cell nuclear transfer as described herein comprising a step of vitrifying a pig embryo. A further aspect of the invention relates to pig embryos obtained, or obtainable by the methods provided herein.

Mitochondria

Cells of the tissue of the modified non-human mammals and/or non-human embryos obtainable by the present invention may harbour mitochondria of different maternal sources. In a preferred embodiment the non-human mammals and/or non-human embryos may harbour mitochondria from only one maternal source. However, in another preferred embodiment the non-human mammals and/or non-human embryos may harbour mitochondria from at least two maternal sources, such as three maternal sources, for example four maternal sources, such as five maternal sources, for example six maternal sources, such as seven maternal sources, for example eight maternal sources, such as nine maternal sources, for example ten maternal sources. The probability of having a specific number of maternal sources can be calculated based on the observed types of mitochondria.

Evaluation of Treatment

At present no cure exists for Alzheimer's disease and the interest in being able to identify and test whether a drug or treatment is suitable for treatment of Alzheimer's disease is significant.

The present invention offers a method for screening the efficacy of a pharmaceutical composition, wherein the method comprises the steps of i) providing the pig model of the present invention, ii) expressing in said pig model the genetic determinant and exerting said phenotype for said disease, iii) administering to the pig model a pharmaceutical composition the efficacy of which is to be evaluated, and iv) evaluating the effect, if any, of the pharmaceutical composition on the phenotype exerted by the genetic determinant when expressed in the pig model.

Furthermore, within the scope of the present invention is a method for evaluating the response of a therapeutical treatment of Alzheimer's disease, wherein the method comprises the steps of i) providing the pig model of the present invention, ii) treating said pig model with a pharmaceutical composition exerting an effect on said phenotype, and iii) evaluating the effect observed. Based on the evaluation one could further advise on the treatment based on the observed effects.

In addition, the present invention relates to a method for treatment of a human being suffering from Alzheimer's disease, wherein the method comprises the initial steps of i) providing the pig model of the present invention, ii) expressing in said pig model said genetic determinant and exerting said phenotype for said disease, iii) administering to said pig model a pharmaceutical composition the efficacy of which is to be evaluated, and v) evaluating the effect observed, and v) treating said human being suffering from Alzheimer's disease based on the effects observed in the pig model.

EXAMPLES

Example 1

Production of APPsw Transgenic Pigs

1. Cloning of Constructs

Example of a transgene that could be used to produce a modified pig as a disease model for Alzheimers are the human or porcine APP genes and/or the porcine or the human PS1 gene.

A donor cell comprising APP695sw was produced in which a cDNA minigene was constructed of the neuron specific splice variant of the human amyloid precursor protein gene, APP695, which lacks exons 7 and 8 of the 19 exons of the APP gene (Neve et al. Neuron 1988; Tanzi et al. Brain Res Mol Brain Res 1993; Selkoe Rev Neurosci 1994) and including the so-called Swedish mutation (APP695sw). This mutation causes autosomal dominant Alzheimer's disease (Mullan et al. Nature 1992). The APPsw is herein also referred to as APP LysMet670/671AsnLeu.

In short, an artificial 5'-UTR was inserted in front of the APP695sw open reading frame, and it consists of a fragment that includes b-globin exon 1, intron 1, and exon 2 sequences. This UTR was introduced to facilitate splicing of the derived APP695sw transcript. A human platelet-derived growth factor (PDGF)-b promoter fragment of 1 kb was subsequently fused to the b-globin sequences. The PDGF-b promoter targets expression preferentially to the cortex, hippocampus, hypothalamus and cerebellum of transgenic animals (Sasahara et al. Cell 1991) and has been shown to drive hAPP minigene expression in brain tissue of transgenic mice (Games et al. Nature 1995, Rockenstein et al. JBC 1995). The PDGF-b promoter is active also in fibroblasts and, accordingly, we have shown that it can drive expression of the eGFP and the APP695sw genes in Göttingen minipig fibrobasts (data not shown and data shown below). After transfection of the donor cells (74114) and geneticin selection 15 cell colonies, well defined and widely spaced, were isolated and grown to 80% in 25 cm2 flasks for storage at −135° C. (⅔ of the cells) and total RNA isolation (⅓ of the cells). cDNA was produced and tested for transgene expression using one primer that requires the splicing of the b-globin sequences fo the transgene and a primer located in the APP sequences. Four of the 15 cell colonies clearly showed transgene expression, and one of them, Trans35 clone 2, was selected for HMC.

For construction of vectors was as a plasmid background used the pEGFP-N1plasmid (Clontech) which contains an expression cassette including the CMV promoter regulated EGFP gene and a SV40 promoter regulated neomycin resistance gene and an SV40 polyadenylation signal. The cassette is flanked by an Ase 1 site 5' and a Not 1 site 3' which does not include the SV40 polyadenylation site. The cassette was removed step-by-step and substituted by our construct consisting of 5' human PDGF β promoter fragment—β globing gene fragment—APP or PS1-SV40 polyadenylation signal—3'. The DNA sequences are included.

The human PDGF promoter fragment was PCR amplified from the human genome as a 1 kb Ase 1-Sal 1 fragment. The pEGFP-N1 CMV promoter was excised by AseI/BglII and instead a 1 kb fragment of the human PDGFb promoter was inserted. The PDGFb promoter fragment was generated by PCR (forward: 5'-GGGATTAATGATCCACAGTCTCCTGAGTAGCTG-3'; reverse: 5'-GGGAGATCTGGGAGGCAGGCAGGCCGCTC-3') on human genomic DNA. The PDGFb promoter fragment includes 27 bp of the 5'-UTR lacking ATG codons. Downstream of the PDGFb promoter fragment was in the XhoI site inserted the b-globin intron II with flanking exon sequences as a SalI/XhoI fragment. The b-globin sequence was amplified by PCR (forward: 5'-GGGGTCGACGATCCTGACAACTTCAGGGTG-3'; reverse: 5'-GGGCTCGAGGCCCTATAGTGAGTCGTATTAC-3') using the vector pSG5 as template. The Sal 1-Xho 1 β-globin fragment from the pSG5 plasmid was ligated to the promoter fragment and the polylinker from pEGFP-N1.

The transgene human or procine APP or variant thereof, or human or porcine PS1) was subsequently ligated as a Hind III-Not 1 fragment to the polylinker and the Not 1 site of the vector thereby using the SV40 polyadenylation signal of pEGFP-N1.

Thus, for construction of the APPsw expression vector, pPDGFbgAPPsw, the EGFP gene was excised from pPDGFbgEGFP by HindIII/NotI. The open reading frame of APP695sw was amplified by PCR (forward:5'-GGGGTCGACAAGCTTGCCACCATGCTGCCCGGTTTGGCACTG-3'; reverse:5'-GGGGTCGACGCGGCCGCCTAGTTCTGCATCTGCTCAAAG-3') using pcDNA3APPsw as template (obtained from Dr. P. Fraser). The PCR fragment cloned into the HindIII/NotI sites. The forward primer sequence includes a consensus Kozak motif for translational initiation in front of the ATG codon.

The PDGF-APP Sequence is as Follows attaatgatccacagtctcctgagtagctgggactacaggagcttgttaccacacccagctccagtttataaattcatctcca gtttataaaggaggaaaccgaggtactgagaggttaaaaaaccttcctgcagacacttgtccagcaagtggccactcca ggatttggaccaaggtgatgtgtcttcaggctgtgtctctgccactgtgccacgctgctgggtggtaggcagcagtgggtgg gtgcctgcagtggtctgtaaagaccacctgagatgtccttcctcctctgttccaccctgtccaggtccaagaagacagtctat gaagagagagcaggtgtgactctctcagtgtgctcctctgtgagaagcaggctgacatcccaaagggaagggcggata acagagacagtgcaagcggaggagatgagggtgcctcaaagccgggaggctgggtgatgcaggagcctgcgtgtcc cgaggggggtgctgggcccagtgtgagtacgtgtgactgtgactgagacagtgtgactgctgaaggcagggacacagc agctccctgactgggggcagaaggcgttaactgtgtgaaggctggttgtgggtgggtgggctctgggcctcgaacccgg gggctgagggagatagtaaacagcagggtgactgacgggaagatcatgttggtagccctgcgaagatgctgcagggc tgtgggggtttgtgtgactttgcagttcaacaaattcaaattcagccaacgctggcagggcctgttgtgccaggcaaccag ctaggaggaggagactcggacccagcttgcagctgaagggcgctggctgccgggttctgtgggttcaccttgcggtgtctt cccttgctaacactgagtccttacaatagccccatctccaggttgaggctagatggaggggacagagggaagtgacttgc ccaaggtgacccaagctcccgagtgccagggcaggatctgaattcaggctctcagactgcagagcctgagtccctccct gccatgcctgtgccagggtggaaatgtctggtcctggaggggagcgtggactcctggccttggctctggagacatccccc tagaccacgtgggctcctaacctgtccatggtcactgtgctgaggggcgggacggtgggtcacccctagttctttttcccca gggccagattcatggactgaagggttgctcggctctcagagacccccctaagcgccccgccctggccccaagccctccc ccagctcccgcgtcccccccctcctggcgctgactccgggccagaagaggaaaggctgtctccacccacctctcgcact ctcccttctcctttataaaggccggaacagctgaaagggtggcaacttctcctcctgcagccgggagcggcctgcctgcct cccgtcgacgatcctgagaacttcagggtgagtttggggacccttgattgttctttctttttcgctattgtaaaattcatgttatatg gaggggcaaagttttcagggtgttgtttagaatgggaagatgtcccttgtatcaccatggaccctcatgataattttgtttcttt cactttctactctgttgacaaccattgtctcctcttattttcttttcattttctgtaacttttcgttaaactttagcttgcatttgtaacgaa tttttaaattcacttttgtttatttgtcagattgtaagtactttctctaatcactttttttttcaaggcaatcagggtatattatattgtacttc agcacagttttagagaacaattgttataattaaatgataaggtagaatatttctgcatataaattctggctggcgtggaaatat tcttattggtagaaacaactacatcctggtcatcatcctgcctttctctttatggttacaatgatatacactgtttgagatgaggat aaaatactctgagtccaaaccgggcccctctgctaaccatgttcatgccttcttctttttcctacagctcctgggcaacgtgct ggttattgtgctgtctcatcattttggcaaagaattgtaatacgactcactatagggcaagcttatgctgcccggtttggcactg ctcctgctggccgcctggacggctcgggcgctggaggtacccactgatggtaatgctggcctgctggctgaaccccagat tgccatgttctgtggcagactgaacatgcacatgaatgtccagaatgggaagtgggattcagatccatcagggaccaaa acctgcattgataccaaggaaggcatcctgcagtattgccaagaagtctaccctgaactgcagatcaccaatgtggtaga agccaaccaaccagtgaccatccagaactggtgcaagcggggccgcaagcagtgcaagacccatccccactttgtga ttccctaccgctgcttagttggtgagtttgtaagtgatgcccttctcgttcctgacaagtgcaaattcttacaccaggagaggat ggatgtttgcgaaactcatcttcactggcacaccgtcgccaaagagacatgcagtgagaagagtaccaacttgcatgact acggcatgttgctgccctgcggaattgacaagttccgaggggtagagtttgtgtgttgcccactggctgaagaaagtgaca atgtggattctgctgatgcggaggaggatgactcggatgtctggtggggcggagcagacacagactatgcagatggga gtgaagacaaagtagtagaagtagcagaggaggaagaagtggctgaggtggaagaagaagaagccgatgatgac gaggacgatgaggatggtgatgaggtagaggaagaggctgaggaaccctacgaagaagccacagagagaaccac cagcattgccaccaccaccaccaccaccacagagtctgtggaagaggtggttcgagaggtgtgctctgaacaagccg agacggggccgtgccgagcaatgatctcccgctggtactttgatgtgactgaagggaagtgtgccccattcttttacggcg gatgtggcggcaaccggaacaactttgacacagaagagtactgcatggccgtgtgtggcagcgccatgtcccaaagttt actcaagactacccaggaacctcttgcccgagatcctgttaaacttcctacaacagcagccagtacccctgatgccgttg -continued

```
acaagtatctcgagacacctggggatgagaatgaacatgcccatttccagaaagccaaagagaggcttgaggccaag

caccgagagagaatgtcccaggtcatgagagaatgggaagaggcagaacgtcaagcaaagaacttgcctaaagctg

ataagaaggcagttatccagcatttccaggagaaagtggaatctttggaacaggaagcagccaacgagagacagca

gctggtggagacacacatggccagagtggaagccatgctcaatgaccgccgccgcctggccctggagaactacatca

ccgctctgcaggctgttcctcctcggcctcgtcacgtgttcaatatgctaaagaagtatgtccgcgcagaacagaaggac

agacagcacaccctaaagcatttcgagcatgtgcgcatggtggatcccaagaaagccgctcagatccggtcccaggtt

atgacacacctccgtgtgatttatgagcgcatgaatcagtctctctccctgctctacaacgtgcctgcagtggccgaggag

attcaggatgaagttgatgagctgcttcagaaagagcaaaactattcagatgacgtcttggccaacatgattagtgaacc

aaggatcagttacggaaacgatgctctcatgccatctttgaccgaaacgaaaaccaccgtggagctccttcccgtgaatg

gagagttcagcctggacgatctccagccgtggcattcttttggggctgactctgtgccagccaacacagaaaacgaagtt

gagcctgttgatgcccgccctgctgccgaccgaggactgaccactcgaccaggttctgggttgacaaatatcaagacgg

aggagatctctgaagtgaagatggatgcagaattccgacatgactcaggatatgaagttcatcatcaaaaattggtgttctt

tgcagaagatgtgggttcaaacaaaggtgcaatcattggactcatggtgggcggtgttgtcatagcgacagtgatcgtcat

caccttggtgatgctgaagaagaaacagtacacatccattcatcatggtgtggtggaggttgacgccgctgtcaccccag

aggagcgccacctgtccaagatgcagcagaacggctacgaaaatccaacctacaagttctttgagcagatgcagaact

aggcggccgcaacttgtttattgcagcttataatggttacaaataaagcaatagcatcacaaatttcacaaataaagcatttt

tttcactgcattctagttgtggtttgtccaaactcatcaatgtatcttatcatgtctg
```

Similarly, for construction of the PS1(Pro117Leu) (expression vector, pPDGFbg$_{PS1(P117L)}$, the EGFP gene was excised from pPDGFbgEGFP by HindIII/NotI. The open reading frame of S1 (Pro117Leu (P117L)) was amplified by PCR (forward PS1fSal1Hind3:5'-GGGGTC GAC AAG CTT GCC ACC ATG ACA GAG TTA CCT GCA C-3'; reverse PS1 r Sal 1 Not1:5'-GGG GTC GAC GCG GCC GCC TAG ATA TAA AAT TGA TGG AAT G-3') using pcDNA3PS1 human as template (obtained from Dr. P. Fraser). The forward primer sequence includes a consensus Kozak motif for translational initiation in front of the ATG codon as described for the pPDGFbg APPsw vector. The PCR fragment was cloned by HindIII/NotI into the HindIII/NotI sites of the EGFP excised pPDGFbgEGFP vector. By this the construct pPDGFbgPS1 was generated. To generate the Pro117Leu mutation a site directed mutagenesis was performed with the primers pPS1P117L+(5'-GCA GCT AAT CTA TAC CCT ATT CAC AGA AGA TAC CG-3')) and pPS1P117L-(5'-CGG TAT CTT CTG TGA ATA GGG TAT AGA TTA GCT GC-3') on the pPDGFbgPS1 vector and the corresponding pPDGFbgPS1P117L construct thereby was constructed

```
SEQ ID NO 35: PDGF-PS1(P117L)(human) sequence
attaatgatccacagtctcctgagtagctgggactacaggagcttgttaccacacccagctccagtttataaattcatctcca

gtttataaaggaggaaaccgaggtactgagaggttaaaaaaccttcctgcagacacttgtccagcaagtggccactcca

ggatttggaccaaggtgatgtgtcttcaggctgtgtctctgccactgtgccacgctgctgggtggtaggcagcagtgggtgg

gtgcctgcagtggtctgtaaagaccacctgagatgtccttcctcctctgttccaccctgtccaggtccaagaagacagtctat

gaagagagagcaggtgtgactctctcagtgtgctcctctgtgagaagcaggctgacatcccaaagggaagggcggata

acagagacagtgcaagcggaggagatgagggtgcctcaaagccgggaggctgggtgatgcaggagcctgcgtgtcc

cgagggggtgctgggcccagtgtgagtacgtgtgactgtgactgagacagtgtgactgctgaaggcagggacacagc

agctccctgactgggggcagaaggcgttaactgtgtgaaggctggttgtgggtgggtgggctctgggcctcgaacccgg

gggctgagggagatagtaaacagcagggtgactgacgggaagatcatgttggtagccctgcgaagatgctgcagggc

tgtgggggtttgtgtgactttgcagttcaacaaattcaaattcagccaacgctggcagggcctgttgtgccaggcaaccag

ctaggaggaggagactcggacccagcttgcagctgaagggcgctggctgccgggttctgtgggttcaccttgcggtgtctt

cccttgctaacactgagtccttacaatagccccatctccaggttgaggctagatggaggggacagagggaagtgacttgc

ccaaggtgacccaagctcccgagtgccagggcaggatctgaattcaggctctcagactgcagagcctgagtccctccct

gccatgcctgtgccagggtggaaatgtctggtcctggaggggagcgtggactcctggccttggctctggagacatccccc
```

-continued

```
tagaccacgtgggctcctaacctgtccatggtcactgtgctgaggggcgggacggtgggtcacccctagttctttttcccca

gggccagattcatggactgaagggttgctcggctctcagagacccctaagcgccccgccctggccccaagccctccc

ccagctcccgcgtcccccccctcctggcgctgactccgggccagaagaggaaaggctgtctccacccacctctcgcact

ctcccttctcctttataaaggccggaacagctgaaagggtggcaacttctcctcctgcagccgggagcggcctgcctgcct

cccgtcgacgatcctgagaacttcagggtgagtttggggacccttgattgttctttctttttcgctattgtaaaattcatgttatatg

gaggggggcaaagttttcagggtgttgtttagaatgggaagatgtcccttgtatcaccatggaccctcatgataatttgtttcttt

cactttctactctgttgacaaccattgtctcctcttattttcttttcattttctgtaactttttcgttaaactttagcttgcatttgtaacgaa

tttttaaattcactttgtttatttgtcagattgtaagtactttctctaatcactttttttcaaggcaatcagggtatattatattgtacttc

agcacagttttagagaacaattgttataattaaatgataaggtagaatatttctgcatataaattctggctggcgtggaaatat

tcttattggtagaaacaactacatcctggtcatcatcctgcctttctctttatggttacaatgatatacactgtttgagatgaggat

aaaatactctgagtccaaaccgggcccctctgctaaccatgttcatgccttcttctttttcctacagctcctgggcaacgtgct

ggttattgtgctgtctcatcattttggcaaagaattgtaatacgactcactatagggcaagcttatgacagagttacctgcacc

gttgtcctacttccagaatgcacagatgtctgaggacaaccacctgagcaatactgtacgtagccagaatgacaataga

gaacggcaggagcacaacgacagacggagccttggccaccctgagccattatctaatggacgaccccagggtaact

cccggcaggtggtggagcaagatgaggaagaagatgaggagctgacattgaaatatggcgccaagcatgtgatcatg

ctctttgtccctgtgactctctgcatggtggtggtcgtggctaccattaagtcagtcagcttttatacccggaaggatgggcag

ctaatctatacccTattcacagaagataccgagactgtgggccagagagccctgcactcaattctgaatgctgccatcat

gatcagtgtcattgttgtcatgactatcctcctggtggttctgtataaatacaggtgctataaggtcatccatgcctggcttattat

atcatctctattgttgctgttctttttttcattcatttacttgggggaagtgtttaaaacctataacgttgctgtggactacattactgtt

gcactcctgatctggaattttggtgtggtgggaatgatttccattcactggaaaggtccacttcgactccagcaggcatatctc

attatgattagtgccctcatggccctggtgtttatcaagtacctccctgaatggactgcgtggctcatcttggctgtgatttcagt

atatgatttagtggctgttttgtgtccgaaaggtccacttcgtatgctggttgaaacagctcaggagagaaatgaaacgctttt

tccagctctcatttactcctcaacaatggtgtggttggtgaatatggcagaaggagacccggaagctcaaaggagagtat

ccaaaaattccaagtataatgcagaaagcacagaaagggagtcacaagacactgttgcagagaatgatgatggcgg

gttcagtgaggaatgggaagcccagagggacagtcatctagggcctcatcgctctacacctgagtcacgagctgctgtc

caggaactttccagcagtatcctcgctggtgaagacccagaggaaaggggagtaaaacttggattgggagatttcattttc

tacagtgttctggttggtaaagcctcagcaacagccagtggagactggaacacaaccatagcctgtttcgtagccatatta

attggtttgtgccttacattattactccttgccattttcaagaaagcattgccagctcttccaatctccatcacctttgggcttgtttt

ctactttgccacagattatcttgtacagccttttatggaccaattagcattccatcaattttatatctaggcggccgcaacttgttt

attgcagcttataatggttacaaataaagcaatagcatcacaaatttcacaaataaagcatttttttcactgcattctagttgtg

gtttgtccaaactcatcaatgtatcttatcatgtctg
```

2. Generation of Transgenic Donor Cells

Fibroblasts were cultured from ear biopsies of newborn Göttingen minipig no. 74114 (Ellegaard Göttingen Minnipigs A/S, Sorø Landevej 302, DK-4261 Dalmose, Denmark). Cells were grown to 50% confluence in a 75 cm3 flask (TPP, Switzerland), trypsinized and resuspended in 40 ml medium (DMEN, Lonza, Switzerland)) of which 10 ml were subsequently poured into a 10 cm petri dish. The cells were transfected with 6 ug of vector DNA in FuGENE 6 transfection reagent according to the protocol of the manufacturer (Roche Applied Science). The cells were grown under geneticin (Gibco Invitrogen) selection (1 mg/ml) for 8 days, cell colonies were isolated, and each colony was transferred to a 1.9 cm2 well (24-well plate, TPP, Switzerland) and grown to 80% confluence. Each colony was transferred to 9.4 cm2 well (6-well plate TPP, Switzerland), grown to 80% confluence, and ⅓ of the cells was used for RNA isolation and ⅔ of the cells were transferred to a 25 cm2 flask, grown to 80% confluence and stored at −135 C in 10% DMSO until use in handmade cloning.

3. Handmade Cloning (HMC) and Establishment of Pregnancies

For the cloning and delivery of transgenic piglets APP695sw transgenic donor cells (Trans 35 clone 2) were used in HMC. The development of reconstructed embryos to the blastocyst stage were 33.3% (59/177, n=3) and 40.5% (102/252, n=4) at respectively day 5 and 6 after reconstruction. Two recipient sows received a total of respectively 65 and 68 of a mixture of day 5 and 6 blastocysts. One recipient sow became pregnant and delivered 7 healthy piglets by Cesarean section. That the piglets (No. 5, 6, 7, 47, 48, 49, 50) were clones originating from the donor cell (74114) and genetically unrelated to the surrogate sow (SO1867) was confirmed by genotyping 10 microsatellite loci located on different porcine chromosomes.

Except where otherwise indicated all chemicals were obtained from Sigma Chemical Co. (St Louis, Mo., USA).

Oocyte Collection and In Vitro Maturation (IVM)

Cumulus-oocyte complexes (COCs) were aspirated from 2 to 6 mm follicles from slaughterhouse-derived sow ovaries and matured in groups of 50 in 400 μl IVM medium consisting of bicarbonate-buffered TCM-199 (GIBCO BRL) supplemented with 10% (v/v) cattle serum (CS), 10% (v/v) pig follicular fluid, 10 IU/ml eCG, 5 IU/ml hCG (Suigonan Vet; Skovlunde, Denmark) at 38.5° C. in 5% $CO_2$ in humidified air in the Submarine Incubation System (SIS; Vajta et al., 1997) for 41-44 h.

HMC was performed by a procedure based on partial digestion of the zona pellucida, as described earlier (Du et al., 2005 and 2007). Matured COCs was freed from cumulum cells in 1 mg/ml hyaluronidase in Hepes-buffered TCM-199. From this point (except where otherwise indicated) all manipulations were performed on a heated stage adjusted to 39° C., and all drops used for handling oocytes were of 20 μl covered with mineral oil. Zonae pellucidae of were partially digested with 3.3 mg/ml pronase solution dissolved in T33 (T for Hepes-buffered TCM 199 medium; the number means percentage (v:v) of CS supplement, here 33%) for 20 s, then oocytes were washed quickly in T2 and T20 drops. Oocytes with distended and softened zonae pellucidae were lined up in T20 drops supplemented with 2.5 μg/ml cytochalasin B. With a finely drawn glass pipette, oocytes were rotated to locate the polar body on the surface. By oriented bisection with an Ultra Sharp Splitting Blade (AB Technology, Pullman, Wash., USA) less than half of the cytoplasm close to the polar body was removed manually from the remaining putative cytoplast.

APPsw transgenic donor fibroblasts grown to a confluent monolayer in DMEM supplemented with 10% FCS were trypsinized and kept in T20 (Kragh et al., 2004). Fusion was performed in two steps. For the first step, 50% of the available cytoplasts were transferred into 1 mg/ml of phytohemagglutinin (PHA; ICN Pharmaceuticals, Australia) dissolved in T0 for 3 s, then each one was quickly dropped over a single APPsw transgenic fibroblast. After attachment, cytoplast-fibroblast cell pairs were equilibrated in fusion medium (0.3 M mannitol and 0.01% PVA) for 10 s and transferred to the fusion chamber (BTX microslide 0.5 mm fusion chamber, model 450; BTX, San Diego, Calif., USA). Using an alternating current (AC) of 0.6 kV/cm and 700 kHz, pairs were aligned to the wire of a fusion chamber with the somatic cells farthest from the wire, then fused with a direct current of 2.0 kV/cm for 9 μs. After the electrical pulse, cell pairs were incubated in T10 drops to observe whether fusion had occurred.

Approximately 1 h after the first fusion, each pair was fused with another cytoplast and activated simultaneously in activation medium (0.3 M mannitol, 0.1 mM $MgSO_4$, 0.1 mM $CaCl_2$ and 0.01% PVA). By using an AC of 0.6 kV/cm and 700 kHz, one fused pair and one cytoplast was aligned to one wire of the fusion chamber, with fused pairs contacting the wire, followed by a single DC pulse of 0.85 kV/cm for 80 μs. When fusion had been observed in T10 drops, reconstructed embryos were transferred into porcine zygote medium 3 (PZM-3; Yoshioka et al., 2002) supplemented with 5 μg/ml cytochalasin B and 10 μg/ml cycloheximide. After a 4 h incubation at 38.5° C. in 5% $CO_2$, 5% $O_2$ and 90% $N_2$ with maximum humidity, embryos were washed three times in PZM-3 medium before culture Embryo Culture and Transfer Embryos were cultured at 38.5° C. in 5% $CO_2$, 5% $O_2$ and 90% $N_2$ with maximum humidity in PZM-3 medium in the well of well system (WOWs; Vajta et al., 2000). Day 5 and 6 blastocysts with clearly visible inner cell mass were surgically transferred to Danish landrace sows on day 4 or 5 after weaning. Pregnancies were diagnosed by ultrasonography on day 21 and confirmed every second week. Piglets were delivered by Caesarean section on day 114, 24 h after treatment with prostaglandin F2.

Figure 3:
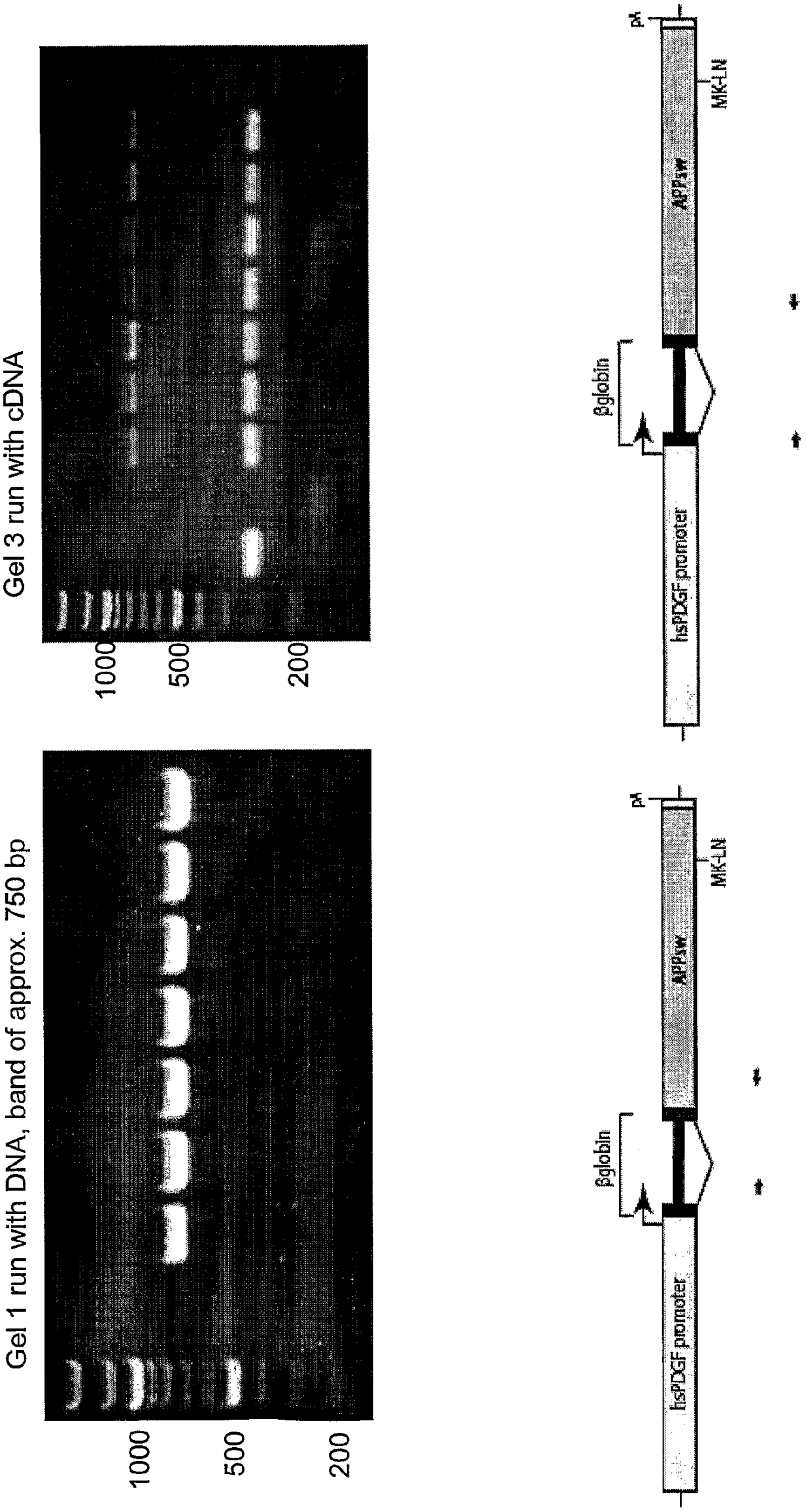
FIG. 3 shows the presence of the mutated APP gene in the genetically modified pig by analysing the length of the transcripts and the presence of the mutation.

4. Analysis of Transgenic Pigs Harbouring the APP Gene According to the Present Invention In Another Embodiment the Transgenic Pigs as Described in Transgenic pigs for the mutated APP were analysed for the presence of the full length transcript of the mutated APP gene. FIG. 3 shows that the full length transcript is present and that it harbours the mutation of APP as shown by restriction analysis.

Determination of Transgene Copy Number

Figure 4:
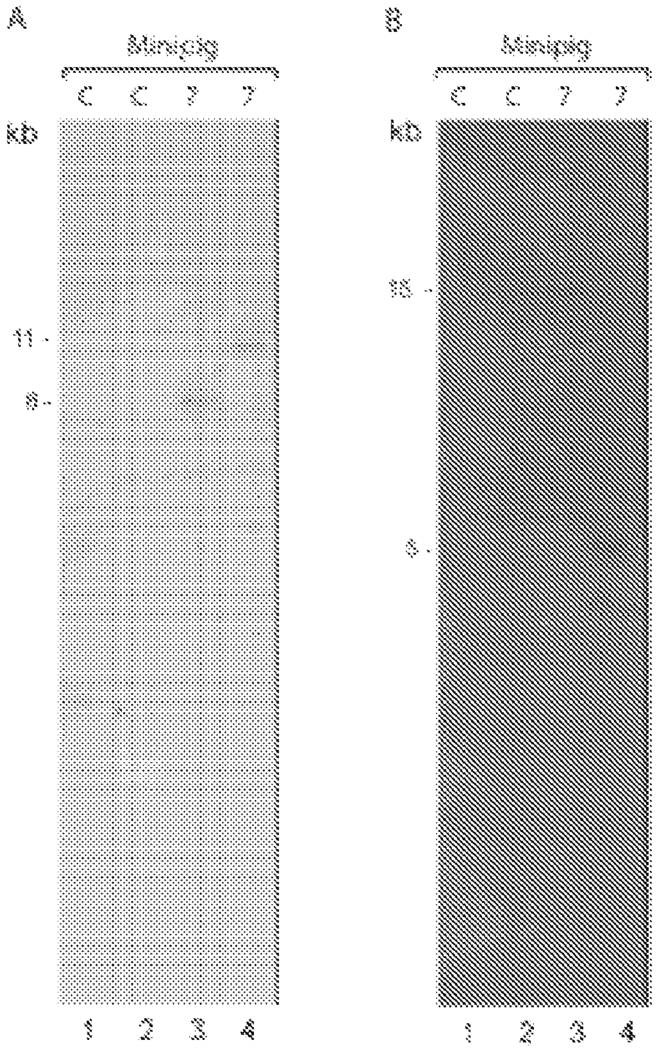
FIG. 4 shows Southern blot analysis of the transgenic insertion. A) Southern blot analysis with a human PDGFβ promoter probe on XbaI and AflII digested genomic DNA. Control porcine DNA is present in lane 1 and 2. Porcine DNA from cloned piglet no. 7 is present in lane 3 and 4. Lane 1 and 3 represent DNA digested with AflII and XbaI while lane 2 and 4 represent DNA digested only with XbaI. An intense band approximately 8 kb is observed in lane 3. In lane 4 an intense band approximately 11 kb is observed. B) Southern blot analysis with a human PDGFβ promoter probe on SpeI and AflII digested genomic DNA. Control porcine DNA is present in lane 1 and 2. DNA from transgenic piglet no. 7 is present in lane 3 and 4. Lane 1 and 3 represent DNA digested with only SpeI. Lane 2 and 4 represent DNA digested with SpeI and AflII. A band about 15 kb is observed in lane 3. In lane 4 a band about 5 kb is observed. X-ray film was visualised after 10 days exposure.

Transgenesis using plasmid vectors have possibility to generate multiple transgene insertions and transgene tandem repeats. To address the transgene insertion in the piglets we performed a Southern blot analysis. Genomic DNA from a control pig and the transgenic piglet No. 7 was digested with XbaI which cuts at one position just downstream of the APP cDNA within the transgene vector. As probe in the Southern blot analysis was used a 600 bp fragment encompassing a part of the PDGFβ promoter sequence. As control for copy numbers was used a serial dilution of the plasmid vector used for transgenesis. The result of the Southern blot showed the presence of a single band sized 11 kb only in DNA from the transgenic piglet, see FIG. 4 This is in agreement with a single transgene insertion as several insertions would be expected to contribute each with a unique sequence tag from the genomic context and thereby generate fragments of different sizes. The absence of tandem repeats is also very likely as digestion of such repeats should result in a band representing the vector having the size of maximum the vector size (7.5 kb). These indications of a single copy transgene insertion were further examined by other enzyme digestions. Double digestion of the genomic DNA with XbaI and AflII (both cutting the vector at single locations and placed at a distance of 0.2 kb from each other) resulted in a single band sized 8 kb in the Southern blot analysis. Genomic DNA was also digested with SpeI which have no recognition sites within the vector used for transgenesis. A single band of 15 kb was detected in the transgenic pig. Double digestion with SpeI and AflII resulted in the presence of a single band sized 5 kb. Altogether the Southern blot analysis is consistent with the presence of a single integration of at least the probed part of the transgene vector and the restriction mapping analysis together with the observed equal intensity of the various probed bands shows that no vector concatameres are present within this integration site.

Thus, a very simple method for transgenesis of the donor fibroblast cells can result in a single copy transgene insertion. The obstacle tandem repeats represent in transgenesis due to their assembly into non-transcribed heterochromatin structures is thereby overcome. Moreover a dispersed insertion of transgenes could result in deregulation of numerous cellular genes and thereby interfere with the usefulness of the established transgenic animal model.

Detection of the APP695sw Transgene and its Transcript

DNA/RNA Extraction and cDNA Synthesis.

Genomic DNAs of bloodsamples of the 7 transgenic piglets and the surrogate mother were extracted from according to the Chemagen DNA-extractor protocol. Fibroblasts of ear biopsies from the 7 transgenic piglets were grown to 50% confluence in a 75 $cm^3$ flask (TPP, Switzerland), and total RNA was isolated from the fibroblasts using TRI reagent (T 9424, Sigma), as recommended by the manufacturer. 50-100 mg of flash frozen dissected brain regions were transferred to an RNase-free tissue-grinder (Wheaton #357542), 2 ml TriReagent added and the tissue was homogenized. Total RNA was extracted using chloroform and isopropanol precipitation. The RNA pellet was resuspended in 50 ul DEPC-$H_2O$. Production of cDNA was done either with the iScript cDNA Synthesis Kit from BioRad or TermoScript Reverse Transcriptase Kit from Invitrogen in a volume of 20 μl.

Microsatellite Analysis.

Figure 5:
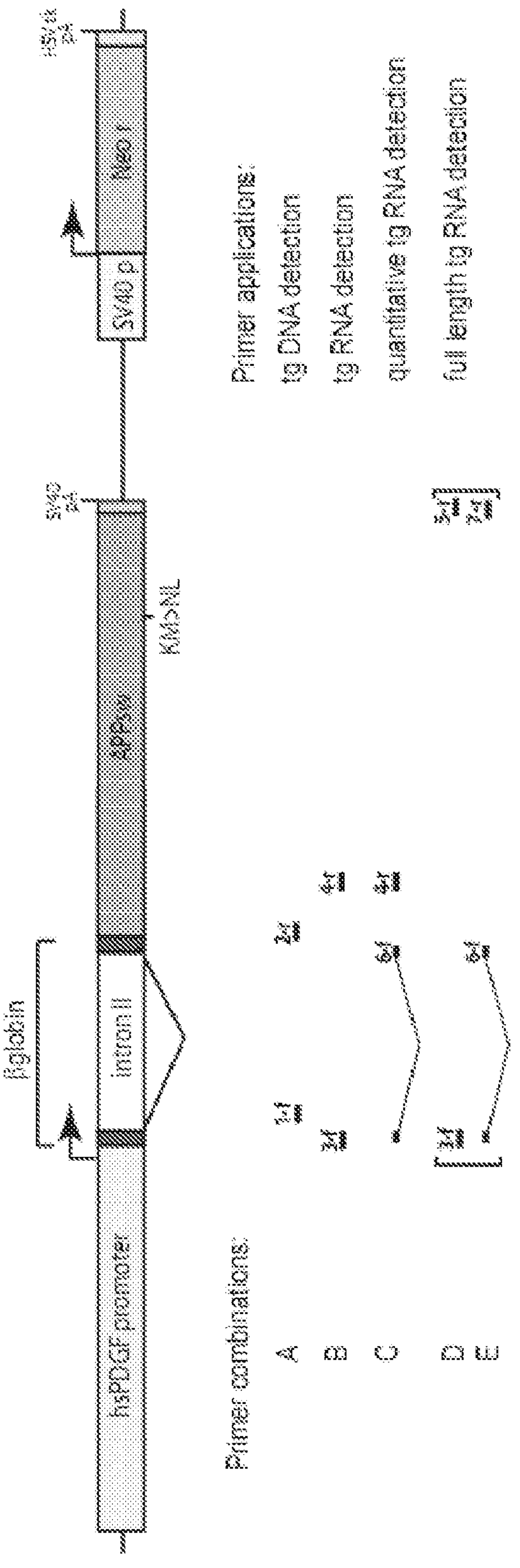
FIG. 5 is a graphical presentation of the mutated APP construct introduced into a pig. The various primer combinations, primer positions and application of the primers are shown.

0.1 μg genomic DNA from each of the 7 newborn piglets (no. 5-7, 47-50), the surrogate sow (SO1867), and from donor fibroblasts (cell no. 74114) were used in a 3-color multiplex touchdown PCR with primer pairs flanking 10 polymorphic microsatellite loci (SW886, SW58, SW2116, SW1989, SW152, SW378, KS139, SO167, SW1987, SW957) located on different porcine chromosomes (www.marc.usda.gov/genome eller Rohrer et al. 1994, Alexander er al. 1996). The PCR products were analyzed on the Genetic Analyzer 3130 X1 (Applied Biosystems) using the program Gene Mapper 3.7. The seven piglets and the donor cell had identical genotypes in all 10 loci while the surrogate sow shared the genotype at only 1 locus and did not share any allele at 7 of the 10 loci (see Table 3.

cDNA from fibroblasts of the 7 transgenic piglets and donor cells was done with 3 μl of the 3 μl cDNA reaction as template and forward primer 3 (5'-GTC GAC GAT CCT GAG AAC TTC AG-3') located in exon 1 of the b-globin sequences and reverse primer 4 (5'-GGG TTC AGC CAG CAG GCC AG-3') located in the 5' end of the APP transgene (primer combination B, FIG. 5).

Figure 6:
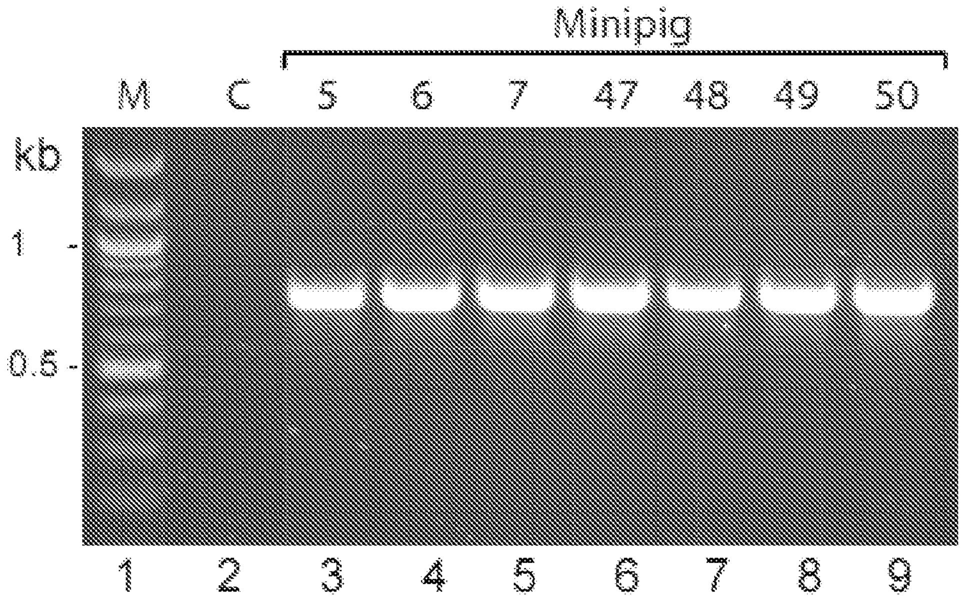
FIG. 6 shows that the transgene is present in the genome of all 7 piglets. Genomic DNA from each of the 7 piglets were subjected to PCR with forward primer 1, which extends from b-globin exon 1 into intronic sequences and requires an unspliced genomic template, and reverse primer 2 located in the APP sequences (FIG. 5). The calculated length of the PCR product is 740 bp, and a band of that length was found in all 7 piglets (lanes 3-9). As expected, no PCR product was obtained when genomic DNA from the donor cell was used as template (lane 2).

PCR of full-length APP cDNA was done with 2 μl from the 20 μl TermoScript cDNA reaction and primer 3 as forward and primer 5 (5'-CTA GTT CTG CAT CTG CTC AAA G-3'), located at the very 3' end of the APP transgene, as reverse primer and nested PCR with forward primer 6 (5'-TTC TGA GAA CTT CAG GCT C-3') and reverse primer 7 (5'-CTT GTA GGT TGG ATT TTC GTA G-3') (primer combinations D and E, respectively, FIG. 5). An expected PCR fragment of about 2200 bp representing full-length cDNA was identified in the agarose gel (FIG. 6). The fragment was purified and its entire sequence determined using the sequencing kit BigDye Terminator 3.1 (ABI) and ABI 3100 sequencing system.

Quantitative real-time PCR. Quantitative real-time PCR was performed essential as described (Blechingberg et al. 2007). Briefly, reactions were performed in a 20 ml volume using the Dynamo HS SYBR green PCR kit (Finnzymes). Two microliters of cDNA was used as template together with 6 pmol of each primer (forward primer 6; reverse primer 4, primer combination C in FIG. 5). The expression values for the APP mRNA were normalized to the expression values

TABLE 3

| Loci | Piglet no. 5 | Piglet no. 6 | Piglet no. 07 | Piglet no. 47 | Piglet no. 48 | Piglet no. 49 | Piglet no. 50 | Donor cell 74114 | Surrogate Sow SO1867 |
|---|---|---|---|---|---|---|---|---|---|
| SW886 | 171 | 171 | 171 | 171 | 171 | 171 | 171 | 171 | 154 |
| | 173 | 173 | 173 | 173 | 173 | 173 | 173 | 173 | 154 |
| SO167 | 198 | 198 | 198 | 198 | 198 | 198 | 198 | 198 | 217 |
| | 198 | 198 | 198 | 198 | 198 | 198 | 198 | 198 | 217 |
| SW378 | 120 | 120 | 120 | 120 | 120 | 120 | 120 | 120 | 120 |
| | 120 | 120 | 120 | 120 | 120 | 120 | 120 | 120 | 120 |
| KS139 | 158 | 158 | 158 | 158 | 158 | 158 | 158 | 158 | 170 |
| | 173 | 173 | 173 | 173 | 173 | 173 | 173 | 173 | 179 |
| SW152 | 178 | 178 | 178 | 178 | 178 | 178 | 178 | 178 | 168 |
| | 178 | 178 | 178 | 178 | 178 | 178 | 178 | 178 | 178 |
| SW1987 | 155 | 155 | 155 | 155 | 155 | 155 | 155 | 155 | 162 |
| | 155 | 155 | 155 | 155 | 155 | 155 | 155 | 155 | 167 |
| SW957 | 130 | 130 | 130 | 130 | 130 | 130 | 130 | 130 | 110 |
| | 139 | 139 | 139 | 139 | 139 | 139 | 139 | 139 | 136 |
| SW2116 | 115 | 115 | 115 | 115 | 115 | 115 | 115 | 115 | 128 |
| | 128 | 128 | 128 | 128 | 128 | 128 | 128 | 128 | 136 |
| SW58 | 214 | 214 | 214 | 214 | 214 | 214 | 214 | 214 | 216 |
| | 214 | 214 | 214 | 214 | 214 | 214 | 214 | 214 | 222 |
| SW1989 | 257 | 257 | 257 | 257 | 257 | 257 | 257 | 257 | 234 |
| | 257 | 257 | 257 | 257 | 257 | 257 | 257 | 257 | 245 |

PCR of DNA/cDNA and DNA Sequencing.

The PCRs were done according to standard protocols in a volume of 50 μl with TAQ-polymerase (GE Healthcare) or Phusion-polymerase (Finnzymes) for long-range PCR. After 35 cycles 10 μl of the PCR products were loaded on a 1.2% LE agarose gel, run at 100 mA for 45 min and the ethidium bromide stained gel photographed.

PCR of 50 ng genomic DNA from each of the 7 piglets, the surrogate sow, and the donor fibroblast cells was done with forward primer 1 (5'-GGG GTC GAC GAT CCT GAG AAC TTC AGG GTG-3') located in the intronic b-globin sequences of the transgene and reverse primer 2 (5'-GAT CGG TAC CTC CAG CGC CCG AGC CGT CC-3') located in the 5' end of the APP transgene (primer combination A, FIG. 5). PCR of obtained for GAPDH. The identity of the PCR products was confirmed by melting-curve analysis and gel electrophoresis.

Figure 7:
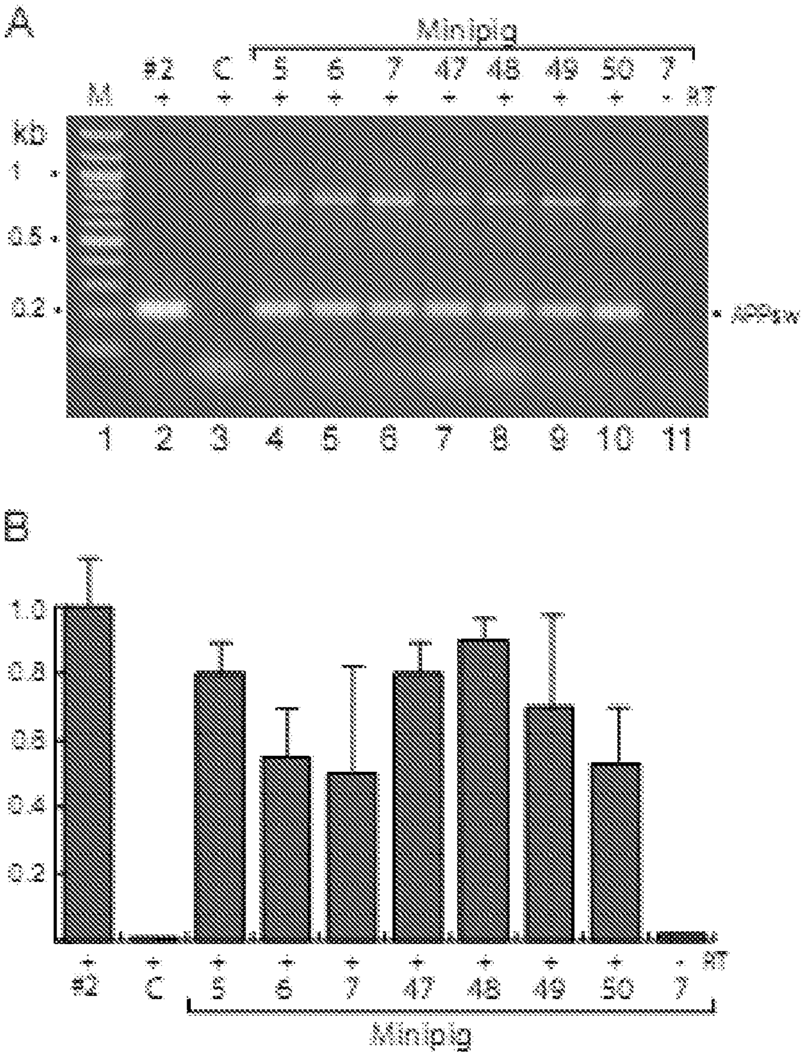
FIG. 7 shows in a) an agarose gel shows that the transgene is expressed in fibroblasts from all 7 piglets (lanes 4-10) and in the transgenic donor cells Trans 35, clone 2 (lane 2), but not in the original non-transgenic donor cell (lane 3). The cDNAs representing the piglets and the donor cells were PCR amplified with forward primer 3 located in b-globin exon 1 and reverse primer 4 located in the APP sequences (FIG. 5); b) shows a quantitative real time PCR analysis performed on the derived cDNAs. Primers 6 and 4 (FIG. 5) were used to amplify specifically the spliced form of the APPsw transcript.

FIG. 7 shows that the transgene is present in the genome of all 7 piglets. Genomic DNA from each of the 7 piglets were subjected to PCR with forward primer 1, which extends from b-globin exon 1 into intronic sequences and requires an unspliced genomic template, and reverse primer 2 located in the APP sequences (FIG. 5). The calculated length of the PCR product is 740 bp, and a band of that length was found in all 7 piglets (lanes 3-9). As expected, no PCR product was obtained when genomic DNA from the donor cell was used as template (lane 2).

The agarose gel in FIG. 8*a* shows that the transgene is expressed in fibroblasts from all 7 piglets (lanes 4-10) and in the transgenic donor cells Trans 35, clone 2 (lane 2), but not in the original non-transgenic donor cell (lane 3). The cDNAs representing the piglets and the donor cells were PCR amplified with forward primer 3 located in b-globin exon 1 and reverse primer 4 located in the APP sequences (FIG. 5). Thus, cDNAs of both unspliced and spliced transcripts of the transgene are expected to be amplified with a PCR fragment length of 794 bp and 201 bp, respectively. A strong band with the length of about 200 bp representing the spliced transcript is amplified from cDNA of the transgenic donor cell (lane 2) and all the piglets (lanes 4-10), but is absent, as expected, when cDNA from the non-transgenic donor cell is used as template (lane 3). A longer, but weaker band of about 800 bp, which represents amplified cDNA of the unspliced transcript, is present only in lanes 4-10. This indicates that some 20% of the transgene transcripts are unspliced in fibroblasts from the piglets, while all the transcripts appear to be spliced in the transgenic donor cell (lane 2). If the cDNA used in lane 6 is produced without reverse transcriptase in the reaction no band is amplified, as seen in lane 11, confirming that the templates of the PCR reactions originate from RNA.

To measure if the mRNA expression level of the APPsw transgene was similar in the fibroblasts from the 7 piglets, as it appears in FIG. 8*a*, a quantitative real time PCR analysis was performed on the derived cDNAs (FIG. 8*b*). Primers 6 and 4 (FIG. 5) were used to amplify specifically the spliced form of the APPsw transcript. To correct for variation in the amount of cDNA from the different samples the APPsw expression values were normalized to the expression values for GAPDH. The analysis showed that in all of the seven fibroblast cultures derived from the cloned piglets the APPsw expression was comparable to the expression level in the transgenic donor cell used for cloning. Thus, we have no indications for neither silencing of the APPsw transgene within fibroblasts as a consequence of the cloning procedure nor epigenetic caused differences in the APPsw transgene expression level between individuals.

The agarose gel in FIG. 6*a* shows that a cDNA derived from a full-length transcript of the transgene is present in the transgenic donor cell and in fibroblasts from the 7 piglets and not, as expected, in the non-transgenic donor cell. Accordingly, a robust band of about 2 kb in length is present in lanes 2, 6, 8, 10, 12, 14, 16, and 18 and represents the product of a nested PCR reaction of cDNA using forward primer 3 and reverse primer 5 in the first PCR reaction and forward primer 6 and reverse primer 7 (FIG. 5) in the nested PCR. No band is present in lane 4 as the cDNA used was made from total RNA from the non-transgenic donor cell. No band is present if reverse transcriptase was omitted in the cDNA synthesis from total RNA from the transgenic donor cell and from the fibroblasts of the piglets (lanes 3, 7, 9, 11, 13, 15, 17, 19). The entire DNA sequence was determined of the cDNA representing the full-length transcript of one of the piglets and it was found to be identical to the human APP695 sequence (NCBI database) except for a silent nucleotide polymorphism (T to C) at position 260 and the Swedish mutation at positions 2204 (G to T) and 2205 (A to C) (FIG. 6*b*).

In order to study transgene expression in brain tissue and other tissues we sacrificed piglet No. 7 at the age of 3 months. cDNA was produced from total RNA extracted from cerebral cortex, cerebellum, the hippocampus, basal ganglia, brain stem, heart, and liver. PCR was done on these cDNAs with the same primers 6 and 4 (primer combination C in FIG. 5) that were used for quantitation of the transcript of the transgene (FIG. 8*b*). The agarose gel in FIG. 9*a* shows that the transgene is highly expressed in all the brain regions and not in heart and liver tissue.

Detection of the Transgenic Protein APP695sw

A Western blot using a commercial anti-APP antibody (6E10), Sigma, was performed according to the manufacturer's recommendations. The Western blot was performed on extracts from fibroblast cells of a transgenic pig (lanes 1 and 2) and on extracts from fibroblast cells of a wt pig (lanes 3 and 4), see FIG. 10. In lane 1 the fibroblasts have been treated with the protease inhibitor ALLN, whereas the fibroblasts of lane 2 have not received treatment. It is evident that in ALLN treated fibroblasts bands of lower molecular weight as compared to the molecular weight of mutated APPis bands have increased in intensity. In contrast, the lower molecular weight products are not present in similar amounts as in lane 2. Lanes 3 and 4 contain extracts of fibroblasts from wt pigs and no effect of ALLN treatment is evident in comparison to the extracts of transgenic pigs.

For the results of the Western blotting described the following procedure was employed:

a) Non-transgenic donor fibroblasts (74114 cells) and fibroblasts from transgenic minipiglet No. 47 were grown to 80% confluence in a 75 cm2 flask. The cells from each flask were resuspended in 24 ml medium and transferred to a 6-well plate (TPP, Schwitzerland) with 2.5 ml of the cell suspension in each well. Medium was changed the following day with 2 ml fresh medium containing the chemical at the indicated concentration were added to the wells of both plates: well No. 1, 5 μM Lactacystin; well No. 2, 20 μM Leupeptin; well No. 3, 20 μl DMSO; well No. 4, 20 μM ALLN; well No. 5, 2.5 mM NH4Cl. After 6 hrs incubation the cells from each well were harvested and transferred to an 1.5 ml Eppendorf tube. 30 μl ddH20, 2 μl reducing agent and 8 μl loading buffer (Fermentas) were added, the tubes were placed in boiling water for 5 min. and spun at full speed for 1 min. in an Eppendorf centrifuge. 15 μl of each sample were loaded on a 4-15% polyacrylamid gel (BioRad), run at 45 mAmp for 90 min. Transfer to PVDF membrane (GE Healthcare) was done at 75 volt for 30 min., and the membrane was stained with anti-human APP monoclonal antibody 6E10 (SIGNET) at dilution 1:1000, and as secondary antibody polyclonal goat anti-mouse immunoglobulines/HRP (Dako Cytomation) at dilution 1:2000.

b) Extraction of protein from brain tissue was done with 100-200 mg flash frozen cortical tissue homogenized in a tissue-grinder with 3 ml lysis buffer (Tris-HCl 50 mM, EDTA 10 mM, SDS 1%, Triton X-100 0.5%, ⅓ Protease Inhibitor Cocktail Tablet (Roche), pH 8.0). The solution was transferred to an Eppendorf tube (1 ml), centrifuged at 12,000 rpm for 2 min at 4° C. and supernatant transferred to a new tube. After vortexing the tube was frozen in dry ice for 3 min, thawed at 37° C. for 3 min, and this freeze/thaw step was repeated 3 times. Finally, the solution was centrifuged at 14,000 rpm (4° C.) for 10 min, the pellet discarded and the protein concentration of the supernatant determined. 8 μg protein extract was loaded in each lane of the polyacrylamid gel. Western blotting was done as described above.

Skin fibroblasts of transgenic piglet No. 47 and non-transgenic donor fibroblasts (No. 74114) were grown in medium with and without protease inhibitors. Equal amounts of cell lysates were loaded on a gel for western blotting, and the monoclonal antibody 6E10 was used to detect the APP695sw protein product. The antibody recognizes amino acid residues 1-17 of human Abeta, and the corresponding amino acid sequence in the mouse differs at 3 positions which may explain why the antibody does not detect mouse APP. By contrast, the corresponding porcine sequence is identical to the human sequence (Oerum et al. Biochimica et Biophysics Acta 1759 (2006) 378-384). It was therefore predicted that the antibody 6E10 would recognize also porcine APP.

In FIG. 11 is shown the result of western blotting. Lanes 1 and 2 represent fibroblasts from the transgenic piglet and lanes 3 and 4 represent non-transgenic donor cells. The cells in lanes 1 and 3 have been grown in the presence of the protease inhibitor ALLN. The western blot shows that porcine fibroblasts (lane 4) express endogenous APP, predominantly the APP770 splice variant and, to a much lesser extend, the neuronal splice variant APP695 represented by a less intensely stained band. No band representing the APP751 splice variant was observed. As indicated by equal intensities of the APP770 bands, the fibroblasts of the transgenic piglet (lane 2) express the APP770 splice variant at a similar level.

By contrast, the APP695 band appears more intense in lane 2 than in lane 4 indicating that the level of the APP695 spice variant is increased in fibroblasts from the transgenic piglet. This increase is explained by the protein product derived from the APP695sw transgenic transcript. RT-PCR of the corresponding transcripts and their relative amounts in non-transgenic donor cells, transgenic donor cells, and fibroblasts from transgenic piglet was consistent with the western blot (data not shown). This difference in intensity of the APP695 bands of the western blot becomes more pronounced if the cells are grown in the presence of 20 μM ALLN (compare lanes 1 and 3). Similar effect was obtained if the medium contained 10 mM lactacystin, which is also a proteasome inhibitor, while the presence of the lysosomal protease inhibitors leupeptin or ammonium chloride had no such effect (data not shown). This is consistent with the finding by other that intracellular degradation of overexpressed APP695 is sensitive to proteasome inhibitors (Chen, Kimura, and Schubert, JCB 2002). It is concluded that the protein product of the APP695sw transgene accounts for the increase in the intensity of the APP695 band in lanes 1 and 2, FIG. 11. Thus, the APP695sw transgene is expressed in fibroblasts of transgenic piglet No. 47 and, by inference, in all 7 cloned piglets.

The western blot in FIG. 10 contains protein extraction from cerebral cortex of a non-transgenic minipig (lane 1) and protein extraction from cerebral cortex of transgenic minipig no. 7 (lane 2). The anti-APP antibody 6E10 detects a weak band around 117 kD representing endogenous APP695. The intensity of this band is more than 10 fold increased in lane 2 representing the APP695sw transgenic protein product.

Examination of Phenotype of Transgenic APP Pigs

A: Behavioural Tests

In order to examine the transgenic pigs for signs of AD symptoms three different behavioural tests are used:

1) Test of olfaction with an Olfactometer Test

2) Test of semantic memory with Object-Recognition Test

3) Test of visuo-spatial memory with Labyrinth Test

All three tests are based on knowledge about the neuropsychological deficits in AD in humans and the assumption that development of AD in pigs will result in comparable deficits.

Re 1) In humans, one of the first signs of AD is affection of olfactory system (Eibenstein et al., 2005a,b) and a relatively simple test has been developed for testing olfaction in humans (Pocket Smell Test, Sensonics) (Doty et al., 1984).

In rodents, olfaction can be tested using an olfactometer (Bodyak & Slotnick, 1999, Slotnick and Bodyak, 2002), in which the animals are trained using a Knosys olfactometer and operant conditioning.

We have modified the rodent olfactometer (Knosys Inc.) described by Bodyak and Slotnick to fit pigs. The modified olfactometer consists of a test chamber, 8 independent lines for administration of odorants and a digital interface. Each line consists of a 200 ml odor saturator plastic bottle containing 50 ml odorant (dissolved in water or glycerol) and air saturated with the odorant. The lines (C-flex tubing) to and from the bottles are controlled by valves that are normally shut. When a valve opens, a 50 ml/min stream of odor-saturated air from the 200 ml saturator bottle is added to a 1950 ml/min stream of clean air and the mixture is led to a test chamber as described in Slotnick and Bodyak, 2002.

The test chamber is an open box placed on wheels and measuring 115.5×66×70 cm. The front panel contains a circular opening (diameter 8 cm) for the pig's nose, a light for signalling stimulus, a pedal for operant response, a magnetic buzzer for signalling correct answer, and a bowl for delivering reward (M&Ms) after correct answer. The hind panel is a door that can be opened to let the pig in and out of the test chamber. The walls are made from plastic covered 1.6 cm thick plates.

The system works by delivering an air stream with +/− odorant. When the air stream is delivered, a short flash is seen to alert the pig. The pigs are trained to press a pedal if the air stream contains an odorant and are rewarded with a short beep sound from the buzzer and chocolate (M&Ms) for a correct answer.

The olfactometer is directed by a PC programmed (software developed by Knosys Inc. and adapted to pig by Slotnick) to give repetitive air with odorants added at random and to deliver M&Ms in a designated dispenser when the pigs are rewarded. All pushes on the pedal are registered by the PC and related to +/− odorant in the air stream to calculate the percentage correct answers.

The initial phase consists of habituating the pigs to the olfactometer, motivation by decreasing the food amount, habituation to the test chamber, habituation to receiving a reward, shaping to operation of the pedal, shaping to odor sampling, shaping to operant response to stimulus, shaping to go/no-go task.

After the initial phase, training ensues. Each training session has a duration of 30 minutes and includes 5-10 trials, each consisting of 20 runs with (+S) or without (−S) odorants (10 +S, 10 −S, randomly distributed). When an animal has 85% correct pushes on the pedal the training is complete. If the animal has more than 85% correct pushes on the pedal after 5 trials training is stopped, otherwise it continues until 10 trials have been done.

The odorants of choice are ethanol and ethyl acetate. Decreasing concentrations are titrated to find the threshold of detection for each animal.

A total of 6 normal (non-transgenic) Göttingen minipigs have been trained to do the task and have been tested with different odorants (ethanol and ethyl acetate).

The threshold for detection of the odorant has also been determined in the pigs.

To further validate the olfactometer test, surgical removal of the olfactory bulb was performed in 4 pigs (bulbectomy) whereas the remaining two pigs were sham-operated.

FIG. 12 shows the results of the training of the 6 pigs. After session 12, the olfactometer was adjusted causing a break in the training lasting 1 month. Sessions 13 to 17 represent renewed training after adjusting the apparatus. Bulbectomy was performed after session 17 in 4 pigs and sessions 18 to 20 represent testing after the operation. The bulbectomized pigs have only 50% correct answers whereas the sham-operated pigs still have 85% correct answers.

The transgenic pigs are tested using the same olfactometer and we have chosen a level of 80% correct answers as normal, implicating that olfaction is decreased when the number of correct answers is below 80%. The transgenic pigs are tested at 6, 12, 18, 24, and 24+ months and each animal serves as it own control. A decrease in olfaction is one of the first symptoms of AD in the pigs to be reflected in a decreased number of correct answers (i.e. the % correct answers decreases below 80%).

Re 2) The cardinal symptom of AD in humans is affection of the memory. Several neuropsychological tests can be used in humans to test different elements of memory (i.e. episodic memory, semantic memory, working memory, perceptual speed test), but a rather simple test of semantic memory, the Mini Mental State Examination (MMSE), has found widespread use in the day-to-day testing of humans. The test consists of a total of 30 different questions and is easily performed. A score below 23 indicates memory deficit corresponding to dementia. A correlate to this test in animals is the object-recognition test in which spontaneous exploration of objects is evaluated. The animals are initially allowed to explore two identical objects. After a certain time lapse, the animals are exposed to two objects—one identical with the objects in the initial session—the other differing from them. The difference in time spent to explore the two objects indicates recognition of the object from the first session. Application of such a test for pigs has already been described by others (Moustgaard et al., 2002) and is used to test the transgenic pigs at the same times as above.

Re 3) In addition to affection of memory, cognitive disturbances develop as a consequence of affection of more widespread cortical areas in the brain. AD patients particularly suffer from visuo-spatial disturbances and this is commonly tested with the clock-drawing test in which the patients are asked to draw a clock with correct numbers and arms. AD patients are unable to do this. A correlate to this test in animals is the Morris Water Maze designed for rodents and several tests have been designed for pigs (e.g. Hagl et al., 2005). Briefly, the pigs learns in which of different compartments food is stored in order to obtain a reward (food). The complexity of the test can be varied to increase the difficulty. This test is applied to the transgenic pigs at the same times as above.

B: Neuropathological Changes

The histological hallmarks of AD in humans is the presence of intraneuronal neurofibrillary tangles consisting of hyperphosphorylated tau protein and extracellular plaques consisting of Abeta protein species. The first changes are believed to be diffuse plaques (without a central amyloid core) containing Abeta 1-42 protein that is toxic to neurons. Later, the diffuse plaques transform into definitive or neuritic or amyloid plaques that contain an amyloid core and consists of various Abeta species, chiefly Abeta 1-40.

One of the transgenic pigs was sacrificed at age of 3 months. In addition to performing the gene expression analyses, we have performed neuropathological examination of the brain tissue, see FIG. 13. Interestingly, we find accumulation of protein in brain tissue that stains positive with an antibody raised against Abeta 1-42 (Signet Lab—SIG-39142-500 batch 06KCO2476), FIG. 13*a*. The protein is located in neuronal somata in the cortex including the hippocampus as well as in the neurpil surrounding small blood vessels in the tissue. A neuropathological examination of the brain tissue, hippocampus, of 3 month old Göttingen minipig (normal control) stained with the same antibody against Abeta1-42 in the same staining procedure, does not disclose plaque-like immunoreactive deposits in the tissue and no staining of neuronal somata in any parts of the brain examined, FIG. 13*b*. Thus, accumulations have not been seen in nontransgenic age matched pigs.

We believe these changes represent the very earliest AD-like changes in the transgenic pigs.

The Use of a Porcine Model of Alzheimer's Disease in Testing Preventive and Therapeutic Strategies Immunotherapy Active Immunization Schenk et al. (1999) was the first to show that subcutaneous immunization with 100 ug Abeta 1-42 antigen in complete Freund adjuvant reduces the accumulation of plaques in the brain of the socalled PDAPP transgenic mouse that carries a mutated APP gene driven by a PDGF promoter similar to the transgenic construct of the porcine model.

The transition to clinical studies, however, was quickly stopped because of development of meningoencephalitis in 6% of the patients. This effect illustrates the problem of translating mouse data to humans and stresses the need for a large animal model.

A similar strategy is used in the porcine model with dosis and frequency adapted to minipigs—both transgenic and non-transgenic. Immunization begins at 6 months of age before any sign of Alzheimer's disease pathology and, for comparison, sham immunization of transgenic minipigs is also performed. The immunization is repeated once every month in a 12 months period and the effect of the treatment is be monitored by PE-scan, test of olfaction and behavioural tests, as described elsewhere herein. A the end of the trial the brains of immunized minipigs are subjected to neuropathological evaluation of the effect of the strategy.

Passive Immunization

Asami-Odaka et al. (2005) and Levites et al. (2006) were first to show that serial intraperitonal injections of 0.5-1 mg of a monoclonal antibody against the C-terminus of Abeta 1-42 have preventive effect on Abeta deposition in the brain of the Tg2576 transgenic mouse.

A strategy using intravenous injection in the porcine model is attractive and dosis and frequency can be optimized. First injection before signs of pathology at the age of 6 months and repeated every second week during a 12 months period. Also 1 year old transgenic minipigs with Alzheimer's disease pathology are passively immunized to study therapeutic effect.

During the trials the minipigs are followed by PIB-scan, olfaction test, and behavioural tests to monitor the effect of the treatment. The brains of the animals are subjected to neuropathological examination after conclusion of the trials.

The porcine model serves an important function as a large animal in pre-clinical testing. Both when addressing safety issues and the immunogenic effect of various Abeta epitopes on Abeta clearance, and in testing different delivery systems. Also in developing safe anti-Abeta antibodies to specifically target neurotoxic Abeta species and efficiently clear them from the brain.

Pharmacological Intervention

Determination of Beta—Secretase Inhibition

Abeta 1-42 (and 1-40) is produced by β-secretase and β-secretase cleavage of APP. β-secretase being a rate limiting enzyme is an attractive target in a therapeutic approach, and even more so as Luo et al. (2001) showed that knock-out mice deficient of β-secretase have normal phenotype. Hussain et al. (2007) have shown that oral administration of a non-peptidic β-secretase inhibitor (GSK188909) results in significant lowering of brain Abeta in APP transgenic mice.

We use a similar approach to lower Abeta production in the brain of our APP transgenic porcine model to support, using a large animal model, the development of safe β-secretase inhibitors for the treatment of Alzheimer's disease.

The transport of the b-secretase inhibitor GSK188909 across the brood brain barrier of the minipig is tested with a peroral dose of 250 mg/kg of the drug transporter p-glycoprotein (pgp) inhibitor GF120918 (Hyafil et al. 1993) 5 hrs. prior to peroral administration of 250 mg/kg of the β-secretase inhibitor GSK188909. 12 hrs. later brain extraxts from treated and untreated minipigs are analyzed for quantitative proteolytic fragments of the APP (sAPP β, aAPPα, CTFβ, CTFα, Abeta) that indicate a shift from β-secretase to α-secretase proteolysis and thus, by inference, β-secretase inhibition. Specific antibodies for the relevant proteolytic fragments are commercially available.

A similar experiment is conducted but without the pgp inhibitor to test whether a subchronic dosing of the b-secretase inhibitor alone is sufficient to lower Abeta load of the brain. Peroral dosis of GSK188909 (250 mg/kg) is administrated twice daily for 1, 2, and 3 weeks, respectively. Brain extracts from treated and untreated minipigs are analyzed as outlined above.

Location of the Transgene PDGF/Beta Globin Intron/APPsw Construct in the Alzheimer Pig Genome to Porcine Chromosome 1q18

The transgene is located in the longest intron between exon exon 3 and exon 4 in the GLIS3 gene on chromosome 9 (9p24.3-p23) in the human corresponding to chromosome 1 (q18) in the pig. A map of the transgene and its porcine genomic context is attached.

Using monohybrid analysis, Kim et al. (2003) found that GLIS3 could function as an activator and repressor of transcription. Deletion analysis showed that both the N and C termini were important for GLIS3 transactivation function.

Kim et al. (2003) determined that the GLIS3 gene spans more than 300 kb and contains 9 exons. Exons 2 through 4 encode the zinc finger domain.

By genomic sequence analysis, Kim et al. (2003) mapped the GLIS3 gene to human chromosome 9p24.3-p23. They mapped the mouse gene to chromosome 19C1.

Example 2

Establishing a Transgenic Porcine Fibroblast Cell Using Constructs for Site-Specific Recombination Based on the well-described mechanisms of SB transposition (4-8) and Flp recombination (9, 10), the present invention discloses a new target vector for site-specific integration into the genome. This vector carries within the context of a SB transposon vector a bicistronic gene cassette containing (i) the FRT recombination site embedded in the coding sequence of eGFP and (ii) an IRES-driven puromycin resistance gene. We demonstrate efficient selective plasmid insertion into SB-tagged genomic loci. In an attempt to further improve the performance of these vectors, we have analyzed the effect of insulator elements, believed to protect inserted foreign genes against transcriptional silencing, within the context of SB vectors. Our investigations indicate that insulators flanking the FRT gene expression cassette may serve to maintain and stabilize gene expression of Flp-inserted transgenes.

Two nonviral integration technologies are employed in the present invention, the SB transposon system and the Flp recombinase, in a combined effort to achieve active locus detection, mediated by SB, and site-directed insertion at an attractive site, mediated by Flp. A bi-phased technology is disclosed in which an integrating SB vector, carrying a reporter gene and a selective marker gene, may first serve as a reporter for continuous gene expression and hence as a target for gene insertion (FIG. 14). By using an actively integrated vector as opposed to plasmid DNA that is randomly recombined into the genome we certify (i) that only a single copy, and not concatemers, of the vector are inserted and, moreover, (ii) that the reporter cassette is not flanked by sequences derived from the bacterial plasmid backbone which may have a detrimental effect on the locus activity over time. In a second modification step this vector may serve as a target for insertion of one or more gene expression cassettes in a well-characterized locus.

Vector Construction

The SB transposon-based vector used in this study was derived from the pSBT/SV40-GFIP.IoxP vector. This vector contains, within the context of a SB transposon, a bicistronic FRTeGFP-IRES-puro (GFIP) cassette flanked upstream by an ATG start codon and downstream by a poly A sequence. Moreover, the vector contains a recognition site for the Cre recombinase (IoxP) located between the upper inverted repeat of the vector and the SV40 promoter driving expression of the FRTeGFP-IRES-puro cassette.

Construction of pSBT/SV40-GFIP.IoxP Vector

The pSBT/RSV-GFIP vector contains the terminal inverted of the SB DNA transposon flanking a FRT-GFP.IRES.puro bicistronic gene cassette driven by a promotor derived from Rous sarcoma virus (RSV). The eGFP sequence was amplified from peGFP.N1 (Clontech) using a forward primer containing the 48-bp FRT sequence. To analyze FRT-GFP functionality, the FRT-eGFP fusion was inserted into an expression vector containing the SV40 promoter. The PCR-fragment containing FRT-tagged eGFP fusion gene was digested with MluI and XmaI and inserted into MluI/XmaI-digested pSBT/RSV-hAAT (pT/hAAT in ref. (8), obtained from Mark Kay, Stanford University, USA), generating a transposon vector with RSV-driven eGFP expression (pSBT/RSV-eGFP). An IRES-puro cassette was PCR-amplified from pecoenv-IRES-puro (provided by Finn Skou Pedersen, University of Aarhus, Denmark), digested with XmaI, and inserted into XmaI-digested pSBT/RSV-eGFP, generating pSBT/RSV-GFIP (see FIG. 15). Alternative versions of this vector containing the SV40 promoter (pSBT/SV40-GFIP) and the promoter derived from the human ubiquitin gene (pSBT/Ubi-GFIP), were generated. In addition, by inserting a Cre recombination target site (IoxP) into the MluI site located between the left inverted repeat of the transposon and the SV40 promoter of pSBT/SV40-GFIP, the vector pSBT/SV40-GFIP.IoxP was created. The donor plasmid pcDNA5/FRT, containing a FRT-hygro fusion gene without a start codon, was obtained from Invitrogen. The Flp-encoding plasmid, pCMV-Flp was obtained from A. Francis Stewart, University of California San Francisco, USA). This plasmid encodes the enhanced Flp variant designated Flpx9 (11). A SB-vector containing two copies of the 1.2-kb chicken DNase hypersensitive site 4 (cHS4)-derived insulator element (12, 13) was generated by inserting PCR-amplified cHS4 sequences and an intervening linker into NotI/SpeI-digested pSBT/PGK-puro (obtained from Mark Kay, Stanford University, USA). The PGK-puro cassette was cloned back into construct by using restriction sites located in the linker, generating pSBT/cHS4.PGK-puro.cHS4

For further use in pigs an alternative Cre recognition site (IoxP-257) was inserted into a unique AscI site that was created by mutagenesis at a position located between the poly A sequence and the lower inverted repeat of the vector. This vector was designated pSBT/IoxP.SV40-GFIP.IoxP257. The presence of two Cre recombination sites allows Cre recombinase-mediated cassette exchange after Flp-based plasmid insertion, thereby facilitating, if needed, removal of plasmid sequences and selection genes.

SB Transposition in Primary Pig Fibroblasts

The SB transposon vectors, either SBT/PGK-puro or the target transposon SBT/IoxP.RSV-GFIP.IoxP257, were inserted into the genome of pig fibroblast by co-transfecting (using Fugene-6 from Roche) 1.5 μg pSBT/Iox.RSV-GFIP.IoxP257 (or pSBT/PGK-puro) with 1.5 μg pCMV-SB (or 1.5 μg pCMV-mSB as a negative control). pCMV-SB (rights held by Perry Hackett, University of Minnesota, Minnesota, USA) encodes the Sleeping Beauty transposase reconstructed from fossil DNA transposable elements of salmoid fish. pCMV-SB, pCMV-mSB, and the hyperactive variant pCMV-HSB3 were obtained from Mark Kay, Stanford University, USA. SB-tagged cell clones appeared as a result of selecting transfected cells with puromycin (0.5 μg/ml). Colonies were fixed and stained in methylene blue in methanol and subsequently counted.

Solid SB Transposition in Primary Pig Fibroblasts

SB transposes efficiently in most mammal cells but with higher efficacy in human cells than in murine cells. Transposition of SB vectors has never been analyzed in porcine cells, and we therefore initially tested activity in primary pig fibroblasts. We utilized a standard transposon encoding a puromycin resistance gene (SBT/PGK-puro) and found decent levels of transposition, resulting in about 75 drug-resistant colonies in cultures of fibroblasts co-transfected with pSBT/PGK-puro and pCMV-SB (FIG. 16). Less than 3 colonies appeared after transfection with pSBT/PGK-puro and pCMV-mSB, the latter which encodes an inactive version of the transposase. Interestingly, a mean of almost 140 colonies was obtained using the hyperactive transposase variant HSB3, indicating that HSB3 also in porcine cells mediates higher levels of transposition compared to the original SB transposase.

Efficient Insertion of a FRT-Tagged SB Vector in Pig Fibroblasts

To generate SB-tagged cell clones containing a Flp recombination target site for site-specific gene insertion, we co-transfected the pSBT/IoxP.SV40-IopP257 plasmid with pCMV-mSB, pCMV-SB, and pCMV-HSB3, respectively. HSB3 again showed the highest activity, resulting in about 30 drug-resistant colonies after transfection of 3 H $10^4$ fibroblasts (FIG. 17).

Puromycin-resistant colonies were isolated and expanded. Clone analysis by fluorescence microscopy demonstrated efficient FRTeGFP expression (FIG. 18), demonstrating vector functionality and easy FRTeGFP detection in pig fibroblasts. These fluorescent cell clones carrying the FIp FRT recombination sequence are currently being used for creation of cloned transgenic animals by hand-made cloning.

Verification of SBT/IoxP.SV40-GFIP.IoxP257 as Target for FIp Recombination

Due to limitations of long-term growth of primary pig fibroblasts in tissue culture we were not able to demonstrate Flp-based gene insertion into FRT-tagged SB vectors in pig fibroblasts. We therefore chose to test functionality of the FRT-containing vector by a standard set of recombination experiments carried out in HEK-293 cells. We generated clones of HEK-293 cells containing the transposed SBT/IoxP.SV40-GFIP.IoxP257 vector. By co-transfection of such clones with (i) a pcDNA5/FRT-derived substrate plasmid containing a FRT-hygro fusion gene and a red fluorescent protein (RFP) expression cassette and (ii) a plasmid encoding the FIp recombinase (pCMV-Flpx9), we subsequently identified hygromycin B resistant colonies. By fluorescence microscopy we observed that site-specifically engineered clones, as expected, turned-off eGFP expression and turned-on RFP expression (data not shown). This 'green-to-red' phenotypic change indicates that the integrated SB-derived target vector serves as acceptor site for Flp-based recombination.

Controlled Integration of Transgenes by Gene-Shifting

Some of the main concerns in creating transgenic cells and animals are the risk of disturbing the cells genome by random integration of the foreign DNA. Furthermore, expression of transgenes is often influenced by the site of integration, possibly leading to transgene silencing. Here we present a method, bypassing these problems by creating a gene shift with the help of the Sleeping Beauty (SB) DNA transposon technology and Flpe recombination. We inserted into HEK 293 cells a SB transposon containing an eGFP gene and an frt site. The frt site enables gene shifting with a donor plasmid containing the RFP gene as well as an frt site (see FIG. 19). Cells which underwent complete gene shifting, changed colour from green to red fluorescence and also changed antibiotic resistance, as the eGFP is linked to a puromycin resistance gene, and the RFP to a hygromycine B resistance gene. One clone with such characteristics was examined by LM-PCR and the location of the transposon, including the eGFP and frt site was found on chromosome 10. The insertion site showed typical signs of SB integration in the form of TA duplication flanked by distinctive consensus sequences. The transposon was sequenced before and after gene shifting, which confirmed that the transposon was intact, initially without the RFP gene, and with RFP after gene shifting (FIGS. 20 and 21).

These findings imply that gene shifting can be controlled at a precise place in the genome. The potential of SB and the transposon was investigated in minipig cells. The results showed that primary pig fibroblasts also support SB insertion thus creating a platform for gene shifting in pig cells (see FIG. 22). We prepared minipig cells for SB-mediated gene shifting, and by hand made cloning (HMC) we show that such cells give rise to viable blastocysts expressing the transgene (see FIG. 23).

In conclusion, the Sleeping Beauty DNA transposon-based vector of the present invention serves in its integrated form as a target for recombinase-based gene insertion. The SB vector is efficiently transferred by cut-and-paste transposition into the genome of primary porcine fibroblasts and therefore is not flanked by plasmid-derived bacterial sequences. Use of these genetically engineered primary cells in for example microinjection and hand-made cloning allows subsequent detailed analyses of SB vector-derived eGFP expression in cloned pigs and identification of animals with attractive expression profiles (e.g. ubiquitous, tissue-specific). Primary fibroblasts from such 'master pigs' is further modified by Flp-based recombination, allowing site-directed gene insertion in a SB vector-tagged locus which is not silenced in the tissue of interest. Cloned pigs harboring a site-specifically inserted disease gene of interest as described herein i.e. mutated APP or PS1 genes of procine or human origin or a shRNA expression cassette for downregulation of endogenous genes can be generated by a second round of animal cloning.

Example 3

Production of Pig Model by Handmade Cloning

Except where otherwise indicated all chemicals were obtained from Sigma Chemical Co. (St Louis, Mo., USA).

Oocyte Collection and In Vitro Maturation (IVM)

Cumulus-oocyte complexes (COCs) were aspirated from 2-6 mm follicles from slaughterhouse-derived sow or gilt ovaries. COCs were matured in groups of 50 in 400 μl bicarbonate-buffered TCM-199 (GIBCO BRL) supplemented with 10% (v/v) cattle serum (CS), 10% (v/v) pig follicular fluid, 10 IU/ml eCG, 5 IU/ml hCG (Suigonan Vet; Skovlunde, Denmark) at 38.5° C. in the "Submarine Incubation System" (SIS; Vajta, et al. 1997) in 5% $CO_2$ in humidified air for 41-44 hours.

In Vitro Fertilization (IVF)

IVF experiments were performed with in vitro matured oocytes in 3 identical replicates. After maturation, COCs were washed twice with mTBM containing 2 mM caffeine ($mTBM_{fert}$) and transferred in groups of 50 to 400 µl $mTBM_{fert}$. Freshly ejaculated semen was treated as described previously (Booth, et al., in press). After 2 h capacitation at 38.5° C. and in 5% $CO_2$ in humidified air, sperm was added to the oocytes with the adjusted final concentration of $1\times10^5$ sperm/ml. Fertilization was performed at 38.5° C. and in 5% $CO_2$ in humidified air in the SIS for 3 h. After the insemination, the presumptive zygotes were vortexed in $mTBM_{fert}$ to remove cumulus cells before washing in IVC medium and placing in culture dishes (see Embryo culture and evaluation).

Handmade Cloning (HMC)

The applied HMC method was based on our previous work in cattle and pig (Kragh, et al., 2004; Peura and Vajta, 2003; Vajta, et al., 2003), but with significant modifications. Briefly, at 41 h after the start of maturation, the cumulus investment of the COCs was removed by repeated pipetting in 1 mg/ml hyaluronidase in Hepes-buffered TCM199. From this point (except where otherwise indicated), all manipulations were performed on a heated stage adjusted to 39° C., and all drops used for handling oocytes were of 20 µl volume covered with mineral oil. Oocytes were briefly incubated in 3.3 mg/ml pronase dissolved in T33 (T for Hepes-buffered TCM 199 medium; the number means percentage (v/v) of CS supplement, here 33%) for 5 s. Before the oocytes started to become misshaped in pronase solution, they were picked out and washed quickly in T2 and T20 drops. Oocytes with partially digested but still visible zona were lined up in drops of T2 supplemented with 3 mg/ml polyvinyl alcohol (TPVA) and 2.5 µg/ml cytochalasin B. Trisection instead of bisection was performed manually under stereomicroscopic control with Ultra Sharp Splitting Blades (AB Technology, Pullman, Wash., USA; FIG. 25*a*). Fragments of trisected oocytes were collected and stained with 5 µg/ml Hoechst 33342 fluorochrome in TPVA drops for 5 min, then placed into 1 µl drops of the TPVA medium on the bottom of a 60 mm Falcon Petri dish covered with oil (3-4 fragments per drop). Using an inverted microscope and UV light, positions of fragments without chromatin staining (cytoplasts) were registered and later collected under a stereomicroscope in T10 drops until the start of the fusion.

Fetal Fibroblast Cells were Prepared as Described Previously (Kragh, et al., in Press).

Fusion was performed in two steps where the second one included the initiation of activation, as well. For the first step, one third of the selected cytoplasts (preferably the smaller parts) were used. With a finely drawn and fire-polished glass pipette, 10 cytoplasts were transferred as a group to 1 mg/ml of phytohaemagglutinin (PHA; ICN Pharmaceuticals, Australia) for 3 s, then quickly dropped onto one of the few fibroblast cells individually that were sedimented in a T2 drop. After attachment, 10 cytoplast-fibroblast cell pairs were equilibrated in fusion medium (0.3 M mannitol and 0.01% PVA) for 10 s. Using an alternative current (AC) of 0.6 KV/cm and 700 KHz, cell pairs were aligned to the wire of a fusion chamber (BTX microslide 0.5 mm fusion chamber, model 450; BTX, San Diego, Calif., USA) with the donor cells farthest from the wire (FIG. 25*b*), then fused with a direct current (DC) of 2.0 KV/cm for 9 µs. After the electrical pulse, cell pairs were removed carefully from the wire, transferred to T10 drops and incubated to observe whether fusion had occurred.

Approximately 1 hour after the first fusion, fused pairs together with the remaining two thirds of cytoplasts were equilibrated in activation medium drops separately (0.3 M mannitol, 0.1 mM $MgSO_4$, 0.1 mM $CaCl_2$ and 0.01% polyvinylalcohol (PVA)). Under a 0.6 KV/cm AC, cytoplast—fused pair—cytoplast triplets were aligned sequentially to the wire in groups of 10, with fused pairs located in the middle (FIG. 25*c*). A single DC pulse of 0.7 KV/cm for 80 µs was used for the second fusion and initiation of activation. The triplets were then removed from the wire and transferred carefully to T10 drops to check the fusion (FIG. 25*d*). Reconstructed embryos were incubated in culture medium (see Embryo culture and evaluation) supplemented with 5 µg/ml cytochalasin B and 10 µg/ml cycloheximide for 4 h at 38.5° C. in 5% $CO_2$, 5% $O_2$ and 90% $N_2$ with maximum humidity, then washed thoroughly for 3 times in IVC medium before culture.

Parthenogenetic Activation (PA)

Parthenogenetically activated oocytes were produced either separately or in parallel with HMC. Oocytes were denuded in the same way as above except that a longer incubation in pronase was used to get the zona pellucida completely removed. Zona free (ZF) oocytes were then equilibrated for 10 s in activation medium (0.3 M mannitol, 0.1 mM $MgSO_4$, 0.1 mM $CaCl_2$ and 0.01% PVA) and transferred to the fusion chamber (BTX microslide 0.5 mm fusion chamber, model 450; BTX, San Diego, Calif., USA). A single DC pulse of 0.85 KV/cm for 80 µs was generated with a BLS CF-150/B cell fusion machine (BLS, Budapest, Hungary) and applied to ZF oocytes. For zona intact (ZI) oocytes, a single DC pulse of 1.25 KV/cm for 80 µs was used (according to our unpublished preliminary experiments, these parameters resulted in the highest activation and subsequent in vitro development for ZI and ZF oocytes, respectively). The procedure after the electrical pulse was the same as for HMC reconstructed embryos.

Embryo Culture and Evaluation

All porcine embryos produced by the above treatments were cultured in a modified NCSU37 medium (Kikuchi, et al., 2002) containing 4 mg/ml BSA at 38.5° C. in 5% $O_2$, 5% $CO_2$ and 90% $N_2$ with maximum humidity. The culture medium was supplied with 0.17 mm sodium pyruvate and 2.73 mm sodium lactate from Day 0 (the day for fertilization and activation) to Day 2, then sodium lactate and sodium pyruvate was replaced with 5.5 mm glucose from Day 2 to Day 7. All ZF embryos were cultured in the WOW system (Vajta, et al., 2000) in the same culture medium and gas mixture as used above, with careful medium change on Day 2 without removing the embryos from the WOWs. The blastocyst rate was registered on Day 7. To determine total cell numbers, blastocysts were fixed and mounted to a glass microscopic slide in glycerol containing 20 µg/µl Hoechst 33342 fluorochrome. After staining for 24 h, embryos were observed under a Diaphot 200 inverted microscope with epifluorescent attachment and UV-2A filter (Nikon, Tokyo, Japan).

Example 3.1

Differences in developmental competence between sow (2.5 years, 170 Kg in weight) derived oocytes and gilt (5.5~6 months, 75 Kg in weight) derived oocytes were investigated through ZF and ZI PA after 44 h in vitro maturation. Four combined groups were investigated in 3 identical replicates: (1) ZF oocytes from sows (2) ZI oocytes from sows (3) ZF oocytes from gilts (4) ZI oocytes from gilts. For ZF activation, a single DC pulse of 0.85 KV/cm for 80 μs was applied, while a single 1.25 KV/cm pulse was used to activate ZI oocytes. Following 7 days culture as described above, the percentage of blastocysts per activated embryo was determined.

The in vitro developmental competence of parthenogenetically activated oocytes derived from either sows or gilts was investigated. As shown in Table 4, the blastocyst rates of parthenogenetically activated oocytes from sows were significantly higher than those from gilts, either after ZF or ZI PA.

TABLE 4

Blastocyst development of Day 7 parthenogenetically activated sow and gilt oocytes

| | Zona Free | | Zona Intact | |
|---|---|---|---|---|
| | No. of activated oocytes | No. of blastocysts (%)* | No. of activated oocytes | No. of blastocysts (%)* |
| sow | 103 | 43 (42 ± 4)$^a$ | 110 | 61 (55 ± 6)$^c$ |
| gilt | 85 | 17 (20 ± 2)$^b$ | 137 | 36 (26 ± 5)$^d$ |

$^{a,b}$Different superscripts mean significant differences ($p < 0.05$).

$^{c,d}$Different superscripts mean significant differences ($p < 0.05$).

*Percentage (Mean ± S.E.M) of embryos developed to blastocysts.

The difference in oocytes developmental competence between sows and gilts has been examined in in vitro production (IVP) and somatic cell nuclear transfer (SCNT) embryos separately, resulting in a similar conclusion as in the earlier publication of other research groups (Sherrer, et al., 2004; Hyun, et al., 2003), i.e. that embryos from sow-derived oocytes are superior to those from gilt-derived oocytes in supporting blastocyst development. Although gilts used in our study were at the borderline of maturity, the difference between Day 7 blastocyst rates after PA was significant, proving the superior developmental competence of sow oocytes.

Example 3.2

The feasibility of modified porcine HMC was investigated in 6 identical replicates, with IVF and in parallel ZF PA as controls. The more competent sow oocytes (according to Example 1) were used in Example 2. Seven days after reconstruction and/or activation, the number of blastocysts per reconstructed embryo and total cell numbers of randomly selected blastocysts were determined.

More than 90% of oocyte fragments derived from morphologically intact oocytes could be recovered for HMC after the trisection. In average, 37 embryos could be reconstructed out of 100 matured oocytes. The developmental competence of all sources of porcine embryos is shown in Table 5. On Day 7, the development of reconstructed embryos to the blastocyst stage was 17±4% with mean cell number of 46±5, while the blastocyst rates for IVF, and ZF PA were 30±6% and 47±4% (n=243, 170, 97) respectively.

TABLE 5

In vitro development of embryos produced by HMC, IVF and ZF PA

| Embryo origins | No. of embryos/oocytes in culture | No. of blastocysts | blastocyst rates (Mean ± S.E.M). | Mean cell number of blastocysts |
|---|---|---|---|---|
| HMC | 243 | 41 | 17 ± 4$^a$ | 46 ± 5$^d$ |
| IVF | 170 | 52 | 30 ± 6$^b$ | 74 ± 6$^e$ |
| ZF PA | 97 | 46 | 47 ± 4$^c$ | 53 ± 7$^d$ |

$^{a,b,c}$Different superscripts mean significant differences ($p < 0.05$).

$^{d,e}$Different superscripts mean significant differences ($p < 0.05$).

Although the theoretical maximum efficiency was still not approached, the integration of zona partial digestion and oocyte trisection almost doubled the number of reconstructed embryos compared to our earlier system (Kragh, et al., 2004 Reprod. Fertil. Dev 16, 315-318). This increase in reconstruction efficiency may have special benefits in porcine cloning since oocyte recovery after aspiration is more demanding and time-consuming than in cattle. An even more important point is the high embryo number required for establishment of pregnancies following porcine nuclear transfer. IVC in pigs is also regarded as a demanding and inefficient procedure (Reed, et al., 1992 Theriogeneology 37, 95-109). A disadvantage of ZF systems is that the embryos have to reach at least the compacted morula or early blastocyst stage in vitro to avoid disintegration in the oviduct without the protective layer of the zona pellucida. On the other hand, once in the blastocyst stage, zona free embryos can be transferred successfully as proved by calves born after either embryonic or somatic cell nuclear transfer (Peura et al., 1998; Tecirlioglu et al., 2004; Oback et al., 2003; Vajta, et al., 2004) and also by the piglets born after zona-free IVP of oocytes (Wu, et al., 2004). NCSU37 medium has been the most widely and successfully used medium for the culture of pig embryos. However, despite the improved embryo development compared with other media, the viability of IVP porcine embryos is still compromised after IVC. Some reports suggested that glucose is not metabolized readily by early porcine embryos before the eight-cell stage but used in higher amounts in embryos between the compacted morula and blastocysts stages (Flood, et al., 1988). The replacement of glucose with pyruvate and lactate in NCSU37 for the first 2 days culture resulted in a blastocyst rate of 25.3% for IVP porcine embryos in Kikuchi's study (Kukuchi, et al., 2002), which was further corroborated by our present studies with an IVP blastocysts rate of 30% in average. Moreover, the first evaluation of this sequential culture system on porcine HMC and ZF PA embryos has resulted in blastocyst rates of 17% and 47% respectively. Sometimes, the blastocyst rate of ZI PA could even reach levels as high as 90% (Du, unpublished)

Statistical Analysis

ANOVA analysis was performed using SPSS 11.0. A probability of P<0.05 was considered to be statistically significant.

Example 3.3

Vitrification of Hand-Made Cloned Porcine Blastocysts Produced from Delipated In Vitro Matured Oocytes Recently a noninvasive procedure was published for delipation of porcine embryos with centrifugation but without subsequent micromanipulation (Esaki et al. 2004 Biol Reprod. 71, 432-6).

Cryopreservation of embryos/blastocysts was carried out by vitrification using Cryotop (Kitazato Supply Co, Fujinomiya Japan) as described previously (Kuwayama et al. 2005a; 2005b). At the time of vitrification, embryos/blastocysts were transferred into equilibration solution (ES) consisting of 7.5% (V/V) ethylene glycol (EG) and 7.5% dimethylsulfoxide (DMSO) in TCM199 supplemented with 20% synthetic serum substitute (SSS) at 39° C. for 5 to 15 min. After an initial shrinkage, embryos regained their original volume. 4~6 embryos/blastocysts were transferred into 20 ul drop of vitrification solution (VS) consisting of 15% (V/V) EG and 15% (DMSO) and 0.5M sucrose dissolved in TCM199 supplemented with 20% SSS. After incubation for 20 s, embryos were loaded on Cryotop and plunged into liquid nitrogen. The process from exposure in VS to plunging was completed with 1 min.

Embryos/blastocysts were thawed by immersing Cryotop directly into thawing solution (TS) consisting of 1.0M sucrose in TCM199 plus 20% SSS for 1 min, then transferred to dilution solution (DS) consisting of 0.5 M sucrose in TCM199 plus 20% SSS for 3 min. To remove cryoprotectant, embryos/blastocysts were kept twice in a washing solution (WS; TCM199 plus 20% SSS), 5 min for each time. Survival of vitrified blastocysts was determined according to reexpansion rates after 24 h recovery in culture medium supplemented with 10% calf serum (CS).

The non-invasive delipation method was applied to in vitro matured porcine oocytes and further development of delipated oocytes after parthenogenetic activation was investigated in 4 identical replicates. Oocytes were randomly separated into delipation and control groups.

For delipation, oocytes were digested with 1 mg/ml pronase in the presence of 50% cattle serum (CS) for 3 min, and washed in Hepes-buffered TCM-199 medium supplemented with 20% CS which results in partial zona pellucida digestion (FIG. 25*a*). Subsequently 40-50 oocytes were centrifuged (12000×g, 20 min) at room temperature in Hepes-buffered TCM-199 medium supplemented with 2% CS, 3 mg/ml PVA and 7.5 μg/ml cytochalasin B (CB) (FIG. 25*b*). Zonae pellucidea of both centrifuged and intact oocytes were removed completely with further digestion in 2 mg/ml pronase solution. For activation, a single direct current of 85 Kv/cm for 80 us was applied to both groups, followed by 4 h treatment with 5 μg/ml CB and 10 μg/ml cycloheximide (CHX). All embryos were then cultured in the modified NCSU37 medium. Day 7 blastocysts were vitrified and warmed by using the Cryotop technique (Kuwayama et al., RBM Online, in press) at 38.5° C. Survival of vitrified blastocysts was determined according to reexpansion rates after 24 h recovery in culture medium supplemented with 10% CS. Cell numbers of reexpanded blastocysts from both groups were determined after Hoechst staining. Results were compared by ANOVA analysis. Partial zona digestion and centrifugation resulted in successful delipation in 173/192 (90%) of oocytes. The development to blastocysts was not different between delipated and intact oocytes (28±7% vs. 28±5% respectively; P>0.05). However, survival rates of blastocysts derived from delipated oocytes were significantly higher than those developed from intact oocytes (85±6% vs. 32±7% respectively; P<0.01). There is no difference in average cell number of reexpanded blastocysts derived from either delipated or intact oocytes (36±7 vs. 38±9, respectively; P>0.05). The results demonstrate that the simple delipation technique does not hamper the in vitro development competence of activated porcine oocytes, and improves the cryosurvival of the derived blastocysts without significant loss in cell number.

After delipation, zona pellucida of oocytes from both groups was removed completely. The same parameters as described above for electrical activation were applied to both groups. Seven days after activation, blastocyst rates and blastocyst cell numbers were determined.

The feasibility of applying a non-invasive delipation technique to in vitro matured porcine oocytes was investigated. 90% (173/192) oocytes can be delipated successfully. As shown in table 6, the development to blastocysts was not different between delipated and intact oocytes (28±7% vs. 28±5% respectively; P>0.05). However, survival rates of blastocysts derived from delipated oocytes were significantly higher than those developed from intact oocytes (85±6% vs. 32±7% respectively; P<0.01). There is no difference in average cell number of reexpanded blastocysts derived from either delipated or intact oocytes (36±7 vs. 38±9, respectively; P>0.05).

TABLE 6

Developmental competence and cryosurvival of vitrified-thawed embryos from delipated and intact activated oocytes.

| Oocyte treatment | Activated oocyte | Blastocyst rate (%) | Reexpanded blastocyst after warming (%) | Mean cell number of reexpanded blastocysts |
|---|---|---|---|---|
| Delipated | 173 | 28 ± 7 | 85 ± 6 | 36 ± 7 |
| Intact | 156 | 28 ± 5 | 32 ± 7 | 39 ± 9 |

Handmade Cloning of Delipated Oocytes

Delipated oocytes were used for HMC in 5 replicates. Four identical replicates of non-delipated oocytes for HMC were used as a control system. Seven days after reconstruction, blastocysts produced from both groups were vitrified with Cryotop. Survival rates and cell numbers of re-expanded blastocysts were determined as described for the blastocysts produced by PA.

Except where otherwise indicated, all manipulations were performed on a heated stage adjusted to 39° C., and all drops used for handling oocytes were of 20 μl volume covered with mineral oil. For somatic cell nuclear transfer, the handmade cloning (HMC) described in our previous work (Du, et al., 2005) was applied with a single modification: for enucleation of both delipated and control oocytes, bisection instead of trisection was applied.

Briefly, after the removal of cumulus investment, control oocytes were incubated in 3.3 mg/ml pronase dissolved in T33 for 10 s. Before the oocytes started to become misshaped in pronase solution, they were picked out and washed quickly in T2 and T20 drops. Delipated oocytes after centrifugation were digested in the 3.3 mg/ml pronase solution for an additional 5 s.

Both control and delipated oocytes with partially digested, distended and softened zonae pellucidae were lined up in T2 drops supplemented with 2.5 μg/ml cytochalasin B. Bisection was performed manually under stereomicroscopic control (FIG. 7*c*) with Ultra Sharp Splitting Blades (AB Technology, Pullman, Wash., USA). Halves were collected and stained with 5 μg/ml Hoechst 33342 fluorochrome in T2 drops for 5 min, and then placed into 1 μl drops of T2 medium on the bottom of a 60 mm Falcon Petri dish covered with oil (3-4 halves per drop). Using an inverted microscope and UV light, positions of halves without chromatin staining (cytoplasts) were registered. Cytoplasts were later collected under a stereomicroscope and stored in T10 drops.

Porcine foetal fibroblast cells were prepared with trypsin digestion from monolayers as described previously (Kragh, et al., 2005). Fusion was performed in two steps where the second one included the initiation of activation, as well. For the first step, 50% of the available cytoplasts were transferred into 1 mg/ml of phytohaemagglutinin (PHA; ICN Pharmaceuticals, Australia) dissolved in TO for 3 s, then quickly dropped over single fibroblast cells. After attachment, cytoplast-fibroblast cell pairs were equilibrated in fusion medium (0.3 M mannitol and 0.01% PVA) for 10 s and transferred to the fusion chamber. Using an alternating current (AC) of 0.6 KV/cm and 700 KHz, pairs were aligned to the wire of a fusion chamber with the somatic cells farthest from the wire (FIG. 25*d*), then fused with a direct current of 2.0 KV/cm for 9 μs. After the electrical pulse, cell pairs were removed carefully from the wire, transferred to T10 drops and incubated to observe whether fusion had occurred.

Approximately 1 hour after the first fusion, each pair was fused with another cytoplast in activation medium. AC current and a single DC pulse of 0.7 KV/cm for 80 μs were applied as described above. Fusion was detected in T10 drops, then reconstructed embryos were transferred into IVC0-2 medium (see Embryo culture and evaluation) supplemented with 5 μg/ml cytochalasin B and 10 μg/ml cycloheximide. After a 4 h incubation at 38.5° C. in 5% $CO_2$, 5% $O_2$ and 90% $N_2$ with maximum humidity, embryos were washed 3 times in IVC0-2 medium before culture.

TABLE 7

Developmental competence and cryosurvival of vitrified-thawed embryos of SCNT porcine embryos derived from delipated and intact oocytes.

| HMC group | No. of reconstructed embryos | Blastocyst rate (%)* | Reexpanded blastocyst after warming (%)* | Mean cell number of reexpanded blastocysts* |
|---|---|---|---|---|
| Delipated | 240 | 21 ± 6[a] | 79 ± 6[b] | 41 ± 7[d] |
| Intact | 150 | 23 ± 6[a] | 32 ± 8[c] | 39 ± 5[d] |

Different superscripts mean significant differences ($p < 0.05$).
*mean ± S.E.M.

In vitro developmental competence was observed in HMC with delipated oocytes when Day 7 blastocyst rates were compared with control HMC group (21±6% vs. 23±6% respectively; P>0.05; Table 7). Cryosurvival rate after vitrification of cloned blastocysts derived from delipated oocytes was significantly higher than those developed from intact oocytes (79±6% vs. 32±8, respectively; P<0.01).

Example 3.4

Chemically Assisted Handmade Enucleation (CAHE) and Comparison to Existing Methods After 41-42 h maturation in vitro, COCs were further cultured for 45 min in the same solution supplemented by 0.4 μg/ml demecolcine. Cumulus cells were then removed by pipetting in 1 mg/ml hyaluronidase dissolved in Hepes-buffered TCM-199. From this point (except where otherwise indicated), all manipulations were performed on a heated stage adjusted to 39° C. All drops used for handling oocytes were of 20 μl in volume, and were covered with mineral oil.

Basic steps of the HMC procedure have been described elsewhere herein. Briefly, oocytes without cumulus cells were incubated in 3.3 mg/ml pronase dissolved in T33 (T for Hepes-buffered TCM 199 medium; the number means percentage [v/v] of CS supplement, here 33%) for 20 s. When partial lyses of zonae pellucidae and slight deformation of oocytes occurred, they were picked up and washed quickly in T2 and T20 drops. Nine oocytes were lined up in one T2 drop supplemented with 2.5 μg/ml cytochalasin B (CB). By using a finely drawn and fire-polished glass pipette, oocytes were rotated to find a light extrusion cone and/or strongly attached polar body on the surface, and oriented bisection was performed manually under stereomicroscopic control with a microblade (AB Technology, Pullman, Wash., USA). Less than half of the cytoplasm (close to the extrusion or PB) was separated from the remaining part (FIG. 26). After bisection of all 9 oocytes in the drop, larger parts and smaller parts (with the extrusion or attached PB) were collected and placed into separate drops of T2, respectively.

Oriented Handmade Enucleation without Demecolcine Treatment (OHE)

All steps were similar to the previously described procedure, but demecolcine preincubation was not applied.

Random Handmade Bisection for Enucleation (RHE)

Demecolcine preincubation was omitted from the pretreatment of this group, as well. After removal of cumulus cells, zonae pellucidae were partially digested by pronase as described above. Random handmade equal bisection was applied in drops of T2 supplemented with 2.5 μg/ml CB. All demi-oocytes were selected and stained with 10 μg/ml Hoechst 33342 in T2 drops for 10 min, then placed into 1 μl drops of T2 medium covered with mineral oil (three demi-oocytes into each drop). Using an inverted microscope and UV light, the positions of chromatin free demi-oocytes, i.e. cytoplasts were registered. These cytoplasts were later collected under a stereomicroscope and stored in T2 drops before further manipulations.

Fusion and Initiation of Activation

Porcine fetal fibroblast cells were prepared as described previously (Kragh, et al., 2005, Du, et al., 2005). Fusion was performed in two steps, where the second one included the initiation of activation as well. For the first step, with a finely drawn and fire-polished glass pipette, approximately 100 somatic cells were placed into a T2 drop, and 20-30 cytoplasts were placed into a T10 drop. After a short equilibration, groups of 3 cytoplasts were transferred to 1 mg/ml of phytohaemagglutinin (PHA) for 2-3 sec, then each was quickly dropped over a single somatic cell. Following attachment, cytoplast-somatic cell pairs were picked up again and transferred to a fusion medium (0.3 M mannitol supplemented with 0.01% [w/v] PVA). By using an alternative current (AC) of 0.6 KV/cm and 700 KHz, equilibrated pairs were aligned to one wire of a fusion chamber (BTX microslide 0.5 mm fusion chamber, model 450; BTX, San Diego, Calif.) with the somatic cells farthest from the wire, then fused with a single direct current (DC) impulse of 2.0 KV/cm for 9 μsec. Pairs were then removed carefully from the wire to a T10 drop, and incubated further to observe whether fusion had occurred.

Approximately 1 h after the fusion, fused pairs and the remaining cytoplasts were separately equilibrated in activation medium (0.3 M mannitol, 0.1 mM $MgSO_4$, 0.1 mM $CaCl_2$, supplemented with 0.01% [w/v] PVA). By using a 0.6 KV/cm AC, one pair and one cytoplast was aligned to one wire of the fusion chamber, with fused pairs contacting the wire. A single DC pulse of 0.86 KV/cm for 80 μsec was used for the second fusion and initiation of activation. Fusion was checked in after incubation in T10 drops.

Traditional Cloning (TC)

Micromanipulation was conducted with a Diaphot 200 inverted microscope (Nikon, Tokyo, Japan), as described before (Chen et al., 1999; Zhang et al., 2005). Briefly, after 42-44 h in vitro maturation, the cumulus cells were removed as described above. All manipulations were performed on a heated stage adjusted to 39° C. A single 50 μL micromanipulation solution drop was made in the central area on a lid of 60 mm culture dish and covered with mineral oil. Groups of 20-30 oocytes and fetal fibroblast cells were placed in the same drop. After incubation for 15-30 min, the oocyte was secured with a holding pipette (inner diameter=25-35 μm and outer diameter=80-100 μm). After being placed at the position of 5-6 o'clock, the first polar body and the adjacent cytoplasm (approx. 10% of the total volume of the oocyte) presumptively containing metaphase plate were aspirated and removed with a beveled injection pipette (inner diameter=20 μm). A fetal fibroblast cell was then injected into the space through the same slit. After nuclear transfer (NT), reconstructed couplets were transferred into drops of media covered with mineral oil for recovery for 1-1.5 h until fusion and activation was conducted. The recovery medium was NCSU-23 supplemented with 4 mg/mL BSA and 7.5 μg/mL CB. Reconstructed couplets were incubated in fusion medium for 4 min. Couplets were aligned manually using a finely pulled and polished glass capillary to make the contact plane parallel to electrodes. A single, 30 μsec, direct current pulse of 2.0 kV/cm was then applied. After culture in drops of IVC0-2 (specified in "Embryo culture and evaluation") supplemented with 7.5 μg/mL CB for 30-60 min, fusion results were examined under a stereomicroscope. Fused couplets were subjected to a second pulse in activation solution. After 30 min incubation in T10 they were transferred to IVC0-2 to evaluate in vitro development.

Further Steps of Activation

After the activation impulse, all reconstructed embryos were incubated in IVC0-2 supplemented with 5 μg/ml CB and 10 μg/ml cycloheximide at 38.5° C. in 5% $CO_2$, 5% $O_2$, and 90% $N_2$, with maximum humidity.

Embryo Culture and Evaluation 4 h later, all reconstructed and activated embryos were washed and cultured in Nunc four-well dishes in 400 μl IVC0-2 covered by mineral oil at 38.5° C. in 5% $CO_2$, 5% $O_2$, and 90% $N_2$, with maximum humidity. IVC0-2 was a modified NCSU37 medium (Kikuchi, et al., 1999), containing 4 mg/ml BSA, 0.17 mM sodium pyruvate, and 2.73 mM sodium lactate from Day 0 (the day for activation) to Day 2. Sodium pyruvate and sodium lactate were replaced with 5.5 mM glucose from Day 2 to Day 7 (IVC2-7). All zonae free embryos were cultured in the Well of the Well (WOW) system (Vajta et al., 2000) in the same culture medium and gas mixture as used above, with careful medium change on Day 2 without removing the embryos from the WOWs. TC embryos were cultured in groups of 15 to 30 in wells of four-well dishes by using the same medium amount and composition. Cleavage and blastocyst rates were registered on Day 2 and Day 7, respectively. To determine total cell numbers, blastocysts were fixed and mounted to a glass microscope slide in a small amount (<2 μl) of glycerol containing 10 μg/ml Hoechst 33342. After staining for several hours at room temperature, embryos were observed under a Diaphot 200 inverted microscope with epifluorescent attachment and UV-2A filter (Nikon, Tokyo, Japan).

Comparison of Efficiency of CAHE vs. OHE

The efficiency and reliability of CAHE was tested in 12 identical replicates by using a total of 620 oocytes. After 41-42 h maturation, oocytes were subjected to demecolcine incubation. Oriented bisection was performed in oocytes where an extrusion cone and/or a strongly attached PB was detected after partial pronase digestion. Percentages of bisected vs. total oocytes and surviving vs. bisected oocytes were registered. Subsequently both putative cytoplasts and karyoplasts were collected separately and stained with Hoechst 33342 (10 μg/ml in T2 for 10 min). The presence or absence of chromatin was detected under an inverted fluorescent microscope (FIG. 27).

The efficiency and reliability of OHE was investigated in 9 identical replicates using a total of 414 oocytes. After 42-43 h in vitro maturation, oriented bisection was performed in matured oocytes where an extrusion cone and/or a PB was detected after partial pronase digestion. Results were evaluated as described in the previous paragraph.

The Results are Shown in Table 8.

TABLE 8

The efficiency of chemically assisted handmade enucleation (CAHE) and oriented handmade enucleation (OHE)

| Groups | No. of treated oocytes | Bisected/total oocytes (%)* | Cytoplast/bisection (%)* | Cytoplast/total oocyte (%)* |
|---|---|---|---|---|
| CAHE | 620 | 96 ± 1[a] | 94 ± 2[b] | 90 ± 3[c] |
| OHE | 414 | 92 ± 2[a] | 88 ± 3[b] | 81 ± 4[d] |

*mean ± A.D. (absolute deviations)
Different superscripts mean difference ($P < 0.05$)

No differences between groups regarding extrusion cones and/or attached polar bodies allowing oriented bisection or in the lysis rates were detected, and the successful enucleation per bisected oocyte ratio was also similar. However the overall efficiency of the procedure measured by the cytoplast per total oocyte number was higher in the CAHE than in the OHE group.

Comparison of In Vitro Development of Embryos Produced with CAHE, RHE and TC

In 8 replicates, a total of 468 in vitro matured oocytes were randomly distributed and subjected to three of the enucleation procedures described above. Fusion rates between cytoplast and donor fibroblasts were registered. Reconstructed embryos were activated and cultured as described earlier. Cleavage and blastocyst rates were determined on Day 2 and Day 7, respectively. Stereomicroscopic characteristics of the developed blastocysts were compared between groups.

TABLE 9

Developmental competence of embryos derived from chemically assisted handmade enucleation (CAHE), random handmade enucleation (RHE) and traditional, micromanipulator based cloning (TC).

| Groups | No. of reconstructed embryos | Fusion rate (%)* | Cleavage rate (%)* | Blastocyst rate (%)* | Cell no. of blastocysts (Day 7) |
|---|---|---|---|---|---|
| CAHE | 150 | 87 ± 7[a] | 97 ± 6[b] | 28 ± 9[d] | 57 ± 6[e] |
| RHE | 86 | 81 ± 4[a] | 87 ± 8[b] | 21 ± 9[d] | 49 ± 7[e] |
| TC | 178 | 81 ± 10[a] | 69 ± 9[c] | 21 ± 6[d] | 53 ± 6[e] |

*mean ± A.D. (absolute deviations)
Different superscripts mean difference ($P < 0.05$).

Fusion rates after enucleation were similar between CAHE, RHE and TC, respectively. The second fusion and activation resulted in negligible (<1%) losses in the first two groups. Although TC resulted in lower cleavage per reconstructed embryo rates than the other two groups, this difference was not present in the blastocyst per reconstructed embryo rates.

Stereomicroscopic characteristics (size; estimated proportion and outlines of the inner cell mass) did not differ between groups. Cell numbers (57±6 vs. 49±7 vs. 53±6) of the produced blastocysts from CAHE, RHE and TC are shown in Table 9, FIG. 28 and FIG. 29.

Statistical Analysis

AVEDEV was performed by Microsoft XP Excel software and ANOVA was performed by SAS system. A probability of $P<0.05$ was considered to be statistically significant.

Example 3.5

Production of Piglets

Handmade Cloning (HMC)

Forty one hrs after the start of in vitro maturation, the cumulus investment of the COCs was removed by repeated pipetting in 1 mg/ml hyaluronidase in Hepes-buffered TCM199. From this point (except where otherwise indicated) all manipulations were performed on a heated stage adjusted to 39° C., and all drops used for handling oocytes were of 20 μl volume covered with mineral oil. Oocytes were briefly incubated in 3.3 mg/ml pronase dissolved in T33 (T for Hepes-buffered TCM 199 medium; the number means percentage (v/v) of calf serum (CS) supplement, here 33%) for 20 sec and then quickly washed in T2 and T20 drops. Oocytes with partially digested but still visible zona were lined up in drops of T2 supplemented with 2.5 μg/ml cytochalasin B (CB). With a finely drawn and fire-polished glass pipette, oocytes were rotated to find the polar body (PB) on the surface, and oriented bisection was performed manually under stereomicroscopic control with a microblade (AB Technology, Pullman, Wash., USA). Thus, less than half of the oocyte cytoplasm (close to the extrusion or PB) was removed from the remaining putative cytoplast. Cytoplasts were washed twice in T2 drops and collected in a T10 drop.

Fetal fibroblast cells were prepared as described previously (Kragh, P. M. et al. *Theriogenology* 64, 1536-1545 (2005).

Fusion was performed in two steps where the second one included the initiation of activation, as well. For the first step, halves of putative cytoplasts were used. With a finely drawn and fire-polished glass pipette, 10 cytoplasts were transferred as a group to 1 mg/ml of phytohaemagglutinin (PHA; ICN Pharmaceuticals, Australia) for 3 sec, then quickly dropped individually onto one of the few fibroblast cells that were sedimented in a T2 drop. After attachment, 10 cytoplast-fibroblast cell pairs were equilibrated in fusion medium (0.3 M mannitol and 0.01% PVA) for 10 sec. Using an alternative current (AC) of 0.6 KV/cm and 700 KHz, cell pairs were aligned to the wire of a fusion chamber (BTX microslide 0.5 mm fusion chamber, model 450; BTX, San Diego, Calif., USA) with the somatic cells farthest from the wire, then fused with a direct current (DC) of 2.0 KV/cm for 9 μsec. After the electrical pulse, cell pairs were removed carefully from the wire, transferred to T10 drops and incubated to observe whether fusion had occurred.

Approximately 1 hr after the first fusion, fused pairs together with the remaining cytoplasts were equilibrated in activation medium drops separately (0.3 M mannitol, 0.1 mM $MgSO_4$, 0.1 mM $CaCl_2$ and 0.01% PVA). Under a 0.6 KV/cm AC, cytoplast—fused pair were aligned sequentially to the wire in groups of 10, with fused pairs far from the wire. A single DC pulse of 0.7 KV/cm for 80 μsec was used for the second fusion and initiation of activation. The pairs were then removed from the wire and transferred carefully to T10 drops to check the fusion. Reconstructed embryos were incubated in PZM-3 medium supplemented with 5 μg/ml CB and 10 μg/ml cycloheximide for 4 hr at 38.5° C. in 5% $CO_2$, 5% $O_2$ and 90% $N_2$ with maximum humidity, then washed thoroughly before culture.

Traditional Cloning (TC)

Micromanipulation was conducted with a Diaphot 200 inverted microscope (Nikon, Tokyo, Japan). Cumulus cells were removed as described above after 42 to 44 hr maturation. All manipulations were performed on a heated stage adjusted to 39□. A single 50 μL drop of micromanipulation solution (NCSU-23 supplemented with 4 mg/mL BSA and 7.5 μg/mL CB) was made in the central area on a lid of 60 mm culture dish and covered with mineral oil. Groups of 20 to 30 oocytes and fetal fibroblast cells were placed in the same drop. After incubation for 15 to 30 min, one oocyte was secured with a holding pipette (inner diameter=25-35 μm and outer diameter=80-100 μm). After being placed at the position of 5-6 o'clock, the first polar body and the adjacent cytoplasm (approx. 10% of the total volume of the oocyte) presumptively containing metaphase plate were aspirated and removed with a beveled injection pipette (inner diameter=20 μm). A fetal fibroblast cell was then injected into the space through the same slot. After nuclear transfer (NT), reconstructed couplets were transferred into drops of media covered with mineral oil for recovery for 1 to 1.5 hrs until fusion and activation was conducted. Reconstructed couplets were incubated in fusion medium for 4 min. Couplets were aligned manually using a finely pulled and polished glass capillary to make the contact plane parallel to electrodes. A single, 30 μsec, direct current pulse of 2.0 kV/cm was then applied. After culture in drops of PZM-3 medium supplemented with 7.5 μg/mL CB for 30-60 min, fusion results were examined under a stereomicroscope. Fused couplets were subjected to a second pulse in activation solution. After 30 min incubation in T10 they were transferred to PZM-3 medium to evaluate in vitro development.

Embryo Culture and Transfer

Reconstructed embryos were cultured in PZM-3 medium (Dobrinsky, J. T. et al. *Biol Reprod* 55, 1069-1074 (1996) supplemented with 4 mg/ml BSA. Zona-free embryos produced from HMC were cultured in the modified WOWs system (Feltrin, C. Et al. *Reprod Fertil Dev* 18, 126 (2006). Two different cell lines (LW1-2 for HMC, LW2 for TC) were used as nuclear donor cells for HMC and TC to allow the identification of the offspring from the two procedures. LW1-2 and LW2 originate from fetuses from a cross (with Duroc) and pure Danish landrace, respectively.

The average blastocyst per reconstructed embryo rate after in vitro culture for 7 days was 50.1±2.8% (mean±S.E.M), which is significantly higher ($p<0.01$) for HMC than that of TC performed in parallel in our laboratory (Table 10) and also the highest one that has ever been reported in pig cloning.

TABLE 10

In vitro development of embryos produced from handmade cloning and traditional cloning

| Group | Somatic cell donor | No. of reconstructed embryos | Cleavage rate (%) | Blastocyst rate (%) |
|---|---|---|---|---|
| HMC | LW1-2 | 643 | 83.7 ± 4.90[a] | 50.06 ± 2.80[a] |
| TC | LW2 | 831 | 74.86 ± 13.16[b] | 28.98 ± 2.84[b] |

[a,b]Values of different superscripts within columns are significantly different ($p < 0.05$).
*mean ± S.E.M.

Mixed blastocysts produced from both HMC and TC were surgically transferred to 11 naturally synchronized sows on Day 4 or 5 of estrous cycle. Six (55%) recipients were diagnosed pregnant by ultrasonography, 2 aborted and by the time of writing 2 have delivered 3 and 10 piglets, respectively. A litter size of 10 cloned piglets is, according to our knowledge, the largest litter size so far achieved in pig cloning. All of them are healthy and behave normally except one showed rigid flexure of distal joint of one foreleg. %).

Preliminary results suggest that when embryos of similar stages were transferred, recipients on Day 4 of the estrous cycle supported pregnancy establishment better than those of Day 5 (Table 11).

TABLE 11

In vivo development of cloned porcine embryos

| Recipient number | Embryos transferred HMC embryo | TC embryo | Embryo stage (Day) | Recipient cycle (Day) | Pregnancy status | No. of piglets born: piglets from HMC | No. piglets from TC | Gestation length (Day) |
|---|---|---|---|---|---|---|---|---|
| 1327 | 22 | 10 | D5, 6, 7 | 4 | Y | 2 | 1 | 116 |
| 1539 | 36 | 10 | D7 | 4 | Y | 8 | 2 | 115 |
| 1309 | 30 | 28 | D5, 6 | 4 | Y | | | |
| 1553 | 45 | 44 | D5, 6 | 4 | Y | | | |
| 1668 | 48 | 18 | D5, 6 | 5 | Y, aborted | | | |
| 1428 | 78 | 22 | D5, 6 | 5 | Y, aborted | | | |
| 1725 | 44 | 4 | D5, 6, 7 | 5 | N | — | — | — |
| 1643 | 22 | 11 | D5, 6, 7 | 4 | N | — | — | — |
| 1520 | 30 | 26 | D5, 6 | 4 | N | — | — | — |
| 1363 | 37 | 7 | D6, 7 | 5 | N | — | — | — |
| 1560 | 99 | 42 | D5, 6, 7 | 5 | N | — | — | — |

Microsatellite Analysis

Parental analysis using 10 different porcine microsatellite markers confirmed the identical genotype of cloned piglets and donor cells used for nuclear transfer. Identification was done by microsatellite analysis of genomic DNA from each of the newborn piglets, the surrogate sow, and the donor skin fibroblasts LW1-2 and LW2 originating from two fetuses that represent Danish landrace and Duroc, respectively. Ten polymorphic microsatellite loci (SW886, SW58, SW2116, SW1989, SW152, SW378, KS139, SO167, SW1987, SW957) located on different porcine chromosomes were amplified by 3-color multiplex PCR and the products analyzed on the Genetic Analyzer 3130 X1 (Applied Biosystems) using the program Gene Mapper 3.7.

For the second recipient, the offspring per embryo rate (22%) was the highest one ever reported so far in pig cloning (Walker, S. C. et al. *Cloning Stem Cells* 7, 105-112 (2005); Hoshino, Y. et al. *Cloning Stem Cells* 7, 17-26 (2005)). Comparable live birth/transferred embryo efficiencies were obtained in HMC (17%) and TC (15%).

Statistical Analysis

Differences between the experimental groups were evaluated using independent-samples t-test by SPSS 11.5. $P<0.05$ was considered significant.

REFERENCES

Alexander L J, Rohrer G A, Beattie C W. (1996): Cloning and characterization of 414 polymorphic porcine microsatellites. Anim Genet. 27(3):137-48.

Asami-Odaka et al 2005 Asami-Odaka A, Obayashi-Adachi Y, Matsumoto Y, Takahashi H, Fukumoto H, Horiguchi T, Suzuki N, Shoji M. (2005): Passive immunization of the Abeta42(43) C-terminal-specific antibody BC05 in a mouse model of Alzheimer's disease. Neurodegener Dis. 2(1):36-43Book, S. A. and Bustad, L. K. (1974). The fetal and neonatal pig in biomedical research. J. Anim. Sci. 38, 997-1002.

Braak H, Braak E (1991): Neuropathological staging of Alzheimer-related changes. Acta Neuropathol (Berl) 82:239-259

Chen Q, Kimura H, Schubert D. (2002): A novel mechanism for the regulation of amyloid precursor protein metabolism. J Cell Biol. 8; 158(1):79-89.

Doty R L, Shaman P, Kimmelman ChP, Dann M S (1984): University of Pennsylvania smell Identification Test: a rapid quantitative olfactory function test for the clinic. Laryngoscope 94: 176-178

Douglas, W. R. (1972). Of pigs and men and research: a review of applications and analogies of the pig, Sus Scrofa, in human medical research. Space Life Sci. 3, 226-234.

Eibenstein A, Fioretti A B, Lena C, Rosati N, Amabile G, Fusetti M (2005a): Modern psychophysical tests to assess olfactory function. Neurol Sci. 26:147-155

Eibenstein A, Fioretti A B, Simaskou M N, Sucapane P, Mearelli S, Mina C, Amabile G, Fusetti M (2005b): Olfactory screening test in mild cognitive impairment. Neurol Sci. 26:156-160

Games D, Adams D, Alessandrini R, Barbour R, Berthelette P, Blackwell C, Carr T, Clemens J, Donaldson T, Gillespie F, et al. (1995): Alzheimer-type neuropathology in transgenic mice overexpressing V717F beta-amyloid precursor protein. Nature. 373(6514):523-7.

Hagl C, Weisz D J, Khaladj N, Griepp M M, Spiegel D, Yang B-Y, de Asia R A, Bodian C A, Griepp R B (2005): Use of maze to detect cognitive dysfunction in a porcine model of hypothermic arrest. The Society of Thoracic Surgeons 79:1707-1715

Hardy J and D J Selkoe (2002): Normal and abnormal biology of the beta-amyloid precursor protein. Science. 2002 Jul. 19; 297(5580):353-6.

Holm I E, West M J (1994): The hippocampus of the domestic pig. A stereological study of the subdivisional volumes and neuron number. Hippocampus 4: 115-126

Jelsing, J., Olsen, A. K., Cumming, P., Gjedde, A., Hansen, A. K., Arnfred, S., Hemmingsen, R. and Pakkenberg, B. (2005a). A volumetric screening procedure for the Göttingen minipig brain. Exp. Brain Res. 162, 428-435.

Jelsing J, Nielsen R, Olsen A K, Grand N, Hemmingsen R, Pakkenberg B (2006): The postnatal development of neocortical neurons and glial cells in the Göttingen minipig and domestic pig brain. J. Exp. Biol. 209: 1454-1462

Levites et al 2006 Levites Y, Das P, Price R W, Rochette M J, Kostura L A, McGowan E M, Murphy M P, Golde T E. (2006): Anti-Abeta42- and anti-Abeta40-specific mAbs attenuate amyloid deposition in an Alzheimer disease mouse model. J Clin Invest. 116(1):193-201.

Mirra S S, Heyman A, McKeel D, Sumi S M, Crain B J, Brownlee L M, Vogel F S, Hughes J P, van Belle G, Berg L, and participating CERAD neuropathologists (1991): The Consortium to Establish a Registry for Alzheimer's Disease (CERAD). II. Standardization of the neuropathological assessment of Alzheimer's disease. Neurol. 41: 479-486

Moustgaard A, Lind N M, Hemmingsen R, Hansen A K (2002): Spontaneous object recognition in the Göttingen minipig. Neural Plasticity 9: 255-259

Mullan et al 1992 Mullan M, Crawford F, Axelman K, Houlden H, Lilius L, Winblad B, Lannfelt L. (1992): A pathogenic mutation for probable Alzheimer's disease in the APP gene at the N-terminus of beta-amyloid. Nat Genet. 1(5):345-7.

Needleman, S. B. and C. D. Wunsch (1970): A general method applicable to the search for similarities in the amino acid sequence of two proteins. Journal of Molecular Biology 48: 443-53.

Neve R L, E A Finch, L R Dawes (1988): Expression of□the Alzheimer amyloid precursor gene transcripts in the human brain. Neuron, Vol 1, 669-677, October 1988.

Oerum et al. 2006 Oerum M A, Bendixen C, Madsen L B, Larsen K. (2006): Porcine APP cDNAs: molecular cloning and characterization, expression analysis, chromosomal localization and SNP analysis. Biochim Biophys Acta. 1759(7):378-84

Pearson W R, Lipman D J. (1988): Improved tools for biological sequence comparison. Proc Natl Acad Sci USA. 85(8):2444-8.

Pillay P, Paul R. Manger (2007): Order-specific quantitative patterns of cortical gyrification European Journal of Neuroscience 25 (9), 2705-2712

Pond W G, Boleman S L, Fiorotto M L, Ho H, Knabe D A, Mersmann H J, Savell J W, Su D R. (2000): Perinatal ontogeny of brain growth in the domestic pig. Proc Soc Exp Biol Med. 223(1):102-8.

Price D L, Martin L J, Sisodia S S, Wagster M V, Koo E H, Walker L C, Koliatsos V E, Cork L C. (1991): Aged nonhuman primates: an animal model of age-associated neurodegenerative disease. Brain Pathol. 1(4):287-96.

Rockenstein et al 1995 Rockenstein E M, McConlogue L, Tan H, Power M, Masliah E, Mucke L. (1995): Levels and alternative splicing of amyloid beta protein precursor (APP) transcripts in brains of APP transgenic mice and humans with Alzheimer's disease. J Biol Chem. 270(47): 28257-67.

Rohrer et al 1994 Rohrer G A, Alexander L J, Keele J W, Smith T P, Beattie C W. (1994): A microsatellite linkage map of the porcine genome. Genetics. 136(1):231-45.

Sasahara M, Fries J W, Raines E W, Gown A M, Westrum L E, Frosch M P, Bonthron D T, Ross R, Collins T. (1991): PDGF B-chain in neurons of the central nervous system, posterior pituitary, and in a transgenic model. Cell. 64(1): 217-27.

Schenk et al 1999 Schenk D, Barbour R, Dunn W, Gordon G, Grajeda H, Guido T, Hu K, Huang J, Johnson-Wood K, Khan K, Kholodenko D, Lee M, Liao Z, Lieberburg I, Motter R, Mutter L, Soriano F, Shopp G, Vasquez N, Vandevert C, Walker S, Wogulis M, Yednock T, Games D, Seubert P. (1999): Immunization with amyloid-beta attenuates Alzheimer-disease-like pathology in the PDAPP mouse. Nature. 400(6740):173-7.

Selkoe D J. (1993): Physiological production of the beta-amyloid protein and the mechanism of Alzheimer's disease. Trends Neurosci. 16(10):403-9.

Selkoe D J (1994): Normal and abnormal biology of the beta-amyloid precursor protein. Annu Rev Neurosci. 1994; 17:489-517.

Sisodia S S. (1999): Alzheimer's disease: perspectives for the new millennium. J Clin Invest. 104(9):1169-70.

Smith T F, Waterman M S (1981). Identification of common molecular subsequences. J Mol Biol. 147(1):195-7.

Smith D H, Chen X H, Nonaka M, Trojanowski J Q, Lee V M, Saatman K E, Leoni M J, Xu B N, Wolf J A, Meaney D F (1999): Accumulation of amyloid beta and tau and the formation of neurofilament inclusions following diffuse brain injury in the pig. J. Neuropathol Exp Neurol. 58: 982-992

Tanzi R E, Wenniger J J, Hyman B T (1993): Cellular specificity and regional distribution of amyloid beta protein precursor alternative transcripts are unaltered in Alzheimer hippocampal formation. Brain Res Mol Brain Res. 18(3): 246-52.

Watanabe H, Andersen F, Simonsen C Z, Evans S M, Gjedde A, Cumming P; DaNeX Study Group (2001): MR-Based Statistical Atlas of the Göttingen Minipig Brain Neuroimage.; 14(5):1089-96.

National Institute on Aging Reagan Institute working Group on Diagnostic Criteria for the Neuropathological Assessment of Alzheimer's Disease (1997): Consensus recommendations for the post-mortem diagnosis of Alzheimer's Disease. Neurobiol Aging 18: S1-S3.

Bodyak N, Slotnick B (1999): Performance of mice in an automated olfactometer:odor detection, discrimination and odor memory. Chem. Senses 24:637-645.

Slotnick B, Bodyak N (2002): Odor discrimination and odor quality perception in rats with disruption of connections between the olfactory epithelium and olfactory bulbs. J. Neurosci. 22:4205-4216.

Doty R L, Shaman P, Kimmelman ChP, Dann M S (1984): University of Pennsylvania smell Identification Test: a rapid quantitative olfactory function test for the clinic. Laryngoscope 94: 176-178.

Eibenstein A, Fioretti A B, Lena C, Rosati N, Amabile G, Fusetti M (2005a): Modern psychophysical tests to assess olfactory function. Neurol Sci. 26:147-155.

Eibenstein A, Fioretti A B, Simaskou M N, Sucapane P, Mearelli S, Mina C, Amabile G, Fusetti M (2005b): Olfactory screening test in mild cognitive impairment. Neurol Sci. 26:156-160.

Hagl C, Weisz D J, Khaladj N, Griepp M M, Spiegel D, Yang B-Y, de Asia R A, Bodian C A, Griepp R B (2005): Use of maze to detect cognitive dysfunction in a porcine model of hypothermic arrest. The Society of Thoracic Surgeons 79:1307-1315.

Moustgaard A, Lind N M, Hemmingsen R Hansen A K (2002): Spontaneous object recognition in the Göttingen minipig. Neural Plasticity 9:255-259.

SEQUENCES

SEQ ID NO 1
Human APP mRNA isoform 770
LOCUS NM_000484 3641 bp mRNA linear PRI
26-MAR-2006

DEFINITION *Homo sapiens* amyloid beta (A4) precursor protein (peptidase nexin-II, Alzheimer disease) (APP), transcript variant 1, mRNA.
ACCESSION NM_000484
VERSION NM_000484.2 GI: 41406053
KEYWORDS .
SOURCE *Homo sapiens* (human)
FEATURES Location/Qualifiers
source 1 . . . 3641
/organism = "*Homo sapiens*"
/mol_type = "mRNA"
/db_xref = "taxon: 9606"
/chromosome = "21"
/map = "21q21.3"
gene 1 . . . 3641
/gene = "APP"
/note = "synonyms: AAA, AD1, PN2, ABPP, APPI, CVAP, ABETA, CTFgamma"
/db_xref = "GeneID: 351"
/db_xref = "HGNC: 620"
/db_xref = "HPRD: 00100"
/db_xref = "MIM: 104760"
CDS 195 . . . 2507
/gene = "APP"
/go_component = "cell surface [pmid 7593229]; coated pit; extracellular region [pmid 10806211]; integral to plasma membrane [pmid 10806211]; membrane"
/go_function = "copper ion binding; heparin binding; iron ion binding; metal ion binding; protein binding [pmid 2119582] [pmid 8626687] [pmid 10049767] [pmid 10081969] [pmid 14557245]; serine-type endopeptidase inhibitor activity [pmid 10652580] [pmid 11279603]; zinc ion binding"
/go_process = "apoptosis; cell adhesion; copper ion homeostasis [pmid 15910549]; endocytosis; neuromuscular physiological process [pmid 7593229]; Notch signaling pathway"
/note = "precursor, isoform a is encoded by transcript variant 1; amyloid beta (A4) precursor protein (protease nexin-II, Alzheimer disease); cerebral vascular amyloid peptide; amyloid-beta protein; beta-amyloid peptide; A4 amyloid protein"
/codon_start = 1
/product = "amyloid beta A4 protein precursor, isoform a"
/protein_id = "NP_000475.1"
/db_xref = "GI: 4502167"
/db_xref = "GeneID: 351"
/db_xref = "HGNC: 620"
/db_xref = "HPRD: 00100"
/db_xref = "MIM: 104760"
/translation = "MLPGLALLLLAAWTARALEVPTDGNAGLLAEPQIAMFCGRLNMH

MNVQNGKWDSDPSGTKTCIDTKEGILQYCQEVYPELQITNVVEANQPVTIQNWCKRGR

KQCKTHPHFVIPYRCLVGEFVSDALLVPDKCKFLHQERMDVCETHLHWHTVAKETCSE

KSTNLHDYGMLLPCGIDKFRGVEFVCCPLAEESDNVDSADAEEDDSDVWWGGADTDYA

-continued

DGSEDKVVEVAEEEEVAEVEEEEADDDEDDEDGDEVEEEAEEPYEEATERTTSIATTT

TTTTESVEEVVREVCSEQAETGPCRAMISRWYFDVTEGKCAPFFYGGCGGNRNNFDTE

EYCMAVCGSAMSQSLLKTTQEPLARDPVKLPTTAASTPDAVDKYLETPGDENEHAHFQ

KAKERLEAKHRERMSQVMREWEEAERQAKNLPKADKKAVIQHFQEKVESLEQEAANER

QQLVETHMARVEAMLNDRRRLALENYITALQAVPPRPRHVFNMLKKYVRAEQKDRQHT

LKHFEHVRMVDPKKAAQIRSQVMTHLRVIYERMNQSLSLLYNVPAVAEEIQDEVDELL

QKEQNYSDDVLANMISEPRISYGNDALMPSLTETKTTVELLPVNGEFSLDDLQPWHSF

GADSVPANTENEVEPVDARPAADRGLTTRPGSGLTNIKTEEISEVKMDAEFRHDSGYE

VHHQKLVFFAEDVGSNKGAIIGLMVGGVVIATVIVITLVMLKKKQYTSIHHGVVEVDA

AVTPEERHLSKMQQNGYENPTYKFFEQMQN"

```
sig_peptide   195 . . . 245
              /gene = "APP"
mat_peptide   246 . . . 2504
              /gene = "APP"
              /product = "amyloid beta A4 protein isoform a"
STS           1799 . . . 2462
              /gene = "APP"
              /standard_name = "GDB: 585471"
              /db_xref = "UniSTS: 157889"
STS           2442 . . . 3135
              /gene = "APP"
              /standard_name = "APP"
              /db_xref = "UniSTS: 266418"
STS           2493 . . . 2801
              /gene = "APP"
              /standard_name = "GDB: 185159"
              /db_xref = "UniSTS: 155415"
STS           2500 . . . 3385
              /gene = "APP"
              /standard_name = "APP_48"
              /db_xref = "UniSTS: 277004"
STS           2782 . . . 3062
              /gene = "APP"
              /standard_name = "GDB: 185158"
              /db_xref = "UniSTS: 155414"
STS           2800 . . . 2964
              /gene = "APP"
              /standard_name = "G34719"
              /db_xref = "UniSTS: 33374"
STS           2842 . . . 2964
              /gene = "APP"
              /standard_name = "D21S1968"
              /db_xref = "UniSTS: 79221"
STS           2932 . . . 3263
              /gene = "APP"
              /standard_name = "GDB: 192308"
              /db_xref = "UniSTS: 155706"
STS           3096 . . . 3231
              /gene = "APP"
              /standard_name = "WI-18826"
              /db_xref = "UniSTS: 9847"
STS           3161 . . . 3297
              /gene = "APP"
              /standard_name = "RH77727"
              /db_xref = "UniSTS: 67046"
STS           3212 . . . 3460
              /gene = "APP"
              /standard_name = "SHGC-52109"
              /db_xref = "UniSTS: 74484"
STS           3250 . . . 3332
              /gene = "APP"
              /standard_name = "RH67934"
              /db_xref = "UniSTS: 49337"
polyA_signal  3353 . . . 3358
              /gene = "APP"
polyA_site    3371
              /gene = "APP"
              /experiment = "experimental evidence, no additional
              details
              recorded"
```

-continued

```
polyA_signal  3604 . . . 3609
              /gene = "APP"
polyA_site    3624
              /gene = "APP"
              /experiment = "experimental evidence, no additional
              details
              recorded"
polyA_site    3627
              /gene = "APP"
     1 gctgactcgc ctggctctga gccccgccgc cgcgctcggg ctccgtcagt ttcctcggca

    61 gcggtaggcg agagcacgcg gaggagcgtg cgcgggggcc ccgggagacg gcggcggtgg

   121 cggcgcgggc agagcaagga cgcggcggat cccactcgca cagcagcgca ctcggtgccc

   181 cgcgcagggt cgcgatgctg cccggtttgg cactgctcct gctggccgcc
       tggacggctc

   241 gggcgctgga ggtacccact gatggtaatg ctggcctgct ggctgaaccc cagattgcca

   301 tgttctgtgg cagactgaac atgcacatga atgtccagaa tgggaagtgg
       gattcagatc

   361 catcagggac caaaacctgc attgatacca aggaaggcat cctgcagtat
       tgccaagaag

   421 tctaccctga actgcagatc accaatgtgg tagaagccaa ccaaccagtg
       accatccaga

   481 actggtgcaa gcggggccgc aagcagtgca agacccatcc ccactttgtg
       attccctacc

   541 gctgcttagt tggtgagttt gtaagtgatg cccttctcgt tcctgacaag
       tgcaaattct

   601 tacaccagga gaggatggat gtttgcgaaa ctcatcttca ctggcacacc
       gtcgccaaag

   661 agacatgcag tgagaagagt accaacttgc atgactacgg catgttgctg
       ccctgcggaa

   721 ttgacaagtt ccgaggggta gagtttgtgt gttgcccact ggctgaagaa
       agtgacaatg

   781 tggattctgc tgatgcggag gaggatgact cggatgtctg gtggggcgga
       gcagacacag

   841 actatgcaga tgggagtgaa gacaaagtag tagaagtagc agaggaggaa
       gaagtggctg

   901 aggtggaaga agaagaagcc gatgatgacg aggacgatga ggatggtgat
       gaggtagagg

   961 aagaggctga ggaaccctac gaagaagcca cagagagaac caccagcatt
       gccaccacca

  1021 ccaccaccac cacagagtct gtggaagagg tggttcgaga ggtgtgctct
       gaacaagccg

  1081 agacggggcc gtgccgagca atgatctccc gctggtactt tgatgtgact
       gaagggaagt

  1141 gtgccccatt cttttacggc ggatgtggcg gcaaccggaa caactttgac
       acagaagagt

  1201 actgcatggc cgtgtgtggc agcgccatgt cccaaagttt actcaagact
       acccaggaac

  1261 ctcttgcccg agatcctgtt aaacttccta caacagcagc cagtacccct
       gatgccgttg

  1321 acaagtatct cgagacacct ggggatgaga atgaacatgc ccatttccag
       aaagccaaag

  1381 agaggcttga ggccaagcac cgagagagaa tgtcccaggt catgagagaa
       tgggaagagg

  1441 cagaacgtca agcaaagaac ttgcctaaag ctgataagaa ggcagttatc
       cagcatttcc
```

-continued 1501 aggagaaagt ggaatctttg gaacaggaag cagccaacga gagacagcag ctggtggaga 1561 cacacatggc cagagtggaa gccatgctca atgaccgccg ccgcctggcc ctggagaact 1621 acatcaccgc tctgcaggct gttcctcctc ggcctcgtca cgtgttcaat atgctaaaga 1681 agtatgtccg cgcagaacag aaggacagac agcacaccct aaagcatttc gagcatgtgc 1741 gcatggtgga tcccaagaaa gccgctcaga tccggtccca ggttatgaca cacctccgtg 1801 tgatttatga gcgcatgaat cagtctctct ccctgctcta caacgtgcct gcagtggccg 1861 aggagattca ggatgaagtt gatgagctgc ttcagaaaga gcaaaactat tcagatgacg 1921 tcttggccaa catgattagt gaaccaagga tcagttacgg aaacgatgct ctcatgccat 1981 ctttgaccga aacgaaaacc accgtggagc tccttcccgt gaatggagag ttcagcctgg 2041 acgatctcca gccgtggcat tcttttgggg ctgactctgt gccagccaac acagaaaacg 2101 aagttgagcc tgttgatgcc cgccctgctg ccgaccgagg actgaccact cgaccaggtt 2161 ctgggttgac aaatatcaag acggaggaga tctctgaagt gaagatggat gcagaattcc 2221 gacatgactc aggatatgaa gttcatcatc aaaaattggt gttctttgca gaagatgtgg 2281 gttcaaacaa aggtgcaatc attggactca tggtgggcgg tgttgtcata gcgacagtga 2341 tcgtcatcac cttggtgatg ctgaagaaga aacagtacac atccattcat catggtgtgg 2401 tggaggttga cgccgctgtc accccagagg agcgccacct gtccaagatg cagcagaacg 2461 gctacgaaaa tccaacctac aagttctttg agcagatgca gaactagacc cccgccacag 2521 cagcctctga agttggacag caaaaccatt gcttcactac ccatcggtgt ccatttatag 2581 aataatgtgg gaagaaacaa acccgtttta tgatttactc attatcgcct tttgacagct 2641 gtgctgtaac acaagtagat gcctgaactt gaattaatcc acacatcagt aatgtattct 2701 atctctcttt acattttggt ctctatacta cattattaat gggttttgtg tactgtaaag 2761 aatttagctg tatcaaacta gtgcatgaat agattctctc ctgattattt atcacatagc 2821 cccttagcca gttgtatatt attcttgtgg tttgtgaccc aattaagtcc tactttacat 2881 atgctttaag aatcgatggg ggatgcttca tgtgaacgtg ggagttcagc tgcttctctt 2941 gcctaagtat tcctttcctg atcactatgc attttaaagt taaacatttt taagtatttc 3001 agatgcttta gagagatttt ttttccatga ctgcatttta ctgtacagat tgctgcttct 3061 gctatatttg tgatatagga attaagagga tacacacgtt tgtttcttcg tgcctgtttt -continued

```
3121 atgtgcacac attaggcatt gagacttcaa gcttttcttt ttttgtccac
     gtatctttgg

3181 gtctttgata aagaaaagaa tccctgttca ttgtaagcac ttttacgggg
     cgggtgggga

3241 ggggtgctct gctggtcttc aattaccaag aattctccaa aacaattttc
     tgcaggatga

3301 ttgtacagaa tcattgctta tgacatgatc gctttctaca ctgtattaca
     taaataaatt

3361 aaataaaata accccgggca agacttttct ttgaaggatg actacagaca
     ttaaataatc

3421 gaagtaattt tgggtgggga gaagaggcag attcaatttt ctttaaccag
     tctgaagttt

3481 catttatgat acaaaagaag atgaaaatgg aagtggcaat ataaggggat
     gaggaaggca

3541 tgcctggaca aacccttctt ttaagatgtg tcttcaattt gtataaaatg
     gtgttttcat

3601 gtaaataaat acattcttgg aggagcaaaa aaaaaaaaaa a
```

SEQ ID NO 2
Human Presenilin-1 (PS-1) mRNA
LOCUS NM_000021 2763 bp mRNA linear PRI
24-FEB-2008

DEFINITION *Homo sapiens* presenilin 1 (Alzheimer disease 3) (PSEN1), mRNA.
ACCESSION NM_000021
VERSION NM_000021.2 GI: 21536454
KEYWORDS
SOURCE *Homo sapiens* (human)
ORGANISM *Homo sapiens*
Eukaryota; Metazoa; Chordata; Craniata; Vertebrata; Euteleostomi;
Mammalia; Eutheria; Euarchontoglires; Primates; Haplorrhini;
Catarrhini; Hominidae; *Homo*.
REFERENCE 1 (bases 1 to 2763)
AUTHORS Sanchez-Valle, R., Llado, A., Ezquerra, M., Rey, M. J., Rami, L. and Molinuevo, J. L.
TITLE A novel mutation in the PSEN1 gene (L286P) associated with familial early-onset dementia of Alzheimer type and lobar haematomas
JOURNAL Eur. J. Neurol. 14 (12), 1409-1412 (2007)
PUBMED 18028191
REMARK GeneRIF: L286P is a novel mutation in PSEN1 that causes familial early-onset AD and brain haematomas related to amyloid angiopathy.
REFERENCE 2 (bases 1 to 2763)
AUTHORS Anheim, M., Hannequin, D., Boulay, C., Martin, C., Campion, D. and Tranchant, C.
TITLE Ataxic variant of Alzheimer's disease caused by Pro117Ala PSEN1 mutation
JOURNAL J. Neurol. Neurosurg. Psychiatr. 78 (12), 1414-1415 (2007)
PUBMED 18024701
REMARK GeneRIF: present study demonstrates that PSEN1 linked autosomal dominant early onset Alzheimer's disease has to be considered, even when ataxia precedes dementia, the Pro117Ala mutation being responsible for a predominant precocious ataxia
REFERENCE 3 (bases 1 to 2763)
AUTHORS Taniuchi, N., Niidome, T., Goto, Y., Akaike, A., Kihara, T. and Sugimoto, H.
TITLE Decreased proliferation of hippocampal progenitor cells in APPswe/PS1dE9 transgenic mice
JOURNAL Neuroreport 18 (17), 1801-1805 (2007)
PUBMED 18090315
REMARK GeneRIF: neurogenesis is decreased with degrees of Abeta pathology, -continued

```
            and that there is no gender difference in their
            proliferation in
            APPswe/PS1dE9 transgenic mice
REFERENCE   4 (bases 1 to 2763)
AUTHORS     Arango-Lasprilla, J. C., Cuetos, F., Valencia, C., Uribe, C.
            and
            Lopera, F.
TITLE       Cognitive changes in the preclinical phase of familial
            Alzheimer's
            disease
JOURNAL     J Clin Exp Neuropsychol 29 (8), 892-900 (2007)
PUBMED      17852592
REMARK      GeneRIF: Healthy carriers of the E280A presenilin-1 gene
            mutation
            scored significantly lower than noncarriers on naming of
            famous
            faces. Cognitive changes in lexical-semantic tasks can be
            detected
            before the clinical diagnosis of probable familial
            Alzheimer's.
REFERENCE   5 (bases 1 to 2763)
AUTHORS     Alberici, A., Bonato, C., Borroni, B., Cotelli, M.,
            Mattioli, F.,
            Binetti, G., Gennarelli, M., Luca, M. D., Simonati, A.,
            Perani, D.,
            Rossini, P. and Padovani, A.
TITLE       Dementia, delusions and seizures: storage disease or
            genetic AD?
JOURNAL     Eur. J. Neurol. 14 (9), 1057-1059 (2007)
PUBMED      17718701
REMARK      GeneRIF: We describe a case of a young patient suffering
            from a
            rapidly progressive cognitive decline, associated with
            delusions,
            myoclonus and seizures and with no family history for
            dementia
            anddemonstrated a de novo presenilin 1 mutation.
REFERENCE   6 (bases 1 to 2763)
AUTHORS     Sherrington, R., Rogaev, E. I., Liang, Y., Rogaeva, E. A.,
            Levesque, G.,
            Ikeda, M., Chi, H., Lin, C., Li, G., Holman, K. et al.
TITLE       Cloning of a gene bearing missense mutations in early-
            onset
            familial Alzheimer's disease
JOURNAL     Nature 375 (6534), 754-760 (1995)
PUBMED      7596106
REFERENCE   7 (bases 1 to 2763)
AUTHORS     St George-Hyslop, P., Haines, J., Rogaev, E., Mortilla, M.,
            Vaula, G.,
            Pericak-Vance, M., Foncin, J. F., Montesi, M., Bruni, A.,
            Sorbi, S. et
            al.
TITLE       Genetic evidence for a novel familial Alzheimer's disease
            locus on
            chromosome 14
JOURNAL     Nat. Genet. 2 (4), 330-334 (1992)
PUBMED      1303289
REFERENCE   8 (bases 1 to 2763)
AUTHORS     Schellenberg, G. D., Bird, T. D., Wijsman, E. M., Orr, H. T.,
            Anderson, L.,
            Nemens, E., White, J. A., Bonnycastle, L., Weber, J. L.,
            Alonso, M. E. et
            al.
TITLE       Genetic linkage evidence for a familial Alzheimer's
            disease locus
            on chromosome 14
JOURNAL     Science 258 (5082), 668-671 (1992)
PUBMED      1411576
REFERENCE   9 (bases 1 to 2763)
AUTHORS     Schellenberg, G. D., Boehnke, M., Wijsman, E. M., Moore, D. K.,
            Martin, G. M. and Bird, T. D.
TITLE       Genetic association and linkage analysis of the
            apolipoprotein CII
            locus and familial Alzheimer's disease
JOURNAL     Ann. Neurol. 31 (2), 223-227 (1992)
PUBMED      1349467
COMMENT     REVIEWED REFSEQ: This record has been curated by NCBI
            staff. The
            reference sequence was derived from L42110.1.
            On Jun 21, 2002 this sequence version replaced gi: 4506162.
            Summary: Alzheimer's disease (AD) patients with an
```

-continued inherited form
of the disease carry mutations in the presenilin proteins
(PSEN1;
PSEN2) or in the amyloid precursor protein (APP). These
disease-linked mutations result in increased production of
the
longer form of amyloid-beta (main component of amyloid
deposits
found in AD brains). Presenilins are postulated to
regulate APP
processing through their effects on gamma-secretase, an
enzyme that
cleaves APP. Also, it is thought that the presenilins are
involved
in the cleavage of the Notch receptor, such that they
either
directly regulate gamma-secretase activity or themselves
are
protease enzymes. Multiple alternatively spliced
transcript
variants have been identified for this gene, the full-
length
natures of only some have been determined.
Publication Note: This RefSeq record includes a subset of
the
publications that are available for this gene. Please see
the
Entrez Gene record to access additional publications.
COMPLETENESS: full length.

```
FEATURES     Location/Qualifiers
source       1 . . . 2763
             /organism = "Homo sapiens"
             /mol_type = "mRNA"
             /db_xref = "taxon: 9606"
             /chromosome = "14"
             /map = "14q24.3"
gene         1 . . . 2763
             /gene = "PSEN1"
             /note = "presenilin 1 (Alzheimer disease 3);
             synonyms: AD3,
             FAD, PS1, S182"
             /db_xref = "GeneID: 5663"
             /db_xref = "HGNC: 9508"
             /db_xref = "HPRD: 00087"
             /db_xref = "MIM: 104311"
exon         1 . . . 113
             /gene = "PSEN1"
             /inference = "alignment: Splign"
             /number = 1
exon         114 . . . 195
             /gene = "PSEN1"
             /inference = "alignment: Splign"
             /number = 2
exon         196 . . . 335
             /gene = "PSEN1"
             /inference = "alignment: Splign"
             /number = 3
CDS          249 . . . 1652
             /gene = "PSEN1"
             /codon_start = 1
             /product = "presenilin 1"
             /protein_id = "NP_000012.1"
             /db_xref = "GI: 4506163"
             /db_xref = "CCDS: CCDS9812.1"
             /db_xref = "GeneID: 5663"
             /db_xref = "HGNC: 9508"
             /db_xref = "HPRD: 00087"
             /db_xref = "MIM: 104311"
/translation = "MTELPAPLSYFQNAQMSEDNHLSNTVRSQNDNRERQEHNDRRSL

GHPEPLSNGRPQGNSRQVVEQDEEEDEELTLKYGAKHVIMLFVPVTLCMVVVVATIKS

VSFYTRKDGQLIYTPFTEDTETVGQRALHSILNAAIMISVIVVMTILLVVLYKYRCYK

VIHAWLIISSLLLLFFFSFIYLGEVFKTYNVAVDYITVALLIWNFGVVGMISIHWKGP

LRLQQAYLIMISALMALVFIKYLPEWTAWLILAVISVYDLVAVLCPKGPLRMLVETAQ

ERNETLFPALIYSSTMVWLVNMAEGDPEAQRRVSKNSKYNAESTERESQDTVAENDDG

GFSEEWEAQRDSHLGPHRSTPESRAAVQELSSSILAGEDPEERGVKLGLGDFIFYSVL
```

-continued

```
VGKASATASGDWNTTIACFVAILIGLCLTLLLLAIFKKALPALPISITFGLVFYFATD

                    YLVQPFMDQLAFHQFYI"

misc_feature  324 . . . 335
              /gene = "PSEN1"
              /note = "sequence not found in isoforms I-463 and
              I-374;
              Region: exon 4"
exon          336 . . . 586
              /gene = "PSEN1"
              /inference = "alignment: Splign"
              /number = 4
exon          587 . . . 728
              /gene = "PSEN1"
              /inference = "alignment: Splign"
              /number = 5
exon          729 . . . 796
              /gene = "PSEN1"
              /inference = "alignment: Splign"
              /number = 6
exon          797 . . . 1017
              /gene = "PSEN1"
              /inference = "alignment: Splign"
              /number = 7
STS           907 . . . 1010
              /gene = "PSEN1"
              /standard_name = "D14S1440"
              /db_xref = "UniSTS: 153983"
exon          1018 . . . 1116
              /gene = "PSEN1"
              /inference = "alignment: Splign"
              /number = 8
exon          1117 . . . 1203
              /gene = "PSEN1"
              /inference = "alignment: Splign"
              /number = 9
exon          1204 . . . 1377
              /gene = "PSEN1"
              /inference = "alignment: Splign"
              /number = 10
exon          1378 . . . 1496
              /gene = "PSEN1"
              /inference = "alignment: Splign"
              /number = 11
exon          1497 . . . 2763
              /gene = "PSEN1"
              /inference = "alignment: Splign"
              /number = 12
STS           1741 . . . 1942
              /gene = "PSEN1"
              /standard_name = "SHGC-31609"
              /db_xref = "UniSTS: 35446"
STS           1910 . . . 2754
              /gene = "PSEN1"
              /standard_name = "PSEN1_232"
              /db_xref = "UniSTS: 277618"
polyA_site    2763
              /gene = "PSEN1"
ORIGIN
    1  tgggacaggc agctccgggg tccgcggttt cacatcggaa acaaaacagc ggctggtctg

   61  gaaggaacct gagctacgag ccgcggcggc agcggggcgg cggggaagcg tatacctaat

  121  ctgggagcct gcaagtgaca acagcctttg cggtccttag acagcttggc ctggaggaga

  181  acacatgaaa gaaagaacct caagaggctt tgttttctgt gaaacagtat ttctatacag

  241  ttgctccaat gacagagtta cctgcaccgt tgtcctactt ccagaatgca cagatgtctg

  301  aggacaacca cctgagcaat actgtacgta gccagaatga caatagagaa cggcaggagc

  361  acaacgacag acggagcctt ggccaccctg agccattatc taatggacga ccccagggta

  421  actcccggca ggtggtggag caagatgagg aagaagatga ggagctgaca ttgaaatatg

  481  gcgccaagca tgtgatcatg ctctttgtcc ctgtgactct ctgcatggtg gtggtcgtgg

  541  ctaccattaa gtcagtcagc ttttataccc ggaaggatgg gcagctaatc tataccccat
```

-continued

```
 601 tcacagaaga taccgagact gtgggccaga gagccctgca ctcaattctg aatgctgcca
 661 tcatgatcag tgtcattgtt gtcatgacta tcctcctggt ggttctgtat aaatacaggt
 721 gctataaggt catccatgcc tggcttatta tatcatctct attgttgctg ttcttttttt
 781 cattcattta cttgggggaa gtgtttaaaa cctataacgt tgctgtggac tacattactg
 841 ttgcactcct gatctggaat tttggtgtgg tgggaatgat ttccattcac tggaaaggtc
 901 cacttcgact ccagcaggca tatctcatta tgattagtgc cctcatggcc ctggtgttta
 961 tcaagtacct ccctgaatgg actgcgtggc tcatcttggc tgtgatttca gtatatgatt
1021 tagtggctgt tttgtgtccg aaaggtccac ttcgtatgct ggttgaaaca gctcaggaga
1081 gaaatgaaac gctttttcca gctctcattt actcctcaac aatggtgtgg ttggtgaata
1141 tggcagaagg agacccggaa gctcaaagga gagtatccaa aaattccaag tataatgcag
1201 aaagcacaga aagggagtca caagacactg ttgcagagaa tgatgatggc gggttcagtg
1261 aggaatggga agcccagagg gacagtcatc tagggcctca tcgctctaca cctgagtcac
1321 gagctgctgt ccaggaactt tccagcagta tcctcgctgg tgaagaccca gaggaaaggg
1381 gagtaaaact tggattggga gatttcattt tctacagtgt tctggttggt aaagcctcag
1441 caacagccag tggagactgg aacacaacca tagcctgttt cgtagccata ttaattggtt
1501 tgtgccttac attattactc cttgccattt tcaagaaagc attgccagct cttccaatct
1561 ccatcacctt tgggcttgtt ttctactttg ccacagatta tcttgtacag ccttttatgg
1621 accaattagc attccatcaa ttttatatct agcatatttg cggttagaat cccatggatg
1681 tttcttcttt gactataaca aaatctgggg aggacaaagg tgattttcct gtgtccacat
1741 ctaacaaagt caagattccc ggctggactt ttgcagcttc cttccaagtc ttcctgacca
1801 ccttgcacta ttggactttg gaaggaggtg cctatagaaa acgattttga acatacttca
1861 tcgcagtgga ctgtgtccct cggtgcagaa actaccagat ttgagggacg aggtcaagga
1921 gatatgatag gcccggaagt tgctgtgccc catcagcagc ttgacgcgtg gtcacaggac
1981 gatttcactg acactgcgaa ctctcaggac taccgttacc aagaggttag gtgaagtggt
2041 ttaaaccaaa cggaactctt catcttaaac tacacgttga aaatcaaccc aataattctg
2101 tattaactga attctgaact tttcaggagg tactgtgagg aagagcaggc accagcagca
2161 gaatggggaa tggagaggtg ggcaggggtt ccagcttccc tttgattttt tgctgcagac
2221 tcatcctttt taaatgagac ttgttttccc ctctctttga gtcaagtcaa atatgtagat
2281 tgcctttggc aattcttctt ctcaagcact gacactcatt accgtctgtg attgccattt
2341 cttcccaagg ccagtctgaa cctgaggttg ctttatccta aaagttttaa cctcaggttc
2401 caaattcagt aaattttgga aacagtacag ctatttctca tcaattctct atcatgttga
2461 agtcaaattt ggatttccca ccaaattctg aatttgtaga catacttgta cgctcacttg
2521 ccccagatgc ctcctctgtc ctcattcttc tctcccacac aagcagtctt tttctacagc
2581 cagtaaggca gctctgtcgt ggtagcagat ggtcccatta ttctagggtc ttactctttg
2641 tatgatgaaa agaatgtgtt atgaatcggt gctgtcagcc ctgctgtcag accttcttcc
2701 acagcaaatg agatgtatgc ccaaagcggt agaattaaag aagagtaaaa tggctgttga
2761 agc
```

SEQ ID NO 3:
Porcine APP mRNA isoform 770

```
   1 acgcgaacag cagcgcactc ggtgccccgc gcagggtcgc gatgctgccc ggtttggcac
  61 tggtcctgct ggccgcctgg acggctaggg cgctggaggt gcccactgat ggcaatgccg
 121 gcctgcttgc agaaccccag gttgccatgt tctgtggcaa actcaacatg cacatgaatg
```

-continued

```
 181 tgcagaatgg gaagtgggag tcagatccgt cggggaccaa aacctgcatt ggcaccaagg
 241 aaggcatctt gcagtactgc caagaagtct accctgaact gcagatcacc aatgtggtag
 301 aagccaacca accagtgacc atccagaact ggtgcaagag gagccggaag cagtgcaaga
 361 cccacactca cattgtgatt ccgtaccgct gcttagttgg cgagtttgta agcgatgccc
 421 tccttgttcc ggacaagtgc aagttcttac accaggagag gatggatgtt tgcgaaaccc
 481 accttcactg gcacactgtg gccaaagaga cctgtagtga gaagagtacg aacttgcatg
 541 actatggcat gttgctgccc tgtggaattg acaagttccg aggggtggag tttgtgtgtt
 601 gcccactggc cgaggaaagt gacaatatcg actcagcaga tgcagaagag gatgactcgg
 661 acgtctggtg gggtggagca gatacagact atgcagatgg cagtgaagac aaagtcgtgg
 721 aggtcgcaga ggaggaggaa gtggctgatg tcgaggaaga agaagctgag gatgatgagg
 781 atgatgagga tggtgatgag gtagaagaag aggctgagga accctatgaa gaggccacgg
 841 agagaaccac cagcatcgcc acaaccacca ccaccaccac ggagtctgtg gaagaggtgg
 901 tccgagaggt gtgctctgaa caagccgaga cggggccgtg ccgagcaatg atctcccgct
 961 ggtactttga tgtgactgaa gggaagtgcg ccccgttctt ttacggcgga tgtggcggca
1021 accgaaacaa ctttgacaca gaggaatact gcatggccgt gtgtggcagc gtcatgtccc
1081 aaagtttact caagactacc caggaacatc ttccccaaga tcctgttaaa cttcctacaa
1141 cagcagccag caccccagat gccgttgaca agtatcttga gacacctgga gatgagaacg
1201 aacatgcgca tttccagaaa gccaaagaga ggctggaggc caagcaccgc gagagaatgt
1261 cccaggtcat gagagagtgg gaagaggcag aacgtcaagc aaagaacttg cctaaagctg
1321 ataagaaagc agtgatccag catttccagg agaaagtgga gtctctggag caggaagcag
1381 ccaacgagag gcagcagttg gtggagacgc acatggccag agtggaggcc atgcttaacg
1441 accgccggcg cctggccctg gagaattaca tcacggctct tcaggctgtt cctcctcggc
1501 ctcgtcatgt gttcaacatg ctcaagaagt atgtccgtgc cgaacagaaa gacagacagc
1561 acaccctaaa gcattttgaa cacgttcgca tggtagatcc aaagaaagct gctcagatcc
1621 gatcccaggt tatgacacac ctccgtgtga tttacgagcg catgaaccag tctctctccc
1681 tgctctacaa cgttcctgct gtggctgagg aaattcagga tgaagttgat gagctgctgc
1741 agaaagagca aaactactcg gatgatgtct tggccaacat gatcagcgaa ccgaggatca
1801 gttatggaaa cgatgctctc atgccgtctc tgactgaaac caaaaccacc gtggagcttc
1861 ttcctgtgaa tggagagttc agcctggatg atctccagcc ctggcatcct tttggggtag
1921 actctgtgcc tgccaacaca gaaaatgaag tcgagcctgt tgacgcccgc cctgcagccg
1981 accgaggact gaccactcga ccaggttccg ggttgaccaa catcaagacg gaagagatct
2041 ctgaagtgaa gatggatgeg gagttccgac acgattcagg ctatgaggtt catcaccaaa
2101 aactggtgtt cttcgcagaa gatgtgggtt caaacaaagg tgccatcatt ggactcatgg
2161 tgggtggtgt tgtcatagca accgtgattg tcatcacctt agtgatgctg aagaagaaac
2221 agtacacatc catccatcac ggtgtggtgg aggttgacgc agctgtgacc ccggaggagc
2281 gccacctctc caagatgcag cagaatggct atgaaaaccc aacttacaag ttctttgagc
2341 agatgcagaa ctagaccgcc gccacagcag cctctgaagt tggacagcaa aaccattgct
2401 tcactaccca ttggtgttca tttatagaat aatggggaaa gacacaaacc cttctgtttt
2461 attatttact catgatcgcc tttcagcagc tgtgctgtaa cacaagtaga tgcctgaact
2521 tgaattaata ttacgaatca gtaatgtatt ctctctcttt acatttccgg tctctacact
```

-continued

```
2581 acattattaa tgggttttgt gtactgtaaa gaatgaagct gtatcaaact agtgcatgaa
2641 tagattccct cctgattatt tatcatgtag cccccttagcc agttgtatat tattcttgtg
2701 gttttgtgat ccaattaagt cctactttga aatatgcttt aagaatcgat gggggatgct
2761 tcatgtgaac gtgggagttt agctgcttct cttgcctaag tattcttttc ctgatcacta
2821 tgcattttaa aggtaaacat ttttatgtat tccaaatgag ttagagaagt tttttccacg
2881 attgcatttg actgtacaga ttgctgcttc tgctatattt gtgatatagg aattatgagg
2941 atacacgttt atttctttgt gcctgtttta tgtgcacaca ttaggcattg agaattaaaa
3001 cttcttttgt ccgtgtacct tcggatcttt aaaaaaaaaa aaaaaaaaaa a
```

SEQ ID NO 4
porcine Presenilin-1 (PS-1) mRNA

```
   1 aatcggaaac aaaacagcgg ctgctgggga agggacctgg gctgcgagag gtggcggctg
  61 cgacgagaaa gaacctaatc cgggagcctg caacctgtga agttcttaga aagcttggcc
 121 tggaggagaa cacatgaaag aaagaacccc aggaggctct gatttctgtg aaaaagtatt
 181 tctatacggt tgttccaatg acagagttac ctgcaccctt gtcctacttc cagaatgccc
 241 agatgtccga ggacaaccac gtgagcaata acgtaagtag ccagaatgac agtagagagc
 301 ggcatgagca cagcatcgag aggcggaggc gtggcaactc tgagtcgtta tccaatggcg
 361 gagcccaggg aaactcacgc caggtggtgg aacaagaaga agaggaagac gaggagctga
 421 cgttgaaata tggcgccaaa catgtgatca tgctctttgt ccctgtgact ctatgtatgg
 481 tggtggttgt ggccaccatc aaatcagtca gcttttatac ccggaaggat gggcagctga
 541 tctatactcc atttacagaa gacactgaga ctgtagggca gagagccctg cactcaattc
 601 tgaatgctgc tatcatgatt agtgtcattg tcgtcatgac tattctcctg gtggttctct
 661 ataaatacag gtgctataag gtcatccatg cctggcttat tatttcatcc ctattgttgc
 721 tgttcttttt ctcattcatt tacttggggg aagtgtttaa aacctataac gttgccatgg
 781 attacattac ggtggcactc ctgatctgga attttggtgt ggtaggaatg attgccattc
 841 actggaaagg cccattgcga ctccagcagg catatctcat tatgatcagt gccctcatgg
 901 ccctggtgtt tatcaagtac ctcccggaat ggaccgcgtg gctcatcttg gctgtgattt
 961 cagtatacga tttagtggct gttttgtgtc caaatggccc acttcgtttg ctggttgaaa
1021 cagctcagga gagaaatgaa actctctttc cagctcttat ttactcgtca acaatggtgt
1081 ggttggtgaa tatggcagaa ggagacccag aagcccaaag gaaggtatcc aaaaactcca
1141 attataatgc acaaagcaca ggtgaatcac aagactctgt gacagagagt gatgatggtg
1201 gcttcagtga agagtgggaa gcccagaggg acagtcgcct gggacctcat cactctacag
1261 ctgagtcacg atctgctgta caggatcttt ccagaagcat cccagccact gaggacccag
1321 aagaaagggg agtaaaactt ggattaggag atttcatttt ctacagtgtt ctggttggta
1381 aagcttctgc aacagccagt ggagactgga acacaaccat tgcctgtttt gtagccatat
1441 taattggttt gtgccttaca ttactgctcc tcgccatttt caagaaagcg ttgccagctc
1501 ttccaatctc tatcaccttt gggcttgttt tctactttgc cacagattat cttgtgcaac
1561 cctttatgga ccaattagca ttccatcaat tttatatcta gcatatttcc agttagaatc
1621 tcatggattt tttctccttt ggctataata aaatctgggg aaagcaaagg tgattttgct
1681 gtgtccacat ctaacaaagt caggattccc agctggacct
```

-continued

```
LOCUS NM_001078667 1720 bp mRNA linear MAM
26-NOV-2006
DEFINITION   Sus scrofa presenilin 1 (PSEN1), mRNA.
ACCESSION    NM_001078667
VERSION      NM_001078667.1 GI: 118403881
KEYWORDS     .
SOURCE       Sus scrofa (pig)
ORGANISM     Sus scrofa
             Eukaryota; Metazoa; Chordata; Craniata; Vertebrata;
             Euteleostomi;
             Mammalia; Eutheria; Laurasiatheria; Cetartiodactyla;
             Suina; Suidae;
             Sus.
COMMENT      PROVISIONAL REFSEQ: This record has not yet been subject
             to final
             NCBI review. The reference sequence was derived from
             DQ853416.1.
FEATURES     Location/Qualifiers
source       1 . . . 1720
             /organism = "Sus scrofa"
             /mol_type = "mRNA"
             /db_xref = "taxon: 9823"
             /chromosome = "7"
             /map = "7"
gene         1 . . . 1720
             /gene = "PSEN1"
             /note = "presenilin 1"
             /db_xref = "GeneID: 780411"
CDS          198 . . . 1601
             /gene = "PSEN1"
             /codon_start = 1
             /product = "presenilin 1"
             /protein_id = "NP_001072135.1"
             /db_xref = "GI: 118403882"
             /db_xref = "GeneID: 780411"
/translation = "MTELPAPLSYFQNAQMSEDNHVSNNVSSQNDSRERHEHSIERRR

RGNSESLSNGGAQGNSRQVVEQEEEEDEELTLKYGAKHVIMLFVPVTLCMVVVVATIK

SVSFYTRKDGQLIYTPFTEDTETVGQRALHSILNAAIMISVIVVMTILLVVLYKYRCY

KVIHAWLIISSLLLLFFFSFIYLGEVFKTYNVAMDYITVALLIWNFGVVGMIAIHWKG

PLRLQQAYLIMISALMALVFIKYLPEWTAWLILAVISVYDLVAVLCPNGPLRLLVETA

QERNETLFPALIYSSTMVWLVNMAEGDPEAQRKVSKNSNYNAQSTGESQDSVTESDDG

GFSEEWEAQRDSRLGPHHSTAESRSAVQDLSRSIPATEDPEERGVKLGLGDFIFYSVL

VGKASATASGDWNTTIACFVAILIGLCLTLLLLAIFKKALPALPISITFGLVFYFATD

                     YLVQPFMDQLAFHQFYI"

ORIGIN
    1  aatcggaaac aaaacagcgg ctgctgggga agggacctgg gctgcgagag gtggcggctg

   61  cgacgagaaa gaacctaatc cgggagcctg caacctgtga agttcttaga aagcttggcc

  121  tggaggagaa cacatgaaag aaagaacccc aggaggctct gatttctgtg aaaaagtatt

  181  tctatacggt tgttccaatg acagagttac ctgcaccctt gtcctacttc cagaatgccc

  241  agatgtccga ggacaaccac gtgagcaata acgtaagtag ccagaatgac agtagagagc

  301  ggcatgagca cagcatcgag aggcggaggc gtggcaactc tgagtcgtta tccaatggcg

  361  gagcccaggg aaactcacgc caggtggtgg aacaagaaga agaggaagac gaggagctga

  421  cgttgaaata tggcgccaaa catgtgatca tgctctttgt ccctgtgact ctatgtatgg

  481  tggtggttgt ggccaccatc aaatcagtca gcttttatac ccggaaggat gggcagctga

  541  tctatactcc atttacagaa gacactgaga ctgtagggca gagagccctg cactcaattc

  601  tgaatgctgc tatcatgatt agtgtcattg tcgtcatgac tattctcctg gtggttctct

  661  ataaatacag gtgctataag gtcatccatg cctggcttat tatttcatcc ctattgttgc

  721  tgttcttttt ctcattcatt tacttggggg aagtgtttaa aacctataac gttgccatgg

  781  attacattac ggtggcactc ctgatctgga attttggtgt ggtaggaatg attgccattc
```

-continued

```
 841 actggaaagg cccattgcga ctccagcagg catatctcat tatgatcagt gccctcatgg

 901 ccctggtgtt tatcaagtac ctcccggaat ggaccgcgtg gctcatcttg gctgtgattt

 961 cagtatacga tttagtggct gttttgtgtc caaatggccc acttcgtttg ctggttgaaa

1021 cagctcagga gagaaatgaa actctctttc cagctcttat ttactcgtca acaatggtgt

1081 ggttggtgaa tatggcagaa ggagacccag aagcccaaag gaaggtatcc aaaaactcca

1141 attataatgc acaaagcaca ggtgaatcac aagactctgt gacagagagt gatgatggtg

1201 gcttcagtga agagtgggaa gcccagaggg acagtcgcct gggacctcat cactctacag

1261 ctgagtcacg atctgctgta caggatcttt ccagaagcat cccagccact gaggacccag

1321 aagaaagggg agtaaaactt ggattaggag atttcatttt ctacagtgtt ctggttggta

1381 aagcttctgc aacagccagt ggagactgga acacaaccat tgcctgtttt gtagccatat

1441 taattggttt gtgccttaca ttactgctcc tcgccatttt caagaaagcg ttgccagctc

1501 ttccaatctc tatcaccttt gggcttgttt tctactttgc cacagattat cttgtgcaac

1561 cctttatgga ccaattagca ttccatcaat tttatatcta gcatatttcc agttagaatc

1621 tcatggattt tttctccttt ggctataata aaatctgggg aaagcaaagg tgattttgct

1681 gtgtccacat ctaacaaagt caggattccc agctggacct
```

SEQ ID NO 5
Porcine APPsw gene coding sequence isoform 770
As SEQ ID NO 3 except for the inclusion of the Swedish double mutation. This double mutation changes sequence shown in ID 1 at position 2104 from G to T and at position 2105 from A to C. This double mutation is shown in this sequence ID 6 in capital letters.

```
   1 gctgactcgc ctggctctga gccccgccgc cgcgctcggg ctccgtcagt ttcctcggca

  61 gcggtaggcg agagcacgcg gaggagcgtg cgcgggggcc ccgggagacg gcggcggtgg

 121 cggcgcgggc agagcaagga cgcggcggat cccactcgca cagcagcgca ctcggtgccc

 181 cgcgcagggt cgcgatgctg cccggtttgg cactgctcct gctggccgcc tggacggctc

 241 gggcgctgga ggtacccact gatggtaatg ctggcctgct ggctgaaccc cagattgcca

 301 tgttctgtgg cagactgaac atgcacatga atgtccagaa tgggaagtgg gattcagatc

 361 catcagggac caaaacctgc attgatacca aggaaggcat cctgcagtat tgccaagaag

 421 tctaccctga actgcagatc accaatgtgg tagaagccaa ccaaccagtg accatccaga

 481 actggtgcaa gcggggccgc aagcagtgca agacccatcc ccactttgtg attccctacc

 541 gctgcttagt tggtgagttt gtaagtgatg cccttctcgt tcctgacaag tgcaaattct

 601 tacaccagga gaggatggat gtttgcgaaa ctcatcttca ctggcacacc gtcgccaaag

 661 agacatgcag tgagaagagt accaacttgc atgactacgg catgttgctg ccctgcggaa

 721 ttgacaagtt ccgaggggta gagtttgtgt gttgcccact ggctgaagaa agtgacaatg

 781 tggattctgc tgatgcggag gaggatgact cggatgtctg gtggggcgga gcagacacag

 841 actatgcaga tgggagtgaa gacaaagtag tagaagtagc agaggaggaa gaagtggctg

 901 aggtggaaga agaagaagcc gatgatgacg aggacgatga ggatggtgat gaggtagagg

 961 aagaggctga ggaaccctac gaagaagcca cagagagaac caccagcatt gccaccacca

1021 ccaccaccac cacagagtct gtggaagagg tggttcgaga ggtgtgctct gaacaagccg

1081 agacggggcc gtgccgagca atgatctccc gctggtactt tgatgtgact gaagggaagt

1141 gtgccccatt cttttacggc ggatgtggcg gcaaccggaa caactttgac acagaagagt

1201 actgcatggc cgtgtgtggc agcgccatgt cccaaagttt actcaagact acccaggaac

1261 ctcttgcccg agatcctgtt aaacttccta caacagcagc cagtacccct gatgccgttg

1321 acaagtatct cgagacacct ggggatgaga atgaacatgc ccatttccag aaagccaaag
```

-continued 1381 agaggcttga ggccaagcac cgagagagaa tgtcccaggt catgagagaa tgggaagagg
1441 cagaacgtca agcaaagaac ttgcctaaag ctgataagaa ggcagttatc cagcatttcc
1501 aggagaaagt ggaatctttg gaacaggaag cagccaacga gagacagcag ctggtggaga
1561 cacacatggc cagagtggaa gccatgctca atgaccgccg ccgcctggcc ctggagaact
1621 acatcaccgc tctgcaggct gttcctcctc ggcctcgtca cgtgttcaat atgctaaaga
1681 agtatgtccg cgcagaacag aaggacagac agcacaccct aaagcatttc gagcatgtgc
1741 gcatggtgga tcccaagaaa gccgctcaga tccggtccca ggttatgaca cacctccgtg
1801 tgatttatga gcgcatgaat cagtctctct ccctgctcta caacgtgcct gcagtggccg
1861 aggagattca ggatgaagtt gatgagctgc ttcagaaaga gcaaaactat tcagatgacg
1921 tcttggccaa catgattagt gaaccaagga tcagttacgg aaacgatgct ctcatgccat
1981 ctttgaccga aacgaaaacc accgtggagc tccttcccgt gaatggagag ttcagcctgg
2041 acgatctcca gccgtggcat tcttttgggg ctgactctgt gccagccaac acagaaaacg
2101 aagttgagcc tgttgatgcc cgccctgctg ccgaccgagg actgaccact cgaccaggtt
2161 ctgggttgac aaatatcaag acggaggaga tctctgaagt gaaTCtggat gcagaattcc
2221 gacatgactc aggatatgaa gttcatcatc aaaaattggt gttctttgca gaagatgtgg
2281 gttcaaacaa aggtgcaatc attggactca tggtgggcgg tgttgtcata gcgacagtga
2341 tcgtcatcac cttggtgatg ctgaagaaga aacagtacac atccattcat catggtgtgg
2401 tggaggttga cgccgctgtc accccagagg agcgccacct gtccaagatg cagcagaacg
2461 gctacgaaaa tccaacctac aagttctttg agcagatgca gaactagacc cccgccacag
2521 cagcctctga agttggacag caaaaccatt gcttcactac ccatcggtgt ccatttatag
2581 aataatgtgg gaagaaacaa acccgtttta tgatttactc attatcgcct tttgacagct
2641 gtgctgtaac acaagtagat gcctgaactt gaattaatcc acacatcagt aatgtattct
2701 atctctcttt acattttggt ctctatacta cattattaat gggttttgtg tactgtaaag
2761 aatttagctg tatcaaacta gtgcatgaat agattctctc ctgattattt atcacatagc
2821 cccttagcca gttgtatatt attcttgtgg tttgtgaccc aattaagtcc tactttacat
2881 atgctttaag aatcgatggg ggatgcttca tgtgaacgtg ggagttcagc tgcttctctt
2941 gcctaagtat tcctttcctg atcactatgc attttaaagt taaacatttt taagtatttc
3001 agatgcttta gagagatttt ttttccatga ctgcatttta ctgtacagat tgctgcttct
3061 gctatatttg tgatatagga attaagagga tacacacgtt tgtttcttcg tgcctgtttt
3121 atgtgcacac attaggcatt gagacttcaa gcttttcttt ttttgtccac gtatctttgg
3181 gtctttgata aagaaaagaa tccctgttca ttgtaagcac ttttacgggg cgggtgggga
3241 ggggtgctct gctggtcttc aattaccaag aattctccaa aacaatttc tgcaggatga
3301 ttgtacagaa tcattgctta tgacatgatc gctttctaca ctgtattaca taaataaatt
3361 aaataaaata accccgggca agacttttct ttgaaggatg actacagaca ttaaataatc
3421 gaagtaattt tgggtgggga gaagaggcag attcaatttt ctttaaccag tctgaagttt
3481 catttatgat acaaaagaag atgaaaatgg aagtggcaat ataaggggat gaggaaggca
3541 tgcctggaca aacccttctt ttaagatgtg tcttcaattt gtataaaatg gtgttttcat
3601 gtaaataaat acattcttgg aggagcaaaa aaaaaaaaaa a -continued SEQ ID NO 6
Human APPsw mRNA isoform 770
As SEQ ID NO 1 except for the inclusion of the Swedish double mutation. This double mutation changes sequence shown in ID 1 at position 2104 from G to T and at position 2105 from A to C. This double mutation is shown in this sequence ID 6 in capital letters.

```
   1 gctgactcgc ctggctctga gccccgccgc cgcgctcggg ctccgtcagt ttcctcggca

  61 gcggtaggcg agagcacgcg gaggagcgtg cgcgggggcc ccgggagacg gcggcggtgg

 121 cggcgcgggc agagcaagga cgcggcggat cccactcgca cagcagcgca ctcggtgccc

 181 cgcgcagggt cgcgatgctg cccggtttgg cactgctcct gctggccgcc tggacggctc

 241 gggcgctgga ggtacccact gatggtaatg ctggcctgct ggctgaaccc cagattgcca

 301 tgttctgtgg cagactgaac atgcacatga atgtccagaa tgggaagtgg gattcagatc

 361 catcagggac caaaacctgc attgatacca aggaaggcat cctgcagtat tgccaagaag

 421 tctaccctga actgcagatc accaatgtgg tagaagccaa ccaaccagtg accatccaga

 481 actggtgcaa gcggggccgc aagcagtgca agacccatcc ccactttgtg attccctacc

 541 gctgcttagt tggtgagttt gtaagtgatg cccttctcgt tcctgacaag tgcaaattct

 601 tacaccagga gaggatggat gtttgcgaaa ctcatcttca ctggcacacc gtcgccaaag

 661 agacatgcag tgagaagagt accaacttgc atgactacgg catgttgctg ccctgcggaa

 721 ttgacaagtt ccgaggggta gagtttgtgt gttgcccact ggctgaagaa agtgacaatg

 781 tggattctgc tgatgcggag gaggatgact cggatgtctg gtggggcgga gcagacacag

 841 actatgcaga tgggagtgaa gacaaagtag tagaagtagc agaggaggaa gaagtggctg

 901 aggtggaaga agaagaagcc gatgatgacg aggacgatga ggatggtgat gaggtagagg

 961 aagaggctga ggaaccctac gaagaagcca cagagagaac caccagcatt gccaccacca

1021 ccaccaccac cacagagtct gtggaagagg tggttcgaga ggtgtgctct gaacaagccg

1081 agacggggcc gtgccgagca atgatctccc gctggtactt tgatgtgact gaagggaagt

1141 gtgccccatt cttttacggc ggatgtggcg gcaaccggaa caactttgac acagaagagt

1201 actgcatggc cgtgtgtggc agcgccatgt cccaaagttt actcaagact acccaggaac

1261 ctcttgcccg agatcctgtt aaacttccta caacagcagc cagtacccct gatgccgttg

1321 acaagtatct cgagacacct ggggatgaga atgaacatgc ccatttccag aaagccaaag

1381 agaggcttga ggccaagcac cgagagagaa tgtcccaggt catgagagaa tgggaagagg

1441 cagaacgtca agcaaagaac ttgcctaaag ctgataagaa ggcagttatc cagcatttcc

1501 aggagaaagt ggaatctttg gaacaggaag cagccaacga gagacagcag ctggtggaga

1561 cacacatggc cagagtggaa gccatgctca atgaccgccg ccgcctggcc ctggagaact

1621 acatcaccgc tctgcaggct gttcctcctc ggcctcgtca cgtgttcaat atgctaaaga

1681 agtatgtccg cgcagaacag aaggacagac agcacaccct aaagcatttc gagcatgtgc

1741 gcatggtgga tcccaagaaa gccgctcaga tccggtccca ggttatgaca cacctccgtg

1801 tgatttatga gcgcatgaat cagtctctct ccctgctcta caacgtgcct gcagtggccg

1861 aggagattca ggatgaagtt gatgagctgc ttcagaaaga gcaaaactat tcagatgacg

1921 tcttggccaa catgattagt gaaccaagga tcagttacgg aaacgatgct ctcatgccat

1981 ctttgaccga aacgaaaacc accgtggagc tccttcccgt gaatggagag ttcagcctgg

2041 acgatctcca gccgtggcat tcttttgggg ctgactctgt gccagccaac acagaaaacg

2101 aagttgagcc tgttgatgcc cgccctgctg ccgaccgagg actgaccact cgaccaggtt

2161 ctgggttgac aaatatcaag acggaggaga tctctgaagt gaaTCtggat gcagaattcc

2221 gacatgactc aggatatgaa gttcatcatc aaaaattggt gttctttgca gaagatgtgg
```

-continued 2281 gttcaaacaa aggtgcaatc attggactca tggtgggcgg tgttgtcata gcgacagtga 2341 tcgtcatcac cttggtgatg ctgaagaaga aacagtacac atccattcat catggtgtgg 2401 tggaggttga cgccgctgtc accccagagg agcgccacct gtccaagatg cagcagaacg 2461 gctacgaaaa tccaacctac aagttctttg agcagatgca gaactagacc cccgccacag 2521 cagcctctga agttggacag caaaaccatt gcttcactac ccatcggtgt ccatttatag 2581 aataatgtgg gaagaaacaa acccgtttta tgatttactc attatcgcct tttgacagct 2641 gtgctgtaac acaagtagat gcctgaactt gaattaatcc acacatcagt aatgtattct 2701 atctctcttt acattttggt ctctatacta cattattaat gggttttgtg tactgtaaag 2761 aatttagctg tatcaaacta gtgcatgaat agattctctc ctgattattt atcacatagc 2821 cccttagcca gttgtatatt attcttgtgg tttgtgaccc aattaagtcc tactttacat 2881 atgctttaag aatcgatggg ggatgcttca tgtgaacgtg ggagttcagc tgcttctctt 2941 gcctaagtat tcctttcctg atcactatgc attttaaagt taaacatttt taagtatttc 3001 agatgcttta gagagatttt ttttccatga ctgcatttta ctgtacagat tgctgcttct 3061 gctatatttg tgatatagga attaagagga tacacacgtt tgtttcttcg tgcctgtttt 3121 atgtgcacac attaggcatt gagacttcaa gcttttcttt ttttgtccac gtatctttgg 3181 gtctttgata aagaaaagaa tccctgttca ttgtaagcac ttttacgggg cgggtgggga 3241 ggggtgctct gctggtcttc aattaccaag aattctccaa aacaattttc tgcaggatga 3301 ttgtacagaa tcattgctta tgacatgatc gctttctaca ctgtattaca taaataaatt 3361 aaataaaata accccgggca agacttttct ttgaaggatg actacagaca ttaaataatc 3421 gaagtaattt tgggtgggga gaagaggcag attcaatttt ctttaaccag tctgaagttt 3481 catttatgat acaaaagaag atgaaaatgg aagtggcaat ataaggggat gaggaaggca 3541 tgcctggaca aacccttctt ttaagatgtg tcttcaattt gtataaaatg gtgttttcat 3601 gtaaataaat acattcttgg aggagcaaaa aaaaaaaaaa a SEQ ID NO 7
Human APPsw protein isoform 770
Protein sequence derived from translation of SEQ ID No 6
The two amino acid changes due to the Swedish mutation are indicated in bold (NL) and corresponds to the K670N/M671L mutation
MLPGLALLLLAAWTARALEVPTDGNAGLLAEPQIAMFCGRLNMH

MNVQNGKWDSDPSGTKTCIDTKEGILQYCQEVYPELQITNVVEANQPVTIQNWCKRGR

KQCKTHPHFVIPYRCLVGEFVSDALLVPDKCKFLHQERMDVCETHLHWHTVAKETCSE

KSTNLHDYGMLLPCGIDKFRGVEFVCCPLAEESDNVDSADAEEDDSDVWWGGADTDYA

DGSEDKVVEVAEEEEVAEVEEEEADDDEDDEDGDEVEEEAEEPYEEATERTTSIATTT

TTTTESVEEVVREVCSEQAETGPCRAMISRWYFDVTEGKCAPFFYGGCGGNRNNFDTE

EYCMAVCGSAMSQSLLKTTQEPLARDPVKLPTTAASTPDAVDKYLETPGDENEHAHFQ

KAKERLEAKHRERMSQVMREWEEAERQAKNLPKADKKAVIQHFQEKVESLEQEAANER

QQLVETHMARVEAMLNDRRRLALENYITALQAVPPRPRHVFNMLKKYVRAEQKDRQHT

LKHFEHVRMVDPKKAAQIRSQVMTHLRVIYERMNQSLSLLYNVPAVAEEIQDEVDELL

QKEQNYSDDVLANMISEPRISYGNDALMPSLTETKTTVELLPVNGEFSLDDLQPWHSF

GADSVPANTENEVEPVDARPAADRGLTTRPGSGLTNIKTEEISEVNLDAEFRHDSGYE

VHHQKLVFFAEDVGSNKGAIIGLMVGGVVIATVIVITLVMLKKKQYTSIHHGVVEVDA

AVTPEERHLSKMQQNGYENPTYKFFEQMQN

-continued

SEQ ID NO 8
Human APPsw mRNA isoform 695
Sequence used for transgenesis. As SEQ ID NO 9 except for the presence of a silent nucleotide substitution at position 260 changing nucleotide T to nucleotide C. Change is indicated in bold in SEQ ID 8

```
   1 gctgactcgc ctggctctga gccccgccgc cgcgctcggg ctccgtcagt ttcctcggca

  61 gcggtaggcg agagcacgcg gaggagcgtg cgcgggggcc ccgggagacg gcggcggtgg

 121 cggcgcgggc agagcaagga cgcggcggat cccactcgca cagcagcgca ctcggtgccc

 181 cgcgcagggt cgcgatgctg cccggtttgg cactgctcct gctggccgcc tggacggctc

 241 gggcgctgga ggtacccacC gatggtaatg ctggcctgct ggctgaaccc cagattgcca

 301 tgttctgtgg cagactgaac atgcacatga atgtccagaa tgggaagtgg gattcagatc

 361 catcagggac caaaacctgc attgatacca aggaaggcat cctgcagtat tgccaagaag

 421 tctaccctga actgcagatc accaatgtgg tagaagccaa ccaaccagtg accatccaga

 481 actggtgcaa gcggggccgc aagcagtgca agacccatcc ccactttgtg attccctacc

 541 gctgcttagt tggtgagttt gtaagtgatg cccttctcgt tcctgacaag tgcaaattct

 601 tacaccagga gaggatggat gtttgcgaaa ctcatcttca ctggcacacc gtcgccaaag

 661 agacatgcag tgagaagagt accaacttgc atgactacgg catgttgctg ccctgcggaa

 721 ttgacaagtt ccgaggggta gagtttgtgt gttgcccact ggctgaagaa agtgacaatg

 781 tggattctgc tgatgcggag gaggatgact cggatgtctg gtggggcgga gcagacacag

 841 actatgcaga tgggagtgaa gacaaagtag tagaagtagc agaggaggaa gaagtggctg

 901 aggtggaaga agaagaagcc gatgatgacg aggacgatga ggatggtgat gaggtagagg

 961 aagaggctga ggaaccctac gaagaagcca cagagagaac caccagcatt gccaccacca

1021 ccaccaccac cacagagtct gtggaagagg tggttcgag. .......... ..........

     .......... .......... .......... .......... .......... ..........

     .......... .......... ...cttccta caacagcagc cagtacccct gatgccgttg

1321 acaagtatct cgagacacct ggggatgaga atgaacatgc ccatttccag aaagccaaag

1381 agaggcttga ggccaagcac cgagagagaa tgtcccaggt catgagagaa tgggaagagg

1441 cagaacgtca agcaaagaac ttgcctaaag ctgataagaa ggcagttatc cagcatttcc

1501 aggagaaagt ggaatctttg gaacaggaag cagccaacga gagacagcag ctggtggaga

1561 cacacatggc cagagtggaa gccatgctca atgaccgccg ccgcctggcc ctggagaact

1621 acatcaccgc tctgcaggct gttcctcctc ggcctcgtca cgtgttcaat atgctaaaga

1681 agtatgtccg cgcagaacag aaggacagac agcacaccct aaagcatttc gagcatgtgc

1741 gcatggtgga tcccaagaaa gccgctcaga tccggtccca ggttatgaca cacctccgtg

1801 tgatttatga gcgcatgaat cagtctctct ccctgctcta caacgtgcct gcagtggccg

1861 aggagattca ggatgaagtt gatgagctgc ttcagaaaga gcaaaactat tcagatgacg

1921 tcttggccaa catgattagt gaaccaagga tcagttacgg aaacgatgct ctcatgccat

1981 ctttgaccga aacgaaaacc accgtggagc tccttcccgt gaatggagag ttcagcctgg

2041 acgatctcca gccgtggcat tcttttgggg ctgactctgt gccagccaac acagaaaacg

2101 aagttgagcc tgttgatgcc cgccctgctg ccgaccgagg actgaccact cgaccaggtt

2161 ctgggttgac aaatatcaag acggaggaga tctctgaagt gaaTCtggat gcagaattcc

2221 gacatgactc aggatatgaa gttcatcatc aaaaattggt gttctttgca gaagatgtgg

2281 gttcaaacaa aggtgcaatc attggactca tggtgggcgg tgttgtcata gcgacagtga

2341 tcgtcatcac cttggtgatg ctgaagaaga aacagtacac atccattcat catggtgtgg
```

-continued 2401 tggaggttga cgccgctgtc accccagagg agcgccacct gtccaagatg cagcagaacg 2461 gctacgaaaa tccaacctac aagttctttg agcagatgca gaactagacc cccgccacag 2521 cagcctctga agttggacag caaaaccatt gcttcactac ccatcggtgt ccatttatag 2581 aataatgtgg gaagaaacaa acccgtttta tgatttactc attatcgcct tttgacagct 2641 gtgctgtaac acaagtagat gcctgaactt gaattaatcc acacatcagt aatgtattct 2701 atctctcttt acattttggt ctctatacta cattattaat gggttttgtg tactgtaaag 2761 aatttagctg tatcaaacta gtgcatgaat agattctctc ctgattattt atcacatagc 2821 cccttagcca gttgtatatt attcttgtgg tttgtgaccc aattaagtcc tactttacat 2881 atgctttaag aatcgatggg ggatgcttca tgtgaacgtg ggagttcagc tgcttctctt 2941 gcctaagtat tcctttcctg atcactatgc attttaaagt taaacatttt taagtatttc 3001 agatgcttta gagagatttt ttttccatga ctgcatttta ctgtacagat tgctgcttct 3061 gctatatttg tgatatagga attaagagga tacacacgtt tgtttcttcg tgcctgtttt 3121 atgtgcacac attaggcatt gagacttcaa gcttttcttt ttttgtccac gtatctttgg 3181 gtctttgata aagaaaagaa tccctgttca ttgtaagcac ttttacgggg cgggtgggga 3241 ggggtgctct gctggtcttc aattaccaag aattctccaa aacaattttc tgcaggatga 3301 ttgtacagaa tcattgctta tgacatgatc gctttctaca ctgtattaca taaataaatt 3361 aaataaaata accccgggca agacttttct ttgaaggatg actacagaca ttaaataatc 3421 gaagtaattt tgggtgggga gaagaggcag attcaatttt ctttaaccag tctgaagttt 3481 catttatgat acaaaagaag atgaaaatgg aagtggcaat ataaggggat gaggaaggca 3541 tgcctggaca aacccttctt ttaagatgtg tcttcaattt gtataaaatg gtgttttcat 3601 gtaaataaat acattcttgg aggagcaaaa aaaaaaaaaa a Deleted sequence:
a ggtgtgctct gaacaagccg 1081 agacggggcc gtgccgagca atgatctccc gctggtactt tgatgtgact gaagggaagt 1141 gtgccccatt cttttacggc ggatgtggcg gcaaccggaa caactttgac acagaagagt 1201 actgcatggc cgtgtgtggc agcgccatgt cccaaagttt actcaagact acccaggaac 1261 ctcttgcccg agatcctgtt aaa SEQ ID NO 9
Human APPsw mRNA isoform 695
As SEQ ID NO 6 except for deletion of nucleotides from position 1060 to 1283. This deletion is indicated by ( . . . )in the sequence.

1 gctgactcgc ctggctctga gccccgccgc cgcgctcggg ctccgtcagt ttcctcggca 61 gcggtaggcg agagcacgcg gaggagcgtg cgcgggggcc ccgggagacg gcggcggtgg 121 cggcgcgggc agagcaagga cgcggcggat cccactcgca cagcagcgca ctcggtgccc 181 cgcgcagggt cgcgatgctg cccggtttgg cactgctcct gctggccgcc tggacggctc 241 gggcgctgga ggtacccact gatggtaatg ctggcctgct ggctgaaccc cagattgcca 301 tgttctgtgg cagactgaac atgcacatga atgtccagaa tgggaagtgg gattcagatc 361 catcagggac caaaacctgc attgatacca aggaaggcat cctgcagtat tgccaagaag 421 tctaccctga actgcagatc accaatgtgg tagaagccaa ccaaccagtg accatccaga 481 actggtgcaa gcggggccgc aagcagtgca agacccatcc ccactttgtg attccctacc 541 gctgcttagt tggtgagttt gtaagtgatg cccttctcgt tcctgacaag tgcaaattct 601 tacaccagga gaggatggat gtttgcgaaa ctcatcttca ctggcacacc gtcgccaaag 661 agacatgcag tgagaagagt accaacttgc atgactacgg catgttgctg ccctgcggaa -continued

```
 721 ttgacaagtt ccgaggggta gagtttgtgt gttgcccact ggctgaagaa agtgacaatg
 781 tggattctgc tgatgcggag gaggatgact cggatgtctg gtggggcgga gcagacacag
 841 actatgcaga tgggagtgaa gacaaagtag tagaagtagc agaggaggaa gaagtggctg
 901 aggtggaaga agaagaagcc gatgatgacg aggacgatga ggatggtgat gaggtagagg
 961 aagaggctga ggaaccctac gaagaagcca cagagagaac caccagcatt gccaccacca
1021 ccaccaccac cacagagtct gtggaagagg tggttcgag. .......... ..........
     .......... .......... .......... .......... .......... ..........
     .......... .......... ...cttccta caacagcagc cagtacccct gatgccgttg
1321 acaagtatct cgagacacct ggggatgaga atgaacatgc ccatttccag aaagccaaag
1381 agaggcttga ggccaagcac cgagagagaa tgtcccaggt catgagagaa tgggaagagg
1441 cagaacgtca agcaaagaac ttgcctaaag ctgataagaa ggcagttatc cagcatttcc
1501 aggagaaagt ggaatctttg gaacaggaag cagccaacga gagacagcag ctggtggaga
1561 cacacatggc cagagtggaa gccatgctca atgaccgccg ccgcctggcc ctggagaact
1621 acatcaccgc tctgcaggct gttcctcctc ggcctcgtca cgtgttcaat atgctaaaga
1681 agtatgtccg cgcagaacag aaggacagac agcacaccct aaagcatttc gagcatgtgc
1741 gcatggtgga tcccaagaaa gccgctcaga tccggtccca ggttatgaca cacctccgtg
1801 tgatttatga gcgcatgaat cagtctctct ccctgctcta caacgtgcct gcagtggccg
1861 aggagattca ggatgaagtt gatgagctgc ttcagaaaga gcaaaactat tcagatgacg
1921 tcttggccaa catgattagt gaaccaagga tcagttacgg aaacgatgct ctcatgccat
1981 ctttgaccga aacgaaaacc accgtggagc tccttcccgt gaatggagag ttcagcctgg
2041 acgatctcca gccgtggcat tcttttgggg ctgactctgt gccagccaac acagaaaacg
2101 aagttgagcc tgttgatgcc cgccctgctg ccgaccgagg actgaccact cgaccaggtt
2161 ctgggttgac aaatatcaag acggaggaga tctctgaagt gaaTCtggat gcagaattcc
2221 gacatgactc aggatatgaa gttcatcatc aaaaattggt gttctttgca gaagatgtgg
2281 gttcaaacaa aggtgcaatc attggactca tggtgggcgg tgttgtcata gcgacagtga
2341 tcgtcatcac cttggtgatg ctgaagaaga aacagtacac atccattcat catggtgtgg
2401 tggaggttga cgccgctgtc accccagagg agcgccacct gtccaagatg cagcagaacg
2461 gctacgaaaa tccaacctac aagttctttg agcagatgca gaactagacc cccgccacag
2521 cagcctctga agttggacag caaaaccatt gcttcactac ccatcggtgt ccatttatag
2581 aataatgtgg gaagaaacaa acccgtttta tgatttactc attatcgcct tttgacagct
2641 gtgctgtaac acaagtagat gcctgaactt gaattaatcc acacatcagt aatgtattct
2701 atctctcttt acattttggt ctctatacta cattattaat gggttttgtg tactgtaaag
2761 aatttagctg tatcaaacta gtgcatgaat agattctctc ctgattattt atcacatagc
2821 cccttagcca gttgtatatt attcttgtgg tttgtgaccc aattaagtcc tactttacat
2881 atgctttaag aatcgatggg ggatgcttca tgtgaacgtg ggagttcagc tgcttctctt
2941 gcctaagtat tcctttcctg atcactatgc attttaaagt taaacatttt taagtatttc
3001 agatgcttta gagagatttt ttttccatga ctgcatttta ctgtacagat tgctgcttct
3061 gctatatttg tgatatagga attaagagga tacacacgtt tgtttcttcg tgcctgtttt
3121 atgtgcacac attaggcatt gagacttcaa gcttttcttt ttttgtccac gtatctttgg
3181 gtctttgata aagaaaagaa tccctgttca ttgtaagcac ttttacgggg cgggtgggga
3241 ggggtgctct gctggtcttc aattaccaag aattctccaa aacaatttc tgcaggatga
```

-continued 3301 ttgtacagaa tcattgctta tgacatgatc gctttctaca ctgtattaca taaataaatt 3361 aaataaaata accccgggca agacttttct ttgaaggatg actacagaca ttaaataatc 3421 gaagtaattt tgggtgggga gaagaggcag attcaatttt ctttaaccag tctgaagttt 3481 catttatgat acaaaagaag atgaaaatgg aagtggcaat ataaggggat gaggaaggca 3541 tgcctggaca aacccttctt ttaagatgtg tcttcaattt gtataaaatg gtgttttcat 3601 gtaaataaat acattcttgg aggagcaaaa aaaaaaaaaa a Deleted sequence:

a ggtgtgctct gaacaagccg 1081 agacggggcc gtgccgagca atgatctccc gctggtactt tgatgtgact gaagggaagt 1141 gtgccccatt cttttacggc ggatgtggcg gcaaccggaa caactttgac acagaagagt 1201 actgcatggc cgtgtgtggc agcgccatgt cccaaagttt actcaagact acccaggaac 1261 ctcttgcccg agatcctgtt aaa SEQ ID NO 10
Human APPsw protein isoform 695
Protein sequence derived from translation of SEQ ID No 9 and 8
The two amino acid changes due to the Swedish mutation are indicated in bold (NL) and corresponds to the K670N/M671L mutation. The deletion compared to APP770 is indicated by ( . . . ) in the sequence.
MLPGLALLLLAAWTARALEVPTDGNAGLLAEPQIAMFCGRLNMH

MNVQNGKWDSDPSGTKTCIDTKEGILQYCQEVYPELQITNVVEANQPVTIQNWCKRGR

KQCKTHPHFVIPYRCLVGEFVSDALLVPDKCKFLHQERMDVCETHLHWHTVAKETCSE

KSTNLHDYGMLLPCGIDKFRGVEFVCCPLAEESDNVDSADAEEDDSDVWWGGADTDYA

DGSEDKVVEVAEEEEVAEVEEEEADDDEDDEDGDEVEEEAEEPYEEATERTTSIATTT

TTTTESVEEVVRE.............................................

..............................PTTAASTPDAVDKYLETPGDENEHAHFQ

KAKERLEAKHRERMSQVMREWEEAERQAKNLPKADKKAVIQHFQEKVESLEQEAANER

QQLVETHMARVEAMLNDRRRLALENYITALQAVPPRPRHVFNMLKKYVRAEQKDRQHT

LKHFEHVRMVDPKKAAQIRSQVMTHLRVIYERMNQSLSLLYNVPAVAEEIQDEVDELL

QKEQNYSDDVLANMISEPRISYGNDALMPSLTETKTTVELLPVNGEFSLDDLQPWHSF

GADSVPANTENEVEPVDARPAADRGLTTRPGSGLTNIKTEEISEVNLDAEFRHDSGYE

VHHQKLVFFAEDVGSNKGAIIGLMVGGVVIATVIVITLVMLKKKQYTSIHHGVVEVDA

AVTPEERHLSKMQQNGYENPTYKFFEQMQN

SEQ ID NO 11
Porcine APPsw gene coding sequence isoform 770
As SEQ ID NO 3 except for the inclusion of the Swedish double mutation. This double mutation changes sequence shown in ID 3 at position 2051 from G to T and at position 2052 from A to C. This double mutation is shown in this sequence ID 12 in capital letters.

1 acgcgaacag cagcgcactc ggtgccccgc gcagggtcgc gatgctgccc ggtttggcac 61 tggtcctgct ggccgcctgg acggctaggg cgctggaggt gcccactgat ggcaatgccg 121 gcctgcttgc agaaccccag gttgccatgt tctgtggcaa actcaacatg cacatgaatg 181 tgcagaatgg gaagtgggag tcagatccgt cggggaccaa aacctgcatt ggcaccaagg 241 aaggcatctt gcagtactgc caagaagtct accctgaact gcagatcacc aatgtggtag 301 aagccaacca accagtgacc atccagaact ggtgcaagag gagccggaag cagtgcaaga 361 cccacactca cattgtgatt ccgtaccgct gcttagttgg cgagtttgta agcgatgccc 421 tccttgttcc ggacaagtgc aagttcttac accaggagag gatggatgtt tgcgaaaccc 481 accttcactg gcacactgtg gccaaagaga cctgtagtga gaagagtacg aacttgcatg -continued 541 actatggcat gttgctgccc tgtggaattg acaagttccg aggggtggag tttgtgtgtt 601 gcccactggc cgaggaaagt gacaatatcg actcagcaga tgcagaagag gatgactcgg 661 acgtctggtg gggtggagca gatacagact atgcagatgg cagtgaagac aaagtcgtgg 721 aggtcgcaga ggaggaggaa gtggctgatg tcgaggaaga agaagctgag gatgatgagg 781 atgatgagga tggtgatgag gtagaagaag aggctgagga accctatgaa gaggccacgg 841 agagaaccac cagcatcgcc acaaccacca ccaccaccac ggagtctgtg gaagaggtgg 901 tccgagaggt gtgctctgaa caagccgaga cggggccgtg ccgagcaatg atctcccgct 961 ggtactttga tgtgactgaa gggaagtgcg ccccgttctt ttacggcgga tgtggcggca 1021 accgaaacaa ctttgacaca gaggaatact gcatggccgt gtgtggcagc gtcatgtccc 1081 aaagtttact caagactacc caggaacatc ttccccaaga tcctgttaaa cttcctacaa 1141 cagcagccag caccccagat gccgttgaca agtatcttga gacacctgga gatgagaacg 1201 aacatgcgca tttccagaaa gccaaagaga ggctggaggc caagcaccgc gagagaatgt 1261 cccaggtcat gagagagtgg gaagaggcag aacgtcaagc aaagaacttg cctaaagctg 1321 ataagaaagc agtgatccag catttccagg agaaagtgga gtctctggag caggaagcag 1381 ccaacgagag gcagcagttg gtggagacgc acatggccag agtggaggcc atgcttaacg 1441 accgccggcg cctggccctg gagaattaca tcacggctct tcaggctgtt cctcctcggc 1501 ctcgtcatgt gttcaacatg ctcaagaagt atgtccgtgc cgaacagaaa gacagacagc 1561 acaccctaaa gcattttgaa cacgttcgca tggtagatcc aaagaaagct gctcagatcc 1621 gatcccaggt tatgacacac ctccgtgtga tttacgagcg catgaaccag tctctctccc 1681 tgctctacaa cgttcctgct gtggctgagg aaattcagga tgaagttgat gagctgctgc 1741 agaaagagca aaactactcg gatgatgtct tggccaacat gatcagcgaa ccgaggatca 1801 gttatggaaa cgatgctctc atgccgtctc tgactgaaac caaaaccacc gtggagcttc 1861 ttcctgtgaa tggagagttc agcctggatg atctccagcc ctggcatcct tttggggtag 1921 actctgtgcc tgccaacaca gaaaatgaag tcgagcctgt tgacgcccgc cctgcagccg 1981 accgaggact gaccactcga ccaggttccg ggttgaccaa catcaagacg gaagagatct 2041 ctgaagtgaa TCtggatgcg gagttccgac acgattcagg ctatgaggtt catcaccaaa 2101 aactggtgtt cttcgcagaa gatgtgggtt caaacaaagg tgccatcatt ggactcatgg 2161 tgggtggtgt tgtcatagca accgtgattg tcatcacctt agtgatgctg aagaagaaac 2221 agtacacatc catccatcac ggtgtggtgg aggttgacgc agctgtgacc ccggaggagc 2281 gccacctctc caagatgcag cagaatggct atgaaaaccc aacttacaag ttctttgagc 2341 agatgcagaa ctagaccgcc gccacagcag cctctgaagt tggacagcaa aaccattgct 2401 tcactaccca ttggtgttca tttatagaat aatggggaaa gacacaaacc cttctgtttt 2461 attatttact catgatcgcc tttcagcagc tgtgctgtaa cacaagtaga tgcctgaact 2521 tgaattaata ttacgaatca gtaatgtatt ctctctcttt acatttccgg tctctacact 2581 acattattaa tgggttttgt gtactgtaaa gaatgaagct gtatcaaact agtgcatgaa 2641 tagattccct cctgattatt tatcatgtag ccccttagcc agttgtatat tattcttgtg 2701 gttttgtgat ccaattaagt cctactttga aatatgcttt aagaatcgat gggggatgct 2761 tcatgtgaac gtgggagttt agctgcttct cttgcctaag tattcttttc ctgatcacta 2821 tgcattttaa aggtaaacat ttttatgtat tccaaatgag ttagagaagt tttttccacg 2881 attgcatttg actgtacaga ttgctgcttc tgctatattt gtgatatagg aattatgagg -continued

```
2941 atacacgttt atttctttgt gcctgtttta tgtgcacaca ttaggcattg agaattaaaa

3001 cttcttttgt ccgtgtacct tcggatcttt aaaaaaaaaa aaaaaaaaaa a
```

SEQ ID NO 12
Porcine APPsw mRNA isoform 770
As SEQ ID NO 3 except for the inclusion of the Swedish double mutation. This double mutation changes sequence shown in ID 3 at position 2051 from G to T and at position 2052 from A to C. This double mutation is shown in this sequence ID 12 in capital letters.

```
   1 acgcgaacag cagcgcactc ggtgccccgc gcagggtcgc gatgctgccc ggtttggcac

  61 tggtcctgct ggccgcctgg acggctaggg cgctggaggt gcccactgat ggcaatgccg

 121 gcctgcttgc agaaccccag gttgccatgt tctgtggcaa actcaacatg cacatgaatg

 181 tgcagaatgg gaagtgggag tcagatccgt cggggaccaa aacctgcatt ggcaccaagg

 241 aaggcatctt gcagtactgc caagaagtct accctgaact gcagatcacc aatgtggtag

 301 aagccaacca accagtgacc atccagaact ggtgcaagag gagccggaag cagtgcaaga

 361 cccacactca cattgtgatt ccgtaccgct gcttagttgg cgagtttgta agcgatgccc

 421 tccttgttcc ggacaagtgc aagttcttac accaggagag gatggatgtt tgcgaaaccc

 481 accttcactg gcacactgtg gccaaagaga cctgtagtga gaagagtacg aacttgcatg

 541 actatggcat gttgctgccc tgtggaattg acaagttccg aggggtggag tttgtgtgtt

 601 gcccactggc cgaggaaagt gacaatatcg actcagcaga tgcagaagag gatgactcgg

 661 acgtctggtg ggtggagca gatacagact atgcagatgg cagtgaagac aaagtcgtgg

 721 aggtcgcaga ggaggaggaa gtggctgatg tcgaggaaga agaagctgag gatgatgagg

 781 atgatgagga tggtgatgag gtagaagaag aggctgagga accctatgaa gaggccacgg

 841 agagaaccac cagcatcgcc acaaccacca ccaccaccac ggagtctgtg gaagaggtgg

 901 tccgagaggt gtgctctgaa caagccgaga cggggccgtg ccgagcaatg atctcccgct

 961 ggtactttga tgtgactgaa gggaagtgcg ccccgttctt ttacggcgga tgtggcggca

1021 accgaaacaa ctttgacaca gaggaatact gcatggccgt gtgtggcagc gtcatgtccc

1081 aaagtttact caagactacc caggaacatc ttccccaaga tcctgttaaa cttcctacaa

1141 cagcagccag caccccagat gccgttgaca agtatcttga gacacctgga gatgagaacg

1201 aacatgcgca tttccagaaa gccaaagaga ggctggaggc caagcaccgc gagagaatgt

1261 cccaggtcat gagagagtgg gaagaggcag aacgtcaagc aaagaacttg cctaaagctg

1321 ataagaaagc agtgatccag catttccagg agaaagtgga gtctctggag caggaagcag

1381 ccaacgagag gcagcagttg gtggagacgc acatggccag agtggaggcc atgcttaacg

1441 accgccggcg cctggccctg gagaattaca tcacggctct tcaggctgtt cctcctcggc

1501 ctcgtcatgt gttcaacatg ctcaagaagt atgtccgtgc cgaacagaaa gacagacagc

1561 acaccctaaa gcattttgaa cacgttcgca tggtagatcc aaagaaagct gctcagatcc

1621 gatcccaggt tatgacacac ctccgtgtga tttacgagcg catgaaccag tctctctccc

1681 tgctctacaa cgttcctgct gtggctgagg aaattcagga tgaagttgat gagctgctgc

1741 agaaagagca aaactactcg gatgatgtct tggccaacat gatcagcgaa ccgaggatca

1801 gttatggaaa cgatgctctc atgccgtctc tgactgaaac caaaaccacc gtggagcttc

1861 ttcctgtgaa tggagagttc agcctggatg atctccagcc ctggcatcct tttggggtag

1921 actctgtgcc tgccaacaca gaaaatgaag tcgagcctgt tgacgcccgc cctgcagccg

1981 accgaggact gaccactcga ccaggttccg ggttgaccaa catcaagacg gaagagatct

2041 ctgaagtgaa TCtggatgcg gagttccgac acgattcagg ctatgaggtt catcaccaaa

2101 aactggtgtt cttcgcagaa gatgtgggtt caaacaaagg tgccatcatt ggactcatgg
```

-continued

```
2161 tgggtggtgt tgtcatagca accgtgattg tcatcacctt agtgatgctg aagaagaaac
2221 agtacacatc catccatcac ggtgtggtgg aggttgacgc agctgtgacc ccggaggagc
2281 gccacctctc caagatgcag cagaatggct atgaaaaccc aacttacaag ttctttgagc
2341 agatgcagaa ctagaccgcc gccacagcag cctctgaagt tggacagcaa aaccattgct
2401 tcactaccca ttggtgttca tttatagaat aatggggaaa gacacaaacc cttctgtttt
2461 attatttact catgatcgcc tttcagcagc tgtgctgtaa cacaagtaga tgcctgaact
2521 tgaattaata ttacgaatca gtaatgtatt ctctctcttt acatttccgg tctctacact
2581 acattattaa tgggttttgt gtactgtaaa gaatgaagct gtatcaaact agtgcatgaa
2641 tagattccct cctgattatt tatcatgtag ccccttagcc agttgtatat tattcttgtg
2701 gttttgtgat ccaattaagt cctactttga aatatgcttt aagaatcgat gggggatgct
2761 tcatgtgaac gtgggagttt agctgcttct cttgcctaag tattcttttc ctgatcacta
2821 tgcattttaa aggtaaacat ttttatgtat tccaaatgag ttagagaagt tttttccacg
2881 attgcatttg actgtacaga ttgctgcttc tgctatattt gtgatatagg aattatgagg
2941 atacacgttt atttctttgt gcctgtttta tgtgcacaca ttaggcattg agaattaaaa
3001 cttcttttgt ccgtgtacct tcggatcttt aaaaaaaaaa aaaaaaaaaa a
```

SEQ ID NO 13
Porcine APPsw protein isoform 770
Protein sequence derived from translation of SEQ ID No 12
The two amino acid changes due to the Swedish mutation are indicated in bold (NL) and corresponds to the K670N/M671L mutation

MLPGLALVLLAAWTARALEVPTDGNAGLLAEPQVAMFCGKLNMH

MNVQNGKWESDPSGTKTCIGTKEGILQYCQEVYPELQITNVVEANQPVTIQNWCKRSR

KQCKTHTHIVIPYRCLVGEFVSDALLVPDKCKFLHQERMDVCETHLHWHTVAKETCSE

KSTNLHDYGMLLPCGIDKFRGVEFVCCPLAEESDNIDSADAEEDDSDVWWGGADTDYA

DGSEDKVVEVAEEEEVADVEEEEAEDDEDDEDGDEVEEEAEEPYEEATERTTSIATT

TTTTESVEEVVREVCSEQAETGPCRAMISRWYFDVTEGKCAPFFYGGCGGNRNNFDTE

EYCMAVCGSVMSQSLLKTTQEHLPQDPVKLPTTAASTPDAVDKYLETPGDENEHAHFQ

KAKERLEAKHRERMSQVMREWEEAERQAKNLPKADKKAVIQHFQEKVESLEQEAANER

QQLVETHMARVEAMLNDRRRLALENYITALQAVPPRPRHVFNMLKKYVRAEQKDRQHT

LKHFEHVRMVDPKKAAQIRSQVMTHLRVIYERMNQSLSLLYNVPAVAEEIQDEVDELL

QKEQNYSDDVLANMISEPRISYGNDALMPSLTETKTTVELLPVNGEFSLDDLQPWHPF

GVDSVPANTENEVEPVDARPAADRGLTTRPGSGLTNIKTEEISEVNLDAEFRHDSGYE

VHHQKLVFFAEDVGSNKGAIIGLMVGGVVIATVIVITLVMLKKKQYTSIHHGVVEVDA

AVTPEERHLSKMQQNGYENPTYKFFEQMQN

SEQ ID NO 14
Porcine APPsw gene coding sequence isoform 695
As SEQ ID NO 12 except for deletion of nucleotides from position 907 to 1131. The deletion is indicated by ( . . . ) in the sequence.

```
  1 acgcgaacag cagcgcactc ggtgccccgc gcagggtcgc gatgctgccc ggtttggcac
 61 tggtcctgct ggccgcctgg acggctaggg cgctggaggt gcccactgat ggcaatgccg
121 gcctgcttgc agaaccccag gttgccatgt tctgtggcaa actcaacatg cacatgaatg
181 tgcagaatgg gaagtgggag tcagatccgt cggggaccaa aacctgcatt ggcaccaagg
241 aaggcatctt gcagtactgc caagaagtct accctgaact gcagatcacc aatgtggtag
301 aagccaacca accagtgacc atccagaact ggtgcaagag gagccggaag cagtgcaaga
361 cccacactca cattgtgatt ccgtaccgct gcttagttgg cgagtttgta agcgatgccc
```

-continued

```
421  tccttgttcc ggacaagtgc aagttcttac accaggagag gatggatgtt tgcgaaaccc
481  accttcactg gcacactgtg gccaaagaga cctgtagtga gaagagtacg aacttgcatg
541  actatggcat gttgctgccc tgtggaattg acaagttccg aggggtggag tttgtgtgtt
601  gcccactggc cgaggaaagt gacaatatcg actcagcaga tgcagaagag gatgactcgg
661  acgtctggtg ggtggagca gatacagact atgcagatgg cagtgaagac aaagtcgtgg
721  aggtcgcaga ggaggaggaa gtggctgatg tcgaggaaga agaagctgag gatgatgagg
781  atgatgagga tggtgatgag gtagaagaag aggctgagga accctatgaa gaggccacgg
841  agagaaccac cagcatcgcc acaaccacca ccaccaccac ggagtctgtg gaagaggtgg
901  tccgag.... .......... .......... .......... .......... ..........
     .......... .......... .......... .......... .......... ..........
                                                           .ttcctacaa
1141 cagcagccag caccccagat gccgttgaca agtatcttga gacacctgga gatgagaacg
1201 aacatgcgca tttccagaaa gccaaagaga ggctggaggc caagcaccgc gagagaatgt
1261 cccaggtcat gagagagtgg gaagaggcag aacgtcaagc aaagaacttg cctaaagctg
1321 ataagaaagc agtgatccag catttccagg agaaagtgga gtctctggag caggaagcag
1381 ccaacgagag gcagcagttg gtggagacgc acatggccag agtggaggcc atgcttaacg
1441 accgccggcg cctggccctg gagaattaca tcacggctct tcaggctgtt cctcctcggc
1501 ctcgtcatgt gttcaacatg ctcaagaagt atgtccgtgc cgaacagaaa gacagacagc
1561 acaccctaaa gcattttgaa cacgttcgca tggtagatcc aaagaaagct gctcagatcc
1621 gatcccaggt tatgacacac ctccgtgtga tttacgagcg catgaaccag tctctctccc
1681 tgctctacaa cgttcctgct gtggctgagg aaattcagga tgaagttgat gagctgctgc
1741 agaaagagca aaactactcg gatgatgtct tggccaacat gatcagcgaa ccgaggatca
1801 gttatggaaa cgatgctctc atgccgtctc tgactgaaac caaaaccacc gtggagcttc
1861 ttcctgtgaa tggagagttc agcctggatg atctccagcc ctggcatcct tttggggtag
1921 actctgtgcc tgccaacaca gaaaatgaag tcgagcctgt tgacgcccgc cctgcagccg
1981 accgaggact gaccactcga ccaggttccg ggttgaccaa catcaagacg gaagagatct
2041 ctgaagtgaa TCtggatgcg gagttccgac acgattcagg ctatgaggtt catcaccaaa
2101 aactggtgtt cttcgcagaa gatgtgggtt caaacaaagg tgccatcatt ggactcatgg
2161 tgggtggtgt tgtcatagca accgtgattg tcatcacctt agtgatgctg aagaagaaac
2221 agtacacatc catccatcac ggtgtggtgg aggttgacgc agctgtgacc ccggaggagc
2281 gccacctctc caagatgcag cagaatggct atgaaaaccc aacttacaag ttctttgagc
2341 agatgcagaa ctagaccgcc gccacagcag cctctgaagt tggacagcaa aaccattgct
2401 tcactaccca ttggtgttca tttatagaat aatggggaaa gacacaaacc cttctgtttt
2461 attatttact catgatcgcc tttcagcagc tgtgctgtaa cacaagtaga tgcctgaact
2521 tgaattaata ttacgaatca gtaatgtatt ctctctcttt acatttccgg tctctacact
2581 acattattaa tgggttttgt gtactgtaaa gaatgaagct gtatcaaact agtgcatgaa
2641 tagattccct cctgattatt tatcatgtag ccccttagcc agttgtatat tattcttgtg
2701 gttttgtgat ccaattaagt cctactttga aatatgcttt aagaatcgat gggggatgct
2761 tcatgtgaac gtgggagttt agctgcttct cttgcctaag tattcttttc ctgatcacta
2821 tgcattttaa aggtaaacat ttttatgtat tccaaatgag ttagagaagt tttttccacg
```

-continued

```
2881 attgcatttg actgtacaga ttgctgcttc tgctatattt gtgatatagg aattatgagg

2941 atacacgttt atttctttgt gcctgtttta tgtgcacaca ttaggcattg agaattaaaa

3001 cttcttttgt ccgtgtacct tcggatcttt aaaaaaaaaa aaaaaaaaaa a
```

Deleted sequence:

```
            aggt gtgctctgaa caagccgaga cggggccgtg ccgagcaatg atctcccgct

 961 ggtactttga tgtgactgaa gggaagtgcg ccccgttctt ttacggcgga tgtggcggca

1021 accgaaacaa ctttgacaca gaggaatact gcatggccgt gtgtggcagc gtcatgtccc

1081 aaagtttact caagactacc caggaacatc ttccccaaga tcctgttaaa c
```

SEQ ID NO 15
Porcine APPsw mRNA isoform 695
As SEQ ID NO 12 except for deletion of nucleotides from position 907 to 1131. The deletion is indicated by ( . . . . ) in the sequence.

```
   1 acgcgaacag cagcgcactc ggtgccccgc gcagggtcgc gatgctgccc ggtttggcac

  61 tggtcctgct ggccgcctgg acggctaggg cgctggaggt gcccactgat ggcaatgccg

 121 gcctgcttgc agaaccccag gttgccatgt tctgtggcaa actcaacatg cacatgaatg

 181 tgcagaatgg gaagtgggag tcagatccgt cggggaccaa aacctgcatt ggcaccaagg

 241 aaggcatctt gcagtactgc caagaagtct accctgaact gcagatcacc aatgtggtag

 301 aagccaacca accagtgacc atccagaact ggtgcaagag gagccggaag cagtgcaaga

 361 cccacactca cattgtgatt ccgtaccgct gcttagttgg cgagtttgta agcgatgccc

 421 tccttgttcc ggacaagtgc aagttcttac accaggagag gatggatgtt tgcgaaaccc

 481 accttcactg gcacactgtg gccaaagaga cctgtagtga gaagagtacg aacttgcatg

 541 actatggcat gttgctgccc tgtggaattg acaagttccg aggggtggag tttgtgtgtt

 601 gcccactggc cgaggaaagt gacaatatcg actcagcaga tgcagaagag gatgactcgg

 661 acgtctggtg ggtggagcca gatacagact atgcagatgg cagtgaagac aaagtcgtgg

 721 aggtcgcaga ggaggaggaa gtggctgatg tcgaggaaga agaagctgag gatgatgagg

 781 atgatgagga tggtgatgag gtagaagaag aggctgagga accctatgaa gaggccacgg

 841 agagaaccac cagcatcgcc acaaccacca ccaccaccac ggagtctgtg gaagaggtgg

 901 tccgag.... .......... .......... .......... .......... ..........

     .......... .......... .......... .......... .......... ..........

                                                           .ttcctacaa

1141 cagcagccag caccccagat gccgttgaca agtatcttga gacacctgga gatgagaacg

1201 aacatgcgca tttccagaaa gccaaagaga ggctggaggc caagcaccgc gagagaatgt

1261 cccaggtcat gagagagtgg gaagaggcag aacgtcaagc aaagaacttg cctaaagctg

1321 ataagaaagc agtgatccag catttccagg agaaagtgga gtctctggag caggaagcag

1381 ccaacgagag gcagcagttg gtggagacgc acatggccag agtggaggcc atgcttaacg

1441 accgccggcg cctggccctg gagaattaca tcacggctct tcaggctgtt cctcctcggc

1501 ctcgtcatgt gttcaacatg ctcaagaagt atgtccgtgc cgaacagaaa gacagacagc

1561 acaccctaaa gcattttgaa cacgttcgca tggtagatcc aaagaaagct gctcagatcc

1621 gatcccaggt tatgacacac ctccgtgtga tttacgagcg catgaaccag tctctctccc

1681 tgctctacaa cgttcctgct gtggctgagg aaattcagga tgaagttgat gagctgctgc

1741 agaaagagca aaactactcg gatgatgtct tggccaacat gatcagcgaa ccgaggatca

1801 gttatggaaa cgatgctctc atgccgtctc tgactgaaac caaaaccacc gtggagcttc

1861 ttcctgtgaa tggagagttc agcctggatg atctccagcc ctggcatcct tttggggtag
```

-continued

```
1921 actctgtgcc tgccaacaca gaaaatgaag tcgagcctgt tgacgcccgc cctgcagccg
1981 accgaggact gaccactcga ccaggttccg ggttgaccaa catcaagacg gaagagatct
2041 ctgaagtgaa TCtggatgcg gagttccgac acgattcagg ctatgaggtt catcaccaaa
2101 aactggtgtt cttcgcagaa gatgtgggtt caaacaaagg tgccatcatt ggactcatgg
2161 tgggtggtgt tgtcatagca accgtgattg tcatcacctt agtgatgctg aagaagaaac
2221 agtacacatc catccatcac ggtgtggtgg aggttgacgc agctgtgacc ccggaggagc
2281 gccacctctc caagatgcag cagaatggct atgaaaaccc aacttacaag ttctttgagc
2341 agatgcagaa ctagaccgcc gccacagcag cctctgaagt tggacagcaa aaccattgct
2401 tcactaccca ttggtgttca tttatagaat aatggggaaa gacacaaacc cttctgtttt
2461 attatttact catgatcgcc tttcagcagc tgtgctgtaa cacaagtaga tgcctgaact
2521 tgaattaata ttacgaatca gtaatgtatt ctctctcttt acatttccgg tctctacact
2581 acattattaa tgggttttgt gtactgtaaa gaatgaagct gtatcaaact agtgcatgaa
2641 tagattccct cctgattatt tatcatgtag ccccttagcc agttgtatat tattcttgtg
2701 gttttgtgat ccaattaagt cctactttga aatatgcttt aagaatcgat gggggatgct
2761 tcatgtgaac gtgggagttt agctgcttct cttgcctaag tattcttttc ctgatcacta
2821 tgcattttaa aggtaaacat ttttatgtat tccaaatgag ttagagaagt tttttccacg
2881 attgcatttg actgtacaga ttgctgcttc tgctatattt gtgatatagg aattatgagg
2941 atacacgttt atttctttgt gcctgtttta tgtgcacaca ttaggcattg agaattaaaa
3001 cttcttttgt ccgtgtacct tcggatcttt aaaaaaaaaa aaaaaaaaaa a
```

Deleted sequence:

```
            aggt gtgctctgaa caagccgaga cggggccgtg ccgagcaatg atctcccgct
 961 ggtactttga tgtgactgaa gggaagtgcg ccccgttctt ttacggcgga tgtggcggca
1021 accgaaacaa ctttgacaca gaggaatact gcatggccgt gtgtggcagc gtcatgtccc
1081 aaagtttact caagactacc caggaacatc ttccccaaga tcctgttaaa c
```

SEQ ID NO 16
porcine APPsw protein isoform 695
Protein sequence derived from translation of SEQ ID No 15
The two amino acid changes due to the Swedish mutation are indicated in bold (NL) and corresponds to the K670N/M671L mutation. The deletion compared to APP770 is indicated by ( . . . ) in the sequence.

MLPGLALVLLAAWTARALEVPTDGNAGLLAEPQVAMFCGKLNMH

MNVQNGKWESDPSGTKTCIGTKEGILQYCQEVYPELQITNVVEANQPVTIQNWCKRSR

KQCKTHTHIVIPYRCLVGEFVSDALLVPDKCKFLHQERMDVCETHLHWHTVAKETCSE

KSTNLHDYGMLLPCGIDKFRGVEFVCCPLAEESDNIDSADAEEDDSDVWWGGADTDYA

DGSEDKVVEVAEEEEVADVEEEEAEDDEDDEDGDEVEEEAEEPYEEATERTTSIATTT

TTTTESVEEVVRE.........................................

.

.............................PTTAASTPDAVDKYLETPGDENEHAHFQ

KAKERLEAKHRERMSQVMREWEEAERQAKNLPKADKKAVIQHFQEKVESLEQEAANER

QQLVETHMARVEAMLNDRRRLALENYITALQAVPPRPRHVFNMLKKYVRAEQKDRQHT

LKHFEHVRMVDPKKAAQIRSQVMTHLRVIYERMNQSLSLLYNVPAVAEEIQDEVDELL

QKEQNYSDDVLANMISEPRISYGNDALMPSLTETKTTVELLPVNGEFSLDDLQPWHPF

GVDSVPANTENEVEPVDARPAADRGLTTRPGSGLTNIKTEEISEVNLDAEFRHDSGYE

-continued

VHHQKLVFFAEDVGSNKGAIIGLMVGGVVIATVIVITLVMLKKKQYTSIHHGVVEVDA

AVTPEERHLSKMQQNGYENPTYKFFEQMQN

SEQ ID NO 17
Human Presenilin-1 (PS-1) gene coding sequence with Pro117Leu (P117L) mutation. Sequence as SEQ ID NO 2 except for the nucleotide substitution at position 598 changing nucleotide C to nucleotide T. The mutation is indicated in capital letter. The nucleotide mutation results in the P117L mutation in the presenilin-1 protein.

```
   1 tgggacaggc agctccgggg tccgcggttt cacatcggaa acaaaacagc ggctggtctg

  61 gaaggaacct gagctacgag ccgcggcggc agcggggcgg cggggaagcg tatacctaat

 121 ctgggagcct gcaagtgaca acagcctttg cggtccttag acagcttggc ctggaggaga

 181 acacatgaaa gaaagaacct caagaggctt tgttttctgt gaaacagtat ttctatacag

 241 ttgctccaat gacagagtta cctgcaccgt tgtcctactt ccagaatgca cagatgtctg

 301 aggacaacca cctgagcaat actgtacgta gccagaatga caatagagaa cggcaggagc

 361 acaacgacag acggagcctt ggccaccctg agccattatc taatggacga ccccagggta

 421 actcccggca ggtggtggag caagatgagg aagaagatga ggagctgaca ttgaaatatg

 481 gcgccaagca tgtgatcatg ctctttgtcc ctgtgactct ctgcatggtg gtggtcgtgg

 541 ctaccattaa gtcagtcagc ttttataccc ggaaggatgg gcagctaatc tatacccTat

 601 tcacagaaga taccgagact gtgggccaga gagccctgca ctcaattctg aatgctgcca

 661 tcatgatcag tgtcattgtt gtcatgacta tcctcctggt ggttctgtat aaatacaggt

 721 gctataaggt catccatgcc tggcttatta tatcatctct attgttgctg ttcttttttt

 781 cattcattta cttgggggaa gtgtttaaaa cctataacgt tgctgtggac tacattactg

 841 ttgcactcct gatctggaat tttggtgtgg tgggaatgat ttccattcac tggaaaggtc

 901 cacttcgact ccagcaggca tatctcatta tgattagtgc cctcatggcc ctggtgttta

 961 tcaagtacct ccctgaatgg actgcgtggc tcatcttggc tgtgatttca gtatatgatt

1021 tagtggctgt tttgtgtccg aaaggtccac ttcgtatgct ggttgaaaca gctcaggaga

1081 gaaatgaaac gctttttcca gctctcattt actcctcaac aatggtgtgg ttggtgaata

1141 tggcagaagg agacccggaa gctcaaagga gagtatccaa aaattccaag tataatgcag

1201 aaagcacaga aagggagtca caagacactg ttgcagagaa tgatgatggc gggttcagtg

1261 aggaatggga agcccagagg gacagtcatc tagggcctca tcgctctaca cctgagtcac

1321 gagctgctgt ccaggaactt tccagcagta tcctcgctgg tgaagaccca gaggaaaggg

1381 gagtaaaact tggattggga gatttcattt tctacagtgt tctggttggt aaagcctcag

1441 caacagccag tggagactgg aacacaacca tagcctgttt cgtagccata ttaattggtt

1501 tgtgccttac attattactc cttgccattt tcaagaaagc attgccagct cttccaatct

1561 ccatcacctt tgggcttgtt ttctactttg ccacagatta tcttgtacag ccttttatgg

1621 accaattagc attccatcaa ttttatatct agcatatttg cggttagaat cccatggatg

1681 tttcttcttt gactataaca aaatctgggg aggacaaagg tgattttcct gtgtccacat

1741 ctaacaaagt caagattccc ggctggactt ttgcagcttc cttccaagtc ttcctgacca

1801 ccttgcacta ttggactttg gaaggaggtg cctatagaaa acgattttga acatacttca

1861 tcgcagtgga ctgtgtccct cggtgcagaa actaccagat ttgagggacg aggtcaagga

1921 gatatgatag gcccggaagt tgctgtgccc catcagcagc ttgacgcgtg gtcacaggac

1981 gatttcactg acactgcgaa ctctcaggac taccgttacc aagaggttag gtgaagtggt

2041 ttaaaccaaa cggaactctt catcttaaac tacacgttga aaatcaaccc aataattctg

2101 tattaactga attctgaact tttcaggagg tactgtgagg aagagcaggc accagcagca
```

-continued

```
2161 gaatggggaa tggagaggtg ggcaggggtt ccagcttccc tttgattttt tgctgcagac
2221 tcatcctttt taaatgagac ttgttttccc ctctctttga gtcaagtcaa atatgtagat
2281 tgcctttggc aattcttctt ctcaagcact gacactcatt accgtctgtg attgccattt
2341 cttcccaagg ccagtctgaa cctgaggttg ctttatccta aaagttttaa cctcaggttc
2401 caaattcagt aaattttgga aacagtacag ctatttctca tcaattctct atcatgttga
2461 agtcaaattt ggattttcca ccaaattctg aatttgtaga catacttgta cgctcacttg
2521 ccccagatgc ctcctctgtc ctcattcttc tctcccacac aagcagtctt tttctacagc
2581 cagtaaggca gctctgtcgt ggtagcagat ggtcccatta ttctagggtc ttactctttg
2641 tatgatgaaa agaatgtgtt atgaatcggt gctgtcagcc ctgctgtcag accttcttcc
2701 acagcaaatg agatgtatgc ccaaagcggt agaattaaag aagagtaaaa tggctgttga
2761 agc
```

SEQ ID NO 18
Human Presenilin-1 (PS-1) mRNA with Pro117Leu (P117L) mutation.
Sequence as SEQ ID NO 2 except for the nucleotide substitution at position 598 changing nucleotide C to nucleotide T. The mutation is indicated in capital letter. The nucleotide mutation results in the P117L mutation in the presenilin-1 protein.

```
   1 tgggacaggc agctccgggg tccgcggttt cacatcggaa acaaaacagc ggctggtctg
  61 gaaggaacct gagctacgag ccgcggcggc agcggggcgg cggggaagcg tatacctaat
 121 ctgggagcct gcaagtgaca acagcctttg cggtccttag acagcttggc ctggaggaga
 181 acacatgaaa gaaagaacct caagaggctt tgttttctgt gaaacagtat ttctatacag
 241 ttgctccaat gacagagtta cctgcaccgt tgtcctactt ccagaatgca cagatgtctg
 301 aggacaacca cctgagcaat actgtacgta gccagaatga caatagagaa cggcaggagc
 361 acaacgacag acggagcctt ggccaccctg agccattatc taatggacga ccccagggta
 421 actcccggca ggtggtggag caagatgagg aagaagatga ggagctgaca ttgaaatatg
 481 gcgccaagca tgtgatcatg ctctttgtcc ctgtgactct ctgcatggtg gtggtcgtgg
 541 ctaccattaa gtcagtcagc ttttataccc ggaaggatgg gcagctaatc tatacccTat
 601 tcacagaaga taccgagact gtgggccaga gagccctgca ctcaattctg aatgctgcca
 661 tcatgatcag tgtcattgtt gtcatgacta tcctcctggt ggttctgtat aaatacaggt
 721 gctataaggt catccatgcc tggcttatta tatcatctct attgttgctg ttcttttttt
 781 cattcattta cttgggggaa gtgtttaaaa cctataacgt tgctgtggac tacattactg
 841 ttgcactcct gatctggaat tttggtgtgg tgggaatgat ttccattcac tggaaaggtc
 901 cacttcgact ccagcaggca tatctcatta tgattagtgc cctcatggcc ctggtgttta
 961 tcaagtacct ccctgaatgg actgcgtggc tcatcttggc tgtgatttca gtatatgatt
1021 tagtggctgt tttgtgtccg aaaggtccac ttcgtatgct ggttgaaaca gctcaggaga
1081 gaaatgaaac gctttttcca gctctcattt actcctcaac aatggtgtgg ttggtgaata
1141 tggcagaagg agacccggaa gctcaaagga gagtatccaa aaattccaag tataatgcag
1201 aaagcacaga aagggagtca caagacactg ttgcagagaa tgatgatggc gggttcagtg
1261 aggaatggga agcccagagg gacagtcatc tagggcctca tcgctctaca cctgagtcac
1321 gagctgctgt ccaggaactt tccagcagta tcctcgctgg tgaagaccca gaggaaaggg
1381 gagtaaaact tggattggga gatttcattt tctacagtgt tctggttggt aaagcctcag
1441 caacagccag tggagactgg aacacaacca tagcctgttt cgtagccata ttaattggtt
1501 tgtgccttac attattactc cttgccattt tcaagaaagc attgccagct cttccaatct
1561 ccatcacctt tgggcttgtt ttctactttg ccacagatta tcttgtacag ccttttatgg
```

-continued 1621 accaattagc attccatcaa ttttatatct agcatatttg cggttagaat cccatggatg 1681 tttcttcttt gactataaca aaatctgggg aggacaaagg tgattttcct gtgtccacat 1741 ctaacaaagt caagattccc ggctggactt ttgcagcttc cttccaagtc ttcctgacca 1801 ccttgcacta ttggactttg gaaggaggtg cctatagaaa acgattttga acatacttca 1861 tcgcagtgga ctgtgtccct cggtgcagaa actaccagat ttgagggacg aggtcaagga 1921 gatatgatag gcccggaagt tgctgtgccc catcagcagc ttgacgcgtg gtcacaggac 1981 gatttcactg acactgcgaa ctctcaggac taccgttacc aagaggttag gtgaagtggt 2041 ttaaaccaaa cggaactctt catcttaaac tacacgttga aaatcaaccc aataattctg 2101 tattaactga attctgaact tttcaggagg tactgtgagg aagagcaggc accagcagca 2161 gaatggggaa tggagaggtg ggcaggggtt ccagcttccc tttgattttt tgctgcagac 2221 tcatcctttt taaatgagac ttgttttccc ctctctttga gtcaagtcaa atatgtagat 2281 tgcctttggc aattcttctt ctcaagcact gacactcatt accgtctgtg attgccattt 2341 cttcccaagg ccagtctgaa cctgaggttg ctttatccta aaagttttaa cctcaggttc 2401 caaattcagt aaattttgga aacagtacag ctatttctca tcaattctct atcatgttga 2461 agtcaaattt ggatttttcca ccaaattctg aatttgtaga catacttgta cgctcacttg 2521 ccccagatgc ctcctctgtc ctcattcttc tctcccacac aagcagtctt tttctacagc 2581 cagtaaggca gctctgtcgt ggtagcagat ggtcccatta ttctagggtc ttactctttg 2641 tatgatgaaa agaatgtgtt atgaatcggt gctgtcagcc ctgctgtcag accttcttcc 2701 acagcaaatg agatgtatgc ccaaagcggt agaattaaag aagagtaaaa tggctgttga 2761 agc SEQ ID NO 19
Human Presenilin-1 (PS-1) protein with Pro117Leu (P117L) mutation.
Translation of SEQ ID NO 18. The P117L mutation in the presenilin-1 protein is in bold.
MTELPAPLSYFQNAQMSEDNHLSNTVRSQNDNRERQEHNDRRSL

GHPEPLSNGRPQGNSRQVVEQDEEEDEELTLKYGAKHVIMLFVPVTLCMVVVVATIKS

VSFYTRKDGQLIYTLFTEDTETVGQRALHSILNAAIMISVIVVMTILLVVLYKYRCYK

VIHAWLIISSLLLLFFFSFIYLGEVFKTYNVAVDYITVALLIWNFGVVGMISIHWKGP

LRLQQAYLIMISALMALVFIKYLPEWTAWLILAVISVYDLVAVLCPKGPLRMLVETAQ

ERNETLFPALIYSSTMVWLVNMAEGDPEAQRRVSKNSKYNAESTERESQDTVAENDDG

GFSEEWEAQRDSHLGPHRSTPESRAAVQELSSSILAGEDPEERGVKLGLGDFIFYSVL

VGKASATASGDWNTTIACFVAILIGLCLTLLLLAIFKKALPALPISITFGLVFYFATD

YLVQPFMDQLAFHQFYI

SEQ ID NO 20
Porcine Presenilin-1 (PS-1) gene coding sequence with Pro117Leu (P117L) mutation.
Sequence as SEQ ID NO 4 except for the nucleotide substitution at position 550 changing nucleotide C to nucleotide T. The mutation is indicated in capital letter. The nucleotide mutation results in the P117L mutation in the presenilin-1 protein.

1 aatcggaaac aaaacagcgg ctgctgggga agggacctgg gctgcgagag gtggcggctg 61 cgacgagaaa gaacctaatc cgggagcctg caacctgtga agttcttaga aagcttggcc 121 tggaggagaa cacatgaaag aaagaacccc aggaggctct gatttctgtg aaaaagtatt 181 tctatacggt tgttccaatg acagagttac ctgcaccctt gtcctacttc cagaatgccc 241 agatgtccga ggacaaccac gtgagcaata acgtaagtag ccagaatgac agtagagagc 301 ggcatgagca cagcatcgag aggcggaggc gtggcaactc tgagtcgtta tccaatggcg 361 gagcccaggg aaactcacgc caggtggtgg aacaagaaga agaggaagac gaggagctga 421 cgttgaaata tggcgccaaa catgtgatca tgctctttgt ccctgtgact ctatgtatgg -continued 481 tggtggttgt ggccaccatc aaatcagtca gcttttatac ccggaaggat gggcagctga 541 tctatactcT atttacagaa gacactgaga ctgtagggca gagagccctg cactcaattc 601 tgaatgctgc tatcatgatt agtgtcattg tcgtcatgac tattctcctg gtggttctct 661 ataaatacag gtgctataag gtcatccatg cctggcttat tatttcatcc ctattgttgc 721 tgttcttttt ctcattcatt tacttggggg aagtgtttaa aacctataac gttgccatgg 781 attacattac ggtggcactc ctgatctgga attttggtgt ggtaggaatg attgccattc 841 actggaaagg cccattgcga ctccagcagg catatctcat tatgatcagt gccctcatgg 901 ccctggtgtt tatcaagtac ctcccggaat ggaccgcgtg gctcatcttg gctgtgattt 961 cagtatacga tttagtggct gttttgtgtc caaatggccc acttcgtttg ctggttgaaa 1021 cagctcagga gagaaatgaa actctctttc cagctcttat ttactcgtca acaatggtgt 1081 ggttggtgaa tatggcagaa ggagacccag aagcccaaag gaaggtatcc aaaaactcca 1141 attataatgc acaaagcaca ggtgaatcac aagactctgt gacagagagt gatgatggtg 1201 gcttcagtga agagtgggaa gcccagaggg acagtcgcct gggacctcat cactctacag 1261 ctgagtcacg atctgctgta caggatcttt ccagaagcat cccagccact gaggacccag 1321 aagaaagggg agtaaaactt ggattaggag atttcatttt ctacagtgtt ctggttggta 1381 aagcttctgc aacagccagt ggagactgga acacaaccat tgcctgtttt gtagccatat 1441 taattggttt gtgccttaca ttactgctcc tcgccatttt caagaaagcg ttgccagctc 1501 ttccaatctc tatcaccttt gggcttgttt tctactttgc cacagattat cttgtgcaac 1561 cctttatgga ccaattagca ttccatcaat tttatatcta gcatatttcc agttagaatc 1621 tcatggattt tttctccttt ggctataata aaatctgggg aaagcaaagg tgattttgct 1681 gtgtccacat ctaacaaagt caggattccc agctggacct SEQ ID NO 21
Porcine Presenilin-1 (PS-1) mRNA with Pro117Leu (P117L) mutation.
Sequence as SEQ ID NO 4 except for the nucleotide substitution at position 550 changing nucleotide C to nucleotide T. The mutation is indicated in capital letter. The nucleotide mutation results in the P117L mutation in the presenilin-1 protein.

1 aatcggaaac aaaacagcgg ctgctgggga agggacctgg gctgcgagag gtggcggctg 61 cgacgagaaa gaacctaatc cgggagcctg caacctgtga agttcttaga aagcttggcc 121 tggaggagaa cacatgaaag aaagaacccc aggaggctct gatttctgtg aaaaagtatt 181 tctatacggt tgttccaatg acagagttac ctgcacccctt gtcctacttc cagaatgccc 241 agatgtccga ggacaaccac gtgagcaata acgtaagtag ccagaatgac agtagagagc 301 ggcatgagca cagcatcgag aggcggaggc gtggcaactc tgagtcgtta tccaatggcg 361 gagcccaggg aaactcacgc caggtggtgg aacaagaaga agaggaagac gaggagctga 421 cgttgaaata tggcgccaaa catgtgatca tgctctttgt ccctgtgact ctatgtatgg 481 tggtggttgt ggccaccatc aaatcagtca gcttttatac ccggaaggat gggcagctga 541 tctatactcT atttacagaa gacactgaga ctgtagggca gagagccctg cactcaattc 601 tgaatgctgc tatcatgatt agtgtcattg tcgtcatgac tattctcctg gtggttctct 661 ataaatacag gtgctataag gtcatccatg cctggcttat tatttcatcc ctattgttgc 721 tgttcttttt ctcattcatt tacttggggg aagtgtttaa aacctataac gttgccatgg 781 attacattac ggtggcactc ctgatctgga attttggtgt ggtaggaatg attgccattc 841 actggaaagg cccattgcga ctccagcagg catatctcat tatgatcagt gccctcatgg 901 ccctggtgtt tatcaagtac ctcccggaat ggaccgcgtg gctcatcttg gctgtgattt 961 cagtatacga tttagtggct gttttgtgtc caaatggccc acttcgtttg ctggttgaaa -continued

```
1021 cagctcagga gagaaatgaa actctctttc cagctcttat ttactcgtca acaatggtgt

1081 ggttggtgaa tatggcagaa ggagacccag aagcccaaag gaaggtatcc aaaaactcca

1141 attataatgc acaaagcaca ggtgaatcac aagactctgt gacagagagt gatgatggtg

1201 gcttcagtga agagtgggaa gcccagaggg acagtcgcct gggacctcat cactctacag

1261 ctgagtcacg atctgctgta caggatcttt ccagaagcat cccagccact gaggacccag

1321 aagaaagggg agtaaaactt ggattaggag atttcatttt ctacagtgtt ctggttggta

1381 aagcttctgc aacagccagt ggagactgga acacaaccat tgcctgtttt gtagccatat

1441 taattggttt gtgccttaca ttactgctcc tcgccatttt caagaaagcg ttgccagctc

1501 ttccaatctc tatcaccttt gggcttgttt tctactttgc cacagattat cttgtgcaac

1561 cctttatgga ccaattagca ttccatcaat tttatatcta gcatatttcc agttagaatc

1621 tcatggattt tttctccttt ggctataata aaatctgggg aaagcaaagg tgattttgct

1681 gtgtccacat ctaacaaagt caggattccc agctggacct
```

SEQ ID NO 22
Porcine Presenilin-1 (PS-1) protein with Pro117Leu (P117L) mutation.
Translation of SEQ ID NO 21. The P117L mutation in the presenilin-1 protein is in bold.
MTELPAPLSYFQNAQMSEDNHVSNNVSSQNDSRERHEHSIERRR

RGNSESLSNGGAQGNSRQVVEQEEEEDEELTLKYGAKHVIMLFVPVTLCMVVVVATIK

SVSFYTRKDGQLIYTLFTEDTETVGQRALHSILNAAIMISVIVVMTILLVVLYKYRCY

KVIHAWLIISSLLLLFFFSFIYLGEVFKTYNVAMDYITVALLIWNFGVVGMIAIHWKG

PLRLQQAYLIMISALMALVFIKYLPEWTAWLILAVISVYDLVAVLCPNGPLRLLVETA

QERNETLFPALIYSSTMVWLVNMAEGDPEAQRKVSKNSNYNAQSTGESQDSVTESDDG

GFSEEWEAQRDSRLGPHHSTAESRSAVQDLSRSIPATEDPEERGVKLGLGDFIFYSVL

VGKASATASGDWNTTIACFVAILIGLCLTLLLLAIFKKALPALPISITFGLVFYFATD

YLVQPFMDQLAFHQFYI

SEQ ID NO 23
Human APP protein isoform 770
Protein sequence derived from translation of SEQ ID No 1
MLPGLALLLLAAWTARALEVPTDGNAGLLAEPQIAMFCGRLNMH

MNVQNGKWDSDPSGTKTCIDTKEGILQYCQEVYPELQITNVVEANQPVTIQNWCKRGR

KQCKTHPHFVIPYRCLVGEFVSDALLVPDKCKFLHQERMDVCETHLHWHTVAKETCSE

KSTNLHDYGMLLPCGIDKFRGVEFVCCPLAEESDNVDSADAEEDDSDVWWGGADTDYA

DGSEDKVVEVAEEEEVAEVEEEEADDDEDDEDGDEVEEEAEEPYEEATERTTSIATT

TTTTESVEEVVREVCSEQAETGPCRAMISRWYFDVTEGKCAPFFYGGCGGNRNNFDTE

EYCMAVCGSAMSQSLLKTTQEPLARDPVKLPTTAASTPDAVDKYLETPGDENEHAHFQ

KAKERLEAKHRERMSQVMREWEEAERQAKNLPKADKKAVIQHFQEKVESLEQEAANER

QQLVETHMARVEAMLNDRRRLALENYITALQAVPPRPRHVFNMLKKYVRAEQKDRQHT

LKHFEHVRMVDPKKAAQIRSQVMTHLRVIYERMNQSLSLLYNVPAVAEEIQDEVDELL

QKEQNYSDDVLANMISEPRISYGNDALMPSLTETKTTVELLPVNGEFSLDDLQPWHSF

GADSVPANTENEVEPVDARPAADRGLTTRPGSGLTNIKTEEISEVKMDAEFRHDSGYE

VHHQKLVFFAEDVGSNKGAIIGLMVGGVVIATVIVITLVMLKKKQYTSIHHGVVEVDA

AVTPEERHLSKMQQNGYENPTYKFFEQMQN

SEQ ID NO 24
porcine APP protein isoform 770
Protein sequence derived from translation of SEQ ID No 3
MLPGLALVLLAAWTARALEVPTDGNAGLLAEPQVAMFCGKLNMH

MNVQNGKWESDPSGTKTCIGTKEGILQYCQEVYPELQITNVVEANQPVTIQNWCKRSR

KQCKTHTHIVIPYRCLVGEFVSDALLVPDKCKFLHQERMDVCETHLHWHTVAKETCSE

KSTNLHDYGMLLPCGIDKFRGVEFVCCPLAEESDNIDSADAEEDDSDVWWGGADTDYA

DGSEDKVVEVAEEEEVADVEEEEAEDDEDDEDGDEVEEEAEEPYEEATERTTSIATTT

TTTTESVEEVVREVCSEQAETGPCRAMISRWYFDVTEGKCAPFFYGGCGGNRNNFDTE

EYCMAVCGSVMSQSLLKTTQEHLPQDPVKLPTTAASTPDAVDKYLETPGDENEHAHFQ

KAKERLEAKHRERMSQVMREWEEAERQAKNLPKADKKAVIQHFQEKVESLEQEAANER

QQLVETHMARVEAMLNDRRRLALENYITALQAVPPRPRHVFNMLKKYVRAEQKDRQHT

LKHFEHVRMVDPKKAAQIRSQVMTHLRVIYERMNQSLSLLYNVPAVAEEIQDEVDELL

QKEQNYSDDVLANMISEPRISYGNDALMPSLTETKTTVELLPVNGEFSLDDLQPWHPF

GVDSVPANTENEVEPVDARPAADRGLTTRPGSGLTNIKTEEISEVKMDAEFRHDSGYE

VHHQKLVFFAEDVGSNKGAIIGLMVGGVVIATVIVITLVMLKKKQYTSIHHGVVEVDA

AVTPEERHLSKMQQNGYENPTYKFFEQMQN

SEQ ID NO 25
Human presenilin-1 protein
Protein sequence derived from translation of SEQ ID No 2
MTELPAPLSYFQNAQMSEDNHLSNTVRSQNDNRERQEHNDRRSL

GHPEPLSNGRPQGNSRQVVEQDEEEDEELTLKYGAKHVIMLFVPVTLCMVVVVATIKS

VSFYTRKDGQLIYTPFTEDTETVGQRALHSILNAAIMISVIVVMTILLVVLYKYRCYK

VIHAWLIISSLLLLFFFSFIYLGEVFKTYNVAVDYITVALLIWNFGVVGMISIHWKGP

LRLQQAYLIMISALMALVFIKYLPEWTAWLILAVISVYDLVAVLCPKGPLRMLVETAQ

ERNETLFPALIYSSTMVWLVNMAEGDPEAQRRVSKNSKYNAESTERESQDTVAENDDG

GFSEEWEAQRDSHLGPHRSTPESRAAVQELSSSILAGEDPEERGVKLGLGDFIFYSVL

VGKASATASGDWNTTIACFVAILIGLCLTLLLLAIFKKALPALPISITFGLVFYFATD

YLVQPFMDQLAFHQFYI

SEQ ID NO 26
Porcine presenilin-1 protein
Protein sequence derived from translation of SEQ ID No 4
MTELPAPLSYFQNAQMSEDNHVSNNVSSQNDSRERHEHSIERRR

RGNSESLSNGGAQGNSRQVVEQEEEEDEELTLKYGAKHVIMLFVPVTLCMVVVVATIK

SVSFYTRKDGQLIYTPFTEDTETVGQRALHSILNAAIMISVIVVMTILLVVLYKYRCY

KVIHAWLIISSLLLLFFFSFIYLGEVFKTYNVAMDYITVALLIWNFGVVGMIAIHWKG

PLRLQQAYLIMISALMALVFIKYLPEWTAWLILAVISVYDLVAVLCPNGPLRLLVETA

QERNETLFPALIYSSTMVWLVNMAEGDPEAQRKVSKNSNYNAQSTGESQDSVTESDDG

GFSEEWEAQRDSRLGPHHSTAESRSAVQDLSRSIPATEDPEERGVKLGLGDFIFYSVL

VGKASATASGDWNTTIACFVAILIGLCLTLLLLAIFKKALPALPISITFGLVFYFATD

YLVQPFMDQLAFHQFYI

LOCUS       AB032550                3051 bp    mRNA    linear   MAM
23-SEP-1999
DEFINITION  Sus scrofa mRNA for amyloid precursor protein, complete
            cds.
ACCESSION   AB032550
VERSION     AB032550.1  GI: 5921141
KEYWORDS    amyloid precursor protein.
SOURCE      Sus scrofa (pig)

-continued

```
ORGANISM      Sus scrofa
              Eukaryota; Metazoa; Chordata; Craniata; Vertebrata;
              Euteleostomi;
              Mammalia; Eutheria; Laurasiatheria; Cetartiodactyla;
              Suina; Suidae;
              Sus.
REFERENCE     1
AUTHORS       Kimura, A. and Takahashi, T.
TITLE         Amyloid Precursor Protein 770
JOURNAL       Published Only in Database (1999)
REFERENCE     2 (bases 1 to 3051)
AUTHORS       Kimura, A. and Takahashi, T.
TITLE         Direct Submission
JOURNAL       Submitted (18-SEP-1999) Takayuki Takahashi, Hokkaido
              University,
              The Division of Biological Sciences, Graduate School of
              Science;
              kita-10, nishi-8, kita-ku, Sapporo city 060-0810, Japan
              (E-mail: ttakaha@sci.hokudai.ac.jp, Tel: 81-11-706-2748,
              Fax: 81-11-706-4851)
FEATURES      Location/Qualifiers
source        1 . . . 3051
              /organism = "Sus scrofa"
              /mol_type = "mRNA"
              /db_xref = "taxon: 9823"
CDS           42 . . . 2354
              /codon_start = 1
              /product = "amyloid precursor protein"
              /protein_id = "BAA84580.1"
              /db_xref = "GI: 5921142"
/translation = "MLPGLALVLLAAWTARALEVPTDGNAGLLAEPQVAMFCGKLNMH

MNVQNGKWESDPSGTKTCIGTKEGILQYCQEVYPELQITNVVEANQPVTIQNWCKRSR

KQCKTHTHIVIPYRCLVGEFVSDALLVPDKCKFLHQERMDVCETHLHWHTVAKETCSE

KSTNLHDYGMLLPCGIDKFRGVEFVCCPLAEESDNIDSADAEEDDSDVWWGGADTDYA

DGSEDKVVEVAEEEEVADVEEEEAEDDEDDEDGDEVEEEAEEPYEEATERTTSIATTT

TTTTESVEEVVREVCSEQAETGPCRAMISRWYFDVTEGKCAPFFYGGCGGNRNNFDTE

EYCMAVCGSVMSQSLLKTTQEHLPQDPVKLPTTAASTPDAVDKYLETPGDENEHAHFQ

KAKERLEAKHRERMSQVMREWEEAERQAKNLPKADKKAVIQHFQEKVESLEQEAANER

QQLVETHMARVEAMLNDRRRLALENYITALQAVPPRPRHVFNMLKKYVRAEQKDRQHT

LKHFEHVRMVDPKKAAQIRSQVMTHLRVIYERMNQSLSLLYNVPAVAEEIQDEVDELL

QKEQNYSDDVLANMISEPRISYGNDALMPSLTETKTTVELLPVNGEFSLDDLQPWHPF

GVDSVPANTENEVEPVDARPAADRGLTTRPGSGLTNIKTEEISEVKMDAEFRHDSGYE

VHHQKLVFFAEDVGSNKGAIIGLMVGGVVIATVIVITLVMLKKKQYTSIHHGVVEVDA

                    AVTPEERHLSKMQQNGYENPTYKFFEQMQN"

ORIGIN
     1  acgcgaacag cagcgcactc ggtgccccgc gcagggtcgc gatgctgccc
        ggtttggcac

    61  tggtcctgct ggccgcctgg acggctaggg cgctggaggt gcccactgat
        ggcaatgccg

   121  gcctgcttgc agaaccccag gttgccatgt tctgtggcaa actcaacatg
        cacatgaatg

   181  tgcagaatgg gaagtgggag tcagatccgt cggggaccaa aacctgcatt
        ggcaccaagg

   241  aaggcatctt gcagtactgc caagaagtct accctgaact gcagatcacc
        aatgtggtag

   301  aagccaacca accagtgacc atccagaact ggtgcaagag gagccggaag
        cagtgcaaga

   361  cccacactca cattgtgatt ccgtaccgct gcttagttgg cgagtttgta
        agcgatgccc
```

-continued 421 tccttgttcc ggacaagtgc aagttcttac accaggagag gatggatgtt tgcgaaaccc 481 accttcactg gcacactgtg gccaaagaga cctgtagtga gaagagtacg aacttgcatg 541 actatggcat gttgctgccc tgtggaattg acaagttccg aggggtggag tttgtgtgtt 601 gcccactggc cgaggaaagt gacaatatcg actcagcaga tgcagaagag gatgactcgg 661 acgtctggtg gggtggagca gatacagact atgcagatgg cagtgaagac aaagtcgtgg 721 aggtcgcaga ggaggaggaa gtggctgatg tcgaggaaga agaagctgag gatgatgagg 781 atgatgagga tggtgatgag gtagaagaag aggctgagga accctatgaa gaggccacgg 841 agagaaccac cagcatcgcc acaaccacca ccaccaccac ggagtctgtg gaagaggtgg 901 tccgagaggt gtgctctgaa caagccgaga cggggccgtg ccgagcaatg atctcccgct 961 ggtactttga tgtgactgaa gggaagtgcg ccccgttctt ttacggcgga tgtggcggca 1021 accgaaacaa ctttgacaca gaggaatact gcatggccgt gtgtggcagc gtcatgtccc 1081 aaagtttact caagactacc caggaacatc ttccccaaga tcctgttaaa cttcctacaa 1141 cagcagccag caccccagat gccgttgaca agtatcttga gacacctgga gatgagaacg 1201 aacatgcgca tttccagaaa gccaaagaga ggctggaggc caagcaccgc gagagaatgt 1261 cccaggtcat gagagagtgg gaagaggcag aacgtcaagc aaagaacttg cctaaagctg 1321 ataagaaagc agtgatccag catttccagg agaaagtgga gtctctggag caggaagcag 1381 ccaacgagag gcagcagttg gtggagacgc acatggccag agtggaggcc atgcttaacg 1441 accgccggcg cctggccctg gagaattaca tcacggctct tcaggctgtt cctcctcggc 1501 ctcgtcatgt gttcaacatg ctcaagaagt atgtccgtgc cgaacagaaa gacagacagc 1561 acaccctaaa gcattttgaa cacgttcgca tggtagatcc aaagaaagct gctcagatcc 1621 gatcccaggt tatgacacac ctccgtgtga tttacgagcg catgaaccag tctctctccc 1681 tgctctacaa cgttcctgct gtggctgagg aaattcagga tgaagttgat gagctgctgc 1741 agaaagagca aaactactcg gatgatgtct tggccaacat gatcagcgaa ccgaggatca 1801 gttatggaaa cgatgctctc atgccgtctc tgactgaaac caaaaccacc gtggagcttc 1861 ttcctgtgaa tggagagttc agcctggatg atctccagcc ctggcatcct tttggggtag 1921 actctgtgcc tgccaacaca gaaaatgaag tcgagcctgt tgacgcccgc cctgcagccg 1981 accgaggact gaccactcga ccaggttccg ggttgaccaa catcaagacg gaagagatct -continued 2041 ctgaagtgaa gatggatgcg gagttccgac acgattcagg ctatgaggtt catcaccaaa 2101 aactggtgtt cttcgcagaa gatgtgggtt caaacaaagg tgccatcatt ggactcatgg 2161 tgggtggtgt tgtcatagca accgtgattg tcatcacctt agtgatgctg aagaagaaac 2221 agtacacatc catccatcac ggtgtggtgg aggttgacgc agctgtgacc ccggaggagc 2281 gccacctctc caagatgcag cagaatggct atgaaaaccc aacttacaag ttctttgagc 2341 agatgcagaa ctagaccgcc gccacagcag cctctgaagt tggacagcaa aaccattgct 2401 tcactaccca ttggtgttca tttatagaat aatggggaaa gacacaaacc cttctgtttt 2461 attatttact catgatcgcc tttcagcagc tgtgctgtaa cacaagtaga tgcctgaact 2521 tgaattaata ttacgaatca gtaatgtatt ctctctcttt acatttccgg tctctacact 2581 acattattaa tgggttttgt gtactgtaaa gaatgaagct gtatcaaact agtgcatgaa 2641 tagattccct cctgattatt tatcatgtag ccccttagcc agttgtatat tattcttgtg 2701 gttttgtgat ccaattaagt cctactttga aatatgcttt aagaatcgat gggggatgct 2761 tcatgtgaac gtgggagttt agctgcttct cttgcctaag tattcttttc ctgatcacta 2821 tgcattttaa aggtaaacat tttatgtat tccaaatgag ttagagaagt tttttccacg 2881 attgcatttg actgtacaga ttgctgcttc tgctatattt gtgatatagg aattatgagg 2941 atacacgttt atttctttgt gcctgtttta tgtgcacaca ttaggcattg agaattaaaa 3001 cttcttttgt ccgtgtacct tcggatcttt aaaaaaaaaa aaaaaaaaaa a Presenilin 1:
Porcine Presenilin 1 (PS1) Protein 1 mtelpaplsy fqnaqmsedn hvsnnvssqn dsrerhehsi errrrgnses lsnggaqgns 61 rqvveqeeee deeltlkyga khvimlfvpv tlcmvvvvat iksvsfytrk dgqliytpft 121 edtetvgqra lhsilnaaim isvivvmtil lvvlykyrcy kvihawliis sllllfffsf 181 iylgevfkty nvamdyitva lliwnfgvvg miaihwkgpl rlqqaylimi salmalvfik 241 ylpewtawli lavisvydlv avlcpngplr llvetaqern etlfpaliys stmvwlvnma 301 egdpeaqrkv sknsnynaqs tgesqdsvte sddggfseew eaqrdsrlgp hhstaesrsa 361 vqdlsrsipa tedpeergvk lglgdfifys vlvgkasata sgdwnttiac fvailiglcl 421 tllllaifkk alpalpisit fglvfyfatd ylvqpfmdql afhqfyi SEQ ID NO.: 4 Porcine Presenilin 1 (PS1) DNA 1 aatcggaaac aaaacagcgg ctgctgggga agggacctgg gctgcgagag gtggcggctg 61 cgacgagaaa gaacctaatc cgggagcctg caacctgtga agttcttaga aagcttggcc 121 tggaggagaa cacatgaaag aaagaacccc aggaggctct gatttctgtg aaaaagtatt 181 tctatacggt tgttccaatg acagagttac ctgcaccctt gtcctacttc cagaatgccc 241 agatgtccga ggacaaccac gtgagcaata acgtaagtag ccagaatgac agtagagagc 301 ggcatgagca cagcatcgag aggcggaggc gtggcaactc tgagtcgtta tccaatggcg -continued 361 gagcccaggg aaactcacgc caggtggtgg aacaagaaga agaggaagac gaggagctga 421 cgttgaaata tggcgccaaa catgtgatca tgctctttgt ccctgtgact ctatgtatgg 481 tggtggttgt ggccaccatc aaatcagtca gcttttatac ccggaaggat gggcagctga 541 tctatactcc atttacagaa gacactgaga ctgtagggca gagagccctg cactcaattc 601 tgaatgctgc tatcatgatt agtgtcattg tcgtcatgac tattctcctg gtggttctct 661 ataaatacag gtgctataag gtcatccatg cctggcttat tatttcatcc ctattgttgc 721 tgttcttttt ctcattcatt tacttggggg aagtgtttaa aacctataac gttgccatgg 781 attacattac ggtggcactc ctgatctgga attttggtgt ggtaggaatg attgccattc 841 actggaaagg cccattgcga ctccagcagg catatctcat tatgatcagt gccctcatgg 901 ccctggtgtt tatcaagtac ctcccggaat ggaccgcgtg gctcatcttg gctgtgattt 961 cagtatacga tttagtggct gttttgtgtc caaatggccc acttcgtttg ctggttgaaa 1021 cagctcagga gagaaatgaa actctctttc cagctcttat ttactcgtca acaatggtgt 1081 ggttggtgaa tatggcagaa ggagacccag aagcccaaag gaaggtatcc aaaaactcca 1141 attataatgc acaaagcaca ggtgaatcac aagactctgt gacagagagt gatgatggtg 1201 gcttcagtga agagtgggaa gcccagaggg acagtcgcct gggacctcat cactctacag 1261 ctgagtcacg atctgctgta caggatcttt ccagaagcat cccagccact gaggacccag 1321 aagaaagggg agtaaaactt ggattaggag atttcatttt ctacagtgtt ctggttggta 1381 aagcttctgc aacagccagt ggagactgga acacaaccat tgcctgtttt gtagccatat 1441 taattggttt gtgccttaca ttactgctcc tcgccatttt caagaaagcg ttgccagctc 1501 ttccaatctc tatcaccttt gggcttgttt tctactttgc cacagattat cttgtgcaac 1561 cctttatgga ccaattagca ttccatcaat tttatatcta gcatatttcc agttagaatc 1621 tcatggattt tttctccttt ggctataata aaatctgggg aaagcaaagg tgattttgct 1681 gtgtccacat ctaacaaagt caggattccc agctggacct Human Presenilin 1 mRNA and protein
LOCUS NM_000021 2763 bp mRNA linear PRI 14-JAN-2007
DEFINITION *Homo sapiens* presenilin 1 (Alzheimer disease 3) (PSEN1), mRNA.
ACCESSION NM_000021
VERSION NM_000021.2 GI: 21536454
KEYWORDS .
SOURCE *Homo sapiens* (human)
ORGANISM *Homo sapiens*
Eukaryota; Metazoa; Chordata; Craniata; Vertebrata; Euteleostomi; Mammalia; Eutheria; Euarchontoglires; Primates; Haplorrhini; Catarrhini; Hominidae; *Homo*.
REFERENCE 1 (bases 1 to 2763)
AUTHORS Sato, C., Morohashi, Y., Tomita, T. and Iwatsubo, T.
TITLE Structure of the catalytic pore of gamma-secretase probed by the accessibility of substituted cysteines
JOURNAL J. Neurosci. 26 (46), 12081-12088 (2006)
PUBMED 17108181
REMARK GeneRIF: Collectively, our data suggest that the active site of gamma-secretase resides in a catalytic pore filled with water within the lipid bilayer and is tapered around the catalytic aspartates.
REFERENCE 2 (bases 1 to 2763)
AUTHORS Tsuchiya, D., Kitamura, Y., Takata, K., Taniguchi, T., Uemura, K., Miki, H., Takenawa, T. and Shimohama, S.
TITLE Morphological change by overexpression of D385A dominant negative presenilin 1 in human neuroblastoma SH-SY5Y cells
JOURNAL J. Pharmacol. Sci. 102 (3), 354-358 (2006)
PUBMED 17099291
REMARK GeneRIF: PS1 may be involved in neuritogenesis and morphological change in SH-SY5Y cells, and P117L mutation may linked to Alzheimer's disease by different mechanisms
REFERENCE 3 (bases 1 to 2763)
AUTHORS Fang, B., Jia, L. and Jia, J.

-continued

```
TITLE       Chinese Presenilin-1 V97L mutation enhanced Abeta42 levels in
            SH-SY5Y neuroblastoma cells
JOURNAL     Neurosci. Lett. 406 (1-2), 33-37 (2006)
PUBMED      16916581
REMARK      GeneRIF: Our data reveal that the Presenilin-1 V97L variant can
            elevate Abeta42 levels both intracellularly and extracellularly,
            and was a potentially pathogenic mutation for this Chinese FAD
            pedigree.
REFERENCE   4 (bases 1 to 2763)
AUTHORS     Dumanchin, C., Tournier, I., Martin, C., Didic, M., Belliard, S.,
            Carlander, B., Rouhart, F., Duyckaerts, C., Pellissier, J. F.,
            Latouche, J. B., Hannequin, D., Frebourg, T., Tosi, M. and Campion, D.
TITLE       Biological effects of four PSEN1 gene mutations causing Alzheimer
            disease with spastic paraparesis and cotton wool plaques
JOURNAL     Hum. Mutat. 27 (10), 1063 (2006)
PUBMED      16941492
REMARK      GeneRIF: PSEN1 gene mutations resulting in large increases in
            secreted Abeta42 levels or loss of PSEN1 exons 8 or 9 may cause
            Alzheimer disease with spastic paraparesis and cotton wool
            plaques.
REFERENCE   5 (bases 1 to 2763)
AUTHORS     Parisiadou, L., Fassa, A., Fotinopoulou, A., Bethani, I. and
            Efthimiopoulos, S.
TITLE       Presenilin 1 and cadherins: stabilization of cell-cell adhesion
            and
            proteolysis-dependent regulation of transcription
JOURNAL     Neurodegener Dis 1 (4-5), 184-191 (2004)
PUBMED      16908988
REMARK      GeneRIF: PS1 mutations associated with FAD abolish production of
            the N-cadherin intracellular fragment
REFERENCE   6 (bases 1 to 2763)
AUTHORS     Sherrington, R., Rogaev, E. I., Liang, Y., Rogaeva, E. A., Levesque, G.,
            Ikeda, M., Chi, H., Lin, C., Li, G., Holman, K. et al.
TITLE       Cloning of a gene bearing missense mutations in early-onset
            familial Alzheimer's disease
JOURNAL     Nature 375 (6534), 754-760 (1995)
PUBMED      7596406
REFERENCE   7 (bases 1 to 2763)
AUTHORS     St George-Hyslop, P., Haines, J., Rogaev, E., Mortilla, M., Vaula, G.,
            Pericak-Vance, M., Foncin, J. F., Montesi, M., Bruni, A., Sorbi, S. et
            al.
TITLE       Genetic evidence for a novel familial Alzheimer's disease locus on
            chromosome 14
JOURNAL     Nat. Genet. 2 (4), 330-334 (1992)
PUBMED      1303289
REFERENCE   8 (bases 1 to 2763)
AUTHORS     Schellenberg, G. D., Bird, T. D., Wijsman, E. M., Orr, H. T., Anderson, L.,
            Nemens, E., White, J. A., Bonnycastle, L., Weber, J. L., Alonso, M. E. et
            al.
TITLE       Genetic linkage evidence for a familial Alzheimer's disease locus
            on chromosome 14
JOURNAL     Science 258 (5082), 668-671 (1992)
PUBMED      1411576
REFERENCE   9 (bases 1 to 2763)
AUTHORS     Schellenberg, G. D., Boehnke, M., Wijsman, E. M., Moore, D. K.,
            Martin, G. M. and Bird, T. D.
TITLE       Genetic association and linkage analysis of the
            apolipoprotein CII
            locus and familial Alzheimer's disease
JOURNAL     Ann. Neurol. 31 (2), 223-227 (1992)
PUBMED      1349467
COMMENT     REVIEWED REFSFQ: This record has been curated by NCBI
            staff. The
            reference sequence was derived from L42110.1.
            On Jun. 21, 2002 this sequence version replaced gi: 4506162.
            Summary: Alzheimer's disease (AD) patients with an inherited form
            of the disease carry mutations in the presenilin proteins (PSEN1;
            PSEN2) or in the amyloid precursor protein (APP). These
            disease-linked mutations result in increased production of the
            longer form of amyloid-beta (main component of amyloid deposits
            found in AD brains). Presenilins are postulated to regulate APP
            processing through their effects on gamma-secretase, an enzyme
            that
            cleaves APP. Also, it is thought that the presenilins are involved
            in the cleavage of the Notch receptor, such that they either
            directly regulate gamma-secretase activity or themselves are
            protease enzymes. Multiple alternatively spliced transcript
            variants have been identified for this gene, the full-length
            natures of only some have been determined.
            Publication Note: This RefSeq record includes a subset of the
            publications that are available for this gene. Please see the
```

-continued

```
            Entrez Gene record to access additional publications.
            COMPLETENESS: full length.
FEATURES    Location/Qualifiers
source      1 . . . 2763
            /organism = "Homo sapiens"
            /mol_type = "mRNA"
            /db_xref = "taxon: 9606"
            /chromosome = "14"
            /map = "14q24.3"
gene        1 . . . 2763
            /gene = "PSEN1"
            /note = "presenilin 1 (Alzheimer disease 3); synonyms: AD3,
            FAD, PS1, S182"
            /db_xref = "GeneID: 5663"
            /db_xref = "HGNC: 9508"
            /db_xref = "HPRD: 00087"
            /db_xref = "MIM: 104311"
CDS         249 . . . 1652
            /gene = "PSEN1"
            /GO_component = "endoplasmic reticulum [pmid 15274632];
            Golgi apparatus [pmid 15274632]; integral to nuclear
            inner
            membrane [pmid 9298903]; integral to plasma membrane
            [pmid
            15274632]; kinetochore [pmid 9298903]; membrane; membrane
            fraction [pmid 8878479]; mitochondrion [pmid 12377771]"
            /GO_function = "peptidase activity; protein binding [pmid
            9689133] [pmid 10551805] [pmid 12297508]"
            /GO_process = "amyloid precursor protein catabolism [pmid
            15274632]; anti-apoptosis [pmid 10805794]; apoptosis;
            cell
            adhesion; chromosome organization and biogenesis (sensu
            Eukaryota) [pmid 9298903]; chromosome segregation [pmid
            10206644]; intracellular signaling cascade; membrane
            protein ectodomain proteolysis [pmid 15274632]; Notch
            receptor processing [pmid 15274632]; positive regulation
            of enzyme activity [pmid 15274632]; protein processing
            [pmid 15274632]; regulation of phosphorylation [pmid
            9689133]"
            /codon_start = 1
            /product = "presenilin 1"
            /protein_id = "NP_000012.1"
            /db_xref = "GI: 4506163"
            /db_xref = "CCDS: CCDS9812.1"
            /db_xref = "GeneID: 5663"
            /db_xref = "HGNC: 9508"
            /db_xref = "HPRD: 00087"
            /db_xref = "MIM: 104311"
            /translation = "
MTELPAPLSYFQNAQMSEDNHLSNTVRSQNDNRERQEHNDRRSL

GHPEPLSNGRPQGNSRQVVEQDEEEDEELTLKYGAKHVIMLFVPVTLCMVVVVATIKS

VSFYTRKDGQLIYTPFTEDTETVGQRALHSILNAAIMISVIVVMTILLVVLYKYRCYK

VIHAWLIISSLLLLFFFSFIYLGEVFKTYNVAVDYITVALLIWNFGVVGMISIHWKGP

LRLQQAYLIMISALMALVFIKYLPEWTAWLILAVISVYDLVAVLCPKGPLRMLVETAQ

ERNETLFPALIYSSTMVWLVNMAEGDPEAQRRVSKNSKYNAESTERESQDTVAENDDG

GFSEEWEAQRDSHLGPHRSTPESRAAVQELSSSILAGEDPEERGVKLGLGDFIFYSVL

VGKASATASGDWNTTIACFVAILIGLCLTLLLLAIFKKALPALPISITFGLVFYFATD

                     YLVQPFMDQLAFHQFYI"

misc_feature  324 . . . 335
              /gene = "PSEN1"
              /note = "sequence not found in isoforms I-463 and
              1374;
              Region: exon 4"
STS           907 . . . 1010
              /gene = "PSEN1"
              /standard_name = "D14S1440"
              /db_xref = "UniSTS: 153983"
STS           1741 . . . 1942
              /gene = "PSEN1"
              /standard_name = "SHGC-31609"
              /db_xref = "UniSTS: 35446"
```

-continued

```
STS           1910 . . . 2754
              /gene = “PSEN1”
              /standard_name = “PSEN1_232”
              /db_xref = “UniSTS: 277618”
polyA_site    2763
              /gene = “PSEN1”
ORIGIN
     1 tgggacaggc agctccgggg tccgcggttt cacatcggaa acaaaacagc ggctggtctg

    61 gaaggaacct gagctacgag ccgcggcggc agcggggcgg cggggaagcg tatacctaat

   121 ctgggagcct gcaagtgaca acagcctttg cggtccttag acagcttggc ctggaggaga

   181 acacatgaaa gaaagaacct caagaggctt tgttttctgt gaaacagtat ttctatacag

   241 ttgctccaat gacagagtta cctgcaccgt tgtcctactt ccagaatgca cagatgtctg

   301 aggacaacca cctgagcaat actgtacgta gccagaatga caatagagaa cggcaggagc

   361 acaacgacag acggagcctt ggccaccctg agccattatc taatggacga ccccagggta

   421 actcccggca ggtggtggag caagatgagg aagaagatga ggagctgaca ttgaaatatg

   481 gcgccaagca tgtgatcatg ctctttgtcc ctgtgactct ctgcatggtg gtggtcgtgg

   541 ctaccattaa gtcagtcagc ttttataccc ggaaggatgg gcagctaatc tataccccat

   601 tcacagaaga taccgagact gtgggccaga gagccctgca ctcaattctg aatgctgcca

   661 tcatgatcag tgtcattgtt gtcatgacta tcctcctggt ggttctgtat aaatacaggt

   721 gctataaggt catccatgcc tggcttatta tatcatctct attgttgctg ttcttttttt

   781 cattcattta cttgggggaa gtgtttaaaa cctataacgt tgctgtggac tacattactg

   841 ttgcactcct gatctggaat tttggtgtgg tgggaatgat ttccattcac tggaaaggtc

   901 cacttcgact ccagcaggca tatctcatta tgattagtgc cctcatggcc ctggtgttta

   961 tcaagtacct ccctgaatgg actgcgtggc tcatcttggc tgtgatttca gtatatgatt

  1021 tagtggctgt tttgtgtccg aaaggtccac ttcgtatgct ggttgaaaca gctcaggaga

  1081 gaaatgaaac gctttttcca gctctcattt actcctcaac aatggtgtgg ttggtgaata

  1141 tggcagaagg agacccggaa gctcaaagga gagtatccaa aaattccaag tataatgcag

  1201 aaagcacaga aagggagtca caagacactg ttgcagagaa tgatgatggc gggttcagtg

  1261 aggaatggga agcccagagg gacagtcatc tagggcctca tcgctctaca cctgagtcac

  1321 gagctgctgt ccaggaactt tccagcagta tcctcgctgg tgaagaccca gaggaaaggg

  1381 gagtaaaact tggattggga gatttcattt tctacagtgt tctggttggt aaagcctcag

  1441 caacagccag tggagactgg aacacaacca tagcctgttt cgtagccata ttaattggtt

  1501 tgtgccttac attattactc cttgccattt tcaagaaagc attgccagct cttccaatct

  1561 ccatcacctt tgggcttgtt ttctactttg ccacagatta tcttgtacag ccttttatgg

  1621 accaattagc attccatcaa ttttatatct agcatatttg cggttagaat cccatggatg

  1681 tttcttcttt gactataaca aaatctgggg aggacaaagg tgattttcct gtgtccacat

  1741 ctaacaaagt caagattccc ggctggactt ttgcagcttc cttccaagtc ttcctgacca

  1801 ccttgcacta ttggactttg gaaggaggtg cctatagaaa acgattttga acatacttca

  1861 tcgcagtgga ctgtgtccct cggtgcagaa actaccagat ttgagggacg aggtcaagga

  1921 gatatgatag gcccggaagt tgctgtgccc catcagcagc ttgacgcgtg gtcacaggac

  1981 gatttcactg acactgcgaa ctctcaggac taccgttacc aagaggttag gtgaagtggt

  2041 ttaaaccaaa cggaactctt catcttaaac tacacgttga aaatcaaccc aataattctg

  2101 tattaactga attctgaact tttcaggagg tactgtgagg aagagcaggc accagcagca

  2161 gaatggggaa tggagaggtg ggcaggggtt ccagcttccc tttgattttt tgctgcagac
```

-continued

```
2221 tcatcctttt taaatgagac ttgttttccc ctctctttga gtcaagtcaa atatgtagat

2281 tgcctttggc aattcttctt ctcaagcact gacactcatt accgtctgtg attgccattt

2341 cttcccaagg ccagtctgaa cctgaggttg ctttatccta aaagttttaa cctcaggttc

2401 caaattcagt aaattttgga aacagtacag ctatttctca tcaattctct atcatgttga

2461 agtcaaattt ggatttttcca ccaaattctg aatttgtaga catacttgta cgctcacttg

2521 ccccagatgc ctcctctgtc ctcattcttc tctcccacac aagcagtctt tttctacagc

2581 cagtaaggca gctctgtcgt ggtagcagat ggtcccatta ttctagggtc ttactctttg

2641 tatgatgaaa agaatgtgtt atgaatcggt gctgtcagcc ctgctgtcag accttcttcc

2701 acagcaaatg agatgtatgc ccaaagcggt agaattaaag aagagtaaaa tggctgttga

2761 agc
```

APP
Porcine APP Protein

```
  1 mlpglalvll aawtaralev ptdgnaglla epqvamfcgk lnmhmnvqng kwesdpsgtk

 61 tcigtkegil qycqevypel qitnvveanq pvtiqnwckr srkqckthth ivipyrclvg

121 efvsdallvp dkckflhqer mdvcethlhw htvaketcse kstnlhdygm llpcgidkfr

181 gvefvccpla eesdnidsad aeeddsdvww ggadtdyadg sedkvvevae eeevadveee

241 eaeddedded gdeveeeaee pyeeatertt siattttttt esveevvrev cseqaetgpc

301 ramisrwyfd vtegkcapff yggcggnrnn fdteeycmav cgsvmsqsll kttqehlpqd

361 pvklpttaas tpdavdkyle tpgdenehah fqkakerlea khrermsqvm reweeaerqa

421 knlpkadkka viqhfqekve sleqeaaner qqlvethmar veamlndrrr lalenyital

481 qavpprprhv fnmlkkyvra eqkdrqhtlk hfehvrmvdp kkaaqirsqv mthlrviyer

541 mnqslsllyn vpavaeeiqd evdellqkeq nysddvlanm iseprisygn dalmpsltet

601 kttvellpvn gefslddlqp whpfgvdsvp antenevepv darpaadrgl ttrpgsgltn

661 ikteeisevk mdaefrhdsg yevhhqklvf faedvgsnkg aiiglmvggv viatvivitl

721 vmlkkkqyts ihhgvvevda avtpeerhls kmqqngyenp tykffeqmqn
```

LOCUS NP_999537 770 aa linear MAM 11-FEB-
2007

| | |
|---|---|
| DEFINITION | amyloid beta A4 protein [*Sus scrofa*]. |
| ACCESSION | NP_999537 |
| VERSION | NP_999537.1 GI: 47523800 |
| DBSOURCE | REFSEQ: accession NM_214372.1 |
| KEYWORDS | . |
| SOURCE | *Sus scrofa* (pig) |
| ORGANISM | *Sus scrofa*<br>Eukaryota; Metazoa; Chordata; Craniata; Vertebrata; Euteleostomi; Mammalia; Eutheria; Laurasiatheria; Cetartiodactyla; Suina; Suidae;<br>*Sus*. |
| REFERENCE | 1 (residues 1 to 770) |
| AUTHORS | Oerum, M. A., Bendixen, C., Madsen, L. B. and Larsen, K. |
| TITLE | Porcine APP cDNAs: molecular cloning and characterization, expression analysis, chromosomal localization and SNP analysis |
| JOURNAL | Biochim. Biophys. Acta 1759 (7), 378-384 (2006) |
| PUBMED | 16934345 |
| REMARK | GeneRIF: Two novel transcript variants of porcine APP have been identified, producing isoforms of 695 and 751 amino acids, respectively. |
| REFERENCE | 2 (residues 1 to 770) |
| AUTHORS | Lahdo, R. and De La Fourniere-Bessueille, L. |
| TITLE | Insertion of the amyloid precursor protein into lipid monolayers: effects of cholesterol and apolipoprotein E |
| JOURNAL | Biochem. J. 382 (PT 3), 987-994 (2004) |
| PUBMED | 15202933 |
| REMARK | GeneRIF: These experiments demonstrate the roles of Chol and ApoE in the modulation of membrane insertion of APP. |
| COMMENT | PROVISIONAL REFSEQ: This record has not yet been subject to final NCBI review. The reference sequence was derived from AB032550.1. |
| FEATURES | Location/Qualifiers |

-continued

```
source         1 . . . 770
               /organism = "Sus scrofa"
               /db_xref = "taxon: 9823"
               /chromosome = "13"
               /map = "13"
Protein        1 . . . 770
               /product = "amyloid beta A4 protein"
               /note = "amyloid precursor protein variant 1; amyloid
               precursor protein variant 2"
               /calculated_mol_wt = 86831
Region         24 . . . 188
               /region_name = "A4_EXTRA"
               /note = "amyloid A4; amyloid A4 precursor of Alzheimers
               disease; smart00006"
               /db_xref = "CDD: 47362"
Region         291 . . . 342
               /region_name = "KU"
               /note = "BPTI/Kunitz family of serine protease inhibitors;
               Structure is a disulfide rich alpha + beta fold; cd00109"
               /db_xref = "CDD: 29009"
Region         <384 . . . 580
               /region_name = "SbcC"
               /note = "ATPase involved in DNA repair [DNA replication,
               recombination, and repair]; COG0419"
               /db_xref = "CDD: 30768"
Region         675 . . . >705
               /region_name = "Beta-APP"
               /note = "Beta-amyloid peptide (beta-APP); pfam03494"
               /db_xref = "CDD: 43420"
CDS            1 . . . 770
               /gene = "APP"
               /coded_by = "NM_214372.1: 42 . . . 2354"
               /db_xref = "GeneID: 397663"
ORIGIN
    1 mlpglalvll aawtaralev ptdgnaglla epqvamfcgk lnmhmnvqng kwesdpsgtk

   61 tcigtkegil qycqevypel qitnvveanq pvtiqnwckr srkqckthth ivipyrclvg

  121 efvsdallvp dkckflhqer mdvcethlhw htvaketcse kstnlhdygm llpcgidkfr

  181 gvefvccpla eesdnidsad aeeddsdvww ggadtdyadg sedkvvevae eeevadveee

  241 eaeddedded gdeveeeaee pyeeatertt siattttttt esveevvrev cseqaetgpc

  301 ramisrwyfd vtegkcapff yggcggnrnn fdteeycmav cgsvmsqsll kttqehlpqd

  361 pvklpttaas tpdavdkyle tpgdenehah fqkakerlea khrermsqvm reweeaerqa

  421 knlpkadkka viqhfqekve sleqeaaner qqlvethmar veamlndrrr lalenyital

  481 qavpprprhv fnmlkkyvra eqkdrqhtlk hfehvrmvdp kkaaqirsqv mthlrviyer

  541 mnqslsllyn vpavaeeiqd evdellqkeq nysddvlanm iseprisygn dalmpsltet

  601 kttvellpvn gefslddlqp whpfgvdsvp antenevepv darpaadrgl ttrpgsgltn

  661 ikteeisevk mdaefrhdsg yevhhqklvf faedvgsnkg aiiglmvggv viatvivitl

  721 vmlkkkqyts ihhgvvevda avtpeerhls kmqqngyenp tykffeqmqn

Porcine APP mRNA
    1 acgcgaacag cagcgcactc ggtgccccgc gcagggtcgc gatgctgccc ggtttggcac

   61 tggtcctgct ggccgcctgg acggctaggg cgctggaggt gcccactgat ggcaatgccg

  121 gcctgcttgc agaaccccag gttgccatgt tctgtggcaa actcaacatg cacatgaatg

  181 tgcagaatgg gaagtgggag tcagatccgt cggggaccaa aacctgcatt ggcaccaagg

  241 aaggcatctt gcagtactgc caagaagtct accctgaact gcagatcacc aatgtggtag

  301 aagccaacca accagtgacc atccagaact ggtgcaagag gagccggaag cagtgcaaga

  361 cccacactca cattgtgatt ccgtaccgct gcttagttgg cgagtttgta agcgatgccc

  421 tccttgttcc ggacaagtgc aagttcttac accaggagag gatggatgtt tgcgaaaccc

  481 accttcactg gcacactgtg gccaaagaga cctgtagtga gaagagtacg aacttgcatg

  541 actatggcat gttgctgccc tgtggaattg acaagttccg aggggtggag tttgtgtgtt
```

-continued

```
 601 gcccactggc cgaggaaagt gacaatatcg actcagcaga tgcagaagag gatgactcgg
 661 acgtctggtg gggtggagca gatacagact atgcagatgg cagtgaagac aaagtcgtgg
 721 aggtcgcaga ggaggaggaa gtggctgatg tcgaggaaga agaagctgag gatgatgagg
 781 atgatgagga tggtgatgag gtagaagaag aggctgagga accctatgaa gaggccacgg
 841 agagaaccac cagcatcgcc acaaccacca ccaccaccac ggagtctgtg gaagaggtgg
 901 tccgagaggt gtgctctgaa caagccgaga cggggccgtg ccgagcaatg atctcccgct
 961 ggtactttga tgtgactgaa gggaagtgcg ccccgttctt ttacggcgga tgtggcggca
1021 accgaaacaa ctttgacaca gaggaatact gcatggccgt gtgtggcagc gtcatgtccc
1081 aaagtttact caagactacc caggaacatc ttccccaaga tcctgttaaa cttcctacaa
1141 cagcagccag caccccagat gccgttgaca agtatcttga gacacctgga gatgagaacg
1201 aacatgcgca tttccagaaa gccaaagaga ggctggaggc caagcaccgc gagagaatgt
1261 cccaggtcat gagagagtgg gaagaggcag aacgtcaagc aaagaacttg cctaaagctg
1321 ataagaaagc agtgatccag catttccagg agaaagtgga gtctctggag caggaagcag
1381 ccaacgagag gcagcagttg gtggagacgc acatggccag agtggaggcc atgcttaacg
1441 accgccggcg cctggccctg gagaattaca tcacggctct tcaggctgtt cctcctcggc
1501 ctcgtcatgt gttcaacatg ctcaagaagt atgtccgtgc cgaacagaaa gacagacagc
1561 acaccctaaa gcattttgaa cacgttcgca tggtagatcc aaagaaagct gctcagatcc
1621 gatcccaggt tatgacacac ctccgtgtga tttacgagcg catgaaccag tctctctccc
1681 tgctctacaa cgttcctgct gtggctgagg aaattcagga tgaagttgat gagctgctgc
1741 agaaagagca aaactactcg gatgatgtct tggccaacat gatcagcgaa ccgaggatca
1801 gttatggaaa cgatgctctc atgccgtctc tgactgaaac caaaaccacc gtggagcttc
1861 ttcctgtgaa tggagagttc agcctggatg atctccagcc ctggcatcct tttggggtag
1921 actctgtgcc tgccaacaca gaaaatgaag tcgagcctgt tgacgcccgc cctgcagccg
1981 accgaggact gaccactcga ccaggttccg ggttgaccaa catcaagacg gaagagatct
2041 ctgaagtgaa gatggatgcg gagttccgac acgattcagg ctatgaggtt catcaccaaa
2101 aactggtgtt cttcgcagaa gatgtgggtt caaacaaagg tgccatcatt ggactcatgg
2161 tgggtggtgt tgtcatagca accgtgattg tcatcacctt agtgatgctg aagaagaaac
2221 agtacacatc catccatcac ggtgtggtgg aggttgacgc agctgtgacc ccggaggagc
2281 gccacctctc caagatgcag cagaatggct atgaaaaccc aacttacaag ttctttgagc
2341 agatgcagaa ctagaccgcc gccacagcag cctctgaagt tggacagcaa aaccattgct
2401 tcactaccca ttggtgttca tttatagaat aatggggaaa gacacaaacc cttctgtttt
2461 attatttact catgatcgcc tttcagcagc tgtgctgtaa cacaagtaga tgcctgaact
2521 tgaattaata ttacgaatca gtaatgtatt ctctctcttt acatttccgg tctctacact
2581 acattattaa tgggttttgt gtactgtaaa gaatgaagct gtatcaaact agtgcatgaa
2641 tagattccct cctgattatt tatcatgtag ccccttagcc agttgtatat tattcttgtg
2701 gttttgtgat ccaattaagt cctactttga aatatgcttt aagaatcgat gggggatgct
2761 tcatgtgaac gtgggagttt agctgcttct cttgcctaag tattcttttc ctgatcacta
2821 tgcattttaa aggtaaacat ttttatgtat tccaaatgag ttagagaagt tttttccacg
2881 attgcatttg actgtacaga ttgctgcttc tgctatattt gtgatatagg aattatgagg
2941 atacacgttt atttctttgt gcctgtttta tgtgcacaca ttaggcattg agaattaaaa
3001 cttcttttgt ccgtgtacct tcggatcttt aaaaaaaaaa aaaaaaaaaa a
```

-continued

```
LOCUS AB032550 3051 bp mRNA linear MAM 23-SEP-1999
DEFINITION    Sus scrofa mRNA for amyloid precursor protein, complete cds.
ACCESSION     AB032550
VERSION       AB032550.1 GI: 5921141
KEYWORDS      amyloid precursor protein.
SOURCE        Sus scrofa (pig)
ORGANISM      Sus scrofa
              Eukaryota; Metazoa; Chordata; Craniata; Vertebrata; Euteleostomi;
              Mammalia; Eutheria; Laurasiatheria; Cetartiodactyla; Suina; Suidae;
              Sus.
REFERENCE     1
AUTHORS       Kimura, A. and Takahashi, T.
TITLE         Amyloid Precursor Protein 770
JOURNAL       Published Only in Database (1999)
REFERENCE     2 (bases 1 to 3051)
AUTHORS       Kimura, A. and Takahashi, T.
TITLE         Direct Submission
JOURNAL       Submitted (18-SEP-1999) Takayuki Takahashi, Hokkaido University,
              The Division of Biological Sciences, Graduate School of Science;
              kita-10, nishi-8, kita-ku, Sapporo city 060-0810, Japan
              (E-mail: ttakaha@sci.hokudai.ac.jp, Tel: 81-11-706-2748,
              Fax: 81-11-706-4851)
FEATURES      Location/Qualifiers
source        1 . . . 3051
              /organism = "Sus scrofa"
              /mol_type = "mRNA"
              /db_xref = "taxon: 9823"
CDS           42 . . . 2354
              /codon_start = 1
              /product = "amyloid precursor protein"
              /protein_id = "BAA84580.1"
              /db_xref = "GI: 5921142"
/translation = "MLPGLALVLLAAWTARALEVPTDGNAGLLAEPQVAMFCGKLNMH

MNVQNGKWESDPSGTKTCIGTKEGILQYCQEVYPELQITNVVEANQPVTIQNWCKRSR

KQCKTHTHVIPYRCLVGEFVSDALLVPDKCKFLHQERMDVCETHLHWHTVAKETCSE

KSTNLHDYGMLLPCGIDKFRGVEFVCCPLAEESDNIDSADAEEDDSDVWWGGADTDYA

DGSEDKVVEVAEEEEVADVEEEEAEDDEDDEDGDEVEEEAEEPYEEATERTTSIATT

TTTTESVEEVVREVCSEQAETGPCRAMISRWYFDVTEGKCAPFFYGGCGGNRNNFDTE

EYCMAVCGSVMSQSLLKTTQEHLPQDPVKLPTTAASTPDAVDKYLETPGDENEHAHFQ

KAKERLEAKHRERMSQVMREWEEAERQAKNLPKADKKAVIQHFQEKVESLEQEAANER

QQLVETHMARVEAMLNDRRRLALENYITALQAVPPRPRHVFNMLKKYVRAEQKDRQHT

LKHFEHVRMVDPKKAAQIRSQVMTHLRVIYERMNQSLSLLYNVPAVAEEIQDEVDELL

QKEQNYSDDVLANMISEPRISYGNDALMPSLTETKTTVELLPVNGEFSLDDLQPWHPF

GVDSVPANTENEVEPVDARPAADRGLTTRPGSGLTNIKTEEISEVKMDAEFRHDSGYE

VHHQKLVFFAEDVGSNKGAIIGLMVGGVVIATVIVITLVMLKKKQYTSIHHGVVEVDA

AVTPEERHLSKMQQNGYENPTYKFFEQMQN"

ORIGIN
     1  acgcgaacag cagcgcactc ggtgccccgc gcagggtcgc gatgctgccc ggtttggcac

    61  tggtcctgct ggccgcctgg acggctaggg cgctggaggt gcccactgat ggcaatgccg

   121  gcctgcttgc agaaccccag gttgccatgt tctgtggcaa actcaacatg cacatgaatg

   181  tgcagaatgg gaagtgggag tcagatccgt cggggaccaa aacctgcatt ggcaccaagg

   241  aaggcatctt gcagtactgc caagaagtct accctgaact gcagatcacc aatgtggtag

   301  aagccaacca accagtgacc atccagaact ggtgcaagag gagccggaag cagtgcaaga

   361  cccacactca cattgtgatt ccgtaccgct gcttagttgg cgagtttgta agcgatgccc

   421  tccttgttcc ggacaagtgc aagttcttac accaggagag gatggatgtt tgcgaaaccc

   481  accttcactg gcacactgtg gccaaagaga cctgtagtga gaagagtacg aacttgcatg

   541  actatggcat gttgctgccc tgtggaattg acaagttccg aggggtggag tttgtgtgtt
```

-continued

```
 601 gcccactggc cgaggaaagt gacaatatcg actcagcaga tgcagaagag gatgactcgg
 661 acgtctggtg gggtggagca gatacagact atgcagatgg cagtgaagac aaagtcgtgg
 721 aggtcgcaga ggaggaggaa gtggctgatg tcgaggaaga agaagctgag gatgatgagg
 781 atgatgagga tggtgatgag gtagaagaag aggctgagga accctatgaa gaggccacgg
 841 agagaaccac cagcatcgcc acaaccacca ccaccaccac ggagtctgtg gaagaggtgg
 901 tccgagaggt gtgctctgaa caagccgaga cggggccgtg ccgagcaatg atctcccgct
 961 ggtactttga tgtgactgaa gggaagtgcg ccccgttctt ttacggcgga tgtggcggca
1021 accgaaacaa ctttgacaca gaggaatact gcatggccgt gtgtggcagc gtcatgtccc
1081 aaagtttact caagactacc caggaacatc ttccccaaga tcctgttaaa cttcctacaa
1141 cagcagccag caccccagat gccgttgaca agtatcttga gacacctgga gatgagaacg
1201 aacatgcgca tttccagaaa gccaaagaga ggctggaggc caagcaccgc gagagaatgt
1261 cccaggtcat gagagagtgg gaagaggcag aacgtcaagc aaagaacttg cctaaagctg
1321 ataagaaagc agtgatccag catttccagg agaaagtgga gtctctggag caggaagcag
1381 ccaacgagag gcagcagttg gtggagacgc acatggccag agtggaggcc atgcttaacg
1441 accgccggcg cctggccctg gagaattaca tcacggctct tcaggctgtt cctcctcggc
1501 ctcgtcatgt gttcaacatg ctcaagaagt atgtccgtgc cgaacagaaa gacagacagc
1561 acaccctaaa gcattttgaa cacgttcgca tggtagatcc aaagaaagct gctcagatcc
1621 gatcccaggt tatgacacac ctccgtgtga tttacgagcg catgaaccag tctctctccc
1681 tgctctacaa cgttcctgct gtggctgagg aaattcagga tgaagttgat gagctgctgc
1741 agaaagagca aaactactcg gatgatgtct tggccaacat gatcagcgaa ccgaggatca
1801 gttatggaaa cgatgctctc atgccgtctc tgactgaaac caaaaccacc gtggagcttc
1861 ttcctgtgaa tggagagttc agcctggatg atctccagcc ctggcatcct tttggggtag
1921 actctgtgcc tgccaacaca gaaaatgaag tcgagcctgt tgacgcccgc cctgcagccg
1981 accgaggact gaccactcga ccaggttccg ggttgaccaa catcaagacg gaagagatct
2041 ctgaagtgaa gatggatgcg gagttccgac acgattcagg ctatgaggtt catcaccaaa
2101 aactggtgtt cttcgcagaa gatgtgggtt caaacaaagg tgccatcatt ggactcatgg
2161 tgggtggtgt tgtcatagca accgtgattg tcatcacctt agtgatgctg aagaagaaac
2221 agtacacatc catccatcac ggtgtggtgg aggttgacgc agctgtgacc ccggaggagc
2281 gccacctctc caagatgcag cagaatggct atgaaaaccc aacttacaag ttctttgagc
2341 agatgcagaa ctagaccgcc gccacagcag cctctgaagt tggacagcaa aaccattgct
2401 tcactaccca ttggtgttca tttatagaat aatggggaaa gacacaaacc cttctgtttt
2461 attatttact catgatcgcc tttcagcagc tgtgctgtaa cacaagtaga tgcctgaact
2521 tgaattaata ttacgaatca gtaatgtatt ctctctcttt acatttccgg tctctacact
2581 acattattaa tgggttttgt gtactgtaaa gaatgaagct gtatcaaact agtgcatgaa
2641 tagattccct cctgattatt tatcatgtag ccccttagcc agttgtatat tattcttgtg
2701 gttttgtgat ccaattaagt cctactttga aatatgcttt aagaatcgat gggggatgct
2761 tcatgtgaac gtgggagttt agctgcttct cttgcctaag tattcttttc ctgatcacta
2821 tgcattttaa aggtaaacat ttttatgtat tccaaatgag ttagagaagt tttttccacg
2881 attgcatttg actgtacaga ttgctgcttc tgctatattt gtgatatagg aattatgagg
2941 atacacgttt atttctttgt gcctgtttta tgtgcacaca ttaggcattg agaattaaaa
```

-continued

```
3001 cttcttttgt ccgtgtacct tcggatcttt aaaaaaaaaa aaaaaaaaaa a
```

Human APP:

```
LOCUS NM_000484 3641 bp mRNA linear PRI 25-FEB-
2007
DEFINITION   Homo sapiens amyloid beta (A4) precursor protein (peptidase
             nexin-II, Alzheimer disease) (APP), transcript variant 1, mRNA.
ACCESSION    NM_000484
VERSION      NM_000484.2 GI: 41406053
KEYWORDS     .
SOURCE       Homo sapiens (human)
ORGANISM     Homo sapiens
             Eukaryota; Metazoa; Chordata; Craniata; Vertebrata; Euteleostomi;
             Mammalia; Eutheria; Euarchontoglires; Primates; Haplorrhini;
             Catarrhini; Hominidae; Homo.
REFERENCE    1 (bases 1 to 3641)
AUTHORS      Biswas, S. C., Shi, Y., Vonsattel, J. P., Leung, C. L., Troy, C. M. and
             Greene, L. A.
TITLE        Bim is elevated in Alzheimer's disease neurons and is required for
             beta-amyloid-induced neuronal apoptosis
JOURNAL      J. Neurosci. 27 (4), 893-900 (2007)
PUBMED       17251431
REMARK       GeneRIF: beta-amyloid (Abeta) induces the proapoptotic protein
             Bcl-2 interacting mediator of cell death (Bim) in cultured
             hippocampal and cortical neurons.
REFERENCE    2 (bases 1 to 3641)
AUTHORS      Kim, J., Onstead, L., Randle, S., Price, R., Smithson, L.,
             Zwizinski, C.,
             Dickson, D. W., Golde, T. and McGowan, E.
TITLE        Abeta40 inhibits amyloid deposition in vivo
JOURNAL      J. Neurosci. 27 (3), 627-633 (2007)
PUBMED       17234594
REMARK       GeneRIF: Abeta40 has anti-amyloidogenic effect in vivo.
REFERENCE    3 (bases 1 to 3641)
AUTHORS      Carey, B. W., Kim, D. Y. and Kovacs, D. M.
TITLE        Presenilin/gamma-secretase and alpha-secretase-like peptidases
             cleave human MHC Class I proteins
JOURNAL      Biochem. J. 401 (1), 121-127 (2007)
PUBMED       17150042
REMARK       GeneRIF: Class 1 antigens undergo extra-cellular domain cleavage
             mediated by alpha-secretases and the cleavage product is
             subsequently cleaved by PS1/gamma-secretase.
REFERENCE    4 (bases 1 to 3641)
AUTHORS      Saganich, M. J., Schroeder, B. E., Galvan, V., Bredesen, D. E., Koo, E. H.
             and Heinemann, S. F.
TITLE        Deficits in synaptic transmission and learning in amyloid
             precursor
             protein (APP) transgenic mice require C-terminal cleavage of APP
JOURNAL      J. Neurosci. 26 (52), 13428-13436 (2006)
PUBMED       17192425
REMARK       GeneRIF: Cleavage of amyloid precursor protein (APP)may play a
             critical role in the development of synaptic and behavioral
             dysfunction in APP transgenic mice.
REFERENCE    5 (bases 1 to 3641)
AUTHORS      Abad, M. A., Enguita, M., DeGregorio-Rocasolano, N., Ferrer, I. and
             Trullas, R.
TITLE        Neuronal pentraxin 1 contributes to the neuronal damage evoked by
             amyloid-beta and is overexpressed in dystrophic neurites in
             Alzheimer's brain
JOURNAL      J. Neurosci. 26 (49), 12735-12747 (2006)
PUBMED       17151277
REMARK       GeneRIF: Amyloid-beta (Abeta) peptide fragment 1-42 increases
             neuronal pentraxin 1 expression before inducing apoptotic death of
             cortical neurons, indicating that Abeta contributes to the
             pathology of Alzheimer's disease.
REFERENCE    6 (bases 1 to 3641)
AUTHORS      Kamino, K., Orr, H. T., Payami, H., Wijsman, E. M., Alonso, M. E.,
             Pulst, S. M., Anderson, L., O'dahl, S., Nemens, E., White, J. A. et al.
TITLE        Linkage and mutational analysis of familial Alzheimer disease
             kindreds for the APP gene region
JOURNAL      Am. J. Hum. Genet. 51 (5), 998-1014 (1992)
PUBMED       1415269
REFERENCE    7 (bases 1 to 3641)
AUTHORS      Mant, R., Asherson, P., Gill, M., McGuffin, P., Owen, M., Wert, S. E.,
             Gregory, R. J., Smith, A. E., Cohn, J. A., Wilson, J. M. et al.
TITLE        Schizophrenia scepticism
JOURNAL      Nat. Genet. 2 (1), 12 (1992)
PUBMED       1303244
REFERENCE    8 (bases 1 to 3641)
AUTHORS      Mullan, M., Crawford, F., Axelman, K., Houlden, H., Lilius, L.,
             Winblad, B. and Lannfelt, L.
```

-continued

```
TITLE       A pathogenic mutation for probable Alzheimer's disease in the APP
            gene at the N-terminus of beta-amyloid
JOURNAL     Nat. Genet. 1 (5), 345-347 (1992)
PUBMED      1302033
REFERENCE   9 (bases 1 to 3641)
AUTHORS     Jones, C. T., Morris, S., Yates, C. M., Moffoot, A., Sharpe, C.,
            Brock, D. J. and St Clair, D.
TITLE       Mutation in codon 713 of the beta amyloid precursor protein gene
            presenting with schizophrenia
JOURNAL     Nat. Genet. 1 (4), 306-309 (1992)
PUBMED      1307241
REFERENCE   10 (bases 1 to 3641)
AUTHORS     Hendriks, L., van Duijn, C. M., Cras, P., Cruts, M., Van Hul, W., van
            Harskamp, F., Warren, A., McInnis, M. G., Antonarakis, S. E.,
            Martin, J. J.
            et al.
TITLE       Presenile dementia and cerebral haemorrhage linked to a mutation
            at
            codon 692 of the beta-amyloid precursor protein gene
JOURNAL     Nat. Genet. 1 (3), 218-221 (1992)
PUBMED      1303239
COMMENT     REVIEWED REFSEQ: This record has been curated by NCBI staff. The
            reference sequence was derived from BI559391.1, Y00264.1,
            BC018937.2 and BE907745.1.
            On Jan 30, 2004 this sequence version replaced gi: 4502166.
            Summary: This gene encodes a cell surface receptor and
            transmembrane precursor protein that is cleaved by secretases to
            form a number of peptides. Some of these peptides are secreted and
            can bind to the acetyltransferase complex APBB1/TTP60 to promote
            transcriptional activation, while others form the protein basis of
            the amyloid plaques found in the brains of patients with Alzheimer
            disease. Mutations in this gene have been implicated in autosomal
            dominant Alzheimer disease and cerebroarterial amyloidosis
            (cerebral amyloid angiopathy). Multiple transcript variants
            encoding several different isoforms have been found for this gene.
            Transcript Variant: This variant (1) represents the longest
            transcript and encodes the longest isoform (a).
            Publication Note: This RefSeq record includes a subset of the
            publications that are available for this gene. Please see the
            Entrez Gene record to access additional publications.
            COMPLETENESS: complete on the 3' end.
FEATURES    Location/Qualifiers
source      1 . . . 3641
            /organism = "Homo sapiens"
            /mol_type = "mRNA"
            /db_xref = "taxon: 9606"
            /chromosome = "21"
            /map = "21q21.3"
gene        1 . . . 3641
            /gene = "APP"
            /note = "amyloid beta (A4) precursor protein (peptidase
            nexin-II, Alzheimer disease); synonyms: AAA, AD1, PN2,
            ABPP, APPI, CVAP, ABETA, CTFgamma"
            /db_xref = "GeneTD: 351"
            /db_xref = "HGNC: 620"
            /db_xref = "HPRD: 00100"
            /db_xref = "MIM: 104760"
CDS         195 . . . 2507
            /gene = "APP"
            /GO_component = "cell surface [pmid 7593229]; coated pit;
            extracellular region [pmid 10806211]; integral to plasma
            membrane [pmid 10806211]; membrane"
            /GO_function = "copper ion binding; heparin binding; iron
            ion binding; metal ion binding; protein binding [pmid
            2119582] [pmid 8626687] [pmid 10049767] [pmid 10081969]
            [pmid 14557245]; serine-type endopeptidase inhibitor
            activity [pmid 10652580] [pmid 11279603]; zinc ion
            binding"
            /GO_process = "apoptosis; cell adhesion; copper ion
            homeostasis [pmid 15910549]; endocytosis; neuromuscular
            physiological process [pmid 7593229]; Notch signaling
            pathway"
            /note = "precursor, isoform a is encoded by transcript
            variant 1; protease nexin-II; cerebral vascular amyloid
            peptide; amyloid-beta protein; beta-amyloid peptide; A4
            amyloid protein"
            /codon_start = 1
            /product = "amyloid beta A4 protein precursor, isoform a"
            /protein_id = "NP_000475.1"
            /db_xref = "GI: 4502167"
            /db_xref = "CCDS: CCDS13576.1"
```

-continued

```
              /db_xref = "GeneID: 351"
              /db_xref = "HGNC: 620"
              /db_xref = "HPRD: 00100"
              /db_xref = "MIM: 104760"
              /translation = "
MLPGLALLLLAAWTARALEVPTDGNAGLLAEPQIAMFCGRLNMH

MNVQNGKWDSDPSGTKTCIDTKEGILQYCQEVYPELQITNVVEANQPVTIQNWCKRGR

KQCKTHPHFVIPYRCLVGEFVSDALLVPDKCKFLHQERMDVCETHLHWHTVAKETCSE

KSTNLHDYGMLLPCGIDKFRGVEFVCCPLAEESDNVDSADAEEDDSDVWWGGADTDYA

DGSEDKVVEVAEEEEVAEVEEEEADDDEDDEDGDEVEEEAEEPYEEATERTTSIATTT

TTTTESVEEVVREVCSEQAETGPCRAMISRWYFDVTEGKCAPFFYGGCGGNRNNFDTE

EYCMAVCGSAMSQSLLKTTQEPLARDPVKLPTTAASTPDAVDKYLETPGDENEHAHFQ

KAKERLEAKHRERMSQVMREWEEAERQAKNLPKADKKAVIQHFQEKVESLEQEAANER

QQLVETHMARVEAMLNDRRRLALENYITALQAVPPRPRHVFNMLKKYVRAEQKDRQHT

LKHFEHVRMVDPKKAAQIRSQVMTHLRVIYERMNQSLSLLYNVPAVAEEIQDEVDELL

QKEQNYSDDVLANMISEPRISYGNDALMPSLTETKTTVELLPVNGEFSLDDLQPWHSF

GADSVPANTENEVEPVDARPAADRGLTTRPGSGLTNIKTEEISEVKMDAEFRHDSGYE

VHHQKLVFFAEDVGSNKGAIIGLMVGGVVIATVIVITLVMLKKKQYTSIHHGVVEVDA
                     AVTPEERHLSKMQQNGYENPTYKFFEQMQN"

sig_peptide   195 . . . 245
              /gene = "APP"
mat_peptide   246 . . . 2504
              /gene = "APP"
              /product = "amyloid beta A4 protein isoform a"
STS           1799 . . . 2462
              /gene = "APP"
              /standard_name = "GDB: 585471"
              /db_xref = "UniSTS: 157889"
STS           2442 . . . 3135
              /gene = "APP"
              /standard_name = "APP"
              /db_xref = "UniSTS: 266418"
STS           2493 . . . 2801
              /gene = "APP"
              /standard_name = "GDB: 185159"
              /db_xref = "UniSTS: 155415"
STS           2500 . . . 3385
              /gene = "APP"
              /standard_name = "APP_48"
              /db_xref = "UniSTS: 277004"
STS           2782 . . . 3062
              /gene = "APP"
              /standard_name = "GDB: 185158"
              /db_xref = "UniSTS: 155414"
STS           2800 . . . 2964
              /gene = "APP"
              /standard_name = "G34719"
              /db_xref = "UniSTS: 33374"
STS           2842 . . . 2964
              /gene = "APP"
              /standard_name = "D21S1968"
              /db_xref = "UniSTS: 79221"
STS           2932 . . . 3263
              /gene = "APP"
              /standard_name = "GDB: 192308"
              /db_xref = "UniSTS: 155706"
STS           3096 . . . 3231
              /gene = "APP"
              /standard_name = "WI-18826"
              /db_xref = "UniSTS: 9847"
STS           3161 . . . 3297
              /gene = "APP"
              /standard_name = "RH77727"
              /db_xref = "UniSTS: 67046"
STS           3212 . . . 3460
              /gene = "APP"
              /standard_name = "SHGC-52109"
              /db_xref = "UniSTS: 74484"
```

-continued

```
STS            3250 . . . 3332
               /gene = "APP"
               /standard_name = "RH67934"
               /db_xref = "UniSTS: 49337"
polyA_signal   3353 . . . 3358
               /gene = "APP"
polyA_site     3371
               /gene = "APP"
               /experiment = "experimental evidence, no additional details
               recorded"
polyA_signal   3604 . . . 3609
               /gene = "APP"
polyA_site     3624
               /gene = "APP"
               /experiment = "experimental evidence, no additional details
               recorded"
polyA_site     3627
               /gene = "APP"
ORIGIN
     1 gctgactcgc ctggctctga gccccgccgc cgcgctcggg ctccgtcagt ttcctcggca
    61 gcggtaggcg agagcacgcg gaggagcgtg cgcgggggcc ccgggagacg gcggcggtgg
   121 cggcgcgggc agagcaagga cgcggcggat cccactcgca cagcagcgca ctcggtgccc
   181 cgcgcagggt cgcgatgctg cccggtttgg cactgctcct gctggccgcc tggacggctc
   241 gggcgctgga ggtacccact gatggtaatg ctggcctgct ggctgaaccc cagattgcca
   301 tgttctgtgg cagactgaac atgcacatga atgtccagaa tgggaagtgg gattcagatc
   361 catcagggac caaaacctgc attgatacca aggaaggcat cctgcagtat tgccaagaag
   421 tctaccctga actgcagatc accaatgtgg tagaagccaa ccaaccagtg accatccaga
   481 actggtgcaa gcggggccgc aagcagtgca agacccatcc ccactttgtg attccctacc
   541 gctgcttagt tggtgagttt gtaagtgatg cccttctcgt tcctgacaag tgcaaattct
   601 tacaccagga gaggatggat gtttgcgaaa ctcatcttca ctggcacacc gtcgccaaag
   661 agacatgcag tgagaagagt accaacttgc atgactacgg catgttgctg ccctgcggaa
   721 ttgacaagtt ccgaggggta gagtttgtgt gttgcccact ggctgaagaa agtgacaatg
   781 tggattctgc tgatgcggag gaggatgact cggatgtctg gtggggcgga gcagacacag
   841 actatgcaga tgggagtgaa gacaaagtag tagaagtagc agaggaggaa gaagtggctg
   901 aggtggaaga agaagaagcc gatgatgacg aggacgatga ggatggtgat gaggtagagg
   961 aagaggctga ggaaccctac gaagaagcca cagagagaac caccagcatt gccaccacca
  1021 ccaccaccac cacagagtct gtggaagagg tggttcgaga ggtgtgctct gaacaagccg
  1081 agacggggcc gtgccgagca atgatctccc gctggtactt tgatgtgact gaagggaagt
  1141 gtgccccatt cttttacggc ggatgtggcg gcaaccggaa caactttgac acagaagagt
  1201 actgcatggc cgtgtgtggc agcgccatgt cccaaagttt actcaagact acccaggaac
  1261 ctcttgcccg agatcctgtt aaacttccta caacagcagc cagtacccct gatgccgttg
  1321 acaagtatct cgagacacct ggggatgaga atgaacatgc ccatttccag aaagccaaag
  1381 agaggcttga ggccaagcac cgagagagaa tgtcccaggt catgagagaa tgggaagagg
  1441 cagaacgtca agcaaagaac ttgcctaaag ctgataagaa ggcagttatc cagcatttcc
  1501 aggagaaagt ggaatctttg gaacaggaag cagccaacga gagacagcag ctggtggaga
  1561 cacacatggc cagagtggaa gccatgctca atgaccgccg ccgcctggcc ctggagaact
  1621 acatcaccgc tctgcaggct gttcctcctc ggcctcgtca cgtgttcaat atgctaaaga
  1681 agtatgtccg cgcagaacag aaggacagac agcacaccct aaagcatttc gagcatgtgc
  1741 gcatggtgga tcccaagaaa gccgctcaga tccggtccca ggttatgaca cacctccgtg
  1801 tgatttatga gcgcatgaat cagtctctct ccctgctcta caacgtgcct gcagtggccg
```

-continued 1861 aggagattca ggatgaagtt gatgagctgc ttcagaaaga gcaaaactat tcagatgacg 1921 tcttggccaa catgattagt gaaccaagga tcagttacgg aaacgatgct ctcatgccat 1981 ctttgaccga aacgaaaacc accgtggagc tccttcccgt gaatggagag ttcagcctgg 2041 acgatctcca gccgtggcat tcttttgggg ctgactctgt gccagccaac acagaaaacg 2101 aagttgagcc tgttgatgcc cgccctgctg ccgaccgagg actgaccact cgaccaggtt 2161 ctgggttgac aaatatcaag acggaggaga tctctgaagt gaagatggat gcagaattcc 2221 gacatgactc aggatatgaa gttcatcatc aaaaattggt gttctttgca gaagatgtgg 2281 gttcaaacaa aggtgcaatc attggactca tggtgggcgg tgttgtcata gcgacagtga 2341 tcgtcatcac cttggtgatg ctgaagaaga aacagtacac atccattcat catggtgtgg 2401 tggaggttga cgccgctgtc accccagagg agcgccacct gtccaagatg cagcagaacg 2461 gctacgaaaa tccaacctac aagttctttg agcagatgca gaactagacc cccgccacag 2521 cagcctctga agttggacag caaaaccatt gcttcactac ccatcggtgt ccatttatag 2581 aataatgtgg gaagaaacaa acccgtttta tgatttactc attatcgcct tttgacagct 2641 gtgctgtaac acaagtagat gcctgaactt gaattaatcc acacatcagt aatgtattct 2701 atctctcttt acattttggt ctctatacta cattattaat gggttttgtg tactgtaaag 2761 aatttagctg tatcaaacta gtgcatgaat agattctctc ctgattattt atcacatagc 2821 cccttagcca gttgtatatt attcttgtgg tttgtgaccc aattaagtcc tactttacat 2881 atgctttaag aatcgatggg ggatgcttca tgtgaacgtg ggagttcagc tgcttctctt 2941 gcctaagtat tcctttcctg atcactatgc attttaaagt taaacatttt taagtatttc 3001 agatgcttta gagagatttt ttttccatga ctgcatttta ctgtacagat tgctgcttct 3061 gctatatttg tgatatagga attaagagga tacacacgtt tgtttcttcg tgcctgtttt 3121 atgtgcacac attaggcatt gagacttcaa gcttttcttt ttttgtccac gtatctttgg 3181 gtctttgata aagaaaagaa tccctgttca ttgtaagcac ttttacgggg cgggtgggga 3241 ggggtgctct gctggtcttc aattaccaag aattctccaa aacaattttc tgcaggatga 3301 ttgtacagaa tcattgctta tgacatgatc gctttctaca ctgtattaca taaataaatt 3361 aaataaaata accccgggca agacttttct ttgaaggatg actacagaca ttaaataatc 3421 gaagtaattt tgggtgggga gaagaggcag attcaatttt ctttaaccag tctgaagttt 3481 catttatgat acaaaagaag atgaaaatgg aagtggcaat ataaggggat gaggaaggca 3541 tgcctggaca aacccttctt ttaagatgtg tcttcaattt gtataaaatg gtgttttcat 3601 gtaaataaat acattcttgg aggagcaaaa aaaaaaaaaa a SEQ ID NO: 27 pSBT/SV40-GFIP.loxP, sequence
SB inverted repeats
SV40 promoter
Start codon
FRT site
eGFP
Puro
tcgcgcgtttcggtgatgacggtgaaaacctctgacacatgcagctcccggagacggtcacagcttgtctgtaagcggat gccgggagcagacaagcccgtcagggcgcgtcagcgggtgttggcgggtgtcggggctggcttaactatgcggcatca gagcagattgtactgagagtgcaccatatgcggtgtgaaataccgcacagatgcgtaaggagaaaataccgcatcagg cgccattcgccattcaggctgcgcaactgttgggaagggcgatcggtgcgggcctcttcgctattacgccagctggcgaa agggggatgtgctgcaaggcgattaagttgggtaacgccagggttttcccagtcacgacgttgtaaaacgacggccagt gaattcgagctcggtaccctacagttgaagtcggaagtttacatacacttaagttggagtcattaaaactcgtttttcaactac tccacaaatttcttgttaacaaacaatagttttggcaagtcagttaggacatctactttgtgcatgacacaagtcatttttccaa -continued caattgtttacagacagattatttcacttataattcactgtatcacaattccagtgggtcagaagtttacatacactaagttgact gtgcctttaaacagcttggaaaattccagaaaatgatgtcatggctttagaagcttctgatagactaattgacatcatttgagt caattggaggtgtacctgtggatgtatttcaagggaattctgtggaatgtgtgtcagttagggtgtggaaagtccccaggctc cccaggcaggcagaagtatgcaaagcatcgaggatgtacgggccagatatacgcgataacttcgtataatgtatgctat acgaagttatcgcgtgaggttttcaccgtcatcaccgaaacgcgcgaggcagctgtggaatgtgtgtcagttagggtgtgg aaagtccccaggctccccagcaggcagaagtatgcaaagcatgcatctcaattagtcagcaaccaggtgtggaaagtc cccaggctccccagcaggcagaagtatgcaaagcatgcatctcaattagtcagcaaccatagtcccgcccctaactcc gcccatcccgcccctaactccgcccagttccgcccattctccgccccatggctgactaattttttttatttatgcagaggccga ggccgcctcggcctctgagctattccagaagtagtgaggaggcttttttggaggctaccatggagaagttactattccgaa gttcctattctctagaaagtataggaacttcaagcttggcactggtgagcaagggcgaggagctgttcaccggggtggtgc ccatcctggtcgagctggacggcgacgtaaacggccacaagttcagcgtgtccggcgagggcgagggcgatgccac ctacggcaagctgaccctgaagttcatctgcaccaccggcaagctgcccgtgccctggcccaccctcgtgaccaccctg acctacggcgtgcagtgcttcagccgctaccccgaccacatgaagcagcacgacttcttcaagtccgccatgcccgaag gctacgtccaggagcgcaccatcttcttcaaggacgacggcaactacaagacccgcgccgaggtgaagttcgagggc gacaccctggtgaaccgcatcgagctgaagggcatcgacttcaaggaggacggcaacatcctggggcacaagctgg agtacaactacaacagccacaacgtctatatcatggccgacaagcagaagaacggcatcaaggtgaacttcaagatc cgccacaacatcgaggacggcagcgtgcagctcgccgaccactaccagcagaacacccccatcggcgacggcccc gtgctgctgcccgacaaccactacctgagcacccagtccgccctgagcaaagaccccaacgagaagcgcgatcacat ggtcctgctggagttcgtgaccgccgccgggatcactctcggcatggacgagctgtacaagtaaagcggccgcggcca attgggccaccggtgctagcccccctaacgttactggccgaagccgcttggaataaggccggtgtgcgtttgtctatatgttat tttccaccatattgccgtcttttggcaatgtgagggcccggaaacctggccctgtcttcttgacgagcattcctaggggtctttc ccctctcgccaaaggaatgcaaggtctgttgaatgtcgtgaaggaagcagttcctctggaagcttcttgaagacaaacaa cgtctgtagcgaccctttgcaggcagcggaaccccccacctggcgacaggtgcctctgcggccaaaagccacgtgtat aagatacacctgcaaaggcggcacaaccccagtgccacgttgtgagttggatagttgtggaaagagtcaaatggctctc ctcaagcgtattcaacaaggggctgaaggatgcccagaaggtaccccattgtatgggatctgatctggggcctcggtgc acatgctttacatgtgtttagtcgaggttaaaaaacgtctaggccccccgaaccacggggacgtggttttcctttgaaaaac acgataataccatgaccgagtacaagcccacggtgcgcctcgccacccgcgacgacgtccccgggccgtacgcac cctcgccgccgcgttcgccgactaccccgccacgcgccacaccgtcgatccggaccgccacatcgagcgggtcaccg agctgcaagaactcttcctcacgcgcgtcgggctcgacatcggcaaggtgtgggtcgcggacgacggcgccgcggtg gcggtctggaccacgccggagagcgtcgaagcgggggcggtgttcgccgagatcggcccgcgcatggccgagttga gcggttcccggctggccgcgcagcaacagatggaaggcctcctggcgccgcaccggcccaaggagcccgcgtggtt cctggccaccgtcggcgtctcgcccgaccaccagggcaagggtctgggcagcgccgtcgtgctccccggagtggagg cggccgagcgcgccggggtgcccgccttcctggagacctccgcgccccgcaacctccccttctacgagcggctcggctt caccgtcaccgccgacgtcgaggtgcccgaaggaccgcgcacctggtgcatgacccgcaagcccggtgcctgacgc ccgcccacaagacccgcagcgcccgaccgaaaggagcgcacgaccccatgcatcgaatcgatatcgcggccgcga ctctagatcataatcagcccggggggtgatcagcctcgactgtgccttctagttgccagccatctgttgtttgcccctcccccgt gccttccttgaccctggaaggtgccactcccactgtcctttcctaataaaatgaggaaattgcatcgcattgtctgagtaggt gtcattctattctggggggtggggtggggcaggacagcaagggggaggattgggaagacaatagcaggcatgctggg gatgcggtgggctctatggaaccagctggggctcgacattctagttgtggtttgtccaaactcatcaatgtatcttatcatgtct ggatcccatcacaaagctctgacctcaatcctatagaaaggaggaatgagccaaaattcacccaacttattgtgggaag cttgtggaaggctactcgaaatgtttgacccaagttaaacaatttaaaggcaatgctaccaaatactaattgagtgtatgtta -continued acttctgacccactgggaatgtgatgaaagaaataaaagctgaaatgaatcattctctctactattattctgatatttcacattc ttaaaataaagtggtgatcctaactgaccttaagacagggaatctttactcggattaaatgtcaggaattgtgaaaaagtga gtttaaatgtatttggctaaggtgtatgtaaacttccgacttcaactgtagggatcctctagagtcgacctgcaggcatgcaa gcttggcgtaatcatggtcatagctgtttcctgtgtgaaattgttatccgctcacaattccacacaacatacgagccggaagc ataaagtgtaaagcctggggtgcctaatgagtgagctaactcacattaattgcgttgcgctcactgcccgctttccagtcgg gaaacctgtcgtgccagctgcattaatgaatcggccaacgcgcggggagaggcggtttgcgtattgggcgctcttccgctt cctcgctcactgactcgctgcgctcggtcgttcggctgcggcgagcggtatcagctcactcaaaggcggtaatacggttat ccacagaatcaggggataacgcaggaaagaacatgtgagcaaaaggccagcaaaaggccaggaaccgtaaaaa ggccgcgttgctggcgtttttccataggctccgcccccctgacgagcatcacaaaaatcgacgctcaagtcagaggtggc gaaacccgacaggactataaagataccaggcgtttccccctggaagctccctcgtgcgctctcctgttccgaccctgccg cttaccggatacctgtccgcctttctcccttcgggaagcgtggcgctttctcaatgctcacgctgtaggtatctcagttcggtgt aggtcgttcgctccaagctgggctgtgtgcacgaaccccccgttcagcccgaccgctgcgccttatccggtaactatcgtct tgagtccaacccggtaagacacgacttatcgccactggcagcagccactggtaacaggattagcagagcgaggtatgt aggcggtgctacagagttcttgaagtggtggcctaactacggctacactagaaggacagtatttggtatctgcgctctgctg aagccagttaccttcggaaaaagagttggtagctcttgatccggcaaacaaaccaccgctggtagcggtggtttttttgtttg caagcagcagattacgcgcagaaaaaaaggatctcaagaagatcctttgatcttttctacggggtctgacgctcagtgga acgaaaactcacgttaagggattttggtcatgagattatcaaaaaggatcttcacctagatccttttaaattaaaaatgaagt tttaaatcaatctaaagtatatatgagtaaacttggtctgacagttaccaatgcttaatcagtgaggcacctatctcagcgatc tgtctatttcgttcatccatagttgcctgactccccgtcgtgtagataactacgatacgggagggcttaccatctggccccagt gctgcaatgataccgcgagacccacgctcaccggctccagatttatcagcaataaaccagccagccggaagggccga gcgcagaagtggtcctgcaactttatccgcctccatccagtctattaattgttgccgggaagctagagtaagtagttcgcca gttaatagtttgcgcaacgttgttgccattgctacaggcatcgtggtgtcacgctcgtcgtttggtatggcttcattcagctccgg ttcccaacgatcaaggcgagttacatgatcccccatgttgtgcaaaaaagcggttagctccttcggtcctccgatcgttgtc agaagtaagttggccgcagtgttatcactcatggttatggcagcactgcataattctcttactgtcatgccatccgtaagatg cttttctgtgactggtgagtactcaaccaagtcattctgagaatagtgtatgcggcgaccgagttgctcttgcccggcgtcaat acgggataataccgcgccacatagcagaactttaaaagtgctcatcattggaaaacgttcttcggggcgaaaactctca aggatcttaccgctgttgagatccagttcgatgtaacccactcgtgcacccaactgatcttcagcatcttttactttcaccagc gtttctgggtgagcaaaaacaggaaggcaaaatgccgcaaaaaagggaataagggcgacacggaaatgttgaatac tcatactcttcctttttcaatattattgaagcatttatcagggttattgtctcatgagcggatacatatttgaatgtatttagaaaaat aaacaaataggggttccgcgcacatttccccgaaaagtgccacctgacgtctaagaaaccattattatcatgacattaac ctataaaaataggcgtatcacgaggccctttcgtc SEQ ID NO: 28 pSBT/RSV-GFIP, sequence
SB inverted repeats
RSV promoter
Start codon
ERT site
eGEP
Puro
tcgcgcgtttcggtgatgacggtgaaaacctctgacacatgcagctcccggagacggtcacagcttgtctgtaagcggat gccgggagcagacaagcccgtcagggcgcgtcagcgggtgttggcgggtgtcggggctggcttaactatgcggcatca gagcagattgtactgagagtgcaccatatgcggtgtgaaataccgcacagatgcgtaaggagaaaataccgcatcagg cgccattcgccattcaggctgcgcaactgttgggaagggcgatcggtgcgggcctcttcgctattacgccagctggcgaa agggggatgtgctgcaaggcgattaagttgggtaacgccagggttttcccagtcacgacgttgtaaaacgacggccagt gaattcgagctcggtaccctacagttgaagtcggaagtttacatacacttaagttggagtcattaaaactcgtttttcaactac -continued tccacaaatttcttgttaacaaacaatagttttggcaagtcagttaggacatctactttgtgcatgacacaagtcatttttccaa
caattgtttacagacagattatttcacttataattcactgtatcacaattccagtgggtcagaagtttacatacactaagttgact
gtgcctttaaacagcttggaaaattccagaaaatgatgtcatggctttagaagcttctgatagactaattgacatcatttgagt
caattggaggtgtacctgtggatgtatttcaagggaattctgtggaatgtgtgtcagttagggtgtggaaagtccccaggctc
cccaggcaggcagaagtatgcaaagcatcgaggatgtacgggccagatatacgcgtatctgaggggactagggtgtgt
ttaggcgaaaagcggggcttcggttgtacgcggttaggagtcccctcaggatatagtagtttcgcttttgcatagggaggg
ggaaatgtagtcttatgcaatacacttgtagtcttgcaacatggtaacgatgagttagcaacatgccttacaaggagagaa
aaagcaccgtgcatgccgattggtggaagtaaggtggtacgatcgtgccttattaggaaggcaacagacaggtctgaca
tggattggacgaaccactgaattccgcattgcagagataattgtatttaagtgcctagctcgatacaataaacgccatttga
ccattcaccacattggtgtgcacctccaaagcttgatatctaccatggagaagttactattccgaagttcctattctctagaaa
gtataggaacttcaagcttggcactggtgagcaagggcgaggagctgttcaccggggtggtgcccatcctggtcgagct
ggacggcgacgtaaacggccacaagttcagcgtgtccggcgagggcgagggcgatgccacctacggcaagctgac
cctgaagttcatctgcaccaccggcaagctgcccgtgccctggcccaccctcgtgaccaccctgacctacggcgtgcag
tgcttcagccgctaccccgaccacatgaagcagcacgacttcttcaagtccgccatgcccgaaggctacgtccaggagc
gcaccatcttcttcaaggacgacggcaactacaagacccgcgccgaggtgaagttcgagggcgacaccctggtgaac
cgcatcgagctgaagggcatcgacttcaaggaggacggcaacatcctggggcacaagctggagtacaactacaaca
gccacaacgtctatatcatggccgacaagcagaagaacggcatcaaggtgaacttcaagatccgccacaacatcgag
gacggcagcgtgcagctcgccgaccactaccagcagaacacccccatcggcgacggccccgtgctgctgcccgaca
accactacctgagcacccagtccgccctgagcaaagaccccaacgagaagcgcgatcacatggtcctgctggagttc
gtgaccgccgccgggatcactctcggcatggacgagctgtacaagtaaagcatagcggccgtaaattccgcccctctct
ccctcccccccccctaacgttactggccgaagccgcttggaataaggccggtgtgcgtttgtctatatgttattttccaccata
ttgccgtcttttggcaatgtgagggcccggaaacctggccctgtcttcttgacgagcattcctaggggtctttcccctctcgcc
aaaggaatgcaaggtctgttgaatgtcgtgaaggaagcagttcctctggaagcttcttgaagacaaacaacgtctgtagc
gaccctttgcaggcagcggaaccccccacctggcgacaggtgcctctgcggccaaaagccacgtgtataagatacac
ctgcaaaggcggcacaaccccagtgccacgttgtgagttggatagttgtggaaagagtcaaatggctctcctcaagcgt
attcaacaaggggctgaaggatgcccagaaggtaccccattgtatgggatctgatctggggcctcggtgcacatgcttta
catgtgtttagtcgaggttaaaaaacgtctaggccccccgaaccacggggacgtggttttcctttgaaaaacacgatgata
agcttgccacaaccatgaccgagtacaagcccacggtgcgcctcgccacccgcgacgacgtccccgggccgtacg
caccctcgccgccgcgttcgccgactaccccgccacgcgccacaccgtcgatccggaccgccacatcgagcgggtca
ccgagctgcaagaactcttcctcacgcgcgtcgggctcgacatcggcaaggtgtgggtcgcggacgacggcgccgcg
gtggcggtctggaccacgccggagagcgtcgaagcgggggcggtgttcgccgagatcggcccgcgcatggccgagtt
gagcggttcccggctggccgcgcagcaacagatggaaggcctcctggcgccgcaccggcccaaggagcccgcgtg
gttcctggccaccgtcggcgtctcgcccgaccaccagggcaagggtctgggcagcgccgtcgtgctccccggagtgga
ggcggccgagcgcgccggggtgcccgccttcctggagacctccgcgccccgcaacctccccttctacgagcggctcgg
cttcaccgtcaccgccgacgtcgaggtgcccgaaggaccgcgcacctggtgcatgacccgcaagcccggtgcctgaa
gatcccccgggggatcagcctcgactgtgccttctagttgccagccatctgttgtttgcccctcccccgtgccttccttgaccc
tggaaggtgccactcccactgtcctttcctaataaaatgaggaaattgcatcgcattgtctgagtaggtgtcattctattctgg
ggggtggggtggggcaggacagcaagggggaggattgggaagacaatagcaggcatgctggggatgcggtgggct
ctatggaaccagctggggctcgacattctagttgtggtttgtccaaactcatcaatgtatcttatcatgtctggatcccatcaca
aagctctgacctcaatcctatagaaaggaggaatgagccaaaattcacccaacttattgtgggaagcttgtggaaggcta -continued ctcgaaatgtttgacccaagttaaacaatttaaaggcaatgctaccaaatactaattgagtgtatgttaacttctgacccact gggaatgtgatgaaagaaataaaagctgaaatgaatcattctctctactattattctgatatttcacattcttaaaataaagtg gtgatcctaactgaccttaagacagggaatctttactcggattaaatgtcaggaattgtgaaaaagtgagtttaaatgtatttg gctaaggtgtatgtaaacttccgacttcaactgtagggatcctctagagtcgacctgcaggcatgcaagcttggcgtaatc atggtcatagctgtttcctgtgtgaaattgttatccgctcacaattccacacaacatacgagccggaagcataaagtgtaaa gcctggggtgcctaatgagtgagctaactcacattaattgcgttgcgctcactgcccgctttccagtcgggaaacctgtcgt gccagctgcattaatgaatcggccaacgcgcggggagaggcggtttgcgtattgggcgctcttccgcttcctcgctcactg actcgctgcgctcggtcgttcggctgcggcgagcggtatcagctcactcaaaggcggtaatacggttatccacagaatca ggggataacgcaggaaagaacatgtgagcaaaaggccagcaaaaggccaggaaccgtaaaaaggccgcgttgct ggcgtttttccataggctccgcccccctgacgagcatcacaaaaatcgacgctcaagtcagaggtggcgaaacccgac aggactataaagataccaggcgtttccccctggaagctccctcgtgcgctctcctgttccgaccctgccgcttaccggatac ctgtccgcctttctcccttcgggaagcgtggcgctttctcaatgctcacgctgtaggtatctcagttcggtgtaggtcgttcgctc caagctgggctgtgtgcacgaaccccccgttcagcccgaccgctgcgccttatccggtaactatcgtcttgagtccaaccc ggtaagacacgacttatcgccactggcagcagccactggtaacaggattagcagagcgaggtatgtaggcggtgctac agagttcttgaagtggtggcctaactacggctacactagaaggacagtatttggtatctgcgctctgctgaagccagttacc ttcggaaaaagagttggtagctcttgatccggcaaacaaaccaccgctggtagcggtggtttttttgtttgcaagcagcaga ttacgcgcagaaaaaaaggatctcaagaagatcctttgatcttttctacggggtctgacgctcagtggaacgaaaactca cgttaagggattttggtcatgagattatcaaaaaggatcttcacctagatccttttaaattaaaaatgaagttttaaatcaatct aaagtatatatgagtaaacttggtctgacagttaccaatgcttaatcagtgaggcacctatctcagcgatctgtctatttcgttc atccatagttgcctgactccccgtcgtgtagataactacgatacgggagggcttaccatctggccccagtgctgcaatgat accgcgagacccacgctcaccggctccagatttatcagcaataaaccagccagccggaagggccgagcgcagaagt ggtcctgcaactttatccgcctccatccagtctattaattgttgccgggaagctagagtaagtagttcgccagttaatagtttgc gcaacgttgttgccattgctacaggcatcgtggtgtcacgctcgtcgtttggtatggcttcattcagctccggttcccaacgat caaggcgagttacatgatcccccatgttgtgcaaaaaagcggttagctccttcggtcctccgatcgttgtcagaagtaagtt ggccgcagtgttatcactcatggttatggcagcactgcataattctcttactgtcatgccatccgtaagatgcttttctgtgactg gtgagtactcaaccaagtcattctgagaatagtgtatgcggcgaccgagttgctcttgcccggcgtcaatacgggataata ccgcgccacatagcagaactttaaaagtgctcatcattggaaaacgttcttcggggcgaaaactctcaaggatcttaccg ctgttgagatccagttcgatgtaacccactcgtgcacccaactgatcttcagcatcttttactttcaccagcgtttctgggtgag caaaaacaggaaggcaaaatgccgcaaaaaagggaataagggcgacacggaaatgttgaatactcatactcttcctttt ttcaatattattgaagcatttatcagggttattgtctcatgagcggatacatatttgaatgtatttagaaaaataaacaaatagg ggttccgcgcacatttccccgaaaagtgccacctgacgtctaagaaaccattattatcatgacattaacctataaaaatag gcgtatcacgaggccctttcgtc SEQ ID NO: 29 pSBT/SV40-GFIP, sequence
SB inverted repeats
SV40 promoter
Start codon
FRT site
eGFP
Puro
tcgcgcgtttcggtgatgacggtgaaaacctctgacacatgcagctcccggagacggtcacagcttgtctgtaagcggat gccgggagcagacaagcccgtcagggcgcgtcagcgggtgttggcgggtgtcggggctggcttaactatgcggcatca gagcagattgtactgagagtgcaccatatgcggtgtgaaataccgcacagatgcgtaaggagaaaataccgcatcagg cgccattcgccattcaggctgcgcaactgttgggaagggcgatcggtgcgggcctcttcgctattacgccagctggcgaa agggggatgtgctgcaaggcgattaagttgggtaacgccagggttttcccagtcacgacgttgtaaaacgacggccagt -continued gaattcgagctcggtaccctacagttgaagtcggaagtttacatacacttaagttggagtcattaaaactcgtttttcaactac
tccacaaatttcttgttaacaaacaatagttttggcaagtcagttaggacatctactttgtgcatgacacaagtcatttttccaa
caattgtttacagacagattatttcacttataattcactgtatcacaattccagtgggtcagaagtttacatacactaagttgact
gtgcctttaaacagcttggaaaattccagaaaatgatgtcatggctttagaagcttctgatagactaattgacatcatttgagt
caattggaggtgtacctgtggatgtatttcaagggaattctgtggaatgtgtgtcagttagggtgtggaaagtccccaggctc
cccaggcaggcagaagtatgcaaagcatcgaggatgtacgggccagatatacgcgtgaggttttcaccgtcatcaccg
aaacgcgcgaggcagctgtggaatgtgtgtcagttagggtgtggaaagtccccaggctccccagcaggcagaagtatg
caaagcatgcatctcaattagtcagcaaccaggtgtggaaagtccccaggctccccagcaggcagaagtatgcaaag
catgcatctcaattagtcagcaaccatagtcccgcccctaactccgcccatcccgcccctaactccgcccagttccgccc
attctccgccccatggctgactaattttttttatttatgcagaggccgaggccgcctcggcctctgagctattccagaagtagt
gaggaggcttttttggaggctaccatggagaagttactattccgaagttcctattctctagaaagtataggaacttcaagctt
ggcactggtgagcaagggcgaggagctgttcaccggggtggtgcccatcctggtcgagctggacggcgacgtaaacg
gccacaagttcagcgtgtccggcgagggcgagggcgatgccacctacggcaagctgaccctgaagttcatctgcacca
ccggcaagctgcccgtgccctggcccaccctcgtgaccaccctgacctacggcgtgcagtgcttcagccgctaccccga
ccacatgaagcagcacgacttcttcaagtccgccatgcccgaaggctacgtccaggagcgcaccatcttcttcaaggac
gacggcaactacaagacccgcgccgaggtgaagttcgagggcgacaccctggtgaaccgcatcgagctgaagggc
atcgacttcaaggaggacggcaacatcctggggcacaagctggagtacaactacaacagccacaacgtctatatcatg
gccgacaagcagaagaacggcatcaaggtgaacttcaagatccgccacaacatcgaggacggcagcgtgcagctc
gccgaccactaccagcagaacacccccatcggcgacggccccgtgctgctgcccgacaaccactacctgagcaccc
agtccgccctgagcaaagaccccaacgagaagcgcgatcacatggtcctgctggagttcgtgaccgccgccgggatc
actctcggcatggacgagctgtacaagtaaagcggccgcggccaattgggccaccggtgctagcccccctaacgttactg
gccgaagccgcttggaataaggccggtgtgcgtttgtctatatgttattttccaccatattgccgtcttttggcaatgtgagggc
ccggaaacctggccctgtcttcttgacgagcattcctaggggtctttcccctctcgccaaaggaatgcaaggtctgttgaat
gtcgtgaaggaagcagttcctctggaagcttcttgaagacaaacaacgtctgtagcgaccctttgcaggcagcggaacc
ccccacctggcgacaggtgcctctgcggccaaaagccacgtgtataagatacacctgcaaaggcggcacaacccca
gtgccacgttgtgagttggatagttgtggaaagagtcaaatggctctcctcaagcgtattcaacaaggggctgaaggatg
cccagaaggtaccccattgtatgggatctgatctggggcctcggtgcacatgctttacatgtgtttagtcgaggttaaaaaa
cgtctaggccccccgaaccacggggacgtggttttcctttgaaaaacacgataataccatgaccgagtacaagcccacg
gtgcgcctcgccacccgcgacgacgtcccccgggccgtacgcaccctcgccgccgcgttcgccgactaccccgccac
gcgccacaccgtcgatccggaccgccacatcgagcgggtcaccgagctgcaagaactcttcctcacgcgcgtcgggct
cgacatcggcaaggtgtgggtcgcggacgacggcgccgcggtggcggtctggaccacgccggagagcgtcgaagc
gggggcggtgttcgccgagatcggcccgcgcatggccgagttgagcggttcccggctggccgcgcagcaacagatgg
aaggcctcctggcgccgcaccggcccaaggagcccgcgtggttcctggccaccgtcggcgtctcgcccgaccaccag
ggcaagggtctgggcagcgccgtcgtgctccccggagtggaggcggccgagcgcgccggggtgcccgccttcctgga
gacctccgcgccccgcaacctccccttctacgagcggctcggcttcaccgtcaccgccgacgtcgaggtgcccgaagg
accgcgcacctggtgcatgacccgcaagcccggtgcctgacgcccgcccacaagacccgcagcgcccgaccgaaa
ggagcgcacgaccccatgcatcgaatcgatatcgcggccgcgactctagatcataatcagcccgggggtgatcagcct
cgactgtgccttctagttgccagccatctgttgtttgcccctcccccgtgccttccttgaccctggaaggtgccactcccactgt
cctttcctaataaaatgaggaaattgcatcgcattgtctgagtaggtgtcattctattctggggggtggggtggggcaggac
agcaagggggaggattgggaagacaatagcaggcatgctggggatgcggtgggctctatggaaccagctggggctc
gacattctagttgtggtttgtccaaactcatcaatgtatcttatcatgtctggatcccatcacaaagctctgacctcaatcctata -continued gaaaggaggaatgagccaaaattcacccaacttattgtgggaagcttgtggaaggctactcgaaatgtttgacccaagtt aaacaatttaaaggcaatgctaccaaatactaattgagtgtatgttaacttctgacccactgggaatgtgatgaaagaaat aaaagctgaaatgaatcattctctctactattattctgatatttcacattcttaaaataaagtggtgatcctaactgaccttaaga cagggaatctttactcggattaaatgtcaggaattgtgaaaaagtgagtttaaatgtatttggctaaggtgtatgtaaacttcc gacttcaactgtagggatcctctagagtcgacctgcaggcatgcaagcttggcgtaatcatggtcatagctgtttcctgtgtg aaattgttatccgctcacaattccacacaacatacgagccggaagcataaagtgtaaagcctggggtgcctaatgagtg agctaactcacattaattgcgttgcgctcactgcccgctttccagtcgggaaacctgtcgtgccagctgcattaatgaatcg gccaacgcgcggggagaggcggtttgcgtattgggcgctcttccgcttcctcgctcactgactcgctgcgctcggtcgttcg gctgcggcgagcggtatcagctcactcaaaggcggtaatacggttatccacagaatcaggggataacgcaggaaaga acatgtgagcaaaaggccagcaaaaggccaggaaccgtaaaaaggccgcgttgctggcgtttttccataggctccgcc cccctgacgagcatcacaaaaatcgacgctcaagtcagaggtggcgaaacccgacaggactataaagataccaggc gtttccccctggaagctccctcgtgcgctctcctgttccgaccctgccgcttaccggatacctgtccgcctttctcccttcggga agcgtggcgctttctcaatgctcacgctgtaggtatctcagttcggtgtaggtcgttcgctccaagctgggctgtgtgcacga accccccgttcagcccgaccgctgcgccttatccggtaactatcgtcttgagtccaacccggtaagacacgacttatcgcc actggcagcagccactggtaacaggattagcagagcgaggtatgtaggcggtgctacagagttcttgaagtggtggcct aactacggctacactagaaggacagtatttggtatctgcgctctgctgaagccagttaccttcggaaaaagagttggtagc tcttgatccggcaaacaaaccaccgctggtagcggtggtttttttgtttgcaagcagcagattacgcgcagaaaaaaagg atctcaagaagatcctttgatcttttctacggggtctgacgctcagtggaacgaaaactcacgttaagggattttggtcatga gattatcaaaaaggatcttcacctagatccttttaaattaaaaatgaagttttaaatcaatctaaagtatatatgagtaaacttg gtctgacagttaccaatgcttaatcagtgaggcacctatctcagcgatctgtctatttcgttcatccatagttgcctgactcccc gtcgtgtagataactacgatacgggagggcttaccatctggccccagtgctgcaatgataccgcgagacccacgctcac cggctccagatttatcagcaataaaccagccagccggaagggccgagcgcagaagtggtcctgcaactttatccgcctc catccagtctattaattgttgccgggaagctagagtaagtagttcgccagttaatagtttgcgcaacgttgttgccattgctac aggcatcgtggtgtcacgctcgtcgtttggtatggcttcattcagctccggttcccaacgatcaaggcgagttacatgatccc ccatgttgtgcaaaaaagcggttagctccttcggtcctccgatcgttgtcagaagtaagttggccgcagtgttatcactcatg gttatggcagcactgcataattctcttactgtcatgccatccgtaagatgcttttctgtgactggtgagtactcaaccaagtcatt ctgagaatagtgtatgcggcgaccgagttgctcttgcccggcgtcaatacgggataataccgcgccacatagcagaactt taaaagtgctcatcattggaaaacgttcttcggggcgaaaactctcaaggatcttaccgctgttgagatccagttcgatgta acccactcgtgcacccaactgatcttcagcatcttttactttcaccagcgtttctgggtgagcaaaaacaggaaggcaaaa tgccgcaaaaaagggaataagggcgacacggaaatgttgaatactcatactcttcctttttcaatattattgaagcatttatc agggttattgtctcatgagcggatacatatttgaatgtatttagaaaaataaacaaataggggttccgcgcacatttccccg aaaagtgccacctgacgtctaagaaaccattattatcatgacattaacctataaaaataggcgtatcacgaggccctttcg tc SEQ ID NO: 30 pSBT/SV40-GFIP.IoxP, sequence
SB inverted repeats
SV40 promoter
Start codon
FRT site
eGFP
Puro
tcgcgcgtttcggtgatgacggtgaaaacctctgacacatgcagctcccggagacggtcacagcttgtctgtaagcggat gccgggagcagacaagcccgtcagggcgcgtcagcgggtgttggcgggtgtcggggctggcttaactatgcggcatca gagcagattgtactgagagtgcaccatatgcggtgtgaaataccgcacagatgcgtaaggagaaaataccgcatcagg cgccattcgccattcaggctgcgcaactgttgggaagggcgatcggtgcgggcctcttcgctattacgccagctggcgaa -continued agggggatgtgctgcaaggcgattaagttgggtaacgccagggttttcccagtcacgacgttgtaaaacgacggccagt
gaattcgagctcggtaccctacagttgaagtcggaagtttacatacacttaagttggagtcattaaaactcgtttttcaactac
tccacaaatttcttgttaacaaacaatagttttggcaagtcagttaggacatctactttgtgcatgacacaagtcatttttccaa
caattgtttacagacagattatttcacttataattcactgtatcacaattccagtgggtcagaagtttacatacactaagttgact
gtgcctttaaacagcttggaaaattccagaaaatgatgtcatggctttagaagcttctgatagactaattgacatcatttgagt
caattggaggtgtacctgtggatgtatttcaagggaattctgtggaatgtgtgtcagttagggtgtggaaagtccccaggctc
cccaggcaggcagaagtatgcaaagcatcgaggatgtacgggccagatatacgcgataacttcgtataatgtatgctat
acgaagttatcgcgtgaggttttcaccgtcatcaccgaaacgcgcgaggcagctgtggaatgtgtgtcagttagggtgtgg
aaagtccccaggctccccagcaggcagaagtatgcaaagcatgcatctcaattagtcagcaaccaggtgtggaaagtc
cccaggctccccagcaggcagaagtatgcaaagcatgcatctcaattagtcagcaaccatagtcccgcccctaactcc
gcccatcccgcccctaactccgcccagttccgcccattctccgccccatggctgactaattttttttatttatgcagaggccga
ggccgcctcggcctctgagctattccagaagtagtgaggaggcttttttggaggctaccatggagaagttactattccgaa
gttcctattctctagaaagtataggaacttcaagcttggcactggtgagcaagggcgaggagctgttcaccggggtggtgc
ccatcctggtcgagctggacggcgacgtaaacggccacaagttcagcgtgtccggcgagggcgagggcgatgccac
ctacggcaagctgaccctgaagttcatctgcaccaccggcaagctgcccgtgccctggcccaccctcgtgaccaccctg
acctacggcgtgcagtgcttcagccgctaccccgaccacatgaagcagcacgacttcttcaagtccgccatgcccgaag
gctacgtccaggagcgcaccatcttcttcaaggacgacggcaactacaagacccgcgccgaggtgaagttcgagggc
gacaccctggtgaaccgcatcgagctgaagggcatcgacttcaaggaggacggcaacatcctggggcacaagctgg
agtacaactacaacagccacaacgtctatatcatggccgacaagcagaagaacggcatcaaggtgaacttcaagatc
cgccacaacatcgaggacggcagcgtgcagctcgccgaccactaccagcagaacacccccatcggcgacggcccc
gtgctgctgcccgacaaccactacctgagcacccagtccgccctgagcaaagaccccaacgagaagcgcgatcacat
ggtcctgctggagttcgtgaccgccgccgggatcactctcggcatggacgagctgtacaagtaaagcggccgcggcca
attgggccaccggtgctagcccccctaacgttactggccgaagccgcttggaataaggccggtgtgcgtttgtctatatgttat
tttccaccatattgccgtcttttggcaatgtgagggcccggaaacctggccctgtcttcttgacgagcattcctaggggtctttc
ccctctcgccaaaggaatgcaaggtctgttgaatgtcgtgaaggaagcagttcctctggaagcttcttgaagacaaacaa
cgtctgtagcgaccctttgcaggcagcggaaccccccacctggcgacaggtgcctctgcggccaaaagccacgtgtat
aagatacacctgcaaaggcggcacaaccccagtgccacgttgtgagttggatagttgtggaaagagtcaaatggctctc
ctcaagcgtattcaacaaggggctgaaggatgcccagaaggtaccccattgtatgggatctgatctggggcctcggtgc
acatgctttacatgtgtttagtcgaggttaaaaaacgtctaggccccccgaaccacggggacgtggttttcctttgaaaaac
acgataataccatgaccgagtacaagcccacggtgcgcctcgccacccgcgacgacgtcccccgggccgtacgcac
cctcgccgccgcgttcgccgactaccccgccacgcgccacaccgtcgatccggaccgccacatcgagcgggtcaccg
agctgcaagaactcttcctcacgcgcgtcgggctcgacatcggcaaggtgtgggtcgcggacgacggcgccgcggtg
gcggtctggaccacgccggagagcgtcgaagcgggggcggtgttcgccgagatcggcccgcgcatggccgagttga
gcggttcccggctggccgcgcagcaacagatggaaggcctcctggcgccgcaccggcccaaggagcccgcgtggtt
cctggccaccgtcggcgtctcgcccgaccaccagggcaagggtctgggcagcgccgtcgtgctccccggagtggagg
cggccgagcgcgccggggtgcccgccttcctggagacctccgcgccccgcaacctccccttctacgagcggctcggctt
caccgtcaccgccgacgtcgaggtgcccgaaggaccgcgcacctggtgcatgacccgcaagcccggtgcctgacgc
ccgcccacaagacccgcagcgcccgaccgaaaggagcgcacgaccccatgcatcgaatcgatatcgcggccgcga
ctctagatcataatcagcccggggggtgatcagcctcgactgtgccttctagttgccagccatctgttgtttgcccctcccccgt
gccttccttgaccctggaaggtgccactcccactgtcctttcctaataaaatgaggaaattgcatcgcattgtctgagtaggt -continued gtcattctattctggggggtggggtggggcaggacagcaaggggggaggattgggaagacaatagcaggcatgctggg gatgcggtgggctctatggaaccagctggggcgcgattaacttcgtataaagtctcctatacgaagttatcgcgccattcta gttgtggtttgtccaaactcatcaatgtatcttatcatgtctggatcccatcacaaagctctgacctcaatcctatagaaagga ggaatgagccaaaattcacccaacttattgtgggaagcttgtggaaggctactcgaaatgtttgacccaagttaaacaattt aaaggcaatgctaccaaatactaattgagtgtatgttaacttctgacccactgggaatgtgatgaaagaaataaaagctg aaatgaatcattctctctactattattctgatatttcacattcttaaaataaagtggtgatcctaactgaccttaagacagggaat ctttactcggattaaatgtcaggaattgtgaaaaagtgagtttaaatgtatttggctaaggtgtatgtaaacttccgacttcaac tgtagggatcctctagagtcgacctgcaggcatgcaagcttggcgtaatcatggtcatagctgtttcctgtgtgaaattgttat ccgctcacaattccacacaacatacgagccggaagcataaagtgtaaagcctggggtgcctaatgagtgagctaactc acattaattgcgttgcgctcactgcccgctttccagtcgggaaacctgtcgtgccagctgcattaatgaatcggccaacgcg cggggagaggcggtttgcgtattgggcgctcttccgcttcctcgctcactgactcgctgcgctcggtcgttcggctgcggcg agcggtatcagctcactcaaaggcggtaatacggttatccacagaatcaggggataacgcaggaaagaacatgtgag caaaaggccagcaaaaggccaggaaccgtaaaaaggccgcgttgctggcgtttttccataggctccgcccccctgacg agcatcacaaaaatcgacgctcaagtcagaggtggcgaaacccgacaggactataaagataccaggcgtttcccccct ggaagctccctcgtgcgctctcctgttccgaccctgccgcttaccggatacctgtccgcctttctcccttcgggaagcgtggc gctttctcaatgctcacgctgtaggtatctcagttcggtgtaggtcgttcgctccaagctgggctgtgtgcacgaaccccccgt tcagcccgaccgctgcgccttatccggtaactatcgtcttgagtccaacccggtaagacacgacttatcgccactggcag cagccactggtaacaggattagcagagcgaggtatgtaggcggtgctacagagttcttgaagtggtggcctaactacgg ctacactagaaggacagtatttggtatctgcgctctgctgaagccagttaccttcggaaaaagagttggtagctcttgatcc ggcaaacaaaccaccgctggtagcggtggtttttttgtttgcaagcagcagattacgcgcagaaaaaaaggatctcaag aagatcctttgatcttttctacggggtctgacgctcagtggaacgaaaactcacgttaagggattttggtcatgagattatcaa aaaggatcttcacctagatccttttaaattaaaaatgaagttttaaatcaatctaaagtatatatgagtaaacttggtctgaca gttaccaatgcttaatcagtgaggcacctatctcagcgatctgtctatttcgttcatccatagttgcctgactccccgtcgtgta gataactacgatacgggagggcttaccatctggccccagtgctgcaatgataccgcgagacccacgctcaccggctcc agatttatcagcaataaaccagccagccggaagggccgagcgcagaagtggtcctgcaactttatccgcctccatcca gtctattaattgttgccgggaagctagagtaagtagttcgccagttaatagtttgcgcaacgttgttgccattgctacaggcat cgtggtgtcacgctcgtcgtttggtatggcttcattcagctccggttcccaacgatcaaggcgagttacatgatcccccatgtt gtgcaaaaaagcggttagctccttcggtcctccgatcgttgtcagaagtaagttggccgcagtgttatcactcatggttatgg cagcactgcataattctcttactgtcatgccatccgtaagatgcttttctgtgactggtgagtactcaaccaagtcattctgaga atagtgtatgcggcgaccgagttgctcttgcccggcgtcaatacgggataataccgcgccacatagcagaactttaaaag tgctcatcattggaaaacgttcttcggggcgaaaactctcaaggatcttaccgctgttgagatccagttcgatgtaacccact cgtgcacccaactgatcttcagcatcttttactttcaccagcgtttctgggtgagcaaaaacaggaaggcaaaatgccgca aaaaagggaataagggcgacacggaaatgttgaatactcatactcttcctttttcaatattattgaagcatttatcagggttat tgtctcatgagcggatacatatttgaatgtatttagaaaaataaacaaataggggttccgcgcacatttccccgaaaagtgc cacctgacgtctaagaaaccattattatcatgacattaacctataaaaataggcgtatcacgaggccctttcgtc

The invention claimed is:

1. A genetically modified pig as a model for studying Alzheimer's disease, wherein the genome of the modified pig comprises at least one modified gene or combination of modified genes selected from i) human APP gene or an Alzheimer's disease phenotype causing part thereof, ii) human PS1 gene or an Alzheimer's disease phenotype causing part thereof, iii) porcine APP gene or an Alzheimer's disease phenotype causing part thereof, iv) porcine PS1 gene or an Alzheimer's disease phenotype causing part thereof, v) APP gene or an Alzheimer's disease phenotype causing part thereof and at least one PS1 gene or an Alzheimer's disease phenotype causing part thereof, vi) human APP gene comprising a Swedish mutation or an Alzheimer's disease phenotype causing part thereof comprising a Swedish mutation, vii) human APP gene comprising the APPsw695 gene or an Alzheimer's disease phenotype causing part thereof comprising an APPsw695mutation, viii) human PS1 gene encoding a PS1 protein harbouring a Pro117Leu mutation, or an Alzheimer's disease phenotype causing part thereof comprising a mutation encoding a PSi protein harbouring a Pro117Leu mutation, ix) human APP gene encoding a Swedish mutation or an Alzheimer's disease phenotype causing part thereof comprising a Swedish mutation and at least one modified PS1gene encoding a PS1 protein harbouring a Pro117Leu mutation or an Alzheimer's disease phenotype causing part thereof comprising a mutation encoding a PS1 protein harbouring a Pro117Leu mutation, and x) human APP gene comprising the APPsw695 gene or an Alzheimer's disease phenotype causing part thereof comprising an APPsw695 mutation, and at least one human PS1 gene encoding a PS1 protein harbouring a Pro117Leu mutation or an Alzheimer's disease phenotype causing part thereof comprising a mutation encoding a PS1 protein harbouring a Pro117Leu mutation, and wherein the modified pig expresses at least one phenotype associated with Alzheimer's disease.

2. A genetically modified porcine blastocyst derived from the genetically modified pig as defined in claim 1, wherein the genome of the modified pig blastocyst comprises at least one modified gene or combination of modified genes selected from i) human APP gene or an Alzheimer's disease phenotype causing part thereof, ii) human PS1 gene or an Alzheimer's disease phenotype causing part thereof, iii) porcine APP gene or an Alzheimer's disease phenotype causing part thereof, iv) porcine PS1 gene or an Alzheimer's disease phenotype causing part thereof, v) APP gene or an Alzheimer's disease phenotype causing part thereof and at least one modified PS1 gene or an Alzheimer's disease phenotype causing part thereof vi) human APP gene comprising a Swedish mutation or an Alzheimer's disease phenotype causing part thereof comprising a Swedish mutation, vii) human APP gene comprising the APPsw695 gene or an Alzheimer's disease phenotype causing part thereof comprising an APPsw695 mutation viii) human PS1 gene encoding a PS1 protein harbouring a Pro117Leu mutation or an Alzheimer's disease phenotype causing part thereof comprising a mutation encoding a PS1 protein harbouring a Pro117Leu mutation, ix) human APP gene encoding a Swedish mutation or an Alzheimer's disease phenotype causing part thereof comprising a Swedish mutation and at least one modified PS1 gene encoding a PS1 protein harbouring a Pro117Leu mutation or an Alzheimer's disease phenotype causing part thereof comprising a mutation encoding a PS1 protein harbouring a Pro117Leu mutation, and x) human APP gene comprising the APPsw695 gene or an Alzheimer's disease phenotype causing part thereof comprising an APPsw695 mutation, and at least one human PS1 gene encoding a PS1 protein harbouring a Pro117Leu mutation or an Alzheimer's disease phenotype causing part thereof comprising a mutation encoding a PS1 protein harbouring a Pro117Leu mutation.

3. A genetically modified porcine embryo derived from the genetically modified pig as defined in claim 1, wherein the genome of the modified pig embryo comprises at least one modified gene or combination of modified genes selected from i) human APP gene or an Alzheimer's disease phenotype causing part thereof, ii) human PS1 gene or an Alzheimer's disease phenotype causing part thereof, iii) porcine APP gene or an Alzheimer's disease phenotype causing part thereof, iv) porcine PS1 gene or an Alzheimer's disease phenotype causing part thereof, v) APP gene or an Alzheimer's disease phenotype causing part thereof and at least one modified PS1 gene or an Alzheimer's disease phenotype causing part thereof vi) human APP gene comprising a Swedish mutation or an Alzheimer's disease phenotype causing part thereof comprising a Swedish mutation, vii) human APP gene comprising the APPsw695 gene or an Alzheimer's disease phenotype causing part thereof comprising an APPsw695 mutation, viii) human PS1 gene encoding a PS1 protein harbouring a Pro117Leu mutation or an Alzheimer's disease phenotype causing part thereof comprising a mutation encoding a PS1 protein harbouring a Pro117Leu mutation, ix) human APP gene encoding a Swedish mutation or an Alzheimer's disease phenotype causing part thereof comprising a Swedish mutation and at least one modified PS1 gene encoding a PS1 protein harbouring a Pro117Leu mutation or an Alzheimer's disease phenotype causing part thereof comprising a mutation encoding a PS1 protein harbouring a Pro117Leu mutation, and x) human APP gene comprising the APPsw695 gene or an Alzheimer's disease phenotype causing part thereof comprising an APPsw695 mutation, and at least one human PS1 gene encoding a PS1 protein harbouring a Pro117Leu mutation or an Alzheimer's disease phenotype causing part thereof comprising a mutation encoding a PS1 protein harbouring a Pro117Leu mutation.

4. A genetically modified porcine fetus derived from the genetically modified pig as defined in claim 1, wherein the genome of the modified pig fetus comprises at least one modified gene or combination of modified genes selected from i) human APP gene or an Alzheimer's disease phenotype causing part thereof, ii) human PS1 gene or an Alzheimer's disease phenotype causing part thereof, iii) porcine APP gene or an Alzheimer's disease phenotype causing part thereof, iv) porcine PS1 gene or an Alzheimer's disease phenotype causing part thereof, v) APP gene or an Alzheimer's disease phenotype causing part thereof and at least one modified PS1 gene or an Alzheimer's disease phenotype causing part thereof vi) human APP gene comprising a Swedish mutation or an Alzheimer's disease phenotype causing part thereof comprising a Swedish mutation, vii) human APP gene comprising the APPsw695 gene or an Alzheimer's disease phenotype causing part thereof comprising an APPsw695 mutation, viii) human PS1 gene encoding a PS1 protein harbouring a Pro117Leu mutation or an Alzheimer's disease phenotype causing part thereof comprising a mutation encoding a PS1 protein harbouring a Pro117Leu mutation, ix) human APP gene encoding a Swedish mutation or an Alzheimer's disease phenotype causing part thereof comprising a Swedish mutation and at least one modified PS1 gene encoding a PS1 protein harbouring a Pro117Leu mutation or an Alzheimer's disease phenotype causing part thereof comprising a mutation encoding a PS1 protein harbouring a Pro117Leu mutation, and x) human APP gene comprising the APPsw695 gene or an Alzheimer's disease phenotype causing part thereof comprising an APPsw695 mutation, and at least one human PS1 gene encoding a PS1 protein harbouring a Pro117Leu mutation or an Alzheimer's disease phenotype causing part thereof comprising a mutation encoding a PS1 protein harbouring a Pro117Leu mutation.

5. A genetically modified donor cell and/or cell nucleus derived from the genetically modified pig as defined in claim 1, wherein the genome of the donor cell and/or cell nucleus comprises at least one modified gene or combination of modified genes selected from i) human APP gene or an Alzheimer's disease phenotype causing part thereof, ii) human PS1 gene or an Alzheimer's disease phenotype causing part thereof, iii) porcine APP gene or an Alzheimer's disease phenotype causing part thereof, iv) porcine PS1 gene or an Alzheimer's disease phenotype causing part thereof, v) APP gene or an Alzheimer's disease phenotype causing part thereof and at least one modified PS1 gene or an Alzheimer's disease phenotype causing part thereof vi) human APP gene comprising a Swedish mutation or an Alzheimer's disease phenotype causing part thereof comprising a Swedish mutation, vii) human APP gene comprising the APPsw695 gene or an Alzheimer's disease phenotype causing part thereof comprising an APPsw695 mutation, viii) human PS1 gene encoding a PS1 protein harbouring a Pro117Leu mutation or an Alzheimer's disease phenotype causing part thereof comprising a mutation encoding a PS1 protein harbouring a Pro117Leu mutation, ix) human APP gene encoding a Swedish mutation or an Alzheimer's disease phenotype causing part thereof comprising a Swedish mutation and at least one modified PS1 gene encoding a PS1 protein harbouring a Pro117Leu mutation or an Alzheimer's disease phenotype causing part thereof comprising a mutation encoding a PS1 protein harbouring a Pro117Leu mutation, and x) human APP gene comprising the APPsw695 gene or an Alzheimer's disease phenotype causing part thereof comprising an APPsw695 mutation, and at least one human PS1 gene encoding a PS1 protein harbouring a Pro117Leu mutation or an Alzheimer's disease phenotype causing part thereof comprising a mutation encoding a PS1 protein harbouring a Pro117Leu mutation.

6. The genetically modified pig according to claim 1, and/or a porcine blastocyst, embryo, fetus and/or donor cell derived from said genetically modified pig comprising at least one modified gene or combination of modified genes selected from i) human APP gene or an Alzheimer's disease phenotype causing part thereof,
ii) human PS1 gene or an Alzheimer's disease phenotype causing part thereof,
iii) porcine APP gene or an Alzheimer's disease phenotype causing part thereof,
iv) porcine PS1 gene or an Alzheimer's disease phenotype causing part thereof,
v) APP gene or an Alzheimer's disease phenotype causing part thereof and at least one modified PS1 gene or an Alzheimer's disease phenotype causing part thereof
vi) human APP gene comprising a Swedish mutation or an Alzheimer's disease phenotype causing part thereof comprising a Swedish mutation,
vii) human APP gene comprising the APPsw695 gene or an Alzheimer's disease phenotype causing part thereof comprising an APPsw695 mutation,
viii) human PS1 gene encoding a PS1 protein harbouring a Pro117Leu mutation or an Alzheimer's disease phenotype causing part thereof comprising a mutation encoding a PS1 protein harbouring a Pro117Leu mutation,
ix) human APP gene encoding a Swedish mutation or an Alzheimer's disease phenotype causing part thereof comprising a Swedish mutation and at least one modified PS1 gene encoding a PS1 protein harbouring a Pro117Leu mutation or an Alzheimer's disease phenotype causing part thereof comprising a mutation encoding a PS1 protein harbouring a Pro117Leu mutation, and
x) human APP gene comprising the APPsw695 gene or an Alzheimer's disease phenotype causing part thereof comprising an APPsw695 mutation, and at least one human PS1 gene encoding a PS1 protein harbouring a Pro117Leu mutation or an Alzheimer's disease phenotype causing part thereof comprising a mutation encoding a PS1 protein harbouring a Pro117Leu mutation, wherein any of said genetically modified pig model, porcine blastocyst, embryo, fetus and/or donor cell are obtainable by nuclear transfer comprising the steps of i) establishing at least one porcine oocyte having at least a part of a zona pellucida,
ii) separating the porcine oocyte into at least two parts whereby an oocyte having a nucleus and at least one cytoplast is obtained,
iii) establishing a porcine donor cell or membrane surrounded cell nucleus, wherein the genome of the cell or cell nucleus comprises at least one modified gene or combination of modified genes selected from
a.) human APP gene or an Alzheimer's disease phenotype causing part thereof,
b.) human PS1 gene or an Alzheimer's disease phenotype causing part thereof,
c.) porcine APP gene or an Alzheimer's disease phenotype causing part thereof,
d.) porcine PS1 gene or an Alzheimer's disease phenotype causing part thereof,
e.) APP gene or an Alzheimer's disease phenotype causing part thereof and at least one modified PS1 gene or an Alzheimer's disease phenotype causing part thereof
f.) human APP gene comprising a Swedish mutation or an Alzheimer's disease phenotype causing part thereof comprising a Swedish mutation,
g.) human APP gene comprising the APPsw695 gene or an Alzheimer's disease phenotype causing part thereof comprising an APPsw695 mutation,
h.) human PS1 gene encoding a PS1 protein harbouring a Pro117Leu mutation or an Alzheimer's disease phenotype causing part thereof comprising a mutation encoding a PS1 protein harbouring a Pro117Leu mutation,
i.) human APP gene encoding a Swedish mutation or an Alzheimer's disease phenotype causing part thereof comprising a Swedish mutation and at least one modified PS1 gene encoding a PS1 protein harbouring a Pro117Leu mutation or an Alzheimer's disease phenotype causing part thereof comprising a mutation encoding a PS1 protein harbouring a Pro117Leu mutation, and
j.) human APP gene comprising the APPsw695 gene or an Alzheimer's disease phenotype causing part thereof comprising an APPsw695 mutation, and at least one human PS1 gene encoding a PS1 protein harbouring a Pro117Leu mutation or an Alzheimer's disease phenotype causing part thereof comprising a mutation encoding a PS1 protein harbouring a Pro117Leu mutation,
iv) fusing said at least one cytoplast with the donor cell or membrane surrounded cell nucleus,
v) obtaining a reconstructed porcine embryo,
vi) activating the reconstructed embryo to form an embryo and culturing said embryo,
vii) culturing said embryo, and
viii) transferring said cultured embryo to a host porcine mammal such that the embryo develops into a genetically modified fetus, wherein said genetically modified embryo is obtainable by nuclear transfer comprising steps i) to v) and optionally vi), wherein said genetically modified blastocyst is obtainable by nuclear transfer comprising steps i) to vi) and optionally vii), wherein said genetically modified fetus is obtainable by nuclear transfer comprising steps i) to vii)

wherein said genetically modified pig model is obtainable by nuclear transfer comprising steps i) to viii) and permitting term development of the fetus.

7. A method for producing a transgenic pig, porcine blastocyst, embryo, fetus and/or donor cell as a model for Alzheimer's disease comprising:

i) establishing at least one porcine oocyte,
ii) separating the oocyte into at least three parts whereby at least one cytoplast is obtained,
iii) establishing a porcine donor cell or cell nucleus, wherein the genome of the cell or cell nucleus comprises at least one modified gene or combination of modified genes selected from
a.) human APP gene or an Alzheimer's disease phenotype causing part thereof,
b.) human PS1 gene or an Alzheimer's disease phenotype causing part thereof,
c.) porcine APP gene or an Alzheimer's disease phenotype causing part thereof,
d.) porcine PS1 gene or an Alzheimer's disease phenotype causing part thereof,
e.) APP gene or an Alzheimer's disease phenotype causing part thereof and at least one modified PS1 gene or an Alzheimer's disease phenotype causing part thereof
f.) human APP gene comprising a Swedish mutation or an Alzheimer's disease phenotype causing part thereof comprising a Swedish mutation,
g.) human APP gene comprising the APPsw695 gene or an Alzheimer's disease phenotype causing part thereof comprising an APPsw695 mutation,
h.) human PS1 gene encoding a PS1 protein harbouring a Pro117Leu mutation or an Alzheimer's disease phenotype causing part thereof comprising a mutation encoding a PS1 protein harbouring a Pro117Leu mutation, i.) human APP gene encoding a Swedish mutation or an Alzheimer's disease phenotype causing part thereof comprising a Swedish mutation and at least one modified PS1 gene encoding a PS1 protein harbouring a Pro117Leu mutation or an Alzheimer's disease phenotype causing part thereof comprising a mutation encoding a PS1 protein harbouring a Pro117Leu mutation, and j.) human APP gene comprising the APPsw695 gene or an Alzheimer's disease phenotype causing part thereof comprising an APPsw695 mutation, and at least one human PS1 gene encoding a PS1 protein harbouring a Pro117Leu mutation or an Alzheimer's disease phenotype causing part thereof comprising a mutation encoding a PS1 protein harbouring a Pro117Leu mutation, iv) fusing said at least one cytoplast with the donor cell or membrane surrounded cell nucleus, v) obtaining a reconstructed porcine embryo, vi) activating the reconstructed embryo to form an embryo, vii) culturing said embryo, and viii) transferring said cultured embryo to a host porcine mammal such that the embryo develops into a genetically modified fetus, wherein said genetically modified embryo is obtainable by nuclear transfer comprising steps i) to vi) and optionally vii), wherein said genetically modified blastocyst is obtainable by nuclear transfer comprising steps i) to vii), wherein said genetically modified fetus is obtainable by nuclear transfer comprising steps i) to vii)

wherein said genetically modified pig model is obtainable by nuclear transfer comprising steps i) to viii) and permitting term development of the fetus.

8. A method for evaluating the effect of a therapeutic treatment of Alzheimer's disease, said method comprising the steps of i) providing the modified pig according to claim 1, ii) treating said pig with a pharmaceutical composition, and iii) evaluating the modified pig for an effect of the composition on an Alzheimer's disease phenotype expressed by the pig.

9. The method of claim 8 comprising the further step of advising on medical treatment based on the afore-mentioned observed effects.

10. A method for screening the efficacy of a pharmaceutical composition for Alzheimer's disease, said method comprising the steps of i) providing the modified pig according to claim 1, ii) administering to said pig a pharmaceutical composition the efficacy of which is to be evaluated, and iii) evaluating the modified pig for an effect, if any, of the pharmaceutical composition on an Alzheimer's disease phenotype expressed by the modified pig.

11. A method for treatment of a human being suffering from Alzheimer's disease, said method comprising the initial steps of i) providing the modified pig according to claim 1, ii) administering to said pig a pharmaceutical composition the efficacy of which is to be evaluated, and iii) evaluating the effect, if any, of the pharmaceutical composition on an Alzheimer's disease phenotype expressed by the modified pig, and iv) treating a human being suffering from Alzheimer's disease based on the effects observed in the pig.

* * * * *

SEQUENCE LISTING

<160> NUMBER OF SEQ ID NOS: 49

<210> SEQ ID NO 1
<211> LENGTH: 3641

<212> TYPE: DNA
<213> ORGANISM: Homo sapiens

<400> SEQUENCE: 1
gctgactcgc ctggctctga gccccgccgc cgcgctcggg ctccgtcagt ttcctcggca 60
gcggtaggcg agagcacgcg gaggagcgtg cgcgggggcc ccgggagacg gcggcggtgg 120
cggcgcgggc agagcaagga cgcggcggat cccactcgca cagcagcgca ctcggtgccc 180
cgcgcagggt cgcgatgctg cccggtttgg cactgctcct gctggccgcc tggacggctc 240
gggcgctgga ggtacccact gatggtaatg ctggcctgct ggctgaaccc cagattgcca 300
tgttctgtgg cagactgaac atgcacatga atgtccagaa tgggaagtgg gattcagatc 360
catcagggac caaaacctgc attgatacca aggaaggcat cctgcagtat tgccaagaag 420
tctaccctga actgcagatc accaatgtgg tagaagccaa ccaaccagtg accatccaga 480
actggtgcaa gcggggccgc aagcagtgca agacccatcc ccactttgtg attccctacc 540
gctgcttagt tggtgagttt gtaagtgatg cccttctcgt tcctgacaag tgcaaattct 600
tacaccagga gaggatggat gtttgcgaaa ctcatcttca ctggcacacc gtcgccaaag 660
agacatgcag tgagaagagt accaacttgc atgactacgg catgttgctg ccctgcggaa 720
ttgacaagtt ccgaggggta gagtttgtgt gttgcccact ggctgaagaa agtgacaatg 780
tggattctgc tgatgcggag gaggatgact cggatgtctg gtggggcgga gcagacacag 840
actatgcaga tgggagtgaa gacaaagtag tagaagtagc agaggaggaa gaagtggctg 900
aggtggaaga agaagaagcc gatgatgacg aggacgatga ggatggtgat gaggtagagg 960
aagaggctga ggaaccctac gaagaagcca cagagagaac caccagcatt gccaccacca 1020
ccaccaccac cacagagtct gtggaagagg tggttcgaga ggtgtgctct gaacaagccg 1080
agacggggcc gtgccgagca atgatctccc gctggtactt tgatgtgact gaagggaagt 1140
gtgccccatt cttttacggc ggatgtggcg gcaaccggaa caactttgac acagaagagt 1200
actgcatggc cgtgtgtggc agcgccatgt cccaaagttt actcaagact acccaggaac 1260
ctcttgcccg agatcctgtt aaacttccta caacagcagc cagtacccct gatgccgttg 1320
acaagtatct cgagacacct ggggatgaga atgaacatgc ccatttccag aaagccaaag 1380
agaggcttga ggccaagcac cgagagagaa tgtcccaggt catgagagaa tgggaagagg 1440
cagaacgtca agcaaagaac ttgcctaaag ctgataagaa ggcagttatc cagcatttcc 1500
aggagaaagt ggaatctttg gaacaggaag cagccaacga gagacagcag ctggtggaga 1560
cacacatggc cagagtggaa gccatgctca atgaccgccg ccgcctggcc ctggagaact 1620
acatcaccgc tctgcaggct gttcctcctc ggcctcgtca cgtgttcaat atgctaaaga 1680
agtatgtccg cgcagaacag aaggacagac agcacaccct aaagcatttc gagcatgtgc 1740
gcatggtgga tcccaagaaa gccgctcaga tccggtccca ggttatgaca cacctccgtg 1800
tgatttatga gcgcatgaat cagtctctct ccctgctcta caacgtgcct gcagtggccg 1860
aggagattca ggatgaagtt gatgagctgc ttcagaaaga gcaaaactat tcagatgacg 1920
tcttggccaa catgattagt gaaccaagga tcagttacgg aaacgatgct ctcatgccat 1980
ctttgaccga aacgaaaacc accgtggagc tccttcccgt gaatggagag ttcagcctgg 2040
acgatctcca gccgtggcat tcttttgggg ctgactctgt gccagccaac acagaaaacg 2100
aagttgagcc tgttgatgcc cgccctgctg ccgaccgagg actgaccact cgaccaggtt 2160
ctgggttgac aaatatcaag acggaggaga tctctgaagt gaagatggat gcagaattcc 2220
gacatgactc aggatatgaa gttcatcatc aaaaattggt gttctttgca gaagatgtgg 2280
gttcaaacaa aggtgcaatc attggactca tggtgggcgg tgttgtcata gcgacagtga 2340
tcgtcatcac cttggtgatg ctgaagaaga aacagtacac atccattcat catggtgtgg 2400
tggaggttga cgccgctgtc accccagagg agcgccacct gtccaagatg cagcagaacg 2460
gctacgaaaa tccaacctac aagttctttg agcagatgca gaactagacc cccgccacag 2520
cagcctctga agttggacag caaaaccatt gcttcactac ccatcggtgt ccatttatag 2580
aataatgtgg gaagaaacaa acccgtttta tgatttactc attatcgcct tttgacagct 2640
gtgctgtaac acaagtagat gcctgaactt gaattaatcc acacatcagt aatgtattct 2700
atctctcttt acattttggt ctctatacta cattattaat gggttttgtg tactgtaaag 2760
aatttagctg tatcaaacta gtgcatgaat agattctctc ctgattattt atcacatagc 2820
cccttagcca gttgtatatt attcttgtgg tttgtgaccc aattaagtcc tactttacat 2880
atgctttaag aatcgatggg ggatgcttca tgtgaacgtg ggagttcagc tgcttctctt 2940
gcctaagtat tcctttcctg atcactatgc attttaaagt taaacatttt taagtatttc 3000
agatgcttta gagagatttt ttttccatga ctgcatttta ctgtacagat tgctgcttct 3060
gctatatttg tgatatagga attaagagga tacacacgtt tgtttcttcg tgcctgtttt 3120
atgtgcacac attaggcatt gagacttcaa gcttttcttt ttttgtccac gtatctttgg 3180
gtctttgata aagaaaagaa tccctgttca ttgtaagcac ttttacgggg cgggtgggga 3240
ggggtgctct gctggtcttc aattaccaag aattctccaa aacaattttc tgcaggatga 3300
ttgtacagaa tcattgctta tgacatgatc gctttctaca ctgtattaca taaataaatt 3360
aaataaaata accccgggca agacttttct ttgaaggatg actacagaca ttaaataatc 3420
gaagtaattt tgggtgggga gaagaggcag attcaatttt ctttaaccag tctgaagttt 3480
catttatgat acaaaagaag atgaaaatgg aagtggcaat ataaggggat gaggaaggca 3540
tgcctggaca aacccttctt ttaagatgtg tcttcaattt gtataaaatg gtgttttcat 3600
gtaaataaat acattcttgg aggagcaaaa aaaaaaaaaa a 3641

<210> SEQ ID NO 2
<211> LENGTH: 2763
<212> TYPE: DNA
<213> ORGANISM: Homo sapiens

<400> SEQUENCE: 2
tgggacaggc agctccgggg tccgcggttt cacatcggaa acaaaacagc ggctggtctg 60
gaaggaacct gagctacgag ccgcggcggc agcggggcgg cggggaagcg tatacctaat 120
ctgggagcct gcaagtgaca acagcctttg cggtccttag acagcttggc ctggaggaga 180
acacatgaaa gaaagaacct caagaggctt tgttttctgt gaaacagtat ttctatacag 240
ttgctccaat gacagagtta cctgcaccgt tgtcctactt ccagaatgca cagatgtctg 300
aggacaacca cctgagcaat actgtacgta gccagaatga caatagagaa cggcaggagc 360
acaacgacag acggagcctt ggccaccctg agccattatc taatggacga ccccagggta 420
actcccggca ggtggtggag caagatgagg aagaagatga ggagctgaca ttgaaatatg 480
gcgccaagca tgtgatcatg ctctttgtcc ctgtgactct ctgcatggtg gtggtcgtgg 540
ctaccattaa gtcagtcagc ttttataccc ggaaggatgg gcagctaatc tataccccat 600
tcacagaaga taccgagact gtgggccaga gagccctgca ctcaattctg aatgctgcca 660
tcatgatcag tgtcattgtt gtcatgacta tcctcctggt ggttctgtat aaatacaggt 720
gctataaggt catccatgcc tggcttatta tatcatctct attgttgctg ttcttttttt 780

-continued cattcattta cttgggggaa gtgtttaaaa cctataacgt tgctgtggac tacattactg 840
ttgcactcct gatctggaat tttggtgtgg tgggaatgat ttccattcac tggaaaggtc 900
cacttcgact ccagcaggca tatctcatta tgattagtgc cctcatggcc ctggtgttta 960
tcaagtacct ccctgaatgg actgcgtggc tcatcttggc tgtgatttca gtatatgatt 1020
tagtggctgt tttgtgtccg aaaggtccac ttcgtatgct ggttgaaaca gctcaggaga 1080
gaaatgaaac gctttttcca gctctcattt actcctcaac aatggtgtgg ttggtgaata 1140
tggcagaagg agacccggaa gctcaaagga gagtatccaa aaattccaag tataatgcag 1200
aaagcacaga aagggagtca caagacactg ttgcagagaa tgatgatggc gggttcagtg 1260
aggaatggga agcccagagg gacagtcatc tagggcctca tcgctctaca cctgagtcac 1320
gagctgctgt ccaggaactt tccagcagta tcctcgctgg tgaagaccca gaggaaaggg 1380
gagtaaaact tggattggga gatttcattt tctacagtgt tctggttggt aaagcctcag 1440
caacagccag tggagactgg aacacaacca tagcctgttt cgtagccata ttaattggtt 1500
tgtgccttac attattactc cttgccattt tcaagaaagc attgccagct cttccaatct 1560
ccatcacctt tgggcttgtt ttctactttg ccacagatta tcttgtacag ccttttatgg 1620
accaattagc attccatcaa ttttatatct agcatatttg cggttagaat cccatggatg 1680
tttcttcttt gactataaca aaatctgggg aggacaaagg tgattttcct gtgtccacat 1740
ctaacaaagt caagattccc ggctggactt ttgcagcttc cttccaagtc ttcctgacca 1800
ccttgcacta ttggactttg gaaggaggtg cctatagaaa acgattttga acatacttca 1860
tcgcagtgga ctgtgtccct cggtgcagaa actaccagat ttgagggacg aggtcaagga 1920
gatatgatag gcccggaagt tgctgtgccc catcagcagc ttgacgcgtg gtcacaggac 1980
gatttcactg acactgcgaa ctctcaggac taccgttacc aagaggttag gtgaagtggt 2040
ttaaaccaaa cggaactctt catcttaaac tacacgttga aaatcaaccc aataattctg 2100
tattaactga attctgaact tttcaggagg tactgtgagg aagagcaggc accagcagca 2160
gaatggggaa tggagaggtg ggcaggggtt ccagcttccc tttgattttt tgctgcagac 2220
tcatcctttt taaatgagac ttgttttccc ctctctttga gtcaagtcaa atatgtagat 2280
tgcctttggc aattcttctt ctcaagcact gacactcatt accgtctgtg attgccattt 2340
cttcccaagg ccagtctgaa cctgaggttg ctttatccta aaagttttaa cctcaggttc 2400
caaattcagt aaattttgga aacagtacag ctatttctca tcaattctct atcatgttga 2460
agtcaaattt ggattttcca ccaaattctg aatttgtaga catacttgta cgctcacttg 2520
ccccagatgc ctcctctgtc ctcattcttc tctcccacac aagcagtctt tttctacagc 2580
cagtaaggca gctctgtcgt ggtagcagat ggtcccatta ttctagggtc ttactctttg 2640
tatgatgaaa agaatgtgtt atgaatcggt gctgtcagcc ctgctgtcag accttcttcc 2700
acagcaaatg agatgtatgc ccaaagcggt agaattaaag aagagtaaaa tggctgttga 2760
agc 2763

<210> SEQ ID NO 3
<211> LENGTH: 3051
<212> TYPE: DNA
<213> ORGANISM: Sus scrofa

<400> SEQUENCE: 3
acgcgaacag cagcgcactc ggtgccccgc gcagggtcgc gatgctgccc ggtttggcac 60
tggtcctgct ggccgcctgg acggctaggg cgctggaggt gcccactgat ggcaatgccg 120

-continued

```
gcctgcttgc agaaccccag gttgccatgt tctgtggcaa actcaacatg cacatgaatg    180
tgcagaatgg gaagtgggag tcagatccgt cggggaccaa aacctgcatt ggcaccaagg    240
aaggcatctt gcagtactgc caagaagtct accctgaact gcagatcacc aatgtggtag    300
aagccaacca accagtgacc atccagaact ggtgcaagag gagccggaag cagtgcaaga    360
cccacactca cattgtgatt ccgtaccgct gcttagttgg cgagtttgta agcgatgccc    420
tccttgttcc ggacaagtgc aagttcttac accaggagag gatggatgtt tgcgaaaccc    480
accttcactg gcacactgtg gccaaagaga cctgtagtga gaagagtacg aacttgcatg    540
actatggcat gttgctgccc tgtggaattg acaagttccg aggggtggag tttgtgtgtt    600
gcccactggc cgaggaaagt gacaatatcg actcagcaga tgcagaagag gatgactcgg    660
acgtctggtg gggtggagca gatacagact atgcagatgg cagtgaagac aaagtcgtgg    720
aggtcgcaga ggaggaggaa gtggctgatg tcgaggaaga agaagctgag gatgatgagg    780
atgatgagga tggtgatgag gtagaagaag aggctgagga accctatgaa gaggccacgg    840
agagaaccac cagcatcgcc acaaccacca ccaccaccac ggagtctgtg gaagaggtgg    900
tccgagaggt gtgctctgaa caagccgaga cggggccgtg ccgagcaatg atctcccgct    960
ggtactttga tgtgactgaa gggaagtgcg ccccgttctt ttacggcgga tgtggcggca   1020
accgaaacaa ctttgacaca gaggaatact gcatggccgt gtgtggcagc gtcatgtccc   1080
aaagtttact caagactacc caggaacatc ttccccaaga tcctgttaaa cttcctacaa   1140
cagcagccag caccccagat gccgttgaca agtatcttga gacacctgga gatgagaacg   1200
aacatgcgca tttccagaaa gccaaagaga ggctggaggc caagcaccgc gagagaatgt   1260
cccaggtcat gagagagtgg gaagaggcag aacgtcaagc aaagaacttg cctaaagctg   1320
ataagaaagc agtgatccag catttccagg agaaagtgga gtctctggag caggaagcag   1380
ccaacgagag gcagcagttg gtggagacgc acatggccag agtggaggcc atgcttaacg   1440
accgccggcg cctggccctg gagaattaca tcacggctct tcaggctgtt cctcctcggc   1500
ctcgtcatgt gttcaacatg ctcaagaagt atgtccgtgc cgaacagaaa gacagacagc   1560
acaccctaaa gcattttgaa cacgttcgca tggtagatcc aaagaaagct gctcagatcc   1620
gatcccaggt tatgacacac ctccgtgtga tttacgagcg catgaaccag tctctctccc   1680
tgctctacaa cgttcctgct gtggctgagg aaattcagga tgaagttgat gagctgctgc   1740
agaaagagca aaactactcg gatgatgtct tggccaacat gatcagcgaa ccgaggatca   1800
gttatggaaa cgatgctctc atgccgtctc tgactgaaac caaaaccacc gtggagcttc   1860
ttcctgtgaa tggagagttc agcctggatg atctccagcc ctggcatcct tttggggtag   1920
actctgtgcc tgccaacaca gaaaatgaag tcgagcctgt tgacgcccgc cctgcagccg   1980
accgaggact gaccactcga ccaggttccg ggttgaccaa catcaagacg gaagagatct   2040
ctgaagtgaa gatggatgcg gagttccgac acgattcagg ctatgaggtt catcaccaaa   2100
aactggtgtt cttcgcagaa gatgtgggtt caaacaaagg tgccatcatt ggactcatgg   2160
tgggtggtgt tgtcatagca accgtgattg tcatcacctt agtgatgctg aagaagaaac   2220
agtacacatc catccatcac ggtgtggtgg aggttgacgc agctgtgacc ccggaggagc   2280
gccacctctc caagatgcag cagaatggct atgaaaaccc aacttacaag ttctttgagc   2340
agatgcagaa ctagaccgcc gccacagcag cctctgaagt tggacagcaa aaccattgct   2400
tcactaccca ttggtgttca tttatagaat aatggggaaa gacacaaacc cttctgtttt   2460
attatttact catgatcgcc tttcagcagc tgtgctgtaa cacaagtaga tgcctgaact   2520
```

tgaattaata ttacgaatca gtaatgtatt ctctctcttt acatttccgg tctctacact 2580
acattattaa tgggttttgt gtactgtaaa gaatgaagct gtatcaaact agtgcatgaa 2640
tagattccct cctgattatt tatcatgtag ccccttagcc agttgtatat tattcttgtg 2700
gttttgtgat ccaattaagt cctactttga aatatgcttt aagaatcgat gggggatgct 2760
tcatgtgaac gtgggagttt agctgcttct cttgcctaag tattcttttc ctgatcacta 2820
tgcattttaa aggtaaacat ttttatgtat tccaaatgag ttagagaagt tttttccacg 2880
attgcatttg actgtacaga ttgctgcttc tgctatattt gtgatatagg aattatgagg 2940
atacacgttt atttctttgt gcctgtttta tgtgcacaca ttaggcattg agaattaaaa 3000
cttcttttgt ccgtgtacct tcggatcttt aaaaaaaaaa aaaaaaaaaa a 3051

<210> SEQ ID NO 4
<211> LENGTH: 1720
<212> TYPE: DNA
<213> ORGANISM: Sus scrofa

<400> SEQUENCE: 4
aatcggaaac aaaacagcgg ctgctgggga agggacctgg gctgcgagag gtggcggctg 60
cgacgagaaa gaacctaatc cgggagcctg caacctgtga agttcttaga aagcttggcc 120
tggaggagaa cacatgaaag aaagaacccc aggaggctct gatttctgtg aaaaagtatt 180
tctatacggt tgttccaatg acagagttac ctgcaccctt gtcctacttc cagaatgccc 240
agatgtccga ggacaaccac gtgagcaata acgtaagtag ccagaatgac agtagagagc 300
ggcatgagca cagcatcgag aggcggaggc gtggcaactc tgagtcgtta tccaatggcg 360
gagcccaggg aaactcacgc caggtggtgg aacaagaaga agaggaagac gaggagctga 420
cgttgaaata tggcgccaaa catgtgatca tgctctttgt ccctgtgact ctatgtatgg 480
tggtggttgt ggccaccatc aaatcagtca gcttttatac ccggaaggat gggcagctga 540
tctatactcc atttacagaa gacactgaga ctgtagggca gagagccctg cactcaattc 600
tgaatgctgc tatcatgatt agtgtcattg tcgtcatgac tattctcctg gtggttctct 660
ataaatacag gtgctataag gtcatccatg cctggcttat tatttcatcc ctattgttgc 720
tgttcttttt ctcattcatt tacttggggg aagtgtttaa aacctataac gttgccatgg 780
attacattac ggtggcactc ctgatctgga attttggtgt ggtaggaatg attgccattc 840
actggaaagg cccattgcga ctccagcagg catatctcat tatgatcagt gccctcatgg 900
ccctggtgtt tatcaagtac ctcccggaat ggaccgcgtg gctcatcttg gctgtgattt 960
cagtatacga tttagtggct gttttgtgtc caaatggccc acttcgtttg ctggttgaaa 1020
cagctcagga gagaaatgaa actctctttc cagctcttat ttactcgtca acaatggtgt 1080
ggttggtgaa tatggcagaa ggagacccag aagcccaaag gaaggtatcc aaaaactcca 1140
attataatgc acaaagcaca ggtgaatcac aagactctgt gacagagagt gatgatggtg 1200
gcttcagtga agagtgggaa gcccagaggg acagtcgcct gggacctcat cactctacag 1260
ctgagtcacg atctgctgta caggatcttt ccagaagcat cccagccact gaggacccag 1320
aagaaagggg agtaaaactt ggattaggag atttcatttt ctacagtgtt ctggttggta 1380
aagcttctgc aacagccagt ggagactgga acacaaccat tgcctgtttt gtagccatat 1440
taattggttt gtgccttaca ttactgctcc tcgccatttt caagaaagcg ttgccagctc 1500
ttccaatctc tatcaccttt gggcttgttt tctactttgc cacagattat cttgtgcaac 1560
cctttatgga ccaattagca ttccatcaat tttatatcta gcatatttcc agttagaatc 1620
tcatggattt tttctccttt ggctataata aaatctgggg aaagcaaagg tgattttgct 1680
gtgtccacat ctaacaaagt caggattccc agctggacct 1720

<210> SEQ ID NO 5
<211> LENGTH: 3641
<212> TYPE: DNA
<213> ORGANISM: Sus scrofa

<400> SEQUENCE: 5
gctgactcgc ctggctctga gccccgccgc cgcgctcggg ctccgtcagt ttcctcggca 60
gcggtaggcg agagcacgcg gaggagcgtg cgcgggggcc ccgggagacg gcggcggtgg 120
cggcgcgggc agagcaagga cgcggcggat cccactcgca cagcagcgca ctcggtgccc 180
cgcgcagggt cgcgatgctg cccggtttgg cactgctcct gctggccgcc tggacggctc 240
gggcgctgga ggtacccact gatggtaatg ctggcctgct ggctgaaccc cagattgcca 300
tgttctgtgg cagactgaac atgcacatga atgtccagaa tgggaagtgg gattcagatc 360
catcagggac caaaacctgc attgatacca aggaaggcat cctgcagtat tgccaagaag 420
tctaccctga actgcagatc accaatgtgg tagaagccaa ccaaccagtg accatccaga 480
actggtgcaa gcggggccgc aagcagtgca agacccatcc ccactttgtg attccctacc 540
gctgcttagt tggtgagttt gtaagtgatg cccttctcgt tcctgacaag tgcaaattct 600
tacaccagga gaggatggat gtttgcgaaa ctcatcttca ctggcacacc gtcgccaaag 660
agacatgcag tgagaagagt accaacttgc atgactacgg catgttgctg ccctgcggaa 720
ttgacaagtt ccgaggggta gagtttgtgt gttgcccact ggctgaagaa agtgacaatg 780
tggattctgc tgatgcggag gaggatgact cggatgtctg gtggggcgga gcagacacag 840
actatgcaga tgggagtgaa gacaaagtag tagaagtagc agaggaggaa gaagtggctg 900
aggtggaaga agaagaagcc gatgatgacg aggacgatga ggatggtgat gaggtagagg 960
aagaggctga ggaaccctac gaagaagcca cagagagaac caccagcatt gccaccacca 1020
ccaccaccac cacagagtct gtggaagagg tggttcgaga ggtgtgctct gaacaagccg 1080
agacggggcc gtgccgagca atgatctccc gctggtactt tgatgtgact gaagggaagt 1140
gtgccccatt cttttacggc ggatgtggcg gcaaccggaa caactttgac acagaagagt 1200
actgcatggc cgtgtgtggc agcgccatgt cccaaagttt actcaagact acccaggaac 1260
ctcttgcccg agatcctgtt aaacttccta caacagcagc cagtacccct gatgccgttg 1320
acaagtatct cgagacacct ggggatgaga atgaacatgc ccatttccag aaagccaaag 1380
agaggcttga ggccaagcac cgagagagaa tgtcccaggt catgagagaa tgggaagagg 1440
cagaacgtca agcaaagaac ttgcctaaag ctgataagaa ggcagttatc cagcatttcc 1500
aggagaaagt ggaatctttg gaacaggaag cagccaacga gagacagcag ctggtggaga 1560
cacacatggc cagagtggaa gccatgctca atgaccgccg ccgcctggcc ctggagaact 1620
acatcaccgc tctgcaggct gttcctcctc ggcctcgtca cgtgttcaat atgctaaaga 1680
agtatgtccg cgcagaacag aaggacagac agcacaccct aaagcatttc gagcatgtgc 1740
gcatggtgga tcccaagaaa gccgctcaga tccggtccca ggttatgaca cacctccgtg 1800
tgatttatga gcgcatgaat cagtctctct ccctgctcta caacgtgcct gcagtggccg 1860
aggagattca ggatgaagtt gatgagctgc ttcagaaaga gcaaaactat tcagatgacg 1920
tcttggccaa catgattagt gaaccaagga tcagttacgg aaacgatgct ctcatgccat 1980
ctttgaccga aacgaaaacc accgtggagc tccttcccgt gaatggagag ttcagcctgg 2040
acgatctcca gccgtggcat tcttttgggg ctgactctgt gccagccaac acagaaaacg 2100
aagttgagcc tgttgatgcc cgccctgctg ccgaccgagg actgaccact cgaccaggtt 2160
ctgggttgac aaatatcaag acggaggaga tctctgaagt gaatctggat gcagaattcc 2220
gacatgactc aggatatgaa gttcatcatc aaaaattggt gttctttgca gaagatgtgg 2280
gttcaaacaa aggtgcaatc attggactca tggtgggcgg tgttgtcata gcgacagtga 2340
tcgtcatcac cttggtgatg ctgaagaaga aacagtacac atccattcat catggtgtgg 2400
tggaggttga cgccgctgtc accccagagg agcgccacct gtccaagatg cagcagaacg 2460
gctacgaaaa tccaacctac aagttctttg agcagatgca gaactagacc cccgccacag 2520
cagcctctga agttggacag caaaaccatt gcttcactac ccatcggtgt ccatttatag 2580
aataatgtgg gaagaaacaa acccgtttta tgatttactc attatcgcct tttgacagct 2640
gtgctgtaac acaagtagat gcctgaactt gaattaatcc acacatcagt aatgtattct 2700
atctctcttt acattttggt ctctatacta cattattaat gggttttgtg tactgtaaag 2760
aatttagctg tatcaaacta gtgcatgaat agattctctc ctgattattt atcacatagc 2820
cccttagcca gttgtatatt attcttgtgg tttgtgaccc aattaagtcc tactttacat 2880
atgctttaag aatcgatggg ggatgcttca tgtgaacgtg ggagttcagc tgcttctctt 2940
gcctaagtat tcctttcctg atcactatgc attttaaagt taaacatttt taagtatttc 3000
agatgcttta gagagatttt ttttccatga ctgcatttta ctgtacagat tgctgcttct 3060
gctatatttg tgatatagga attaagagga tacacacgtt tgtttcttcg tgcctgtttt 3120
atgtgcacac attaggcatt gagacttcaa gcttttcttt ttttgtccac gtatctttgg 3180
gtctttgata aagaaaagaa tccctgttca ttgtaagcac ttttacgggg cgggtgggga 3240
ggggtgctct gctggtcttc aattaccaag aattctccaa aacaattttc tgcaggatga 3300
ttgtacagaa tcattgctta tgacatgatc gctttctaca ctgtattaca taaataaatt 3360
aaataaaata accccgggca agacttttct ttgaaggatg actacagaca ttaaataatc 3420
gaagtaattt tgggtgggga gaagaggcag attcaatttt ctttaaccag tctgaagttt 3480
catttatgat acaaaagaag atgaaaatgg aagtggcaat ataaggggat gaggaaggca 3540
tgcctggaca aacccttctt ttaagatgtg tcttcaattt gtataaaatg gtgttttcat 3600
gtaaataaat acattcttgg aggagcaaaa aaaaaaaaaa a 3641

<210> SEQ ID NO 6
<211> LENGTH: 3641
<212> TYPE: DNA
<213> ORGANISM: Homo sapiens

<400> SEQUENCE: 6
gctgactcgc ctggctctga gccccgccgc cgcgctcggg ctccgtcagt ttcctcggca 60
gcggtaggcg agagcacgcg gaggagcgtg cgcgggggcc ccgggagacg gcggcggtgg 120
cggcgcgggc agagcaagga cgcggcggat cccactcgca cagcagcgca ctcggtgccc 180
cgcgcagggt cgcgatgctg cccggtttgg cactgctcct gctggccgcc tggacggctc 240
gggcgctgga ggtacccact gatggtaatg ctggcctgct ggctgaaccc cagattgcca 300
tgttctgtgg cagactgaac atgcacatga atgtccagaa tgggaagtgg gattcagatc 360
catcagggac caaaacctgc attgatacca aggaaggcat cctgcagtat tgccaagaag 420
tctaccctga actgcagatc accaatgtgg tagaagccaa ccaaccagtg accatccaga 480
actggtgcaa gcggggccgc aagcagtgca agacccatcc ccactttgtg attccctacc 540

-continued

```
gctgcttagt tggtgagttt gtaagtgatg cccttctcgt tcctgacaag tgcaaattct    600
tacaccagga gaggatggat gtttgcgaaa ctcatcttca ctggcacacc gtcgccaaag    660
agacatgcag tgagaagagt accaacttgc atgactacgg catgttgctg ccctgcggaa    720
ttgacaagtt ccgaggggta gagtttgtgt gttgcccact ggctgaagaa agtgacaatg    780
tggattctgc tgatgcggag gaggatgact cggatgtctg gtggggcgga gcagacacag    840
actatgcaga tgggagtgaa gacaaagtag tagaagtagc agaggaggaa gaagtggctg    900
aggtggaaga agaagaagcc gatgatgacg aggacgatga ggatggtgat gaggtagagg    960
aagaggctga ggaaccctac gaagaagcca cagagagaac caccagcatt gccaccacca   1020
ccaccaccac cacagagtct gtggaagagg tggttcgaga ggtgtgctct gaacaagccg   1080
agacggggcc gtgccgagca atgatctccc gctggtactt tgatgtgact gaagggaagt   1140
gtgccccatt cttttacggc ggatgtggcg gcaaccggaa caactttgac acagaagagt   1200
actgcatggc cgtgtgtggc agcgccatgt cccaaagttt actcaagact acccaggaac   1260
ctcttgcccg agatcctgtt aaacttccta caacagcagc cagtacccct gatgccgttg   1320
acaagtatct cgagacacct ggggatgaga atgaacatgc ccatttccag aaagccaaag   1380
agaggcttga ggccaagcac cgagagagaa tgtcccaggt catgagagaa tgggaagagg   1440
cagaacgtca agcaaagaac ttgcctaaag ctgataagaa ggcagttatc cagcatttcc   1500
aggagaaagt ggaatctttg gaacaggaag cagccaacga gagacagcag ctggtggaga   1560
cacacatggc cagagtggaa gccatgctca atgaccgccg ccgcctggcc ctggagaact   1620
acatcaccgc tctgcaggct gttcctcctc ggcctcgtca cgtgttcaat atgctaaaga   1680
agtatgtccg cgcagaacag aaggacagac agcacaccct aaagcatttc gagcatgtgc   1740
gcatggtgga tcccaagaaa gccgctcaga tccggtccca ggttatgaca cacctccgtg   1800
tgatttatga gcgcatgaat cagtctctct ccctgctcta caacgtgcct gcagtggccg   1860
aggagattca ggatgaagtt gatgagctgc ttcagaaaga gcaaaactat tcagatgacg   1920
tcttggccaa catgattagt gaaccaagga tcagttacgg aaacgatgct ctcatgccat   1980
ctttgaccga aacgaaaacc accgtggagc tccttcccgt gaatggagag ttcagcctgg   2040
acgatctcca gccgtggcat tcttttgggg ctgactctgt gccagccaac acagaaaacg   2100
aagttgagcc tgttgatgcc cgccctgctg ccgaccgagg actgaccact cgaccaggtt   2160
ctgggttgac aaatatcaag acggaggaga tctctgaagt gaatctggat gcagaattcc   2220
gacatgactc aggatatgaa gttcatcatc aaaaattggt gttctttgca gaagatgtgg   2280
gttcaaacaa aggtgcaatc attggactca tggtgggcgg tgttgtcata gcgacagtga   2340
tcgtcatcac cttggtgatg ctgaagaaga aacagtacac atccattcat catggtgtgg   2400
tggaggttga cgccgctgtc accccagagg agcgccacct gtccaagatg cagcagaacg   2460
gctacgaaaa tccaacctac aagttctttg agcagatgca gaactagacc cccgccacag   2520
cagcctctga agttggacag caaaaccatt gcttcactac ccatcggtgt ccatttatag   2580
aataatgtgg gaagaaacaa acccgtttta tgatttactc attatcgcct tttgacagct   2640
gtgctgtaac acaagtagat gcctgaactt gaattaatcc acacatcagt aatgtattct   2700
atctctcttt acattttggt ctctatacta cattattaat gggttttgtg tactgtaaag   2760
aatttagctg tatcaaacta gtgcatgaat agattctctc ctgattattt atcacatagc   2820
cccttagcca gttgtatatt attcttgtgg tttgtgaccc aattaagtcc tactttacat   2880
atgctttaag aatcgatggg ggatgcttca tgtgaacgtg ggagttcagc tgcttctctt   2940
```

```
gcctaagtat tcctttcctg atcactatgc attttaaagt taaacatttt taagtatttc   3000

agatgcttta gagagatttt ttttccatga ctgcatttta ctgtacagat tgctgcttct   3060

gctatatttg tgatatagga attaagagga tacacacgtt tgtttcttcg tgcctgtttt   3120

atgtgcacac attaggcatt gagacttcaa gcttttcttt ttttgtccac gtatctttgg   3180

gtctttgata aagaaaagaa tccctgttca ttgtaagcac ttttacgggg cgggtgggga   3240

ggggtgctct gctggtcttc aattaccaag aattctccaa aacaattttc tgcaggatga   3300

ttgtacagaa tcattgctta tgacatgatc gctttctaca ctgtattaca taaataaatt   3360

aaataaaata accccgggca agacttttct ttgaaggatg actacagaca ttaaataatc   3420

gaagtaattt tgggtgggga gaagaggcag attcaatttt ctttaaccag tctgaagttt   3480

catttatgat acaaaagaag atgaaaatgg aagtggcaat ataaggggat gaggaaggca   3540

tgcctggaca aacccttctt ttaagatgtg tcttcaattt gtataaaatg gtgttttcat   3600

gtaaataaat acattcttgg aggagcaaaa aaaaaaaaaa a                      3641


<210> SEQ ID NO 7
<211> LENGTH: 770
<212> TYPE: PRT
<213> ORGANISM: Homo sapiens

<400> SEQUENCE: 7

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255
```

```
Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Asn Leu Asp
            660                 665                 670

Ala Glu Phe Arg His Asp Ser Gly Tyr Glu Val His His Gln Lys Leu
```

-continued

```
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770


<210> SEQ ID NO 8
<211> LENGTH: 3417
<212> TYPE: DNA
<213> ORGANISM: Homo sapiens

<400> SEQUENCE: 8

gctgactcgc ctggctctga gccccgccgc cgcgctcggg ctccgtcagt ttcctcggca     60

gcggtaggcg agagcacgcg gaggagcgtg cgcgggggcc ccgggagacg gcggcggtgg    120

cggcgcgggc agagcaagga cgcggcggat cccactcgca cagcagcgca ctcggtgccc    180

cgcgcagggt cgcgatgctg cccggtttgg cactgctcct gctggccgcc tggacggctc    240

gggcgctgga ggtacccacc gatggtaatg ctggcctgct ggctgaaccc cagattgcca    300

tgttctgtgg cagactgaac atgcacatga atgtccagaa tgggaagtgg gattcagatc    360

catcagggac caaaacctgc attgatacca aggaaggcat cctgcagtat tgccaagaag    420

tctaccctga actgcagatc accaatgtgg tagaagccaa ccaaccagtg accatccaga    480

actggtgcaa gcggggccgc aagcagtgca agacccatcc ccactttgtg attccctacc    540

gctgcttagt tggtgagttt gtaagtgatg cccttctcgt tcctgacaag tgcaaattct    600

tacaccagga gaggatggat gtttgcgaaa ctcatcttca ctggcacacc gtcgccaaag    660

agacatgcag tgagaagagt accaacttgc atgactacgg catgttgctg ccctgcggaa    720

ttgacaagtt ccgaggggta gagtttgtgt gttgcccact ggctgaagaa agtgacaatg    780

tggattctgc tgatgcggag gaggatgact cggatgtctg gtggggcgga gcagacacag    840

actatgcaga tgggagtgaa gacaaagtag tagaagtagc agaggaggaa gaagtggctg    900

aggtggaaga agaagaagcc gatgatgacg aggacgatga ggatggtgat gaggtagagg    960

aagaggctga ggaaccctac gaagaagcca cagagagaac caccagcatt gccaccacca   1020

ccaccaccac cacagagtct gtggaagagg tggttcgagc ttcctacaac agcagccagt   1080

acccctgatg ccgttgacaa gtatctcgag acacctgggg atgagaatga acatgcccat   1140

ttccagaaag ccaaagagag gcttgaggcc aagcaccgag agagaatgtc ccaggtcatg   1200

agagaatggg aagaggcaga acgtcaagca aagaacttgc ctaaagctga taagaaggca   1260

gttatccagc atttccagga gaaagtggaa tctttggaac aggaagcagc caacgagaga   1320

cagcagctgg tggagacaca catggccaga gtggaagcca tgctcaatga ccgccgccgc   1380

ctggccctgg agaactacat caccgctctg caggctgttc ctcctcggcc tcgtcacgtg   1440

ttcaatatgc taaagaagta tgtccgcgca gaacagaagg acagacagca caccctaaag   1500

catttcgagc atgtgcgcat ggtggatccc aagaaagccg ctcagatccg gtcccaggtt   1560
```

-continued atgacacacc tccgtgtgat ttatgagcgc atgaatcagt ctctctccct gctctacaac 1620
gtgcctgcag tggccgagga gattcaggat gaagttgatg agctgcttca gaaagagcaa 1680
aactattcag atgacgtctt ggccaacatg attagtgaac caaggatcag ttacggaaac 1740
gatgctctca tgccatcttt gaccgaaacg aaaaccaccg tggagctcct tcccgtgaat 1800
ggagagttca gcctggacga tctccagccg tggcattctt ttggggctga ctctgtgcca 1860
gccaacacag aaaacgaagt tgagcctgtt gatgcccgcc ctgctgccga ccgaggactg 1920
accactcgac caggttctgg gttgacaaat atcaagacgg aggagatctc tgaagtgaat 1980
ctggatgcag aattccgaca tgactcagga tatgaagttc atcatcaaaa attggtgttc 2040
tttgcagaag atgtgggttc aaacaaaggt gcaatcattg gactcatggt gggcggtgtt 2100
gtcatagcga cagtgatcgt catcaccttg gtgatgctga agaagaaaca gtacacatcc 2160
attcatcatg gtgtggtgga ggttgacgcc gctgtcaccc cagaggagcg ccacctgtcc 2220
aagatgcagc agaacggcta cgaaaatcca acctacaagt tctttgagca gatgcagaac 2280
tagacccccg ccacagcagc ctctgaagtt ggacagcaaa accattgctt cactacccat 2340
cggtgtccat ttatagaata atgtgggaag aaacaaaccc gttttatgat ttactcatta 2400
tcgccttttg acagctgtgc tgtaacacaa gtagatgcct gaacttgaat taatccacac 2460
atcagtaatg tattctatct ctctttacat tttggtctct atactacatt attaatgggt 2520
tttgtgtact gtaaagaatt tagctgtatc aaactagtgc atgaatagat tctctcctga 2580
ttatttatca catagcccct tagccagttg tatattattc ttgtggtttg tgacccaatt 2640
aagtcctact ttacatatgc tttaagaatc gatgggggat gcttcatgtg aacgtgggag 2700
ttcagctgct tctcttgcct aagtattcct ttcctgatca ctatgcattt taaagttaaa 2760
catttttaag tatttcagat gctttagaga gatttttttt ccatgactgc attttactgt 2820
acagattgct gcttctgcta tatttgtgat ataggaatta agaggataca cacgtttgtt 2880
tcttcgtgcc tgttttatgt gcacacatta ggcattgaga cttcaagctt ttcttttttt 2940
gtccacgtat ctttgggtct ttgataaaga aaagaatccc tgttcattgt aagcactttt 3000
acggggcggg tggggagggg tgctctgctg gtcttcaatt accaagaatt ctccaaaaca 3060
attttctgca ggatgattgt acagaatcat tgcttatgac atgatcgctt tctacactgt 3120
attacataaa taaattaaat aaaataaccc cgggcaagac ttttctttga aggatgacta 3180
cagacattaa ataatcgaag taattttggg tggggagaag aggcagattc aattttcttt 3240
aaccagtctg aagtttcatt tatgatacaa aagaagatga aaatggaagt ggcaatataa 3300
ggggatgagg aaggcatgcc tggacaaacc cttcttttaa gatgtgtctt caatttgtat 3360
aaaatggtgt tttcatgtaa ataaatacat tcttggagga gcaaaaaaaa aaaaaaa 3417

<210> SEQ ID NO 9
<211> LENGTH: 3417
<212> TYPE: DNA
<213> ORGANISM: Homo sapiens

<400> SEQUENCE: 9
gctgactcgc ctggctctga gccccgccgc cgcgctcggg ctccgtcagt ttcctcggca 60
gcggtaggcg agagcacgcg gaggagcgtg cgcgggggcc ccgggagacg gcggcggtgg 120
cggcgcgggc agagcaagga cgcggcggat cccactcgca cagcagcgca ctcggtgccc 180
cgcgcagggt cgcgatgctg cccggtttgg cactgctcct gctggccgcc tggacggctc 240
gggcgctgga ggtacccact gatggtaatg ctggcctgct ggctgaaccc cagattgcca 300

-continued

```
tgttctgtgg cagactgaac atgcacatga atgtccagaa tgggaagtgg gattcagatc    360
catcagggac caaaacctgc attgatacca aggaaggcat cctgcagtat tgccaagaag    420
tctaccctga actgcagatc accaatgtgg tagaagccaa ccaaccagtg accatccaga    480
actggtgcaa gcggggccgc aagcagtgca agacccatcc ccactttgtg attccctacc    540
gctgcttagt tggtgagttt gtaagtgatg cccttctcgt tcctgacaag tgcaaattct    600
tacaccagga gaggatggat gtttgcgaaa ctcatcttca ctggcacacc gtcgccaaag    660
agacatgcag tgagaagagt accaacttgc atgactacgg catgttgctg ccctgcggaa    720
ttgacaagtt ccgaggggta gagtttgtgt gttgcccact ggctgaagaa agtgacaatg    780
tggattctgc tgatgcggag gaggatgact cggatgtctg gtggggcgga gcagacacag    840
actatgcaga tgggagtgaa gacaaagtag tagaagtagc agaggaggaa gaagtggctg    900
aggtggaaga agaagaagcc gatgatgacg aggacgatga ggatggtgat gaggtagagg    960
aagaggctga ggaaccctac gaagaagcca cagagagaac caccagcatt gccaccacca   1020
ccaccaccac cacagagtct gtggaagagg tggttcgagc ttcctacaac agcagccagt   1080
acccctgatg ccgttgacaa gtatctcgag acacctgggg atgagaatga acatgcccat   1140
ttccagaaag ccaaagagag gcttgaggcc aagcaccgag agagaatgtc ccaggtcatg   1200
agagaatggg aagaggcaga acgtcaagca aagaacttgc ctaaagctga taagaaggca   1260
gttatccagc atttccagga gaaagtggaa tctttggaac aggaagcagc caacgagaga   1320
cagcagctgg tggagacaca catggccaga gtggaagcca tgctcaatga ccgccgccgc   1380
ctggccctgg agaactacat caccgctctg caggctgttc ctcctcggcc tcgtcacgtg   1440
ttcaatatgc taaagaagta tgtccgcgca gaacagaagg acagacagca caccctaaag   1500
catttcgagc atgtgcgcat ggtggatccc aagaaagccg ctcagatccg gtcccaggtt   1560
atgacacacc tccgtgtgat ttatgagcgc atgaatcagt ctctctccct gctctacaac   1620
gtgcctgcag tggccgagga gattcaggat gaagttgatg agctgcttca gaaagagcaa   1680
aactattcag atgacgtctt ggccaacatg attagtgaac caaggatcag ttacggaaac   1740
gatgctctca tgccatcttt gaccgaaacg aaaaccaccg tggagctcct tcccgtgaat   1800
ggagagttca gcctggacga tctccagccg tggcattctt ttggggctga ctctgtgcca   1860
gccaacacag aaaacgaagt tgagcctgtt gatgcccgcc ctgctgccga ccgaggactg   1920
accactcgac caggttctgg gttgacaaat atcaagacgg aggagatctc tgaagtgaat   1980
ctggatgcag aattccgaca tgactcagga tatgaagttc atcatcaaaa attggtgttc   2040
tttgcagaag atgtgggttc aaacaaaggt gcaatcattg gactcatggt gggcggtgtt   2100
gtcatagcga cagtgatcgt catcaccttg gtgatgctga agaagaaaca gtacacatcc   2160
attcatcatg gtgtggtgga ggttgacgcc gctgtcaccc cagaggagcg ccacctgtcc   2220
aagatgcagc agaacggcta cgaaaatcca acctacaagt tctttgagca gatgcagaac   2280
tagacccccg ccacagcagc ctctgaagtt ggacagcaaa accattgctt cactacccat   2340
cggtgtccat ttatagaata atgtgggaag aaacaaaccc gttttatgat ttactcatta   2400
tcgccttttg acagctgtgc tgtaacacaa gtagatgcct gaacttgaat taatccacac   2460
atcagtaatg tattctatct ctctttacat tttggtctct atactacatt attaatgggt   2520
tttgtgtact gtaaagaatt tagctgtatc aaactagtgc atgaatagat tctctcctga   2580
ttatttatca catagcccct tagccagttg tatattattc ttgtggtttg tgacccaatt   2640
aagtcctact ttacatatgc tttaagaatc gatgggggat gcttcatgtg aacgtgggag   2700
```

ttcagctgct tctcttgcct aagtattcct ttcctgatca ctatgcattt taaagttaaa 2760
catttttaag tatttcagat gctttagaga gatttttttt ccatgactgc attttactgt 2820
acagattgct gcttctgcta tatttgtgat ataggaatta agaggataca cacgtttgtt 2880
tcttcgtgcc tgttttatgt gcacacatta ggcattgaga cttcaagctt ttcttttttt 2940
gtccacgtat ctttgggtct ttgataaaga aaagaatccc tgttcattgt aagcactttt 3000
acggggcggg tggggagggg tgctctgctg gtcttcaatt accaagaatt ctccaaaaca 3060
attttctgca ggatgattgt acagaatcat tgcttatgac atgatcgctt tctacactgt 3120
attacataaa taaattaaat aaaataaccc cgggcaagac ttttctttga aggatgacta 3180
cagacattaa ataatcgaag taattttggg tggggagaag aggcagattc aatttttcttt 3240 aaccagtctg aagtttcatt tatgatacaa aagaagatga aaatggaagt ggcaatataa 3300
ggggatgagg aaggcatgcc tggacaaacc cttcttttaa gatgtgtctt caatttgtat 3360
aaaatggtgt tttcatgtaa ataaatacat tcttggagga gcaaaaaaaa aaaaaaa 3417

<210> SEQ ID NO 10
<211> LENGTH: 695
<212> TYPE: PRT
<213> ORGANISM: Homo sapiens

<400> SEQUENCE: 10

Met Leu Pro Gly Leu Ala Leu Leu Leu Leu Ala Ala Trp Thr Ala Arg
1 5 10 15

Ala Leu Glu Val Pro Thr Asp Gly Asn Ala Gly Leu Leu Ala Glu Pro
20 25 30

Gln Ile Ala Met Phe Cys Gly Arg Leu Asn Met His Met Asn Val Gln
35 40 45

Asn Gly Lys Trp Asp Ser Asp Pro Ser Gly Thr Lys Thr Cys Ile Asp
50 55 60

Thr Lys Glu Gly Ile Leu Gln Tyr Cys Gln Glu Val Tyr Pro Glu Leu
65 70 75 80

Gln Ile Thr Asn Val Val Glu Ala Asn Gln Pro Val Thr Ile Gln Asn
85 90 95

Trp Cys Lys Arg Gly Arg Lys Gln Cys Lys Thr His Pro His Phe Val
100 105 110

Ile Pro Tyr Arg Cys Leu Val Gly Glu Phe Val Ser Asp Ala Leu Leu
115 120 125

Val Pro Asp Lys Cys Lys Phe Leu His Gln Glu Arg Met Asp Val Cys
130 135 140

Glu Thr His Leu His Trp His Thr Val Ala Lys Glu Thr Cys Ser Glu
145 150 155 160

Lys Ser Thr Asn Leu His Asp Tyr Gly Met Leu Leu Pro Cys Gly Ile
165 170 175

Asp Lys Phe Arg Gly Val Glu Phe Val Cys Cys Pro Leu Ala Glu Glu
180 185 190

Ser Asp Asn Val Asp Ser Ala Asp Ala Glu Glu Asp Asp Ser Asp Val
195 200 205

Trp Trp Gly Gly Ala Asp Thr Asp Tyr Ala Asp Gly Ser Glu Asp Lys
210 215 220

Val Val Glu Val Ala Glu Glu Glu Glu Val Ala Glu Val Glu Glu Glu
225 230 235 240

Glu Ala Asp Asp Asp Glu Asp Asp Glu Asp Gly Asp Glu Val Glu Glu
245 250 255

```
Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Asn Leu Asp Ala Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685
```

Phe Phe Glu Gln Met Gln Asn
690 695

<210> SEQ ID NO 11
<211> LENGTH: 3051
<212> TYPE: DNA
<213> ORGANISM: Sus scrofa

<400> SEQUENCE: 11
acgcgaacag cagcgcactc ggtgccccgc gcagggtcgc gatgctgccc ggtttggcac 60
tggtcctgct ggccgcctgg acggctaggg cgctggaggt gcccactgat ggcaatgccg 120
gcctgcttgc agaaccccag gttgccatgt tctgtggcaa actcaacatg cacatgaatg 180
tgcagaatgg gaagtgggag tcagatccgt cggggaccaa aacctgcatt ggcaccaagg 240
aaggcatctt gcagtactgc caagaagtct accctgaact gcagatcacc aatgtggtag 300
aagccaacca accagtgacc atccagaact ggtgcaagag gagccggaag cagtgcaaga 360
cccacactca cattgtgatt ccgtaccgct gcttagttgg cgagtttgta agcgatgccc 420
tccttgttcc ggacaagtgc aagttcttac accaggagag gatggatgtt tgcgaaaccc 480
accttcactg gcacactgtg gccaaagaga cctgtagtga gaagagtacg aacttgcatg 540
actatggcat gttgctgccc tgtggaattg acaagttccg aggggtggag tttgtgtgtt 600
gcccactggc cgaggaaagt gacaatatcg actcagcaga tgcagaagag gatgactcgg 660
acgtctggtg ggtggagca gatacagact atgcagatgg cagtgaagac aaagtcgtgg 720
aggtcgcaga ggaggaggaa gtggctgatg tcgaggaaga agaagctgag gatgatgagg 780
atgatgagga tggtgatgag gtagaagaag aggctgagga accctatgaa gaggccacgg 840
agagaaccac cagcatcgcc acaaccacca ccaccaccac ggagtctgtg gaagaggtgg 900
tccgagaggt gtgctctgaa caagccgaga cggggccgtg ccgagcaatg atctcccgct 960
ggtactttga tgtgactgaa gggaagtgcg ccccgttctt ttacggcgga tgtggcggca 1020
accgaaacaa ctttgacaca gaggaatact gcatggccgt gtgtggcagc gtcatgtccc 1080
aaagtttact caagactacc caggaacatc ttccccaaga tcctgttaaa cttcctacaa 1140
cagcagccag caccccagat gccgttgaca agtatcttga gacacctgga gatgagaacg 1200
aacatgcgca tttccagaaa gccaaagaga ggctggaggc caagcaccgc gagagaatgt 1260
cccaggtcat gagagagtgg gaagaggcag aacgtcaagc aaagaacttg cctaaagctg 1320
ataagaaagc agtgatccag catttccagg agaaagtgga gtctctggag caggaagcag 1380
ccaacgagag gcagcagttg gtggagacgc acatggccag agtggaggcc atgcttaacg 1440
accgccggcg cctggccctg gagaattaca tcacggctct tcaggctgtt cctcctcggc 1500
ctcgtcatgt gttcaacatg ctcaagaagt atgtccgtgc cgaacagaaa gacagacagc 1560
acaccctaaa gcattttgaa cacgttcgca tggtagatcc aaagaaagct gctcagatcc 1620
gatcccaggt tatgacacac ctccgtgtga tttacgagcg catgaaccag tctctctccc 1680
tgctctacaa cgttcctgct gtggctgagg aaattcagga tgaagttgat gagctgctgc 1740
agaaagagca aaactactcg gatgatgtct tggccaacat gatcagcgaa ccgaggatca 1800
gttatggaaa cgatgctctc atgccgtctc tgactgaaac caaaaccacc gtggagcttc 1860
ttcctgtgaa tggagagttc agcctggatg atctccagcc ctggcatcct tttggggtag 1920
actctgtgcc tgccaacaca gaaaatgaag tcgagcctgt tgacgcccgc cctgcagccg 1980
accgaggact gaccactcga ccaggttccg ggttgaccaa catcaagacg gaagagatct 2040
ctgaagtgaa tctggatgcg gagttccgac acgattcagg ctatgaggtt catcaccaaa 2100
aactggtgtt cttcgcagaa gatgtgggtt caaacaaagg tgccatcatt ggactcatgg 2160
tgggtggtgt tgtcatagca accgtgattg tcatcacctt agtgatgctg aagaagaaac 2220
agtacacatc catccatcac ggtgtggtgg aggttgacgc agctgtgacc ccggaggagc 2280
gccacctctc caagatgcag cagaatggct atgaaaaccc aacttacaag ttctttgagc 2340
agatgcagaa ctagaccgcc gccacagcag cctctgaagt tggacagcaa aaccattgct 2400
tcactaccca ttggtgttca tttatagaat aatggggaaa gacacaaacc cttctgtttt 2460
attatttact catgatcgcc tttcagcagc tgtgctgtaa cacaagtaga tgcctgaact 2520
tgaattaata ttacgaatca gtaatgtatt ctctctcttt acatttccgg tctctacact 2580
acattattaa tgggttttgt gtactgtaaa gaatgaagct gtatcaaact agtgcatgaa 2640
tagattccct cctgattatt tatcatgtag ccccttagcc agttgtatat tattcttgtg 2700
gttttgtgat ccaattaagt cctactttga aatatgcttt aagaatcgat gggggatgct 2760
tcatgtgaac gtgggagttt agctgcttct cttgcctaag tattcttttc ctgatcacta 2820
tgcattttaa aggtaaacat ttttatgtat tccaaatgag ttagagaagt tttttccacg 2880
attgcatttg actgtacaga ttgctgcttc tgctatattt gtgatatagg aattatgagg 2940
atacacgttt atttctttgt gcctgtttta tgtgcacaca ttaggcattg agaattaaaa 3000
cttcttttgt ccgtgtacct tcggatcttt aaaaaaaaaa aaaaaaaaaa a 3051

<210> SEQ ID NO 12
<211> LENGTH: 3051
<212> TYPE: DNA
<213> ORGANISM: Sus scrofa

<400> SEQUENCE: 12
acgcgaacag cagcgcactc ggtgccccgc gcagggtcgc gatgctgccc ggtttggcac 60
tggtcctgct ggccgcctgg acggctaggg cgctggaggt gcccactgat ggcaatgccg 120
gcctgcttgc agaaccccag gttgccatgt tctgtggcaa actcaacatg cacatgaatg 180
tgcagaatgg gaagtgggag tcagatccgt cggggaccaa aacctgcatt ggcaccaagg 240
aaggcatctt gcagtactgc caagaagtct accctgaact gcagatcacc aatgtggtag 300
aagccaacca accagtgacc atccagaact ggtgcaagag gagccggaag cagtgcaaga 360
cccacactca cattgtgatt ccgtaccgct gcttagttgg cgagtttgta agcgatgccc 420
tccttgttcc ggacaagtgc aagttcttac accaggagag gatggatgtt tgcgaaaccc 480
accttcactg gcacactgtg gccaaagaga cctgtagtga gaagagtacg aacttgcatg 540
actatggcat gttgctgccc tgtggaattg acaagttccg aggggtggag tttgtgtgtt 600
gcccactggc cgaggaaagt gacaatatcg actcagcaga tgcagaagag gatgactcgg 660
acgtctggtg gggtggagca gatacagact atgcagatgg cagtgaagac aaagtcgtgg 720
aggtcgcaga ggaggaggaa gtggctgatg tcgaggaaga agaagctgag gatgatgagg 780
atgatgagga tggtgatgag gtagaagaag aggctgagga accctatgaa gaggccacgg 840
agagaaccac cagcatcgcc acaaccacca ccaccaccac ggagtctgtg gaagaggtgg 900
tccgagaggt gtgctctgaa caagccgaga cggggccgtg ccgagcaatg atctcccgct 960
ggtactttga tgtgactgaa gggaagtgcg ccccgttctt ttacggcgga tgtggcggca 1020
accgaaacaa ctttgacaca gaggaatact gcatggccgt gtgtggcagc gtcatgtccc 1080
aaagtttact caagactacc caggaacatc ttccccaaga tcctgttaaa cttcctacaa 1140

-continued

```
cagcagccag caccccagat gccgttgaca agtatcttga gacacctgga gatgagaacg   1200

aacatgcgca tttccagaaa gccaaagaga ggctggaggc caagcaccgc gagagaatgt   1260

cccaggtcat gagagagtgg gaagaggcag aacgtcaagc aaagaacttg cctaaagctg   1320

ataagaaagc agtgatccag catttccagg agaaagtgga gtctctggag caggaagcag   1380

ccaacgagag gcagcagttg gtggagacgc acatggccag agtggaggcc atgcttaacg   1440

accgccggcg cctggccctg gagaattaca tcacggctct tcaggctgtt cctcctcggc   1500

ctcgtcatgt gttcaacatg ctcaagaagt atgtccgtgc cgaacagaaa gacagacagc   1560

acaccctaaa gcattttgaa cacgttcgca tggtagatcc aaagaaagct gctcagatcc   1620

gatcccaggt tatgacacac ctccgtgtga tttacgagcg catgaaccag tctctctccc   1680

tgctctacaa cgttcctgct gtggctgagg aaattcagga tgaagttgat gagctgctgc   1740

agaaagagca aaactactcg gatgatgtct tggccaacat gatcagcgaa ccgaggatca   1800

gttatggaaa cgatgctctc atgccgtctc tgactgaaac caaaaccacc gtggagcttc   1860

ttcctgtgaa tggagagttc agcctggatg atctccagcc ctggcatcct tttggggtag   1920

actctgtgcc tgccaacaca gaaaatgaag tcgagcctgt tgacgcccgc cctgcagccg   1980

accgaggact gaccactcga ccaggttccg ggttgaccaa catcaagacg gaagagatct   2040

ctgaagtgaa tctggatgcg gagttccgac acgattcagg ctatgaggtt catcaccaaa   2100

aactggtgtt cttcgcagaa gatgtgggtt caaacaaagg tgccatcatt ggactcatgg   2160

tgggtggtgt tgtcatagca accgtgattg tcatcacctt agtgatgctg aagaagaaac   2220

agtacacatc catccatcac ggtgtggtgg aggttgacgc agctgtgacc ccggaggagc   2280

gccacctctc caagatgcag cagaatggct atgaaaaccc aacttacaag ttctttgagc   2340

agatgcagaa ctagaccgcc gccacagcag cctctgaagt tggacagcaa aaccattgct   2400

tcactaccca ttggtgttca tttatagaat aatggggaaa gacacaaacc cttctgtttt   2460

attatttact catgatcgcc tttcagcagc tgtgctgtaa cacaagtaga tgcctgaact   2520

tgaattaata ttacgaatca gtaatgtatt ctctctcttt acatttccgg tctctacact   2580

acattattaa tgggttttgt gtactgtaaa gaatgaagct gtatcaaact agtgcatgaa   2640

tagattccct cctgattatt tatcatgtag ccccttagcc agttgtatat tattcttgtg   2700

gttttgtgat ccaattaagt cctactttga aatatgcttt aagaatcgat gggggatgct   2760

tcatgtgaac gtgggagttt agctgcttct cttgcctaag tattcttttc ctgatcacta   2820

tgcattttaa aggtaaacat ttttatgtat tccaaatgag ttagagaagt tttttccacg   2880

attgcatttg actgtacaga ttgctgcttc tgctatattt gtgatatagg aattatgagg   2940

atacacgttt atttctttgt gcctgtttta tgtgcacaca ttaggcattg agaattaaaa   3000

cttcttttgt ccgtgtacct tcggatcttt aaaaaaaaaa aaaaaaaaaa a            3051
```

```
<210> SEQ ID NO 13
<211> LENGTH: 770
<212> TYPE: PRT
<213> ORGANISM: Sus scrofa

<400> SEQUENCE: 13

Met Leu Pro Gly Leu Ala Leu Val Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Val Ala Met Phe Cys Gly Lys Leu Asn Met His Met Asn Val Gln
        35                  40                  45
```

```
Asn Gly Lys Trp Glu Ser Asp Pro Ser Gly Thr Lys Thr Cys Ile Gly
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Ser Arg Lys Gln Cys Lys Thr His Thr His Ile Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Ile Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Asp Val Glu Glu Glu
225                 230                 235                 240

Glu Ala Glu Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Val Met Ser Gln Ser Leu Leu Lys Thr
            340                 345                 350

Thr Gln Glu His Leu Pro Gln Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
```

```
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Pro Phe
    610                 615                 620

Gly Val Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Asn Leu Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770
```

<210> SEQ ID NO 14
<211> LENGTH: 2826
<212> TYPE: DNA
<213> ORGANISM: Sus scrofa

<400> SEQUENCE: 14

```
acgcgaacag cagcgcactc ggtgccccgc gcagggtcgc gatgctgccc ggtttggcac     60

tggtcctgct ggccgcctgg acggctaggg cgctggaggt gcccactgat ggcaatgccg    120

gcctgcttgc agaaccccag gttgccatgt tctgtggcaa actcaacatg cacatgaatg    180

tgcagaatgg gaagtgggag tcagatccgt cggggaccaa aacctgcatt ggcaccaagg    240

aaggcatctt gcagtactgc caagaagtct accctgaact gcagatcacc aatgtggtag    300

aagccaacca accagtgacc atccagaact ggtgcaagag gagccggaag cagtgcaaga    360

cccacactca cattgtgatt ccgtaccgct gcttagttgg cgagtttgta agcgatgccc    420
```

-continued

```
tccttgttcc ggacaagtgc aagttcttac accaggagag gatggatgtt tgcgaaaccc    480
accttcactg gcacactgtg gccaaagaga cctgtagtga gaagagtacg aacttgcatg    540
actatggcat gttgctgccc tgtggaattg acaagttccg aggggtggag tttgtgtgtt    600
gcccactggc cgaggaaagt gacaatatcg actcagcaga tgcagaagag gatgactcgg    660
acgtctggtg gggtggagca gatacagact atgcagatgg cagtgaagac aaagtcgtgg    720
aggtcgcaga ggaggaggaa gtggctgatg tcgaggaaga agaagctgag gatgatgagg    780
atgatgagga tggtgatgag gtagaagaag aggctgagga accctatgaa gaggccacgg    840
agagaaccac cagcatcgcc acaaccacca ccaccaccac ggagtctgtg gaagaggtgg    900
tccgagttcc tacaacagca gccagcaccc cagatgccgt tgacaagtat cttgagacac    960
ctggagatga gaacgaacat gcgcatttcc agaaagccaa agagaggctg gaggccaagc   1020
accgcgagag aatgtcccag gtcatgagag agtgggaaga ggcagaacgt caagcaaaga   1080
acttgcctaa agctgataag aaagcagtga tccagcattt ccaggagaaa gtggagtctc   1140
tggagcagga agcagccaac gagaggcagc agttggtgga gacgcacatg gccagagtgg   1200
aggccatgct taacgaccgc cggcgcctgg ccctggagaa ttacatcacg gctcttcagg   1260
ctgttcctcc tcggcctcgt catgtgttca acatgctcaa gaagtatgtc cgtgccgaac   1320
agaaagacag acagcacacc ctaaagcatt ttgaacacgt tcgcatggta gatccaaaga   1380
aagctgctca gatccgatcc caggttatga cacacctccg tgtgatttac gagcgcatga   1440
accagtctct ctccctgctc tacaacgttc ctgctgtggc tgaggaaatt caggatgaag   1500
ttgatgagct gctgcagaaa gagcaaaact actcggatga tgtcttggcc aacatgatca   1560
gcgaaccgag gatcagttat ggaaacgatg ctctcatgcc gtctctgact gaaaccaaaa   1620
ccaccgtgga gcttcttcct gtgaatggag agttcagcct ggatgatctc cagccctggc   1680
atccttttgg ggtagactct gtgcctgcca acacagaaaa tgaagtcgag cctgttgacg   1740
cccgccctgc agccgaccga ggactgacca ctcgaccagg ttccgggttg accaacatca   1800
agacggaaga gatctctgaa gtgaatctgg atgcggagtt ccgacacgat tcaggctatg   1860
aggttcatca ccaaaaactg gtgttcttcg cagaagatgt gggttcaaac aaaggtgcca   1920
tcattggact catggtgggt ggtgttgtca tagcaaccgt gattgtcatc accttagtga   1980
tgctgaagaa gaaacagtac acatccatcc atcacggtgt ggtggaggtt gacgcagctg   2040
tgaccccgga ggagcgccac ctctccaaga tgcagcagaa tggctatgaa aacccaactt   2100
acaagttctt tgagcagatg cagaactaga ccgccgccac agcagcctct gaagttggac   2160
agcaaaacca ttgcttcact acccattggt gttcatttat agaataatgg ggaaagacac   2220
aaacccttct gttttattat ttactcatga tcgcctttca gcagctgtgc tgtaacacaa   2280
gtagatgcct gaacttgaat taatattacg aatcagtaat gtattctctc tctttacatt   2340
tccggtctct acactacatt attaatgggt tttgtgtact gtaaagaatg aagctgtatc   2400
aaactagtgc atgaatagat tccctcctga ttatttatca tgtagcccct tagccagttg   2460
tatattattc ttgtggtttt gtgatccaat taagtcctac tttgaaatat gctttaagaa   2520
tcgatggggg atgcttcatg tgaacgtggg agtttagctg cttctcttgc ctaagtattc   2580
ttttcctgat cactatgcat tttaaaggta aacattttta tgtattccaa atgagttaga   2640
gaagtttttt ccacgattgc atttgactgt acagattgct gcttctgcta tatttgtgat   2700
ataggaatta tgaggataca cgtttatttc tttgtgcctg ttttatgtgc acacattagg   2760
cattgagaat taaaacttct tttgtccgtg taccttcgga tctttaaaaa aaaaaaaaaa   2820
```

-continued aaaaaa 2826

<210> SEQ ID NO 15
<211> LENGTH: 2826
<212> TYPE: DNA
<213> ORGANISM: Sus scrofa

<400> SEQUENCE: 15
acgcgaacag cagcgcactc ggtgccccgc gcagggtcgc gatgctgccc ggtttggcac 60
tggtcctgct ggccgcctgg acggctaggg cgctggaggt gcccactgat ggcaatgccg 120
gcctgcttgc agaaccccag gttgccatgt tctgtggcaa actcaacatg cacatgaatg 180
tgcagaatgg gaagtgggag tcagatccgt cggggaccaa aacctgcatt ggcaccaagg 240
aaggcatctt gcagtactgc caagaagtct accctgaact gcagatcacc aatgtggtag 300
aagccaacca accagtgacc atccagaact ggtgcaagag gagccggaag cagtgcaaga 360
cccacactca cattgtgatt ccgtaccgct gcttagttgg cgagtttgta agcgatgccc 420
tccttgttcc ggacaagtgc aagttcttac accaggagag gatggatgtt tgcgaaaccc 480
accttcactg gcacactgtg gccaaagaga cctgtagtga gaagagtacg aacttgcatg 540
actatggcat gttgctgccc tgtggaattg acaagttccg aggggtggag tttgtgtgtt 600
gcccactggc cgaggaaagt gacaatatcg actcagcaga tgcagaagag gatgactcgg 660
acgtctggtg ggtggagcca gatacagact atgcagatgg cagtgaagac aaagtcgtgg 720
aggtcgcaga ggaggaggaa gtggctgatg tcgaggaaga agaagctgag gatgatgagg 780
atgatgagga tggtgatgag gtagaagaag aggctgagga accctatgaa gaggccacgg 840
agagaaccac cagcatcgcc acaaccacca ccaccaccac ggagtctgtg gaagaggtgg 900
tccgagttcc tacaacagca gccagcaccc cagatgccgt tgacaagtat cttgagacac 960
ctggagatga gaacgaacat gcgcatttcc agaaagccaa agagaggctg gaggccaagc 1020
accgcgagag aatgtcccag gtcatgagag agtgggaaga ggcagaacgt caagcaaaga 1080
acttgcctaa agctgataag aaagcagtga tccagcattt ccaggagaaa gtggagtctc 1140
tggagcagga agcagccaac gagaggcagc agttggtgga gacgcacatg gccagagtgg 1200
aggccatgct taacgaccgc cggcgcctgg ccctggagaa ttacatcacg gctcttcagg 1260
ctgttcctcc tcggcctcgt catgtgttca acatgctcaa gaagtatgtc cgtgccgaac 1320
agaaagacag acagcacacc ctaaagcatt ttgaacacgt tcgcatggta gatccaaaga 1380
aagctgctca gatccgatcc caggttatga cacacctccg tgtgatttac gagcgcatga 1440
accagtctct ctccctgctc tacaacgttc ctgctgtggc tgaggaaatt caggatgaag 1500
ttgatgagct gctgcagaaa gagcaaaact actcggatga tgtcttggcc aacatgatca 1560
gcgaaccgag gatcagttat ggaaacgatg ctctcatgcc gtctctgact gaaaccaaaa 1620
ccaccgtgga gcttcttcct gtgaatggag agttcagcct ggatgatctc cagccctggc 1680
atccttttgg ggtagactct gtgcctgcca acacagaaaa tgaagtcgag cctgttgacg 1740
cccgccctgc agccgaccga ggactgacca ctcgaccagg ttccgggttg accaacatca 1800
agacggaaga gatctctgaa gtgaatctgg atgcggagtt ccgacacgat tcaggctatg 1860
aggttcatca ccaaaaactg gtgttcttcg cagaagatgt gggttcaaac aaaggtgcca 1920
tcattggact catggtgggt ggtgttgtca tagcaaccgt gattgtcatc accttagtga 1980
tgctgaagaa gaaacagtac acatccatcc atcacggtgt ggtggaggtt gacgcagctg 2040
tgaccccgga ggagcgccac ctctccaaga tgcagcagaa tggctatgaa aacccaactt 2100
acaagttctt tgagcagatg cagaactaga ccgccgccac agcagcctct gaagttggac 2160
agcaaaacca ttgcttcact acccattggt gttcatttat agaataatgg ggaaagacac 2220
aaacccttct gttttattat ttactcatga tcgcctttca gcagctgtgc tgtaacacaa 2280
gtagatgcct gaacttgaat taatattacg aatcagtaat gtattctctc tctttacatt 2340
tccggtctct acactacatt attaatgggt tttgtgtact gtaaagaatg aagctgtatc 2400
aaactagtgc atgaatagat tccctcctga ttatttatca tgtagcccct tagccagttg 2460
tatattattc ttgtggtttt gtgatccaat taagtcctac tttgaaatat gctttaagaa 2520
tcgatggggg atgcttcatg tgaacgtggg agtttagctg cttctcttgc ctaagtattc 2580
ttttcctgat cactatgcat tttaaaggta aacattttta tgtattccaa atgagttaga 2640
gaagtttttt ccacgattgc atttgactgt acagattgct gcttctgcta tatttgtgat 2700
ataggaatta tgaggataca cgtttatttc tttgtgcctg ttttatgtgc acacattagg 2760
cattgagaat taaaacttct tttgtccgtg taccttcgga tctttaaaaa aaaaaaaaaa 2820
aaaaaa 2826

<210> SEQ ID NO 16
<211> LENGTH: 695
<212> TYPE: PRT
<213> ORGANISM: Sus scrofa

<400> SEQUENCE: 16

Met Leu Pro Gly Leu Ala Leu Val Leu Leu Ala Ala Trp Thr Ala Arg
1 5 10 15

Ala Leu Glu Val Pro Thr Asp Gly Asn Ala Gly Leu Leu Ala Glu Pro
20 25 30

Gln Val Ala Met Phe Cys Gly Lys Leu Asn Met His Met Asn Val Gln
35 40 45

Asn Gly Lys Trp Glu Ser Asp Pro Ser Gly Thr Lys Thr Cys Ile Gly
50 55 60

Thr Lys Glu Gly Ile Leu Gln Tyr Cys Gln Glu Val Tyr Pro Glu Leu
65 70 75 80

Gln Ile Thr Asn Val Val Glu Ala Asn Gln Pro Val Thr Ile Gln Asn
85 90 95

Trp Cys Lys Arg Ser Arg Lys Gln Cys Lys Thr His Thr His Ile Val
100 105 110

Ile Pro Tyr Arg Cys Leu Val Gly Glu Phe Val Ser Asp Ala Leu Leu
115 120 125

Val Pro Asp Lys Cys Lys Phe Leu His Gln Glu Arg Met Asp Val Cys
130 135 140

Glu Thr His Leu His Trp His Thr Val Ala Lys Glu Thr Cys Ser Glu
145 150 155 160

Lys Ser Thr Asn Leu His Asp Tyr Gly Met Leu Leu Pro Cys Gly Ile
165 170 175

Asp Lys Phe Arg Gly Val Glu Phe Val Cys Cys Pro Leu Ala Glu Glu
180 185 190

Ser Asp Asn Ile Asp Ser Ala Asp Ala Glu Glu Asp Asp Ser Asp Val
195 200 205

Trp Trp Gly Gly Ala Asp Thr Asp Tyr Ala Asp Gly Ser Glu Asp Lys
210 215 220

Val Val Glu Val Ala Glu Glu Glu Glu Val Ala Asp Val Glu Glu Glu
225 230 235 240

-continued

```
Glu Ala Glu Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Pro Phe Gly Val Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Asn Leu Asp Ala Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670
```

```
His Leu Ser Lys Met Gln Gln Asn Gly Tyr Glu Asn Pro Thr Tyr Lys
        675                 680                 685

Phe Phe Glu Gln Met Gln Asn
    690                 695


<210> SEQ ID NO 17
<211> LENGTH: 2763
<212> TYPE: DNA
<213> ORGANISM: Homo sapiens

<400> SEQUENCE: 17

tgggacaggc agctccgggg tccgcggttt cacatcggaa acaaaacagc ggctggtctg     60

gaaggaacct gagctacgag ccgcggcggc agcggggcgg cggggaagcg tatacctaat    120

ctgggagcct gcaagtgaca acagcctttg cggtccttag acagcttggc ctggaggaga    180

acacatgaaa gaaagaacct caagaggctt tgttttctgt gaaacagtat ttctatacag    240

ttgctccaat gacagagtta cctgcaccgt tgtcctactt ccagaatgca cagatgtctg    300

aggacaacca cctgagcaat actgtacgta gccagaatga caatagagaa cggcaggagc    360

acaacgacag acggagcctt ggccaccctg agccattatc taatggacga ccccagggta    420

actcccggca ggtggtggag caagatgagg aagaagatga ggagctgaca ttgaaatatg    480

gcgccaagca tgtgatcatg ctctttgtcc ctgtgactct ctgcatggtg gtggtcgtgg    540

ctaccattaa gtcagtcagc ttttataccc ggaaggatgg gcagctaatc tataccctat    600

tcacagaaga taccgagact gtgggccaga gagccctgca ctcaattctg aatgctgcca    660

tcatgatcag tgtcattgtt gtcatgacta tcctcctggt ggttctgtat aaatacaggt    720

gctataaggt catccatgcc tggcttatta tatcatctct attgttgctg ttcttttttt    780

cattcattta cttgggggaa gtgtttaaaa cctataacgt tgctgtggac tacattactg    840

ttgcactcct gatctggaat tttggtgtgg tgggaatgat ttccattcac tggaaaggtc    900

cacttcgact ccagcaggca tatctcatta tgattagtgc cctcatggcc ctggtgttta    960

tcaagtacct ccctgaatgg actgcgtggc tcatcttggc tgtgatttca gtatatgatt   1020

tagtggctgt tttgtgtccg aaaggtccac ttcgtatgct ggttgaaaca gctcaggaga   1080

gaaatgaaac gctttttcca gctctcattt actcctcaac aatggtgtgg ttggtgaata   1140

tggcagaagg agacccggaa gctcaaagga gagtatccaa aaattccaag tataatgcag   1200

aaagcacaga aagggagtca caagacactg ttgcagagaa tgatgatggc gggttcagtg   1260

aggaatggga agcccagagg gacagtcatc tagggcctca tcgctctaca cctgagtcac   1320

gagctgctgt ccaggaactt tccagcagta tcctcgctgg tgaagaccca gaggaaaggg   1380

gagtaaaact tggattggga gatttcattt tctacagtgt tctggttggt aaagcctcag   1440

caacagccag tggagactgg aacacaacca tagcctgttt cgtagccata ttaattggtt   1500

tgtgccttac attattactc cttgccattt tcaagaaagc attgccagct cttccaatct   1560

ccatcacctt tgggcttgtt ttctactttg ccacagatta tcttgtacag ccttttatgg   1620

accaattagc attccatcaa ttttatatct agcatatttg cggttagaat cccatggatg   1680

tttcttcttt gactataaca aaatctgggg aggacaaagg tgattttcct gtgtccacat   1740

ctaacaaagt caagattccc ggctggactt ttgcagcttc cttccaagtc ttcctgacca   1800

ccttgcacta ttggactttg gaaggaggtg cctatagaaa acgattttga acatacttca   1860

tcgcagtgga ctgtgtccct cggtgcagaa actaccagat ttgagggacg aggtcaagga   1920

gatatgatag gcccggaagt tgctgtgccc catcagcagc ttgacgcgtg gtcacaggac   1980
```

gatttcactg acactgcgaa ctctcaggac taccgttacc aagaggttag gtgaagtggt 2040
ttaaaccaaa cggaactctt catcttaaac tacacgttga aaatcaaccc aataattctg 2100
tattaactga attctgaact tttcaggagg tactgtgagg aagagcaggc accagcagca 2160
gaatggggaa tggagaggtg ggcaggggtt ccagcttccc tttgattttt tgctgcagac 2220
tcatcctttt taaatgagac ttgttttccc ctctctttga gtcaagtcaa atatgtagat 2280
tgcctttggc aattcttctt ctcaagcact gacactcatt accgtctgtg attgccattt 2340
cttcccaagg ccagtctgaa cctgaggttg ctttatccta aaagttttaa cctcaggttc 2400
caaattcagt aaattttgga aacagtacag ctatttctca tcaattctct atcatgttga 2460
agtcaaattt ggattttcca ccaaattctg aatttgtaga catacttgta cgctcacttg 2520
ccccagatgc ctcctctgtc ctcattcttc tctcccacac aagcagtctt tttctacagc 2580
cagtaaggca gctctgtcgt ggtagcagat ggtcccatta ttctagggtc ttactctttg 2640
tatgatgaaa agaatgtgtt atgaatcggt gctgtcagcc ctgctgtcag accttcttcc 2700
acagcaaatg agatgtatgc ccaaagcggt agaattaaag aagagtaaaa tggctgttga 2760
agc 2763

<210> SEQ ID NO 18
<211> LENGTH: 2763
<212> TYPE: DNA
<213> ORGANISM: Homo sapiens

<400> SEQUENCE: 18
tgggacaggc agctccgggg tccgcggttt cacatcggaa acaaaacagc ggctggtctg 60
gaaggaacct gagctacgag ccgcggcggc agcggggcgg cggggaagcg tatacctaat 120
ctgggagcct gcaagtgaca acagcctttg cggtccttag acagcttggc ctggaggaga 180
acacatgaaa gaaagaacct caagaggctt tgttttctgt gaaacagtat ttctatacag 240
ttgctccaat gacagagtta cctgcaccgt tgtcctactt ccagaatgca cagatgtctg 300
aggacaacca cctgagcaat actgtacgta gccagaatga caatagagaa cggcaggagc 360
acaacgacag acggagcctt ggccaccctg agccattatc taatggacga ccccagggta 420
actcccggca ggtggtggag caagatgagg aagaagatga ggagctgaca ttgaaatatg 480
gcgccaagca tgtgatcatg ctctttgtcc ctgtgactct ctgcatggtg gtggtcgtgg 540
ctaccattaa gtcagtcagc ttttataccc ggaaggatgg gcagctaatc tataccctat 600
tcacagaaga taccgagact gtgggccaga gagccctgca ctcaattctg aatgctgcca 660
tcatgatcag tgtcattgtt gtcatgacta tcctcctggt ggttctgtat aaatacaggt 720
gctataaggt catccatgcc tggcttatta tatcatctct attgttgctg ttcttttttt 780
cattcattta cttgggggaa gtgtttaaaa cctataacgt tgctgtggac tacattactg 840
ttgcactcct gatctggaat tttggtgtgg tgggaatgat ttccattcac tggaaaggtc 900
cacttcgact ccagcaggca tatctcatta tgattagtgc cctcatggcc ctggtgttta 960
tcaagtacct ccctgaatgg actgcgtggc tcatcttggc tgtgatttca gtatatgatt 1020
tagtggctgt tttgtgtccg aaaggtccac ttcgtatgct ggttgaaaca gctcaggaga 1080
gaaatgaaac gctttttcca gctctcattt actcctcaac aatggtgtgg ttggtgaata 1140
tggcagaagg agacccggaa gctcaaagga gagtatccaa aaattccaag tataatgcag 1200
aaagcacaga aagggagtca caagacactg ttgcagagaa tgatgatggc gggttcagtg 1260
aggaatggga agcccagagg gacagtcatc tagggcctca tcgctctaca cctgagtcac 1320

```
gagctgctgt ccaggaactt tccagcagta tcctcgctgg tgaagaccca gaggaaaggg   1380

gagtaaaact tggattggga gatttcattt tctacagtgt tctggttggt aaagcctcag   1440

caacagccag tggagactgg aacacaacca tagcctgttt cgtagccata ttaattggtt   1500

tgtgccttac attattactc cttgccattt tcaagaaagc attgccagct cttccaatct   1560

ccatcacctt tgggcttgtt ttctactttg ccacagatta tcttgtacag ccttttatgg   1620

accaattagc attccatcaa ttttatatct agcatatttg cggttagaat cccatggatg   1680

tttcttcttt gactataaca aaatctgggg aggacaaagg tgattttcct gtgtccacat   1740

ctaacaaagt caagattccc ggctggactt ttgcagcttc cttccaagtc ttcctgacca   1800

ccttgcacta ttggactttg gaaggaggtg cctatagaaa acgattttga acatacttca   1860

tcgcagtgga ctgtgtccct cggtgcagaa actaccagat ttgagggacg aggtcaagga   1920

gatatgatag gcccggaagt tgctgtgccc catcagcagc ttgacgcgtg gtcacaggac   1980

gatttcactg acactgcgaa ctctcaggac taccgttacc aagaggttag gtgaagtggt   2040

ttaaaccaaa cggaactctt catcttaaac tacacgttga aaatcaaccc aataattctg   2100

tattaactga attctgaact tttcaggagg tactgtgagg aagagcaggc accagcagca   2160

gaatggggaa tggagaggtg ggcaggggtt ccagcttccc tttgattttt tgctgcagac   2220

tcatcctttt taaatgagac ttgttttccc ctctctttga gtcaagtcaa atatgtagat   2280

tgcctttggc aattcttctt ctcaagcact gacactcatt accgtctgtg attgccattt   2340

cttcccaagg ccagtctgaa cctgaggttg ctttatccta aaagttttaa cctcaggttc   2400

caaattcagt aaattttgga aacagtacag ctatttctca tcaattctct atcatgttga   2460

agtcaaattt ggattttcca ccaaattctg aatttgtaga catacttgta cgctcacttg   2520

ccccagatgc ctcctctgtc ctcattcttc tctcccacac aagcagtctt tttctacagc   2580

cagtaaggca gctctgtcgt ggtagcagat ggtcccatta ttctagggtc ttactctttg   2640

tatgatgaaa agaatgtgtt atgaatcggt gctgtcagcc ctgctgtcag accttcttcc   2700

acagcaaatg agatgtatgc ccaaagcggt agaattaaag aagagtaaaa tggctgttga   2760

agc                                                                 2763
```

<210> SEQ ID NO 19
<211> LENGTH: 467
<212> TYPE: PRT
<213> ORGANISM: Homo sapiens

<400> SEQUENCE: 19

```
Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110
```

-continued

```
Leu Ile Tyr Thr Leu Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465
```

<210> SEQ ID NO 20
<211> LENGTH: 1720
<212> TYPE: DNA
<213> ORGANISM: Sus scrofa

<400> SEQUENCE: 20

```
aatcggaaac aaaacagcgg ctgctgggga agggacctgg gctgcgagag gtggcggctg      60

cgacgagaaa gaacctaatc cgggagcctg caacctgtga agttcttaga aagcttggcc     120
```

```
tggaggagaa cacatgaaag aaagaacccc aggaggctct gatttctgtg aaaaagtatt    180
tctatacggt tgttccaatg acagagttac ctgcaccctt gtcctacttc cagaatgccc    240
agatgtccga ggacaaccac gtgagcaata acgtaagtag ccagaatgac agtagagagc    300
ggcatgagca cagcatcgag aggcggaggc gtggcaactc tgagtcgtta tccaatggcg    360
gagcccaggg aaactcacgc caggtggtgg aacaagaaga agaggaagac gaggagctga    420
cgttgaaata tggcgccaaa catgtgatca tgctctttgt ccctgtgact ctatgtatgg    480
tggtggttgt ggccaccatc aaatcagtca gcttttatac ccggaaggat gggcagctga    540
tctatactct atttacagaa gacactgaga ctgtagggca gagagccctg cactcaattc    600
tgaatgctgc tatcatgatt agtgtcattg tcgtcatgac tattctcctg gtggttctct    660
ataaatacag gtgctataag gtcatccatg cctggcttat tatttcatcc ctattgttgc    720
tgttcttttt ctcattcatt tacttggggg aagtgtttaa aacctataac gttgccatgg    780
attacattac ggtggcactc ctgatctgga attttggtgt ggtaggaatg attgccattc    840
actggaaagg cccattgcga ctccagcagg catatctcat tatgatcagt gccctcatgg    900
ccctggtgtt tatcaagtac ctcccggaat ggaccgcgtg gctcatcttg gctgtgattt    960
cagtatacga tttagtggct gttttgtgtc caaatggccc acttcgtttg ctggttgaaa   1020
cagctcagga gagaaatgaa actctctttc cagctcttat ttactcgtca acaatggtgt   1080
ggttggtgaa tatggcagaa ggagacccag aagcccaaag gaaggtatcc aaaaactcca   1140
attataatgc acaaagcaca ggtgaatcac aagactctgt gacagagagt gatgatggtg   1200
gcttcagtga agagtgggaa gcccagaggg acagtcgcct gggacctcat cactctacag   1260
ctgagtcacg atctgctgta caggatcttt ccagaagcat cccagccact gaggacccag   1320
aagaaagggg agtaaaactt ggattaggag atttcatttt ctacagtgtt ctggttggta   1380
aagcttctgc aacagccagt ggagactgga acacaaccat tgcctgtttt gtagccatat   1440
taattggttt gtgccttaca ttactgctcc tcgccatttt caagaaagcg ttgccagctc   1500
ttccaatctc tatcaccttt gggcttgttt tctactttgc cacagattat cttgtgcaac   1560
cctttatgga ccaattagca ttccatcaat tttatatcta gcatatttcc agttagaatc   1620
tcatggattt tttctccttt ggctataata aaatctgggg aaagcaaagg tgattttgct   1680
gtgtccacat ctaacaaagt caggattccc agctggacct                         1720
```

<210> SEQ ID NO 21
<211> LENGTH: 1720
<212> TYPE: DNA
<213> ORGANISM: Sus scrofa

<400> SEQUENCE: 21

```
aatcggaaac aaaacagcgg ctgctgggga agggacctgg gctgcgagag gtggcggctg     60
cgacgagaaa gaacctaatc cgggagcctg caacctgtga agttcttaga aagcttggcc    120
tggaggagaa cacatgaaag aaagaacccc aggaggctct gatttctgtg aaaaagtatt    180
tctatacggt tgttccaatg acagagttac ctgcaccctt gtcctacttc cagaatgccc    240
agatgtccga ggacaaccac gtgagcaata acgtaagtag ccagaatgac agtagagagc    300
ggcatgagca cagcatcgag aggcggaggc gtggcaactc tgagtcgtta tccaatggcg    360
gagcccaggg aaactcacgc caggtggtgg aacaagaaga agaggaagac gaggagctga    420
cgttgaaata tggcgccaaa catgtgatca tgctctttgt ccctgtgact ctatgtatgg    480
tggtggttgt ggccaccatc aaatcagtca gcttttatac ccggaaggat gggcagctga    540
```

```
tctatactct atttacagaa gacactgaga ctgtagggca gagagccctg cactcaattc    600

tgaatgctgc tatcatgatt agtgtcattg tcgtcatgac tattctcctg gtggttctct    660

ataaatacag gtgctataag gtcatccatg cctggcttat tatttcatcc ctattgttgc    720

tgttcttttt ctcattcatt tacttggggg aagtgtttaa aacctataac gttgccatgg    780

attacattac ggtggcactc ctgatctgga attttggtgt ggtaggaatg attgccattc    840

actggaaagg cccattgcga ctccagcagg catatctcat tatgatcagt gccctcatgg    900

ccctggtgtt tatcaagtac ctcccggaat ggaccgcgtg gctcatcttg gctgtgattt    960

cagtatacga tttagtggct gttttgtgtc caaatggccc acttcgtttg ctggttgaaa   1020

cagctcagga gagaaatgaa actctctttc cagctcttat ttactcgtca acaatggtgt   1080

ggttggtgaa tatggcagaa ggagacccag aagcccaaag gaaggtatcc aaaaactcca   1140

attataatgc acaaagcaca ggtgaatcac aagactctgt gacagagagt gatgatggtg   1200

gcttcagtga agagtgggaa gcccagaggg acagtcgcct gggacctcat cactctacag   1260

ctgagtcacg atctgctgta caggatcttt ccagaagcat cccagccact gaggacccag   1320

aagaaagggg agtaaaactt ggattaggag atttcatttt ctacagtgtt ctggttggta   1380

aagcttctgc aacagccagt ggagactgga acacaaccat tgcctgtttt gtagccatat   1440

taattggttt gtgccttaca ttactgctcc tcgccatttt caagaaagcg ttgccagctc   1500

ttccaatctc tatcaccttt gggcttgttt tctactttgc cacagattat cttgtgcaac   1560

cctttatgga ccaattagca ttccatcaat tttatatcta gcatatttcc agttagaatc   1620

tcatggattt tttctccttt ggctataata aaatctgggg aaagcaaagg tgattttgct   1680

gtgtccacat ctaacaaagt caggattccc agctggacct                         1720
```

```
<210> SEQ ID NO 22
<211> LENGTH: 467
<212> TYPE: PRT
<213> ORGANISM: Sus scrofa

<400> SEQUENCE: 22

Met Thr Glu Leu Pro Ala Pro Leu Ser Tyr Phe Gln Asn Ala Gln Met
1               5                   10                  15

Ser Glu Asp Asn His Val Ser Asn Asn Val Ser Ser Gln Asn Asp Ser
            20                  25                  30

Arg Glu Arg His Glu His Ser Ile Glu Arg Arg Arg Arg Gly Asn Ser
        35                  40                  45

Glu Ser Leu Ser Asn Gly Gly Ala Gln Gly Asn Ser Arg Gln Val Val
    50                  55                  60

Glu Gln Glu Glu Glu Glu Asp Glu Glu Leu Thr Leu Lys Tyr Gly Ala
65                  70                  75                  80

Lys His Val Ile Met Leu Phe Val Pro Val Thr Leu Cys Met Val Val
                85                  90                  95

Val Val Ala Thr Ile Lys Ser Val Ser Phe Tyr Thr Arg Lys Asp Gly
            100                 105                 110

Gln Leu Ile Tyr Thr Leu Phe Thr Glu Asp Thr Glu Thr Val Gly Gln
        115                 120                 125

Arg Ala Leu His Ser Ile Leu Asn Ala Ala Ile Met Ile Ser Val Ile
    130                 135                 140

Val Val Met Thr Ile Leu Leu Val Val Leu Tyr Lys Tyr Arg Cys Tyr
145                 150                 155                 160

Lys Val Ile His Ala Trp Leu Ile Ile Ser Ser Leu Leu Leu Leu Phe
```

```
                165                 170                 175

Phe Phe Ser Phe Ile Tyr Leu Gly Glu Val Phe Lys Thr Tyr Asn Val
            180                 185                 190

Ala Met Asp Tyr Ile Thr Val Ala Leu Leu Ile Trp Asn Phe Gly Val
        195                 200                 205

Val Gly Met Ile Ala Ile His Trp Lys Gly Pro Leu Arg Leu Gln Gln
    210                 215                 220

Ala Tyr Leu Ile Met Ile Ser Ala Leu Met Ala Leu Val Phe Ile Lys
225                 230                 235                 240

Tyr Leu Pro Glu Trp Thr Ala Trp Leu Ile Leu Ala Val Ile Ser Val
                245                 250                 255

Tyr Asp Leu Val Ala Val Leu Cys Pro Asn Gly Pro Leu Arg Leu Leu
            260                 265                 270

Val Glu Thr Ala Gln Glu Arg Asn Glu Thr Leu Phe Pro Ala Leu Ile
        275                 280                 285

Tyr Ser Ser Thr Met Val Trp Leu Val Asn Met Ala Glu Gly Asp Pro
    290                 295                 300

Glu Ala Gln Arg Lys Val Ser Lys Asn Ser Asn Tyr Asn Ala Gln Ser
305                 310                 315                 320

Thr Gly Glu Ser Gln Asp Ser Val Thr Glu Ser Asp Asp Gly Gly Phe
                325                 330                 335

Ser Glu Glu Trp Glu Ala Gln Arg Asp Ser Arg Leu Gly Pro His His
            340                 345                 350

Ser Thr Ala Glu Ser Arg Ser Ala Val Gln Asp Leu Ser Arg Ser Ile
        355                 360                 365

Pro Ala Thr Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465


<210> SEQ ID NO 23
<211> LENGTH: 770
<212> TYPE: PRT
<213> ORGANISM: Homo sapiens

<400> SEQUENCE: 23

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
```

```
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495
```

```
Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770


<210> SEQ ID NO 24
<211> LENGTH: 770
<212> TYPE: PRT
<213> ORGANISM: Sus scrofa

<400> SEQUENCE: 24

Met Leu Pro Gly Leu Ala Leu Val Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Val Ala Met Phe Cys Gly Lys Leu Asn Met His Met Asn Val Gln
        35                  40                  45

Asn Gly Lys Trp Glu Ser Asp Pro Ser Gly Thr Lys Thr Cys Ile Gly
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95
```

-continued

```
Trp Cys Lys Arg Ser Arg Lys Gln Cys Lys Thr His Thr His Ile Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Ile Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Asp Val Glu Glu Glu
225                 230                 235                 240

Glu Ala Glu Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Val Met Ser Gln Ser Leu Leu Lys Thr
            340                 345                 350

Thr Gln Glu His Leu Pro Gln Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525
```

```
Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Pro Phe
    610                 615                 620

Gly Val Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770


<210> SEQ ID NO 25
<211> LENGTH: 467
<212> TYPE: PRT
<213> ORGANISM: Homo sapiens

<400> SEQUENCE: 25

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125
```

```
Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465


<210> SEQ ID NO 26
<211> LENGTH: 467
<212> TYPE: PRT
<213> ORGANISM: Sus scrofa

<400> SEQUENCE: 26

Met Thr Glu Leu Pro Ala Pro Leu Ser Tyr Phe Gln Asn Ala Gln Met
1               5                   10                  15

Ser Glu Asp Asn His Val Ser Asn Asn Val Ser Ser Gln Asn Asp Ser
            20                  25                  30
```

-continued

```
Arg Glu Arg His Glu His Ser Ile Glu Arg Arg Arg Arg Gly Asn Ser
        35                  40                  45

Glu Ser Leu Ser Asn Gly Gly Ala Gln Gly Asn Ser Arg Gln Val Val
    50                  55                  60

Glu Gln Glu Glu Glu Glu Asp Glu Glu Leu Thr Leu Lys Tyr Gly Ala
65                  70                  75                  80

Lys His Val Ile Met Leu Phe Val Pro Val Thr Leu Cys Met Val Val
                85                  90                  95

Val Val Ala Thr Ile Lys Ser Val Ser Phe Tyr Thr Arg Lys Asp Gly
            100                 105                 110

Gln Leu Ile Tyr Thr Pro Phe Thr Glu Asp Thr Glu Thr Val Gly Gln
        115                 120                 125

Arg Ala Leu His Ser Ile Leu Asn Ala Ala Ile Met Ile Ser Val Ile
    130                 135                 140

Val Val Met Thr Ile Leu Leu Val Val Leu Tyr Lys Tyr Arg Cys Tyr
145                 150                 155                 160

Lys Val Ile His Ala Trp Leu Ile Ile Ser Ser Leu Leu Leu Leu Phe
                165                 170                 175

Phe Phe Ser Phe Ile Tyr Leu Gly Glu Val Phe Lys Thr Tyr Asn Val
            180                 185                 190

Ala Met Asp Tyr Ile Thr Val Ala Leu Leu Ile Trp Asn Phe Gly Val
        195                 200                 205

Val Gly Met Ile Ala Ile His Trp Lys Gly Pro Leu Arg Leu Gln Gln
    210                 215                 220

Ala Tyr Leu Ile Met Ile Ser Ala Leu Met Ala Leu Val Phe Ile Lys
225                 230                 235                 240

Tyr Leu Pro Glu Trp Thr Ala Trp Leu Ile Leu Ala Val Ile Ser Val
                245                 250                 255

Tyr Asp Leu Val Ala Val Leu Cys Pro Asn Gly Pro Leu Arg Leu Leu
            260                 265                 270

Val Glu Thr Ala Gln Glu Arg Asn Glu Thr Leu Phe Pro Ala Leu Ile
        275                 280                 285

Tyr Ser Ser Thr Met Val Trp Leu Val Asn Met Ala Glu Gly Asp Pro
    290                 295                 300

Glu Ala Gln Arg Lys Val Ser Lys Asn Ser Asn Tyr Asn Ala Gln Ser
305                 310                 315                 320

Thr Gly Glu Ser Gln Asp Ser Val Thr Glu Ser Asp Asp Gly Gly Phe
                325                 330                 335

Ser Glu Glu Trp Glu Ala Gln Arg Asp Ser Arg Leu Gly Pro His His
            340                 345                 350

Ser Thr Ala Glu Ser Arg Ser Ala Val Gln Asp Leu Ser Arg Ser Ile
        355                 360                 365

Pro Ala Thr Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
```

450 455 460

Phe Tyr Ile
465

<210> SEQ ID NO 27
<211> LENGTH: 6307
<212> TYPE: DNA
<213> ORGANISM: Artificial Sequence
<220> FEATURE:
<223> OTHER INFORMATION: Plasmid vector

<400> SEQUENCE: 27
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt accctacagt 420
tgaagtcgga agtttacata cacttaagtt ggagtcatta aaactcgttt ttcaactact 480
ccacaaattt cttgttaaca aacaatagtt ttggcaagtc agttaggaca tctactttgt 540
gcatgacaca agtcattttt ccaacaattg tttacagaca gattatttca cttataattc 600
actgtatcac aattccagtg ggtcagaagt ttacatacac taagttgact gtgcctttaa 660
acagcttgga aaattccaga aaatgatgtc atggctttag aagcttctga tagactaatt 720
gacatcattt gagtcaattg gaggtgtacc tgtggatgta tttcaaggga attctgtgga 780
atgtgtgtca gttagggtgt ggaaagtccc caggctcccc aggcaggcag aagtatgcaa 840
agcatcgagg atgtacgggc cagatatacg cgataacttc gtataatgta tgctatacga 900
agttatcgcg tgaggttttc accgtcatca ccgaaacgcg cgaggcagct gtggaatgtg 960
tgtcagttag ggtgtggaaa gtccccaggc tccccagcag gcagaagtat gcaaagcatg 1020
catctcaatt agtcagcaac caggtgtgga aagtccccag gctccccagc aggcagaagt 1080
atgcaaagca tgcatctcaa ttagtcagca accatagtcc cgcccctaac tccgcccatc 1140
ccgcccctaa ctccgcccag ttccgcccat tctccgcccc atggctgact aattttttt 1200 atttatgcag aggccgaggc cgcctcggcc tctgagctat tccagaagta gtgaggaggc 1260
ttttttggag gctaccatgg agaagttact attccgaagt tcctattctc tagaaagtat 1320
aggaacttca agcttggcac tggtgagcaa gggcgaggag ctgttcaccg ggtggtgcc 1380 catcctggtc gagctggacg gcgacgtaaa cggccacaag ttcagcgtgt ccggcgaggg 1440
cgagggcgat gccacctacg gcaagctgac cctgaagttc atctgcacca ccggcaagct 1500
gcccgtgccc tggcccaccc tcgtgaccac cctgacctac ggcgtgcagt gcttcagccg 1560
ctaccccgac cacatgaagc agcacgactt cttcaagtcc gccatgcccg aaggctacgt 1620
ccaggagcgc accatcttct tcaaggacga cggcaactac aagacccgcg ccgaggtgaa 1680
gttcgagggc gacaccctgg tgaaccgcat cgagctgaag ggcatcgact tcaaggagga 1740
cggcaacatc ctggggcaca agctggagta caactacaac agccacaacg tctatatcat 1800
ggccgacaag cagaagaacg gcatcaaggt gaacttcaag atccgccaca acatcgagga 1860
cggcagcgtg cagctcgccg accactacca gcagaacacc cccatcggcg acggccccgt 1920
gctgctgccc gacaaccact acctgagcac ccagtccgcc ctgagcaaag accccaacga 1980

-continued

```
gaagcgcgat cacatggtcc tgctggagtt cgtgaccgcc gccgggatca ctctcggcat   2040
ggacgagctg tacaagtaaa gcggccgcgg ccaattgggc caccggtgct agcccccctaa  2100
cgttactggc cgaagccgct tggaataagg ccggtgtgcg tttgtctata tgttattttc   2160
caccatattg ccgtcttttg gcaatgtgag ggcccggaaa cctggccctg tcttcttgac   2220
gagcattcct aggggtcttt cccctctcgc caaaggaatg caaggtctgt tgaatgtcgt   2280
gaaggaagca gttcctctgg aagcttcttg aagacaaaca acgtctgtag cgaccctttg   2340
caggcagcgg aacccccccac ctggcgacag gtgcctctgc ggccaaaagc cacgtgtata  2400
agatacacct gcaaaggcgg cacaacccca gtgccacgtt gtgagttgga tagttgtgga   2460
aagagtcaaa tggctctcct caagcgtatt caacaagggg ctgaaggatg cccagaaggt   2520
accccattgt atgggatctg atctggggcc tcggtgcaca tgctttacat gtgtttagtc   2580
gaggttaaaa aacgtctagg ccccccgaac cacggggacg tggttttcct ttgaaaaaca   2640
cgataatacc atgaccgagt acaagcccac ggtgcgcctc gccacccgcg acgacgtccc   2700
ccgggccgta cgcaccctcg ccgccgcgtt cgccgactac cccgccacgc gccacaccgt   2760
cgatccggac cgccacatcg agcgggtcac cgagctgcaa gaactcttcc tcacgcgcgt   2820
cgggctcgac atcggcaagg tgtgggtcgc ggacgacggc gccgcggtgg cggtctggac   2880
cacgccggag agcgtcgaag cgggggcggt gttcgccgag atcggcccgc gcatggccga   2940
gttgagcggt tcccggctgg ccgcgcagca acagatggaa ggcctcctgg cgccgcaccg   3000
gcccaaggag cccgcgtggt tcctggccac cgtcggcgtc tcgcccgacc accagggcaa   3060
gggtctgggc agcgccgtcg tgctccccgg agtggaggcg gccgagcgcg ccggggtgcc   3120
cgccttcctg gagacctccg cgccccgcaa cctccccttc tacgagcggc tcggcttcac   3180
cgtcaccgcc gacgtcgagg tgcccgaagg accgcgcacc tggtgcatga cccgcaagcc   3240
cggtgcctga cgcccgccca caagacccgc agcgcccgac cgaaaggagc gcacgacccc   3300
atgcatcgaa tcgatatcgc ggccgcgact ctagatcata atcagcccgg gggtgatcag   3360
cctcgactgt gccttctagt tgccagccat ctgttgtttg cccctccccc gtgccttcct   3420
tgaccctgga aggtgccact cccactgtcc tttcctaata aaatgaggaa attgcatcgc   3480
attgtctgag taggtgtcat tctattctgg ggggtggggt ggggcaggac agcaaggggg   3540
aggattggga agacaatagc aggcatgctg gggatgcggt gggctctatg gaaccagctg   3600
gggctcgaca ttctagttgt ggtttgtcca aactcatcaa tgtatcttat catgtctgga   3660
tcccatcaca aagctctgac ctcaatccta tagaaaggag gaatgagcca aaattcaccc   3720
aacttattgt gggaagcttg tggaaggcta ctcgaaatgt ttgacccaag ttaaacaatt   3780
taaaggcaat gctaccaaat actaattgag tgtatgttaa cttctgaccc actgggaatg   3840
tgatgaaaga aataaaagct gaaatgaatc attctctcta ctattattct gatatttcac   3900
attcttaaaa taaagtggtg atcctaactg accttaagac agggaatctt tactcggatt   3960
aaatgtcagg aattgtgaaa aagtgagttt aaatgtattt ggctaaggtg tatgtaaact   4020
tccgacttca actgtaggga tcctctagag tcgacctgca ggcatgcaag cttggcgtaa   4080
tcatggtcat agctgtttcc tgtgtgaaat tgttatccgc tcacaattcc acacaacata   4140
cgagccggaa gcataaagtg taaagcctgg ggtgcctaat gagtgagcta actcacatta   4200
attgcgttgc gctcactgcc cgctttccag tcgggaaacc tgtcgtgcca gctgcattaa   4260
tgaatcggcc aacgcgcggg gagaggcggt ttgcgtattg ggcgctcttc cgcttcctcg   4320
ctcactgact cgctgcgctc ggtcgttcgg ctgcggcgag cggtatcagc tcactcaaag   4380
```

gcggtaatac ggttatccac agaatcaggg gataacgcag gaaagaacat gtgagcaaaa 4440
ggccagcaaa aggccaggaa ccgtaaaaag gccgcgttgc tggcgttttt ccataggctc 4500
cgcccccctg acgagcatca caaaaatcga cgctcaagtc agaggtggcg aaacccgaca 4560
ggactataaa gataccaggc gtttccccct ggaagctccc tcgtgcgctc tcctgttccg 4620
accctgccgc ttaccggata cctgtccgcc tttctccctt cgggaagcgt ggcgctttct 4680
caatgctcac gctgtaggta tctcagttcg gtgtaggtcg ttcgctccaa gctgggctgt 4740
gtgcacgaac cccccgttca gcccgaccgc tgcgccttat ccggtaacta tcgtcttgag 4800
tccaacccgg taagacacga cttatcgcca ctggcagcag ccactggtaa caggattagc 4860
agagcgaggt atgtaggcgg tgctacagag ttcttgaagt ggtggcctaa ctacggctac 4920
actagaagga cagtatttgg tatctgcgct ctgctgaagc cagttacctt cggaaaaaga 4980
gttggtagct cttgatccgg caaacaaacc accgctggta gcggtggttt ttttgtttgc 5040
aagcagcaga ttacgcgcag aaaaaaagga tctcaagaag atcctttgat cttttctacg 5100
gggtctgacg ctcagtggaa cgaaaactca cgttaaggga ttttggtcat gagattatca 5160
aaaaggatct tcacctagat ccttttaaat taaaaatgaa gttttaaatc aatctaaagt 5220
atatatgagt aaacttggtc tgacagttac caatgcttaa tcagtgaggc acctatctca 5280
gcgatctgtc tatttcgttc atccatagtt gcctgactcc ccgtcgtgta gataactacg 5340
atacgggagg gcttaccatc tggccccagt gctgcaatga taccgcgaga cccacgctca 5400
ccggctccag atttatcagc aataaaccag ccagccggaa gggccgagcg cagaagtggt 5460
cctgcaactt tatccgcctc catccagtct attaattgtt gccgggaagc tagagtaagt 5520
agttcgccag ttaatagttt gcgcaacgtt gttgccattg ctacaggcat cgtggtgtca 5580
cgctcgtcgt ttggtatggc ttcattcagc tccggttccc aacgatcaag gcgagttaca 5640
tgatccccca tgttgtgcaa aaaagcggtt agctccttcg gtcctccgat cgttgtcaga 5700
agtaagttgg ccgcagtgtt atcactcatg gttatggcag cactgcataa ttctcttact 5760
gtcatgccat ccgtaagatg cttttctgtg actggtgagt actcaaccaa gtcattctga 5820
gaatagtgta tgcggcgacc gagttgctct tgcccggcgt caatacggga taataccgcg 5880
ccacatagca gaactttaaa agtgctcatc attggaaaac gttcttcggg gcgaaaactc 5940
tcaaggatct taccgctgtt gagatccagt tcgatgtaac ccactcgtgc acccaactga 6000
tcttcagcat cttttacttt caccagcgtt tctgggtgag caaaaacagg aaggcaaaat 6060
gccgcaaaaa agggaataag ggcgacacgg aaatgttgaa tactcatact cttccttttt 6120
caatattatt gaagcattta tcagggttat tgtctcatga gcggatacat atttgaatgt 6180
atttagaaaa ataaacaaat aggggttccg cgcacatttc cccgaaaagt gccacctgac 6240
gtctaagaaa ccattattat catgacatta acctataaaa ataggcgtat cacgaggccc 6300
tttcgtc 6307

<210> SEQ ID NO 28
<211> LENGTH: 6221
<212> TYPE: DNA
<213> ORGANISM: Artificial Sequence
<220> FEATURE:
<223> OTHER INFORMATION: Plasmid vector

<400> SEQUENCE: 28
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120

-continued

```
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt accctacagt    420
tgaagtcgga agtttacata cacttaagtt ggagtcatta aaactcgttt ttcaactact    480
ccacaaattt cttgttaaca aacaatagtt ttggcaagtc agttaggaca tctactttgt    540
gcatgacaca agtcattttt ccaacaattg tttacagaca gattatttca cttataattc    600
actgtatcac aattccagtg ggtcagaagt ttacatacac taagttgact gtgcctttaa    660
acagcttgga aaattccaga aaatgatgtc atggctttag aagcttctga tagactaatt    720
gacatcattt gagtcaattg gaggtgtacc tgtggatgta tttcaaggga attctgtgga    780
atgtgtgtca gttagggtgt ggaaagtccc caggctcccc aggcaggcag aagtatgcaa    840
agcatcgagg atgtacgggc cagatatacg cgtatctgag gggactaggg tgtgtttagg    900
cgaaaagcgg ggcttcggtt gtacgcggtt aggagtcccc tcaggatata gtagtttcgc    960
ttttgcatag ggagggggaa atgtagtctt atgcaataca cttgtagtct tgcaacatgg   1020
taacgatgag ttagcaacat gccttacaag gagagaaaaa gcaccgtgca tgccgattgg   1080
tggaagtaag gtggtacgat cgtgccttat taggaaggca acagacaggt ctgacatgga   1140
ttggacgaac cactgaattc cgcattgcag agataattgt atttaagtgc ctagctcgat   1200
acaataaacg ccatttgacc attcaccaca ttggtgtgca cctccaaagc ttgatatcta   1260
ccatggagaa gttactattc cgaagttcct attctctaga aagtatagga acttcaagct   1320
tggcactggt gagcaagggc gaggagctgt tcaccggggt ggtgcccatc ctggtcgagc   1380
tggacggcga cgtaaacggc cacaagttca gcgtgtccgg cgagggcgag ggcgatgcca   1440
cctacggcaa gctgaccctg aagttcatct gcaccaccgg caagctgccc gtgccctggc   1500
ccaccctcgt gaccaccctg acctacggcg tgcagtgctt cagccgctac cccgaccaca   1560
tgaagcagca cgacttcttc aagtccgcca tgcccgaagg ctacgtccag gagcgcacca   1620
tcttcttcaa ggacgacggc aactacaaga cccgcgccga ggtgaagttc gagggcgaca   1680
ccctggtgaa ccgcatcgag ctgaagggca tcgacttcaa ggaggacggc aacatcctgg   1740
ggcacaagct ggagtacaac tacaacagcc acaacgtcta tatcatggcc gacaagcaga   1800
agaacggcat caaggtgaac ttcaagatcc gccacaacat cgaggacggc agcgtgcagc   1860
tcgccgacca ctaccagcag aacaccccca tcggcgacgg ccccgtgctg ctgcccgaca   1920
accactacct gagcacccag tccgccctga gcaaagaccc caacgagaag cgcgatcaca   1980
tggtcctgct ggagttcgtg accgccgccg ggatcactct cggcatggac gagctgtaca   2040
agtaaagcat agcggccgta aattccgccc ctctctccct cccccccccc taacgttact   2100
ggccgaagcc gcttggaata aggccggtgt gcgtttgtct atatgttatt ttccaccata   2160
ttgccgtctt ttggcaatgt gagggcccgg aaacctggcc ctgtcttctt gacgagcatt   2220
cctaggggtc tttcccctct cgccaaagga atgcaaggtc tgttgaatgt cgtgaaggaa   2280
gcagttcctc tggaagcttc ttgaagacaa acaacgtctg tagcgaccct ttgcaggcag   2340
cggaaccccc cacctggcga caggtgcctc tgcggccaaa agccacgtgt ataagataca   2400
cctgcaaagg cggcacaacc ccagtgccac gttgtgagtt ggatagttgt ggaaagagtc   2460
aaatggctct cctcaagcgt attcaacaag gggctgaagg atgcccagaa ggtaccccat   2520
```

-continued

```
tgtatgggat ctgatctggg gcctcggtgc acatgcttta catgtgttta gtcgaggtta   2580
aaaaacgtct aggccccccg aaccacgggg acgtggtttt cctttgaaaa acacgatgat   2640
aagcttgcca caaccatgac cgagtacaag cccacggtgc gcctcgccac ccgcgacgac   2700
gtcccccggg ccgtacgcac cctcgccgcc gcgttcgccg actaccccgc cacgcgccac   2760
accgtcgatc cggaccgcca catcgagcgg gtcaccgagc tgcaagaact cttcctcacg   2820
cgcgtcgggc tcgacatcgg caaggtgtgg gtcgcggacg acggcgccgc ggtggcggtc   2880
tggaccacgc cggagagcgt cgaagcgggg gcggtgttcg ccgagatcgg cccgcgcatg   2940
gccgagttga gcggttcccg gctggccgcg cagcaacaga tggaaggcct cctggcgccg   3000
caccggccca aggagcccgc gtggttcctg gccaccgtcg gcgtctcgcc cgaccaccag   3060
ggcaagggtc tgggcagcgc cgtcgtgctc cccggagtgg aggcggccga gcgcgccggg   3120
gtgcccgcct tcctggagac ctccgcgccc cgcaacctcc ccttctacga gcggctcggc   3180
ttcaccgtca ccgccgacgt cgaggtgccc gaaggaccgc gcacctggtg catgacccgc   3240
aagcccggtg cctgaagatc ccccggggga tcagcctcga ctgtgccttc tagttgccag   3300
ccatctgttg tttgcccctc ccccgtgcct tccttgaccc tggaaggtgc cactcccact   3360
gtcctttcct aataaaatga ggaaattgca tcgcattgtc tgagtaggtg tcattctatt   3420
ctggggggtg gggtggggca ggacagcaag ggggaggatt gggaagacaa tagcaggcat   3480
gctggggatg cggtgggctc tatggaacca gctggggctc gacattctag ttgtggtttg   3540
tccaaactca tcaatgtatc ttatcatgtc tggatcccat cacaaagctc tgacctcaat   3600
cctatagaaa ggaggaatga gccaaaattc acccaactta ttgtgggaag cttgtggaag   3660
gctactcgaa atgtttgacc caagttaaac aatttaaagg caatgctacc aaatactaat   3720
tgagtgtatg ttaacttctg acccactggg aatgtgatga aagaaataaa agctgaaatg   3780
aatcattctc tctactatta ttctgatatt tcacattctt aaaataaagt ggtgatccta   3840
actgacctta agacagggaa tctttactcg gattaaatgt caggaattgt gaaaaagtga   3900
gtttaaatgt atttggctaa ggtgtatgta aacttccgac ttcaactgta gggatcctct   3960
agagtcgacc tgcaggcatg caagcttggc gtaatcatgg tcatagctgt ttcctgtgtg   4020
aaattgttat ccgctcacaa ttccacacaa catacgagcc ggaagcataa agtgtaaagc   4080
ctggggtgcc taatgagtga gctaactcac attaattgcg ttgcgctcac tgcccgcttt   4140
ccagtcggga aacctgtcgt gccagctgca ttaatgaatc ggccaacgcg cggggagagg   4200
cggtttgcgt attgggcgct cttccgcttc ctcgctcact gactcgctgc gctcggtcgt   4260
tcggctgcgg cgagcggtat cagctcactc aaaggcggta atacggttat ccacagaatc   4320
aggggataac gcaggaaaga acatgtgagc aaaaggccag caaaaggcca ggaaccgtaa   4380
aaaggccgcg ttgctggcgt ttttccatag gctccgcccc cctgacgagc atcacaaaaa   4440
tcgacgctca agtcagaggt ggcgaaaccc gacaggacta taaagatacc aggcgtttcc   4500
ccctggaagc tccctcgtgc gctctcctgt tccgaccctg ccgcttaccg gatacctgtc   4560
cgcctttctc ccttcgggaa gcgtggcgct ttctcaatgc tcacgctgta ggtatctcag   4620
ttcggtgtag gtcgttcgct ccaagctggg ctgtgtgcac gaaccccccg ttcagcccga   4680
ccgctgcgcc ttatccggta actatcgtct tgagtccaac ccggtaagac acgacttatc   4740
gccactggca gcagccactg gtaacaggat tagcagagcg aggtatgtag gcggtgctac   4800
agagttcttg aagtggtggc ctaactacgg ctacactaga aggacagtat ttggtatctg   4860
cgctctgctg aagccagtta ccttcggaaa aagagttggt agctcttgat ccggcaaaca   4920
```

aaccaccgct ggtagcggtg gtttttttgt ttgcaagcag cagattacgc gcagaaaaaa 4980
aggatctcaa gaagatcctt tgatcttttc tacggggtct gacgctcagt ggaacgaaaa 5040
ctcacgttaa gggattttgg tcatgagatt atcaaaaagg atcttcacct agatcctttt 5100
aaattaaaaa tgaagtttta aatcaatcta aagtatatat gagtaaactt ggtctgacag 5160
ttaccaatgc ttaatcagtg aggcacctat ctcagcgatc tgtctatttc gttcatccat 5220
agttgcctga ctccccgtcg tgtagataac tacgatacgg gagggcttac catctggccc 5280
cagtgctgca atgataccgc gagacccacg ctcaccggct ccagatttat cagcaataaa 5340
ccagccagcc ggaagggccg agcgcagaag tggtcctgca actttatccg cctccatcca 5400
gtctattaat tgttgccggg aagctagagt aagtagttcg ccagttaata gtttgcgcaa 5460
cgttgttgcc attgctacag gcatcgtggt gtcacgctcg tcgtttggta tggcttcatt 5520
cagctccggt tcccaacgat caaggcgagt tacatgatcc cccatgttgt gcaaaaaagc 5580
ggttagctcc ttcggtcctc cgatcgttgt cagaagtaag ttggccgcag tgttatcact 5640
catggttatg gcagcactgc ataattctct tactgtcatg ccatccgtaa gatgcttttc 5700
tgtgactggt gagtactcaa ccaagtcatt ctgagaatag tgtatgcggc gaccgagttg 5760
ctcttgcccg gcgtcaatac gggataatac cgcgccacat agcagaactt taaaagtgct 5820
catcattgga aaacgttctt cggggcgaaa actctcaagg atcttaccgc tgttgagatc 5880
cagttcgatg taacccactc gtgcacccaa ctgatcttca gcatctttta ctttcaccag 5940
cgtttctggg tgagcaaaaa caggaaggca aaatgccgca aaaaagggaa taagggcgac 6000
acggaaatgt tgaatactca tactcttcct ttttcaatat tattgaagca tttatcaggg 6060
ttattgtctc atgagcggat acatatttga atgtatttag aaaaataaac aaataggggt 6120
tccgcgcaca tttccccgaa aagtgccacc tgacgtctaa gaaaccatta ttatcatgac 6180
attaacctat aaaaataggc gtatcacgag gccctttcgt c 6221

<210> SEQ ID NO 29
<211> LENGTH: 6269
<212> TYPE: DNA
<213> ORGANISM: Artificial Sequence
<220> FEATURE:
<223> OTHER INFORMATION: Plasmid vector

<400> SEQUENCE: 29
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt accctacagt 420
tgaagtcgga agtttacata cacttaagtt ggagtcatta aaactcgttt ttcaactact 480
ccacaaattt cttgttaaca aacaatagtt ttggcaagtc agttaggaca tctactttgt 540
gcatgacaca agtcattttt ccaacaattg tttacagaca gattatttca cttataattc 600
actgtatcac aattccagtg ggtcagaagt ttacatacac taagttgact gtgcctttaa 660
acagcttgga aaattccaga aaatgatgtc atggctttag aagcttctga tagactaatt 720
gacatcattt gagtcaattg gaggtgtacc tgtggatgta tttcaaggga attctgtgga 780

```
atgtgtgtca gttagggtgt ggaaagtccc caggctcccc aggcaggcag aagtatgcaa    840
agcatcgagg atgtacgggc cagatatacg cgtgaggttt tcaccgtcat caccgaaacg    900
cgcgaggcag ctgtggaatg tgtgtcagtt agggtgtgga aagtccccag gctccccagc    960
aggcagaagt atgcaaagca tgcatctcaa ttagtcagca accaggtgtg gaaagtcccc   1020
aggctcccca gcaggcagaa gtatgcaaag catgcatctc aattagtcag caaccatagt   1080
cccgccccta actccgccca tcccgcccct aactccgccc agttccgccc attctccgcc   1140
ccatggctga ctaatttttt ttatttatgc agaggccgag gccgcctcgg cctctgagct   1200
attccagaag tagtgaggag gcttttttgg aggctaccat ggagaagtta ctattccgaa   1260
gttcctattc tctagaaagt ataggaactt caagcttggc actggtgagc aagggcgagg   1320
agctgttcac cggggtggtg cccatcctgg tcgagctgga cggcgacgta aacggccaca   1380
agttcagcgt gtccggcgag ggcgagggcg atgccaccta cggcaagctg accctgaagt   1440
tcatctgcac caccggcaag ctgcccgtgc cctggcccac cctcgtgacc accctgacct   1500
acggcgtgca gtgcttcagc cgctaccccg accacatgaa gcagcacgac ttcttcaagt   1560
ccgccatgcc cgaaggctac gtccaggagc gcaccatctt cttcaaggac gacggcaact   1620
acaagacccg cgccgaggtg aagttcgagg gcgacaccct ggtgaaccgc atcgagctga   1680
agggcatcga cttcaaggag gacggcaaca tcctggggca caagctggag tacaactaca   1740
acagccacaa cgtctatatc atggccgaca agcagaagaa cggcatcaag gtgaacttca   1800
agatccgcca caacatcgag gacggcagcg tgcagctcgc cgaccactac cagcagaaca   1860
cccccatcgg cgacggcccc gtgctgctgc ccgacaacca ctacctgagc acccagtccg   1920
ccctgagcaa agaccccaac gagaagcgcg atcacatggt cctgctggag ttcgtgaccg   1980
ccgccgggat cactctcggc atggacgagc tgtacaagta aagcggccgc ggccaattgg   2040
gccaccggtg ctagcccccct aacgttactg gccgaagccg cttggaataa ggccggtgtg   2100
cgtttgtcta tatgttattt tccaccatat tgccgtcttt tggcaatgtg agggcccgga   2160
aacctggccc tgtcttcttg acgagcattc ctaggggtct ttcccctctc gccaaaggaa   2220
tgcaaggtct gttgaatgtc gtgaaggaag cagttcctct ggaagcttct tgaagacaaa   2280
caacgtctgt agcgaccctt tgcaggcagc ggaacccccc acctggcgac aggtgcctct   2340
gcggccaaaa gccacgtgta taagatacac ctgcaaaggc ggcacaaccc cagtgccacg   2400
ttgtgagttg gatagttgtg gaaagagtca aatggctctc ctcaagcgta ttcaacaagg   2460
ggctgaagga tgcccagaag gtaccccatt gtatgggatc tgatctgggg cctcggtgca   2520
catgctttac atgtgtttag tcgaggttaa aaaacgtcta ggccccccga accacgggga   2580
cgtggttttc ctttgaaaaa cacgataata ccatgaccga gtacaagccc acggtgcgcc   2640
tcgccacccg cgacgacgtc ccccgggccg tacgcaccct cgccgccgcg ttcgccgact   2700
accccgccac gcgccacacc gtcgatccgg accgccacat cgagcgggtc accgagctgc   2760
aagaactctt cctcacgcgc gtcgggctcg acatcggcaa ggtgtgggtc gcggacgacg   2820
gcgccgcggt ggcggtctgg accacgccgg agagcgtcga agcgggggcg gtgttcgccg   2880
agatcggccc gcgcatggcc gagttgagcg gttcccggct ggccgcgcag caacagatgg   2940
aaggcctcct ggcgccgcac cggcccaagg agcccgcgtg gttcctggcc accgtcggcg   3000
tctcgcccga ccaccagggc aagggtctgg gcagcgccgt cgtgctcccc ggagtggagg   3060
cggccgagcg cgccggggtg cccgccttcc tggagacctc cgcgccccgc aacctcccct   3120
tctacgagcg gctcggcttc accgtcaccg ccgacgtcga ggtgcccgaa ggaccgcgca   3180
```

-continued

```
cctggtgcat gacccgcaag cccggtgcct gacgcccgcc cacaagaccc gcagcgcccg   3240
accgaaagga gcgcacgacc ccatgcatcg aatcgatatc gcggccgcga ctctagatca   3300
taatcagccc gggggtgatc agcctcgact gtgccttcta gttgccagcc atctgttgtt   3360
tgcccctccc ccgtgccttc cttgaccctg gaaggtgcca ctcccactgt cctttcctaa   3420
taaaatgagg aaattgcatc gcattgtctg agtaggtgtc attctattct ggggggtggg   3480
gtggggcagg acagcaaggg ggaggattgg gaagacaata gcaggcatgc tggggatgcg   3540
gtgggctcta tggaaccagc tggggctcga cattctagtt gtggtttgtc caaactcatc   3600
aatgtatctt atcatgtctg gatcccatca caaagctctg acctcaatcc tatagaaagg   3660
aggaatgagc caaaattcac ccaacttatt gtgggaagct tgtggaaggc tactcgaaat   3720
gtttgaccca agttaaacaa tttaaaggca atgctaccaa atactaattg agtgtatgtt   3780
aacttctgac ccactgggaa tgtgatgaaa gaaataaaag ctgaaatgaa tcattctctc   3840
tactattatt ctgatatttc acattcttaa aataaagtgg tgatcctaac tgaccttaag   3900
acagggaatc tttactcgga ttaaatgtca ggaattgtga aaaagtgagt ttaaatgtat   3960
ttggctaagg tgtatgtaaa cttccgactt caactgtagg gatcctctag agtcgacctg   4020
caggcatgca agcttggcgt aatcatggtc atagctgttt cctgtgtgaa attgttatcc   4080
gctcacaatt ccacacaaca tacgagccgg aagcataaag tgtaaagcct ggggtgccta   4140
atgagtgagc taactcacat taattgcgtt gcgctcactg cccgctttcc agtcgggaaa   4200
cctgtcgtgc cagctgcatt aatgaatcgg ccaacgcgcg gggagaggcg gtttgcgtat   4260
tgggcgctct tccgcttcct cgctcactga ctcgctgcgc tcggtcgttc ggctgcggcg   4320
agcggtatca gctcactcaa aggcggtaat acggttatcc acagaatcag gggataacgc   4380
aggaaagaac atgtgagcaa aaggccagca aaaggccagg aaccgtaaaa aggccgcgtt   4440
gctggcgttt ttccataggc tccgcccccc tgacgagcat cacaaaaatc gacgctcaag   4500
tcagaggtgg cgaaacccga caggactata aagataccag gcgtttcccc ctggaagctc   4560
cctcgtgcgc tctcctgttc cgaccctgcc gcttaccgga tacctgtccg cctttctccc   4620
ttcgggaagc gtggcgcttt ctcaatgctc acgctgtagg tatctcagtt cggtgtaggt   4680
cgttcgctcc aagctgggct gtgtgcacga accccccgtt cagcccgacc gctgcgcctt   4740
atccggtaac tatcgtcttg agtccaaccc ggtaagacac gacttatcgc cactggcagc   4800
agccactggt aacaggatta gcagagcgag gtatgtaggc ggtgctacag agttcttgaa   4860
gtggtggcct aactacggct acactagaag gacagtattt ggtatctgcg ctctgctgaa   4920
gccagttacc ttcggaaaaa gagttggtag ctcttgatcc ggcaaacaaa ccaccgctgg   4980
tagcggtggt ttttttgttt gcaagcagca gattacgcgc agaaaaaaag gatctcaaga   5040
agatcctttg atcttttcta cggggtctga cgctcagtgg aacgaaaact cacgttaagg   5100
gattttggtc atgagattat caaaaaggat cttcacctag atccttttaa attaaaaatg   5160
aagttttaaa tcaatctaaa gtatatatga gtaaacttgg tctgacagtt accaatgctt   5220
aatcagtgag gcacctatct cagcgatctg tctatttcgt tcatccatag ttgcctgact   5280
ccccgtcgtg tagataacta cgatacggga gggcttacca tctggcccca gtgctgcaat   5340
gataccgcga gacccacgct caccggctcc agatttatca gcaataaacc agccagccgg   5400
aagggccgag cgcagaagtg gtcctgcaac tttatccgcc tccatccagt ctattaattg   5460
ttgccgggaa gctagagtaa gtagttcgcc agttaatagt ttgcgcaacg ttgttgccat   5520
tgctacaggc atcgtggtgt cacgctcgtc gtttggtatg gcttcattca gctccggttc   5580
```

ccaacgatca aggcgagtta catgatcccc catgttgtgc aaaaaagcgg ttagctcctt 5640
cggtcctccg atcgttgtca gaagtaagtt ggccgcagtg ttatcactca tggttatggc 5700
agcactgcat aattctctta ctgtcatgcc atccgtaaga tgcttttctg tgactggtga 5760
gtactcaacc aagtcattct gagaatagtg tatgcggcga ccgagttgct cttgcccggc 5820
gtcaatacgg gataataccg cgccacatag cagaacttta aaagtgctca tcattggaaa 5880
acgttcttcg gggcgaaaac tctcaaggat cttaccgctg ttgagatcca gttcgatgta 5940
acccactcgt gcacccaact gatcttcagc atcttttact ttcaccagcg tttctgggtg 6000
agcaaaaaca ggaaggcaaa atgccgcaaa aaagggaata agggcgacac ggaaatgttg 6060
aatactcata ctcttccttt ttcaatatta ttgaagcatt tatcagggtt attgtctcat 6120
gagcggatac atatttgaat gtatttagaa aaataaacaa ataggggttc cgcgcacatt 6180
tccccgaaaa gtgccacctg acgtctaaga aaccattatt atcatgacat taacctataa 6240
aaataggcgt atcacgaggc cctttcgtc 6269

<210> SEQ ID NO 30
<211> LENGTH: 6346
<212> TYPE: DNA
<213> ORGANISM: Artificial Sequence
<220> FEATURE:
<223> OTHER INFORMATION: Plasmid vector

<400> SEQUENCE: 30
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt accctacagt 420
tgaagtcgga agtttacata cacttaagtt ggagtcatta aaactcgttt ttcaactact 480
ccacaaattt cttgttaaca aacaatagtt ttggcaagtc agttaggaca tctactttgt 540
gcatgacaca agtcattttt ccaacaattg tttacagaca gattatttca cttataattc 600
actgtatcac aattccagtg ggtcagaagt ttacatacac taagttgact gtgcctttaa 660
acagcttgga aaattccaga aaatgatgtc atggctttag aagcttctga tagactaatt 720
gacatcattt gagtcaattg gaggtgtacc tgtggatgta tttcaaggga attctgtgga 780
atgtgtgtca gttagggtgt ggaaagtccc caggctcccc aggcaggcag aagtatgcaa 840
agcatcgagg atgtacgggc cagatatacg cgataacttc gtataatgta tgctatacga 900
agttatcgcg tgaggttttc accgtcatca ccgaaacgcg cgaggcagct gtggaatgtg 960
tgtcagttag ggtgtggaaa gtccccaggc tccccagcag gcagaagtat gcaaagcatg 1020
catctcaatt agtcagcaac caggtgtgga aagtccccag gctccccagc aggcagaagt 1080
atgcaaagca tgcatctcaa ttagtcagca accatagtcc cgcccctaac tccgcccatc 1140
ccgcccctaa ctccgcccag ttccgcccat tctccgcccc atggctgact aattttttt 1200 atttatgcag aggccgaggc cgcctcggcc tctgagctat tccagaagta gtgaggaggc 1260
ttttttggag gctaccatgg agaagttact attccgaagt tcctattctc tagaaagtat 1320
aggaacttca agcttggcac tggtgagcaa gggcgaggag ctgttcaccg ggtggtgcc 1380

-continued

```
catcctggtc gagctggacg gcgacgtaaa cggccacaag ttcagcgtgt ccggcgaggg   1440
cgagggcgat gccacctacg gcaagctgac cctgaagttc atctgcacca ccggcaagct   1500
gcccgtgccc tggcccaccc tcgtgaccac cctgacctac ggcgtgcagt gcttcagccg   1560
ctaccccgac cacatgaagc agcacgactt cttcaagtcc gccatgcccg aaggctacgt   1620
ccaggagcgc accatcttct tcaaggacga cggcaactac aagacccgcg ccgaggtgaa   1680
gttcgagggc gacaccctgg tgaaccgcat cgagctgaag ggcatcgact tcaaggagga   1740
cggcaacatc ctggggcaca agctggagta caactacaac agccacaacg tctatatcat   1800
ggccgacaag cagaagaacg gcatcaaggt gaacttcaag atccgccaca acatcgagga   1860
cggcagcgtg cagctcgccg accactacca gcagaacacc cccatcggcg acggccccgt   1920
gctgctgccc gacaaccact acctgagcac ccagtccgcc ctgagcaaag accccaacga   1980
gaagcgcgat cacatggtcc tgctggagtt cgtgaccgcc gccgggatca ctctcggcat   2040
ggacgagctg tacaagtaaa gcggccgcgg ccaattgggc caccggtgct agccccctaa   2100
cgttactggc cgaagccgct tggaataagg ccggtgtgcg tttgtctata tgttattttc   2160
caccatattg ccgtcttttg gcaatgtgag ggcccggaaa cctggccctg tcttcttgac   2220
gagcattcct aggggtcttt cccctctcgc caaaggaatg caaggtctgt tgaatgtcgt   2280
gaaggaagca gttcctctgg aagcttcttg aagacaaaca acgtctgtag cgaccctttg   2340
caggcagcgg aacccccac ctggcgacag gtgcctctgc ggccaaaagc cacgtgtata   2400
agatacacct gcaaaggcgg cacaacccca gtgccacgtt gtgagttgga tagttgtgga   2460
aagagtcaaa tggctctcct caagcgtatt caacaagggg ctgaaggatg cccagaaggt   2520
accccattgt atgggatctg atctggggcc tcggtgcaca tgctttacat gtgtttagtc   2580
gaggttaaaa aacgtctagg ccccccgaac cacggggacg tggttttcct ttgaaaaaca   2640
cgataatacc atgaccgagt acaagcccac ggtgcgcctc gccacccgcg acgacgtccc   2700
ccgggccgta cgcaccctcg ccgccgcgtt cgccgactac cccgccacgc gccacaccgt   2760
cgatccggac cgccacatcg agcgggtcac cgagctgcaa gaactcttcc tcacgcgcgt   2820
cgggctcgac atcggcaagg tgtgggtcgc ggacgacggc gccgcggtgg cggtctggac   2880
cacgccggag agcgtcgaag cgggggcggt gttcgccgag atcggcccgc gcatggccga   2940
gttgagcggt tcccggctgg ccgcgcagca acagatggaa ggcctcctgg cgccgcaccg   3000
gcccaaggag cccgcgtggt tcctggccac cgtcggcgtc tcgcccgacc accagggcaa   3060
gggtctgggc agcgccgtcg tgctccccgg agtggaggcg gccgagcgcg ccggggtgcc   3120
cgccttcctg gagacctccg cgccccgcaa cctccccttc tacgagcggc tcggcttcac   3180
cgtcaccgcc gacgtcgagg tgcccgaagg accgcgcacc tggtgcatga cccgcaagcc   3240
cggtgcctga cgcccgccca caagacccgc agcgcccgac cgaaaggagc gcacgacccc   3300
atgcatcgaa tcgatatcgc ggccgcgact ctagatcata atcagcccgg gggtgatcag   3360
cctcgactgt gccttctagt tgccagccat ctgttgtttg cccctccccc gtgccttcct   3420
tgaccctgga aggtgccact cccactgtcc tttcctaata aaatgaggaa attgcatcgc   3480
attgtctgag taggtgtcat tctattctgg ggggtggggt ggggcaggac agcaaggggg   3540
aggattggga agacaatagc aggcatgctg gggatgcggt gggctctatg gaaccagctg   3600
gggcgcgatt aacttcgtat aaagtctcct atacgaagtt atcgcgccat tctagttgtg   3660
gtttgtccaa actcatcaat gtatcttatc atgtctggat cccatcacaa agctctgacc   3720
tcaatcctat agaaaggagg aatgagccaa aattcaccca acttattgtg ggaagcttgt   3780
```

-continued ggaaggctac tcgaaatgtt tgacccaagt taaacaattt aaaggcaatg ctaccaaata 3840
ctaattgagt gtatgttaac ttctgaccca ctgggaatgt gatgaaagaa ataaaagctg 3900
aaatgaatca ttctctctac tattattctg atatttcaca ttcttaaaat aaagtggtga 3960
tcctaactga ccttaagaca gggaatcttt actcggatta aatgtcagga attgtgaaaa 4020
agtgagttta aatgtatttg gctaaggtgt atgtaaactt ccgacttcaa ctgtagggat 4080
cctctagagt cgacctgcag gcatgcaagc ttggcgtaat catggtcata gctgtttcct 4140
gtgtgaaatt gttatccgct cacaattcca cacaacatac gagccggaag cataaagtgt 4200
aaagcctggg gtgcctaatg agtgagctaa ctcacattaa ttgcgttgcg ctcactgccc 4260
gctttccagt cgggaaacct gtcgtgccag ctgcattaat gaatcggcca acgcgcgggg 4320
agaggcggtt tgcgtattgg gcgctcttcc gcttcctcgc tcactgactc gctgcgctcg 4380
gtcgttcggc tgcggcgagc ggtatcagct cactcaaagg cggtaatacg gttatccaca 4440
gaatcagggg ataacgcagg aaagaacatg tgagcaaaag gccagcaaaa ggccaggaac 4500
cgtaaaaagg ccgcgttgct ggcgtttttc cataggctcc gcccccctga cgagcatcac 4560
aaaaatcgac gctcaagtca gaggtggcga aacccgacag gactataaag ataccaggcg 4620
tttccccctg gaagctccct cgtgcgctct cctgttccga ccctgccgct taccggatac 4680
ctgtccgcct ttctcccttc gggaagcgtg gcgctttctc aatgctcacg ctgtaggtat 4740
ctcagttcgg tgtaggtcgt tcgctccaag ctgggctgtg tgcacgaacc ccccgttcag 4800
cccgaccgct gcgccttatc cggtaactat cgtcttgagt ccaacccggt aagacacgac 4860
ttatcgccac tggcagcagc cactggtaac aggattagca gagcgaggta tgtaggcggt 4920
gctacagagt tcttgaagtg gtggcctaac tacggctaca ctagaaggac agtatttggt 4980
atctgcgctc tgctgaagcc agttaccttc ggaaaaagag ttggtagctc ttgatccggc 5040
aaacaaacca ccgctggtag cggtggtttt tttgtttgca agcagcagat tacgcgcaga 5100
aaaaaaggat ctcaagaaga tcctttgatc ttttctacgg ggtctgacgc tcagtggaac 5160
gaaaactcac gttaagggat tttggtcatg agattatcaa aaaggatctt cacctagatc 5220
cttttaaatt aaaaatgaag ttttaaatca atctaaagta tatatgagta aacttggtct 5280
gacagttacc aatgcttaat cagtgaggca cctatctcag cgatctgtct atttcgttca 5340
tccatagttg cctgactccc cgtcgtgtag ataactacga tacgggaggg cttaccatct 5400
ggccccagtg ctgcaatgat accgcgagac ccacgctcac cggctccaga tttatcagca 5460
ataaaccagc cagccggaag ggccgagcgc agaagtggtc ctgcaacttt atccgcctcc 5520
atccagtcta ttaattgttg ccgggaagct agagtaagta gttcgccagt taatagtttg 5580
cgcaacgttg ttgccattgc tacaggcatc gtggtgtcac gctcgtcgtt tggtatggct 5640
tcattcagct ccggttccca acgatcaagg cgagttacat gatcccccat gttgtgcaaa 5700
aaagcggtta gctccttcgg tcctccgatc gttgtcagaa gtaagttggc cgcagtgtta 5760
tcactcatgg ttatggcagc actgcataat tctcttactg tcatgccatc cgtaagatgc 5820
ttttctgtga ctggtgagta ctcaaccaag tcattctgag aatagtgtat gcggcgaccg 5880
agttgctctt gcccggcgtc aatacgggat aataccgcgc cacatagcag aactttaaaa 5940
gtgctcatca ttggaaaacg ttcttcgggg cgaaaactct caaggatctt accgctgttg 6000
agatccagtt cgatgtaacc cactcgtgca cccaactgat cttcagcatc ttttactttc 6060
accagcgttt ctgggtgagc aaaaacagga aggcaaaatg ccgcaaaaaa gggaataagg 6120
gcgacacgga aatgttgaat actcatactc ttcctttttc aatattattg aagcatttat 6180
cagggttatt gtctcatgag cggatacata tttgaatgta tttagaaaaa taaacaaata 6240
ggggttccgc gcacatttcc ccgaaaagtg ccacctgacg tctaagaaac cattattatc 6300
atgacattaa cctataaaaa taggcgtatc acgaggccct ttcgtc 6346

<210> SEQ ID NO 31
<211> LENGTH: 33
<212> TYPE: DNA
<213> ORGANISM: Artificial
<220> FEATURE:
<223> OTHER INFORMATION: Primer

<400> SEQUENCE: 31
gggattaatg atccacagtc tcctgagtag ctg 33

<210> SEQ ID NO 32
<211> LENGTH: 29
<212> TYPE: DNA
<213> ORGANISM: Artificial
<220> FEATURE:
<223> OTHER INFORMATION: Primer

<400> SEQUENCE: 32
gggagatctg ggaggcaggc aggccgctc 29

<210> SEQ ID NO 33
<211> LENGTH: 30
<212> TYPE: DNA
<213> ORGANISM: Artificial
<220> FEATURE:
<223> OTHER INFORMATION: Primer

<400> SEQUENCE: 33
ggggtcgacg atcctgacaa cttcagggtg 30

<210> SEQ ID NO 34
<211> LENGTH: 31
<212> TYPE: DNA
<213> ORGANISM: Artificial
<220> FEATURE:
<223> OTHER INFORMATION: Primer

<400> SEQUENCE: 34
gggctcgagg ccctatagtg agtcgtatta c 31

<210> SEQ ID NO 35
<211> LENGTH: 3661
<212> TYPE: DNA
<213> ORGANISM: Artificial
<220> FEATURE:
<223> OTHER INFORMATION: PDGF-PS1(P117L)

<400> SEQUENCE: 35
attaatgatc cacagtctcc tgagtagctg ggactacagg agcttgttac cacacccagc 60
tccagtttat aaattcatct ccagtttata aaggaggaaa ccgaggtact gagaggttaa 120
aaaaccttcc tgcagacact tgtccagcaa gtggccactc caggatttgg accaaggtga 180
tgtgtcttca ggctgtgtct ctgccactgt gccacgctgc tgggtggtag gcagcagtgg 240
gtgggtgcct gcagtggtct gtaaagacca cctgagatgt ccttcctcct ctgttccacc 300
ctgtccaggt ccaagaagac agtctatgaa gagagagcag gtgtgactct ctcagtgtgc 360
tcctctgtga gaagcaggct gacatcccaa agggaagggc ggataacaga gacagtgcaa 420
gcggaggaga tgagggtgcc tcaaagccgg gaggctgggt gatgcaggag cctgcgtgtc 480

```
ccgagggggg tgctgggccc agtgtgagta cgtgtgactg tgactgagac agtgtgactg    540
ctgaaggcag ggacacagca gctccctgac tgggggcaga aggcgttaac tgtgtgaagg    600
ctggttgtgg gtgggtgggc tctgggcctc gaacccgggg gctgagggag atagtaaaca    660
gcagggtgac tgacgggaag atcatgttgg tagccctgcg aagatgctgc agggctgtgg    720
gggtttgtgt gactttgcag ttcaacaaat tcaaattcag ccaacgctgg cagggcctgt    780
tgtgccaggc aaccagctag gaggaggaga ctcggaccca gcttgcagct gaagggcgct    840
ggctgccggg ttctgtgggt tcaccttgcg gtgtcttccc ttgctaacac tgagtcctta    900
caatagcccc atctccaggt tgaggctaga tggaggggac agagggaagt gacttgccca    960
aggtgaccca agctcccgag tgccagggca ggatctgaat tcaggctctc agactgcaga   1020
gcctgagtcc ctccctgcca tgcctgtgcc agggtggaaa tgtctggtcc tggaggggag   1080
cgtggactcc tggccttggc tctggagaca tccccctaga ccacgtgggc tcctaacctg   1140
tccatggtca ctgtgctgag gggcgggacg gtgggtcacc cctagttctt ttttccccag   1200
ggccagattc atggactgaa gggttgctcg gctctcagag accccctaag cgccccgccc   1260
tggccccaag ccctccccca gctcccgcgt ccccccctc ctggcgctga ctccgggcca    1320
gaagaggaaa ggctgtctcc acccacctct cgcactctcc cttctccttt ataaaggccg   1380
gaacagctga aagggtggca acttctcctc ctgcagccgg gagcggcctg cctgcctccc   1440
gtcgacgatc ctgagaactt cagggtgagt ttggggaccc ttgattgttc tttcttttc    1500
gctattgtaa aattcatgtt atatggaggg ggcaaagttt tcagggtgtt gtttagaatg   1560
ggaagatgtc ccttgtatca ccatggaccc tcatgataat tttgtttctt tcactttcta   1620
ctctgttgac aaccattgtc tcctcttatt ttcttttcat tttctgtaac tttttcgtta   1680
aactttagct tgcatttgta acgaattttt aaattcactt ttgtttattt gtcagattgt   1740
aagtactttc tctaatcact tttttttcaa ggcaatcagg gtatattata ttgtacttca   1800
gcacagtttt agagaacaat tgttataatt aaatgataag gtagaatatt tctgcatata   1860
aattctggct ggcgtggaaa tattcttatt ggtagaaaca actacatcct ggtcatcatc   1920
ctgcctttct ctttatggtt acaatgatat acactgtttg agatgaggat aaaatactct   1980
gagtccaaac cgggcccctc tgctaaccat gttcatgcct tcttcttttt cctacagctc   2040
ctgggcaacg tgctggttat tgtgctgtct catcattttg gcaaagaatt gtaatacgac   2100
tcactatagg gcaagcttat gacagagtta cctgcaccgt tgtcctactt ccagaatgca   2160
cagatgtctg aggacaacca cctgagcaat actgtacgta gccagaatga caatagagaa   2220
cggcaggagc acaacgacag acggagcctt ggccaccctg agccattatc taatggacga   2280
ccccagggta actcccggca ggtggtggag caagatgagg aagaagatga ggagctgaca   2340
ttgaaatatg gcgccaagca tgtgatcatg ctctttgtcc ctgtgactct ctgcatggtg   2400
gtggtcgtgg ctaccattaa gtcagtcagc ttttataccc ggaaggatgg gcagctaatc   2460
tataccctat tcacagaaga taccgagact gtgggccaga gagccctgca ctcaattctg   2520
aatgctgcca tcatgatcag tgtcattgtt gtcatgacta tcctcctggt ggttctgtat   2580
aaatacaggt gctataaggt catccatgcc tggcttatta tatcatctct attgttgctg   2640
ttcttttttt cattcattta cttgggggaa gtgtttaaaa cctataacgt tgctgtggac   2700
tacattactg ttgcactcct gatctggaat tttggtgtgg tgggaatgat ttccattcac   2760
tggaaaggtc cacttcgact ccagcaggca tatctcatta tgattagtgc cctcatggcc   2820
ctggtgttta tcaagtacct ccctgaatgg actgcgtggc tcatcttggc tgtgatttca   2880
```

-continued

```
gtatatgatt tagtggctgt tttgtgtccg aaaggtccac ttcgtatgct ggttgaaaca   2940

gctcaggaga gaaatgaaac gctttttcca gctctcattt actcctcaac aatggtgtgg   3000

ttggtgaata tggcagaagg agacccggaa gctcaaagga gagtatccaa aaattccaag   3060

tataatgcag aaagcacaga aagggagtca caagacactg ttgcagagaa tgatgatggc   3120

gggttcagtg aggaatggga agcccagagg gacagtcatc tagggcctca tcgctctaca   3180

cctgagtcac gagctgctgt ccaggaactt tccagcagta tcctcgctgg tgaagaccca   3240

gaggaaaggg gagtaaaact tggattggga gatttcattt tctacagtgt tctggttggt   3300

aaagcctcag caacagccag tggagactgg aacacaacca tagcctgttt cgtagccata   3360

ttaattggtt tgtgccttac attattactc cttgccattt tcaagaaagc attgccagct   3420

cttccaatct ccatcacctt tgggcttgtt ttctactttg ccacagatta tcttgtacag   3480

ccttttatgg accaattagc attccatcaa ttttatatct aggcggccgc aacttgttta   3540

ttgcagctta taatggttac aaataaagca atagcatcac aaatttcaca aataaagcat   3600

tttttcact gcattctagt tgtggtttgt ccaaactcat caatgtatct tatcatgtct   3660

g                                                                   3661
```

<210> SEQ ID NO 36
<211> LENGTH: 42
<212> TYPE: DNA
<213> ORGANISM: Artificial
<220> FEATURE:
<223> OTHER INFORMATION: Primer

<400> SEQUENCE: 36

```
ggggtcgaca agcttgccac catgctgccc ggtttggcac tg                        42
```

<210> SEQ ID NO 37
<211> LENGTH: 39
<212> TYPE: DNA
<213> ORGANISM: Artificial
<220> FEATURE:
<223> OTHER INFORMATION: Primer

<400> SEQUENCE: 37

```
ggggtcgacg cggccgccta gttctgcatc tgctcaaag                            39
```

<210> SEQ ID NO 38
<211> LENGTH: 4570
<212> TYPE: DNA
<213> ORGANISM: Artificial
<220> FEATURE:
<223> OTHER INFORMATION: PDGF-APP

<400> SEQUENCE: 38

```
attaatgatc cacagtctcc tgagtagctg ggactacagg agcttgttac cacacccagc     60

tccagtttat aaattcatct ccagtttata aaggaggaaa ccgaggtact gagaggttaa    120

aaaaccttcc tgcagacact tgtccagcaa gtggccactc caggatttgg accaaggtga    180

tgtgtcttca ggctgtgtct ctgccactgt gccacgctgc tgggtggtag gcagcagtgg    240

gtgggtgcct gcagtggtct gtaaagacca cctgagatgt ccttcctcct ctgttccacc    300

ctgtccaggt ccaagaagac agtctatgaa gagagagcag gtgtgactct ctcagtgtgc    360

tcctctgtga gaagcaggct gacatcccaa agggaagggc ggataacaga gacagtgcaa    420

gcggaggaga tgagggtgcc tcaaagccgg gaggctgggt gatgcaggag cctgcgtgtc    480

ccgagggggg tgctgggccc agtgtgagta cgtgtgactg tgactgagac agtgtgactg    540
```

-continued

```
ctgaaggcag ggacacagca gctccctgac tgggggcaga aggcgttaac tgtgtgaagg    600
ctggttgtgg gtgggtgggc tctgggcctc gaacccgggg gctgagggag atagtaaaca    660
gcagggtgac tgacgggaag atcatgttgg tagccctgcg aagatgctgc agggctgtgg    720
gggtttgtgt gactttgcag ttcaacaaat tcaaattcag ccaacgctgg cagggcctgt    780
tgtgccaggc aaccagctag gaggaggaga ctcggaccca gcttgcagct gaagggcgct    840
ggctgccggg ttctgtgggt tcaccttgcg gtgtcttccc ttgctaacac tgagtcctta    900
caatagcccc atctccaggt tgaggctaga tggaggggac agagggaagt gacttgccca    960
aggtgaccca agctcccgag tgccagggca ggatctgaat tcaggctctc agactgcaga   1020
gcctgagtcc ctccctgcca tgcctgtgcc agggtggaaa tgtctggtcc tggaggggag   1080
cgtggactcc tggccttggc tctggagaca tccccctaga ccacgtgggc tcctaacctg   1140
tccatggtca ctgtgctgag ggcgggacg gtgggtcacc cctagttctt ttttccccag    1200
ggccagattc atggactgaa gggttgctcg gctctcagag accccctaag cgccccgccc   1260
tggccccaag ccctccccca gctcccgcgt cccccccctc ctggcgctga ctccgggcca   1320
gaagaggaaa ggctgtctcc acccacctct cgcactctcc cttctccttt ataaaggccg   1380
gaacagctga aagggtggca acttctcctc ctgcagccgg gagcggcctg cctgcctccc   1440
gtcgacgatc ctgagaactt cagggtgagt ttggggaccc ttgattgttc tttcttttc    1500
gctattgtaa aattcatgtt atatggaggg ggcaaagttt tcagggtgtt gtttagaatg   1560
ggaagatgtc ccttgtatca ccatggaccc tcatgataat tttgtttctt tcactttcta   1620
ctctgttgac aaccattgtc tcctcttatt ttcttttcat tttctgtaac tttttcgtta   1680
aactttagct tgcatttgta acgaattttt aaattcactt ttgtttattt gtcagattgt   1740
aagtactttc tctaatcact tttttttcaa ggcaatcagg gtatattata ttgtacttca   1800
gcacagtttt agagaacaat tgttataatt aaatgataag gtagaatatt tctgcatata   1860
aattctggct ggcgtggaaa tattcttatt ggtagaaaca actacatcct ggtcatcatc   1920
ctgcctttct ctttatggtt acaatgatat acactgtttg agatgaggat aaaatactct   1980
gagtccaaac cgggcccctc tgctaaccat gttcatgcct tcttcttttt cctacagctc   2040
ctgggcaacg tgctggttat tgtgctgtct catcattttg gcaaagaatt gtaatacgac   2100
tcactatagg gcaagcttat gctgcccggt ttggcactgc tcctgctggc cgcctggacg   2160
gctcgggcgc tggaggtacc cactgatggt aatgctggcc tgctggctga accccagatt   2220
gccatgttct gtggcagact gaacatgcac atgaatgtcc agaatgggaa gtgggattca   2280
gatccatcag ggaccaaaac ctgcattgat accaaggaag gcatcctgca gtattgccaa   2340
gaagtctacc ctgaactgca gatcaccaat gtggtagaag ccaaccaacc agtgaccatc   2400
cagaactggt gcaagcgggg ccgcaagcag tgcaagaccc atccccactt tgtgattccc   2460
taccgctgct tagttggtga gtttgtaagt gatgcccttc tcgttcctga caagtgcaaa   2520
ttcttacacc aggagaggat ggatgtttgc gaaactcatc ttcactggca caccgtcgcc   2580
aaagagacat gcagtgagaa gagtaccaac ttgcatgact acggcatgtt gctgccctgc   2640
ggaattgaca agttccgagg ggtagagttt gtgtgttgcc cactggctga agaaagtgac   2700
aatgtggatt ctgctgatgc ggaggaggat gactcggatg tctggtgggg cggagcagac   2760
acagactatg cagatgggag tgaagacaaa gtagtagaag tagcagagga ggaagaagtg   2820
gctgaggtgg aagaagaaga agccgatgat gacgaggacg atgaggatgg tgatgaggta   2880
gaggaagagg ctgaggaacc ctacgaagaa gccacagaga gaaccaccag cattgccacc   2940
```

accaccacca ccaccacaga gtctgtggaa gaggtggttc gagaggtgtg ctctgaacaa 3000
gccgagacgg ggccgtgccg agcaatgatc tcccgctggt actttgatgt gactgaaggg 3060
aagtgtgccc cattctttta cggcggatgt ggcggcaacc ggaacaactt tgacacagaa 3120
gagtactgca tggccgtgtg tggcagcgcc atgtcccaaa gtttactcaa gactacccag 3180
gaacctcttg cccgagatcc tgttaaactt cctacaacag cagccagtac ccctgatgcc 3240
gttgacaagt atctcgagac acctggggat gagaatgaac atgcccattt ccagaaagcc 3300
aaagagaggc ttgaggccaa gcaccgagag agaatgtccc aggtcatgag agaatgggaa 3360
gaggcagaac gtcaagcaaa gaacttgcct aaagctgata agaaggcagt tatccagcat 3420
ttccaggaga aagtggaatc tttggaacag gaagcagcca acgagagaca gcagctggtg 3480
gagacacaca tggccagagt ggaagccatg ctcaatgacc gccgccgcct ggccctggag 3540
aactacatca ccgctctgca ggctgttcct cctcggcctc gtcacgtgtt caatatgcta 3600
aagaagtatg tccgcgcaga acagaaggac agacagcaca ccctaaagca tttcgagcat 3660
gtgcgcatgg tggatcccaa gaaagccgct cagatccggt cccaggttat gacacacctc 3720
cgtgtgattt atgagcgcat gaatcagtct ctctccctgc tctacaacgt gcctgcagtg 3780
gccgaggaga ttcaggatga agttgatgag ctgcttcaga aagagcaaaa ctattcagat 3840
gacgtcttgg ccaacatgat tagtgaacca aggatcagtt acggaaacga tgctctcatg 3900
ccatctttga ccgaaacgaa aaccaccgtg gagctccttc ccgtgaatgg agagttcagc 3960
ctggacgatc tccagccgtg gcattctttt ggggctgact ctgtgccagc caacacagaa 4020
aacgaagttg agcctgttga tgcccgccct gctgccgacc gaggactgac cactcgacca 4080
ggttctgggt tgacaaatat caagacggag gagatctctg aagtgaagat ggatgcagaa 4140
ttccgacatg actcaggata tgaagttcat catcaaaaat tggtgttctt tgcagaagat 4200
gtgggttcaa acaaaggtgc aatcattgga ctcatggtgg gcggtgttgt catagcgaca 4260
gtgatcgtca tcaccttggt gatgctgaag aagaaacagt acacatccat tcatcatggt 4320
gtggtggagg ttgacgccgc tgtcacccca gaggagcgcc acctgtccaa gatgcagcag 4380
aacggctacg aaaatccaac ctacaagttc tttgagcaga tgcagaacta ggcggccgca 4440
acttgtttat tgcagcttat aatggttaca aataaagcaa tagcatcaca aatttcacaa 4500
ataaagcatt tttttcactg cattctagtt gtggtttgtc caaactcatc aatgtatctt 4560
atcatgtctg 4570

<210> SEQ ID NO 39
<211> LENGTH: 40
<212> TYPE: DNA
<213> ORGANISM: Artificial
<220> FEATURE:
<223> OTHER INFORMATION: Primer

<400> SEQUENCE: 39
ggggtcgaca agcttgccac catgacagag ttacctgcac 40

<210> SEQ ID NO 40
<211> LENGTH: 39
<212> TYPE: DNA
<213> ORGANISM: Artificial
<220> FEATURE:
<223> OTHER INFORMATION: Primer

<400> SEQUENCE: 40
ggggtcgacg cggccgccta gatataaaat tgatggaat 39

-continued

<210> SEQ ID NO 41
<211> LENGTH: 35
<212> TYPE: DNA
<213> ORGANISM: Artificial
<220> FEATURE:
<223> OTHER INFORMATION: Primer

<400> SEQUENCE: 41
gcagctaatc tataccctat tcacagaaga taccg 35

<210> SEQ ID NO 42
<211> LENGTH: 35
<212> TYPE: DNA
<213> ORGANISM: Artificial
<220> FEATURE:
<223> OTHER INFORMATION: Primer

<400> SEQUENCE: 42
cggtatcttc tgtgaatagg gtatagatta gctgc 35

<210> SEQ ID NO 43
<211> LENGTH: 30
<212> TYPE: DNA
<213> ORGANISM: Artificial
<220> FEATURE:
<223> OTHER INFORMATION: Primer

<400> SEQUENCE: 43
ggggtcgacg atcctgagaa cttcagggtg 30

<210> SEQ ID NO 44
<211> LENGTH: 29
<212> TYPE: DNA
<213> ORGANISM: Artificial
<220> FEATURE:
<223> OTHER INFORMATION: Primer

<400> SEQUENCE: 44
gatcggtacc tccagcgccc gagccgtcc 29

<210> SEQ ID NO 45
<211> LENGTH: 23
<212> TYPE: DNA
<213> ORGANISM: Artificial
<220> FEATURE:
<223> OTHER INFORMATION: Primer

<400> SEQUENCE: 45
gtcgacgatc ctgagaactt cag 23

<210> SEQ ID NO 46
<211> LENGTH: 20
<212> TYPE: DNA
<213> ORGANISM: Artificial
<220> FEATURE:
<223> OTHER INFORMATION: Primer

<400> SEQUENCE: 46
gggttcagcc agcaggccag 20

<210> SEQ ID NO 47
<211> LENGTH: 22
<212> TYPE: DNA
<213> ORGANISM: Artificial
<220> FEATURE:
<223> OTHER INFORMATION: Primer -continued

```
<400> SEQUENCE: 47

ctagttctgc atctgctcaa ag                                          22


<210> SEQ ID NO 48
<211> LENGTH: 19
<212> TYPE: DNA
<213> ORGANISM: Artificial
<220> FEATURE:
<223> OTHER INFORMATION: Primer

<400> SEQUENCE: 48

ttctgagaac ttcaggctc                                              19


<210> SEQ ID NO 49
<211> LENGTH: 22
<212> TYPE: DNA
<213> ORGANISM: Artificial
<220> FEATURE:
<223> OTHER INFORMATION: Primer

<400> SEQUENCE: 49

cttgtaggtt ggattttcgt ag                                          22
```